US007365168B2

(12) United States Patent
Hinton et al.

(10) Patent No.: US 7,365,168 B2
(45) Date of Patent: *Apr. 29, 2008

(54) ALTERATION OF FCRN BINDING AFFINITIES OR SERUM HALF-LIVES OF ANTIBODIES BY MUTAGENESIS

(75) Inventors: Paul Hinton, Sunnyvale, CA (US); Naoya Tsurushita, Palo Alto, CA (US); J. Yun Tso, Menlo Park, CA (US); Maximiliano Vasquez, Palo Alto, CA (US)

(73) Assignee: PDL BioPharma, Inc., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/102,621

(22) Filed: Apr. 8, 2005

(65) Prior Publication Data

US 2005/0276799 A1 Dec. 15, 2005

Related U.S. Application Data

(63) Continuation-in-part of application No. 10/822,300, filed on Apr. 9, 2004, which is a continuation-in-part of application No. 10/687,118, filed on Oct. 15, 2003.

(60) Provisional application No. 60/499,048, filed on Aug. 29, 2003, provisional application No. 60/475,762, filed on Jun. 3, 2003, provisional application No. 60/462,014, filed on Apr. 10, 2003, provisional application No. 60/418,972, filed on Oct. 15, 2002.

(51) Int. Cl.
*C12P 21/08* (2006.01)
*C07K 1/00* (2006.01)

(52) U.S. Cl. .............................. 530/387.3; 530/388.1; 530/388.15; 530/388.22

(58) Field of Classification Search ..................... None
See application file for complete search history.

(56) References Cited

U.S. PATENT DOCUMENTS

| | | | |
|---|---|---|---|
| 5,530,101 | A | 6/1996 | Queen et al. |
| 5,834,597 | A | 11/1998 | Tso et al. |
| 5,994,514 | A | 11/1999 | Jardieu et al. |
| 6,165,745 | A | 12/2000 | Ward et al. |
| 6,197,297 | B1 | 3/2001 | Kunikata et al. |
| 6,277,375 | B1 | 8/2001 | Ward |
| 6,329,511 | B1 | 12/2001 | Vasquez et al. |
| 6,383,487 | B1 | 5/2002 | Amlot et al. |
| 6,528,624 | B1 | 3/2003 | Idusogie et al. |
| 6,797,493 | B2 | 9/2004 | Sun et al. |
| 7,083,784 | B2 | 8/2006 | Dall'Acqua et al. |
| 7,163,681 | B2 | 1/2007 | Giles-Komar et al. |
| 2001/0033842 | A1 | 10/2001 | Jardieu et al. |
| 2002/0098193 | A1 | 7/2002 | Ward |
| 2002/0142000 | A1 | 10/2002 | Digan et al. |
| 2003/0003098 | A1 | 1/2003 | Strom |
| 2003/0044858 | A1 | 3/2003 | Jardieu et al. |
| 2005/0014934 | A1 | 1/2005 | Hinton et al. |
| 2005/0032114 | A1 | 2/2005 | Hinton et al. |
| 2005/0226864 | A1 | 10/2005 | Hinton et al. |
| 2005/0276799 | A1 | 12/2005 | Hinton et al. |
| 2006/0198840 | A1 | 9/2006 | Dall'Acqua et al. |

FOREIGN PATENT DOCUMENTS

| | | | |
|---|---|---|---|
| EP | 1260521 | A2 | 11/2002 |
| WO | WO93/04173 | A1 | 8/1991 |
| WO | WO96/31229 | A1 | 4/1995 |
| WO | WO97/28267 | A1 | 2/1996 |
| WO | WO97/34631 | A1 | 3/1996 |
| WO | WO98/05787 | A1 | 8/1996 |
| WO | WO98/47531 | A1 | 4/1997 |
| WO | WO99/02709 | A1 | 7/1997 |
| WO | WO97/34621 | A1 | 9/1997 |
| WO | WO98/23289 | A1 | 6/1998 |
| WO | WO00/42072 | A2 | 1/1999 |
| WO | WO00/47625 | A1 | 2/1999 |
| WO | WO99/51642 | A2 | 10/1999 |
| WO | WO99/58572 | A1 | 11/1999 |
| WO | WO01/58957 | A1 | 2/2000 |
| WO | WO00/68381 | A1 | 11/2000 |
| WO | WO02/060919 | A2 | 8/2002 |
| WO | WO2004/092219 | A2 | 10/2004 |

OTHER PUBLICATIONS

Li et al. Biochemistry 2000. 39:6296-6309.*

Achatz, et al. "The IgE antigen Receptor: a Key Regulator for the Production of IgE Antibodies", *Int. Arch. Allergy Immunol.* (2001) 124(1-3):31-4.

Alegre, et al. "Effect of a single amino acid mutation on the activating and immunosuppressive properties of a humanized OKT3 monoclonal antibody", *J. Immunol.* (1992) 148(11):3461-8.

Angal, et al. "A single amino acid substitution abolishes the heterogeneity of chimeric mouse/human (IgG4) antibody", *Mol. Immunol* (1993) 30(1):105-8.

Armour, et al. "Recombinant human IgG molecules lacking Fcgamma receptor 1 binding and monocyte triggering activities", *Eur J. Immunol.* (1999) 29(8):2613-24.

(Continued)

*Primary Examiner*—Maher M. Haddad
*Assistant Examiner*—Chun Crowder
(74) *Attorney, Agent, or Firm*—Townsend and Townsend and Crew, LLP

(57) ABSTRACT

The present invention provides for a modified antibody of class IgG, in which at least one amino acid from the heavy chain constant region selected from the group consisting of amino acid residues 250, 314, and 428 is substituted with another amino acid which is different from that present in the unmodified antibody, thereby altering the binding affinity for FcRn and/or the serum half-life in comparison to the unmodified antibody.

8 Claims, 29 Drawing Sheets

OTHER PUBLICATIONS

Armour, et al. The Contrasting IgG-Binding Interactions of Human and Herpes Simplex Virus Fc Receptors, *Biochem Soc. Trans.* (2002) 30(4):495-500.
Arya, et al. "Mapping of amino acid residues in the C mu 3 domain of mouse IgM important in macromolecular assembly and complement-dependent cytolysis", *J. Immunol* (1994) 152(3):1206-12.
Attwood, Teresa K. "The Babel of Bioinformatics", *Science* (2000) 290:1-5 (html format).
Batra, et al. "Insertion of Constant Region Domains of Human IgG1 into CD4-PE40 Increases Its Plasma Half-Life", *Molec. Immunol.* (1993) 30(4):379-386.
Brekke, et al. "Human IgG isotype-specific amino acid residues affecting complment-mediated cell lysis and phagocytosis", *Eur. J. Immunol.* (1994) 24(10):2542-7.
Burmeister, et al. Crystal structure of the complex of rat neonatal Fc receptor with Fc *Nature* (1994) 372:379-383.
Canfield "The binding affinity of human IgG for its high affinity Fc receptor is determined by multiple amino acids in the CH2 domain and is modulated by the hinge region", *J. Exp. Med.* (1991) 173(6):1483-91.
Caron, et al. Engineered humanized dimeric forms of IgG are more effective antibodies, *J. Exp. Med.* (1992) 176(4): 1191-5.
Chapman, et al. "Characterization of the Interaction Between the Herpes Simplex Virus Type 1 Fc Receptor and Immunoglobulin G", *J. Biol. Chem.* (1999) 274(11):6911-9.
Chappel, et al. "Identification of a secondary Fc gamma R1 binding site within a genetically engineered human IgG antibody", *J. Biol. Chem.* (1993) 268(33):25124-31.
Chaudhury, et al. "The Major Histocompatibility Complex-related Fc Receptor for IgG (FcRn) Binds Albumin and Prolongs Its Lifespan", *J. Exp. Med.* (2003) 197(3):315-322.
Chintalacharuvu, et al. "Hybrid IgA2/IgG1 Antibodies with Tailor-Made Effector Functions", *Clin. Imm.* (2001) 101(1):21-31.
Cole, et al. "HuM291, A Humanized Anti-CD3 Antibody, is Immunosuppressive to T cells While Exhibiting Reduced Mitogenicity in Vitro", *Transplanation* (1999) 68(4):563-71.
Cole, et al. "Human IgG2 variants of chimerical anti-CD3 are nonmitogenic to T cells", *J. Immunol.* (1997) 159(7):3613-21.
Dall'Acqua, et al. "Increasing the Affinity of a Human IgG1 for the Neonatal Fc Receptor: Biological Consequences", *J. Immunol.* (2002) 169(9):5171-80.
Deisenhofer "Crystallographic refinement and atomic models of a human Fc fragment and its complex with fragment B of protein A from *Staphylococcus aureus* at 2.9- and 2.8-A resolution", *Biochemistry* (1981) 20:2361-2370.
Delano, et al. "Convergent Solutions to Binding at a Protein-Protein Interface", *Science* (2000) 287(5456):1279-83.
Dorai, et al. "Role of inter-heavy and light chain disulfide bonds in the effector functions of human immunoglobulin IgG1", *Mol. Immunol.* (1992) 29(12):1487-91.
Duncan, et al. "The binding site for C1q on IgG", *Nature* (1988) 332(6166):738-40.
Ehrlich, et al. "Characterization of human monoclonal antibodies directed against hepatitis B surface antigen", *Hum. Antibodies Hybridomas* (1992) 3:2-7.
El-Amine, et al. "In Vivo Induction of Tolerance by an Ig Peptide is not Affected by the Deletion of FcR or a Mutated IgG Fc Fragment", *Int. Immunol.* (220) 14(7):761-6.
Ellison, Jay, et al. "Linkage and sequence homology of two human immunoglobulin y heavy chain constant region genes", *Proc. Natl. Acad. Sci USA* (1982) 79:1984-1988.
Firan, et al. "The MHC Class I-Related Receptor FcRn, Plays an Essential Role in the Matermofetal Transfer of Gamma-Globulin in Humans", *Int. Immunol.* (2001) 13(8):993-1002.
Ghetie and Ward "Multiple roles for the major histocompatibility complex class I-related receptor FcRn", *Annu. Rev. Immunol.* (2000) 18:739-766.
Ghetie, et al. "Increasing the serum persistence of an IgG fragment by random mutagenesis", *Nat: Biotechnol.* (1997) 15:637-640.
He X-y, et al. "Humanization and Pharmacokinetics of a Monoclonal Antibody with Specificity for Both E- and P-selectin", *The American Association of Immunologists* (1998).
Helm, et al. "Identification of the high affinity receptor binding region in human immunoglobulin E", *J. Biol. Chem.* (1996) 271(13):7494-500.
Hezareh, et al. "Effector Function Activities of a Panel of Mutants of a Broadly Neutralizing Antibody Against Human Immunodeficiency Virus Type", *J. Virol.* (2001) 75(24):12161-8.
Hinton, et al. "Engineered Human IgG Antibodies with Longer Serum Half-lives in Primate", *J. Biol. Chem.* (2004) 279(8):6213-6216.
Hornick, et al. "Single Amino Acid Substitution in the Fc Region of Chimeric TNT-3 Antibody Accelerates Clearance and Improves Immunoscintigraphy of Solid Tumors", *J. Nucl. Med.* (2000) 41(2):355-62.
Isaacs, et al. "Therapy with monoclonal antibodies. II. The contribution of Fc gamma receptor binding and the influence of C(H)1 and C(H)3 domains on in vivo effector function", . *J. Immunol.* (1998) 161(8):3862-9.
Ito, et al. "[An amino acid substitution determining G1m(x) allotypic marker]," *Nippon Hoigaku Zasshi* (1989) 43(2):155-60.
Jendeberg, et al. "Engineering of Fc(1) and Fc(3) from human immunoglobulin G to analyse subclass specificity for staphylococcal protein A", *J. Immunol Methods* (1997) 201(1):25-34.
Jollife, "Humanized antibodies: enhancing therapeutic utility through antibody engineering", *Int. Rev. Immunol.* (1993) 10(2-3):241-50.
Kim, et al. "Mapping the site on human IgG for binding of the MHC class I-related receptor, FcRn", *Eur. J. Immunol.* (1999) 29:2819-2825.
Kim, et al. "Catabolism of the Murine IgG1 Molecule: Evidence that Both CH2-CH3 Domain Interfaces are Required for Persistence of IgG1 in the Circulation of Mice", *Scand. J. Immunol.*, (1994) 40:457-465.
Kim, et al. "Localization of the site of the murine IgG1 molecule that is involved in binding to the murine intestinal Fc receptor", *Eur. J. Immunol.* (1994) 24(10):2429-34.
Kostelny, et al. "Humanization and characterization of the anti-HLA-DR antibody 1D10", *Int. J. Cancer* (2001) 93:556-565.
Krueger, James G., et al. "Successful in vivo blockade of CD25 (high affinity interleukin 2 receptor) on T cells by administration of humanized anti-Tac antibody to patients with psoriasis", *J. Am. Acad. Dermatol.* (2000) 43(3):448-458.
Lund, et al. "Human Fc gamma RI and Fc gamma RII interact with distinct but overlapping sites on human IgG", *J. Immunol.* (1991) 147(8):2657-62.
Lund, et al. "Multiple binding sites on the CH 2 domain of IgG for mouse Fc gamma R11", *Mol. Immunol.* (1992) 29(1):53-9.
Lund, et al. "Multiple interactions of IgG with its core oligosaccharide can modulate recognition by complment and human Fc gamma receptor 1 and influence the synthesis of its oligosaccharide chains", *J. Immunol.* (1996) 157(11):4963-9.
Martin, et al. "Crystal structure at 2.8 A of an FcRn/heterodimeric Fc complex: mechanism of pH-dependent binding", *Molecular Cell* (2001) 7:867-877.
Martin, W. L., et al. "Protein-Protein Recognition: The Neonatal Fc Receptor and Immunoglobulin G", Doctoral dissertation, California Institute of Technology.
McDonnell, et al. "The Structure of the IgE Cepsilon2 Domain and its Role in Stabilizing the Complex with its High-Affinity receptor FcepsilonRIalpha", *Nat. Struc. Biol.* (2001) 8(5):437-41.
Medesan, et al. "Comparative studies of rat IgG to further delineate the Fc:FcRn interaction site", *Eur. J. Immunol.* (1998) 28:2092-2100.
Medesan, et al. "Delineation of the amino acid residues involved in transcytosis and catabolism of mouse IgG1", *J. Immunol.* (1997) 158(5): 2211-7.
Morrison, et al. Sequences in Antibody Molecules Important for Receptor-Mediated Transport Into the Chicken Egg Yolk, *Mol. Immunol.* (2002) 38(8):619-25.

Muraoka "Structural requirements for IgM assembly and cytolytic activity. Effects of mutations in the oligosaccharide acceptor site at Asn402", *J. Immunol.* (1989) 142(2):695-701.

Nagaoka, et al. "Single Amino Acid Substitution in the Mouse IgG1 Fc region induces drastic enhancement of the affinity to Protein A", *Protein Eng.*, (2003) 16(4):243-5.

Newman, et al. "Modification of the Fc Region of a Primatized IgG Antibody to Human CD4 Retains its Ability to Modulate CD4 Receptors But Does Not Deplete CD4(+) T Cells in Chimpanzees", *Clin. Immunol.* (2001) 98(2):164-74.

Ogata, et al. "Markedly prolonged incubation period of hepatitis B in a chimpanzee passively immunized with a human monoclonal antibody to the $\alpha$ determinant of hepatitis B surface antigen", *Proc. Natl. Acad. Sci. USA* (1993) 90:3014-3018.

Popov, et al. "The stoichiometry and affinity of the interaction of murine Fc fragments with the MHC class I-related receptor, FcRn", *Mol. Immunol.* (1996) 33(6):521-30.

Radaev, et al. "Recognition of Immunoglobulins by Fc gamma Receptors", *Mol. Immunol.* (2001) 38(14):1073-83.

Raghavan, et al. "Investigation of the interaction between the class I MHC-related Fc receptor and its immunoglobulin G ligand", *Immunity* (1994) 1:303-315.

Raghavan, et al. "Analysis of the pH dependence of the neonatal Fc receptor/immunoglobulin G interaction using antibody and receptor variants", *Biochemistry* (1995) 34(45):14649-57.

Reff, et al. "A review of modifications to recombinant antibodies: attempt to increase efficacy in oncology applications", *Critical Review in Oncology/Hematology* (2001) 40:25-35.

Saper, et al. "Refined structure of the human histocompatibility antigen HLA-A2 at 2.6 A resolution", *J. Mol. Biol.* (1991) 219:277-319.

Sarmay, et al. "Mapping and comparison of the interaction sites on the Fc region of IgG responsible for triggering antibody dependent cellular cytotoxicity (ADCC) through different types of human Fc gamma receptor", *Mol. Immunol.* (1992) 29(5):633-9.

Shields, et al. "High resolution mapping of the binding site on human IgG1 for Fc gamma RI, Fc gamma RII, Fc gamma RIII, and FcRn and design of IgG1 variants with improved binding to the Fc gamma R", *J. Biol. Chem.* (2001) 276:6591-6604.

Shopes, "A genetically engineered human IgG mutant with enhanced cytolytic activity", *J. Immunol.* (1992) 148(9):218-22.

Simister and Mostov, "An Fc receptor structurally related to MHC class I antigens", *Nature* (1989) 337:184-187.

Skolnick, Jeffrey, et al. *Trends in Biotechnology* (2000) 18(1):34-39.

Tao, "Studies of aglycosylated chimeric mouse-human IgG. Role of carbohydrate in the structure and effector functions mediated by the human IgG constant region", *J. Immunol.* (2002) 143(8):2595-601.

Taylor, et al. "In Vitro and in Vivo Activities of OX40 (CD134)-IgG Fusion Protein Isoforms with Different Levels of Immune-Effector Functions", *J. Leukoc. Biol.* (2002) 72(3):522-9.

Ward and Ghetie, "The effector functions of immunoglobulins: implications for therapy", *Ther. Immunol.* (1995) 2:77-94.

Ward, et al. "Evidence to Support the Cellular Mechanism Involved in Serum IgG Homeostasis in Humans", *Int'l Immunol.* (2003) 15(2):187-195.

Wawrzynczak, et al. "Recombinant mouse monoclonal antibodies with single amino acid substitutions affecting Clq and high affinity Fc receptor binding have identical serum half-lives in the BALB/c mouse", *Mol. Immunol* . (1992) 29(2):221-7.

Weng, et al. "Computational determination of the structure of rat Fc bound to the neonatal Fc receptor", *J. Mol. Biol.* (1998) 282:217-225.

West and Bjorkman, "Crystal structure and immunoglobulin G binding properties of the human major histocompatibility complex-related Fc receptor", *Biochemistry* (2000) 29:9698-9708.

Datta-Mannan, A., et al. "Humanized $IgG_1$ Variants With Differential Binding Properties to the Neonatal Fc Receptor: Relationship to Pharmacokinetics in Mice and Primates", *Drug Metabolism and Disposition*, [published on Oct. 18, 2006 as doi:10.1124/dmd.106.011734-DMD#11734, pp. 1-47].

Datta-Mannan, A. et al. "Monoclonal Antibody Clearance: Impact of modulating the interactions of IgG with FcRn", *Journal of Biological Chemistry* [in press—published on Nov. 29, 2006 as Ms. M607161200, pp. 1-24].

Dall'Acqua, William F., et al. "Properties of Human IgG1s Engineered for Enhanced Binding to the Neonatal Fc Receptor (FcRn)", *Journal of Biological Chemistry* (2006) 281(33):23514-23524.

International PCT Search Report mailed Sep. 24, 2007 (directed to corresponding PCT publication number WO/2005/123780 A3).

* cited by examiner

| | |
|---|---|
| ▭ | domains |
| ⋀⋀ | inter-domain sections |
| — | interchain disulphide bonds |
| V | variable |
| C | constant |
| L | light chain |
| H | heavy chain |

Amino Acid Sequences of Hu1D10-IgG2M3, Hu1D10-IgG1, Hu1D10-IgG3, Hu1D10-IgG4

Hu1D10-VH (SEQ ID NO:6)
QVQLQESGPGLVKPSETLSLTCTVSGFSLTNYGVHWVRQSPGKGLEWIGVKWSGGSTEYNAAFISRLTISKDTSKN
QVSLKLNSLTAADTAVYYCARNDRYAMDYWGQGTLVTVSS

Hu1D10-VL (SEQ ID NO:8)
DIQMTQSPSSLSASVGDRVTITCRASENIYSYLAWYQQKPGKAPKLLVSNAKTLAEGVPSRFSGSGSGKQFTLTIS
SLQPEDFATYYCQHHYGNSYPFGQGTKLEIK

IgG2M3-CH (SEQ ID NO:2)
ASTKGPSVFPLAPCSRSTSESTAALGCLVKDYFPEPVTVSWNSGALTSGVHTFPAVLQSSGLYSLSSVVTVPSSNF
GTQTYTCNVDHKPSNTKVDKTVERKCCVECPPCPAPPAAAPSVFLFPPKPKDTLMISRTPEVTCVVVDVSHEDPEV
QFNWYVDGVEVHNAKTKPREEQFNSTFRVVSVLTVVHQDWLNGKEYKCKVSNKGLPAPIEKTISKTKGQPREPQVY
TLPPSREEMTKNQVSLTCLVKGFYPSDIAVEWESNGQPENNYKTTPPMLDSDGSFFLYSKLTVDKSRWQQGNVFSC
SVMHEALHNHYTQKSLSLSPSK

IgG1-CH (SEQ ID NO:7)
ASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFFLYSKLTVDKSRWQQGN
VFSCSVMHEALHNHYTQKSLSLSPGK

IgG3-CH (SEQ ID NO:113)
ASTKGPSVFPLAPCSRSTSGGTAALGCLVKDYFPEPVTVSWNSGALTSGVHTFPAVLQSSGLYSLSSVVTVPSSSL
GTQTYTCNVNHKPSNTKVDKRVELKTPLGDTTHTCPRCPEPKSCDTPPPCPRCPEPKSCDTPPPCPRCPEPKSCDT
PPPCPRCPAPELLGGPSVFLFPPKPKDTLMISRTPEVTCVVVDVSHEDPEVQFKWYVDGVEVHNAKTKLREEQYNS
TFRVVSVLTVLHQDWLNGKEYKCKVSNKALPAPIEKTISKAKGQPREPQVYTLPPSREEMTKNQVSLTCLVKGFYP
SDIAVEWESNGQPENNYNTTPPMLDSDGSFFLYSKLTVDKSRWQQGNIFSCSVMHEALHNRYTQKSLSLSPGK

IgG4-CH (SEQ ID NO:114)
ASTKGPSVFPLAPCSRSTSESTAALGCLVKDYFPEPVTVSWNSGALTSGVHTFPAVLQSSGLYSLSSVVTVPSSSL
GTKTYTCNVDHKPSNTKVDKRVESKYGPPCPSCPAPEFLGGPSVFLFPPKPKDTLMISRTPEVTCVVVDVSQEDPE
VQFNWYVDGVEVHNAKTKPREEQFNSTYRVVSVLTVLHQDWLNGKEYKCKVSNKGLPSSIEKTISKAKGQPREPQV
YTLPPSQEEMTKNQVSLTCLVKGFYPSDIAVEWESNGQPENNYKTTPPVLDSDGSFFLYSRLTVDKSRWQEGNVFS
CSVMHEALHNHYTQKSLSLSLGK

KAPPA-CL (SEQ ID NO:9)
RTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC

FIG. 3

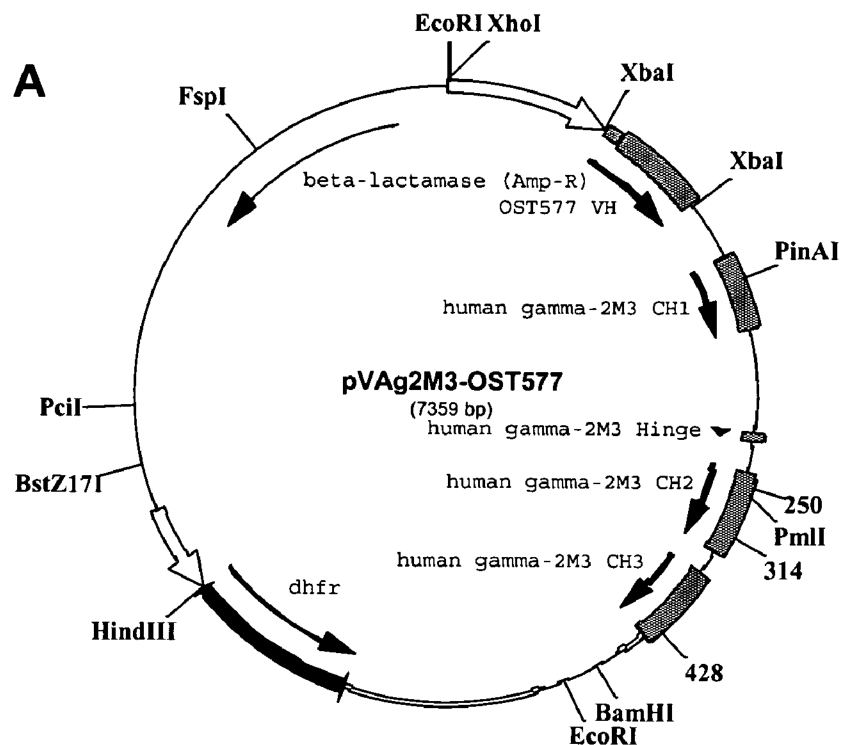
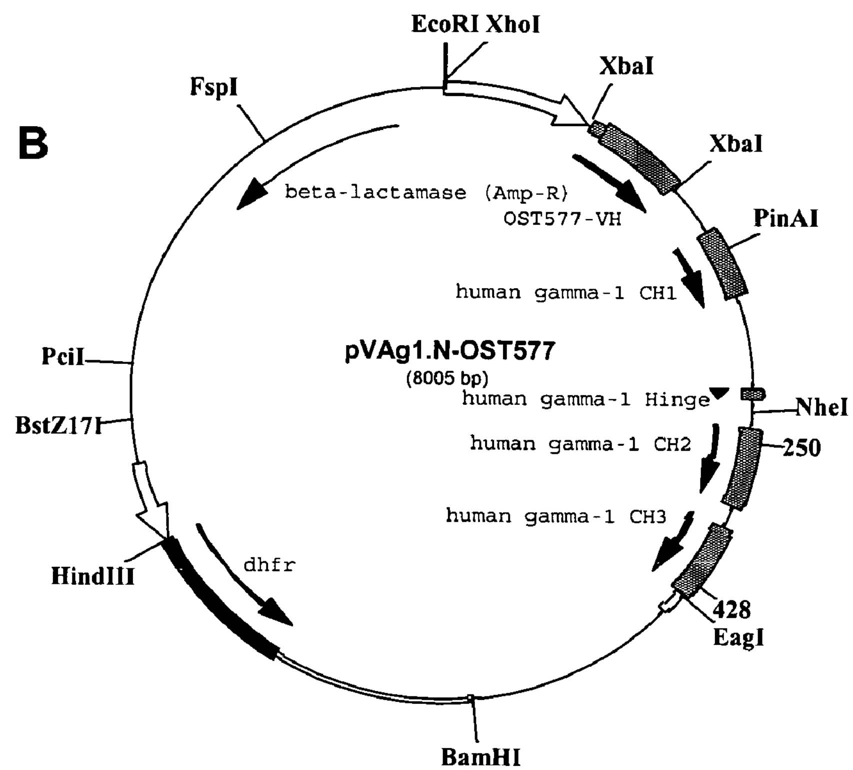
FIG. 5

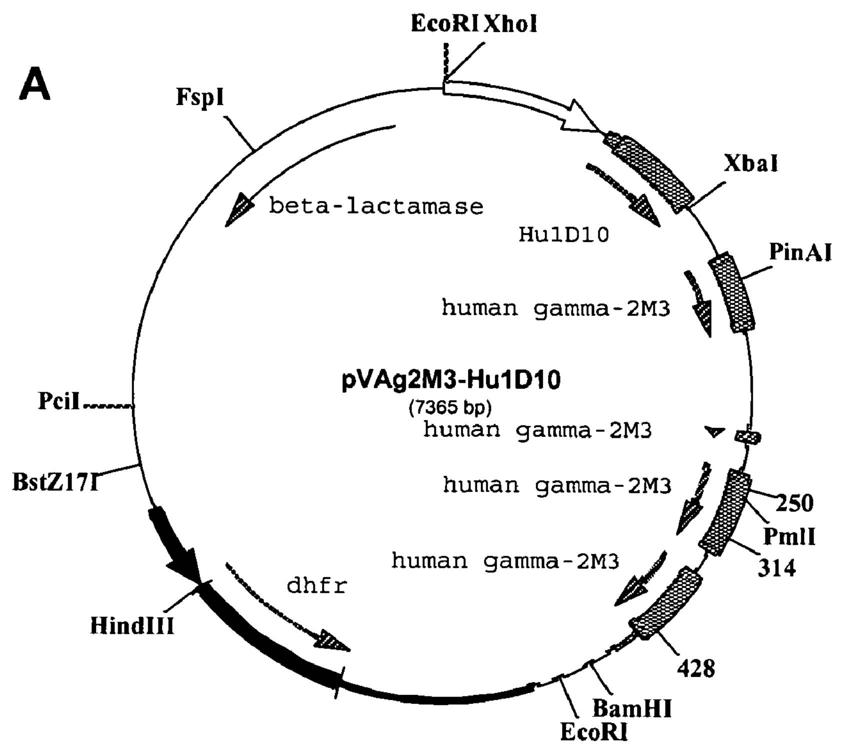
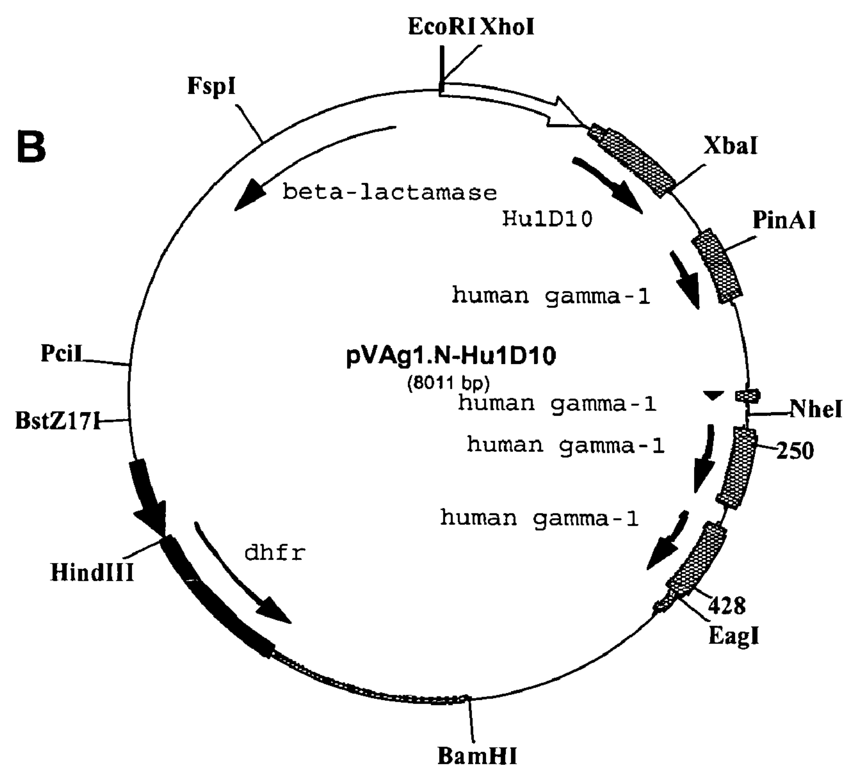
FIG. 7

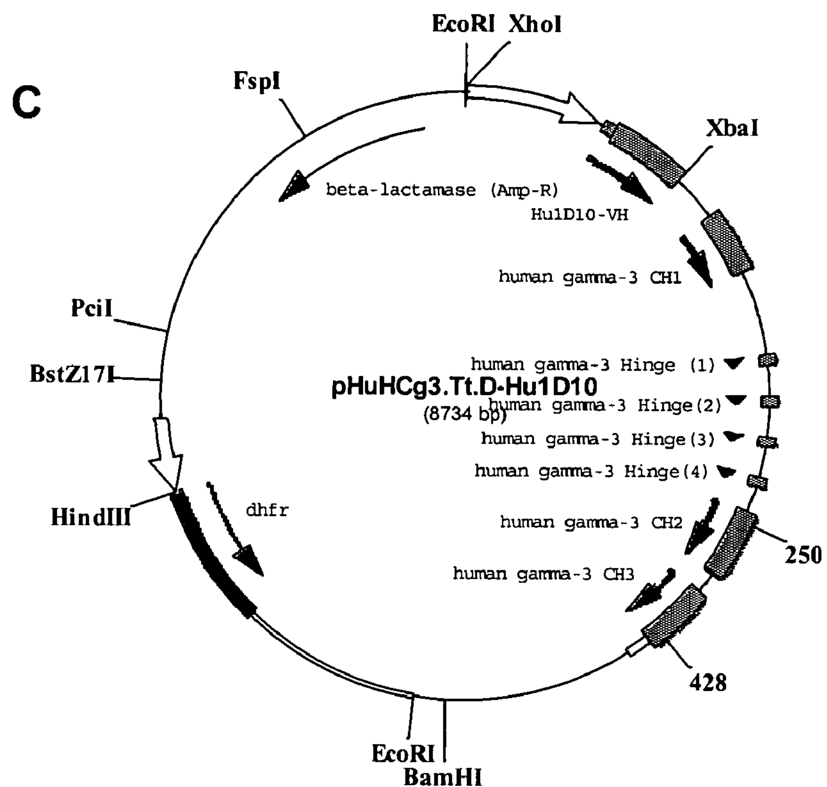
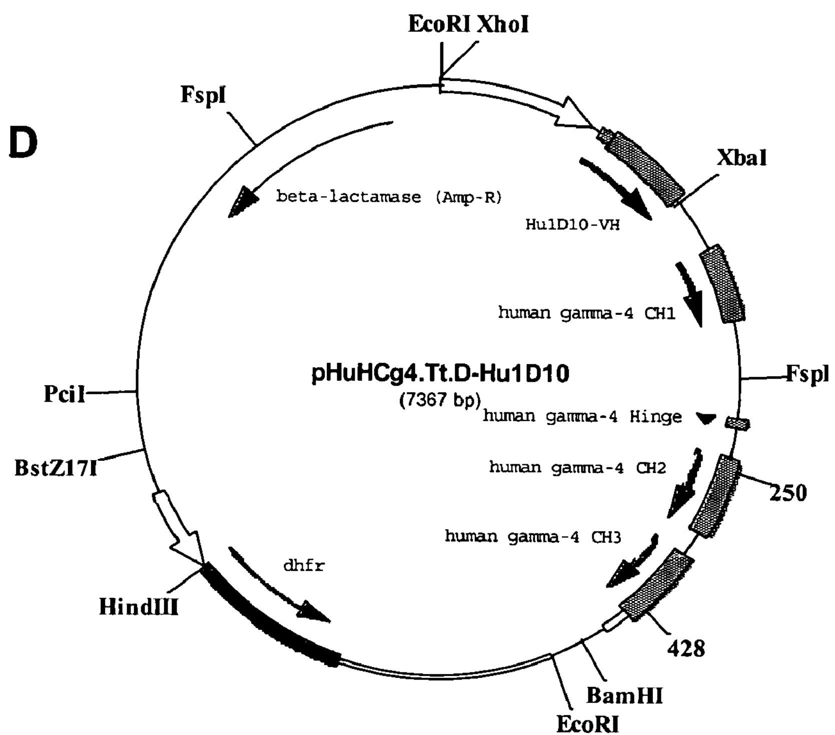
FIG. 7

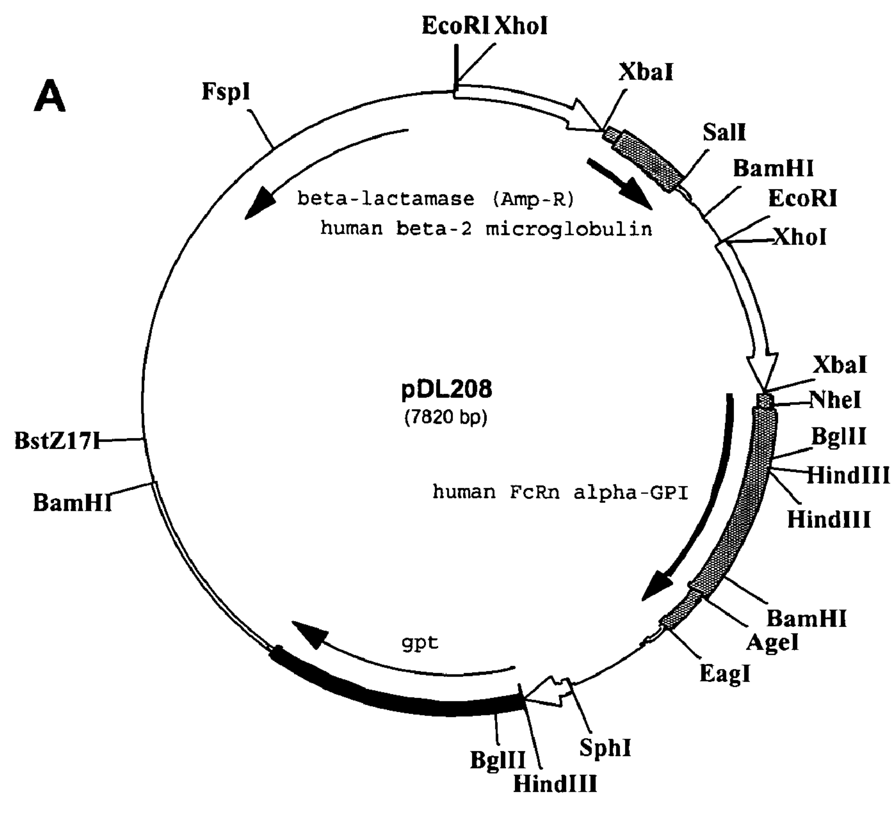
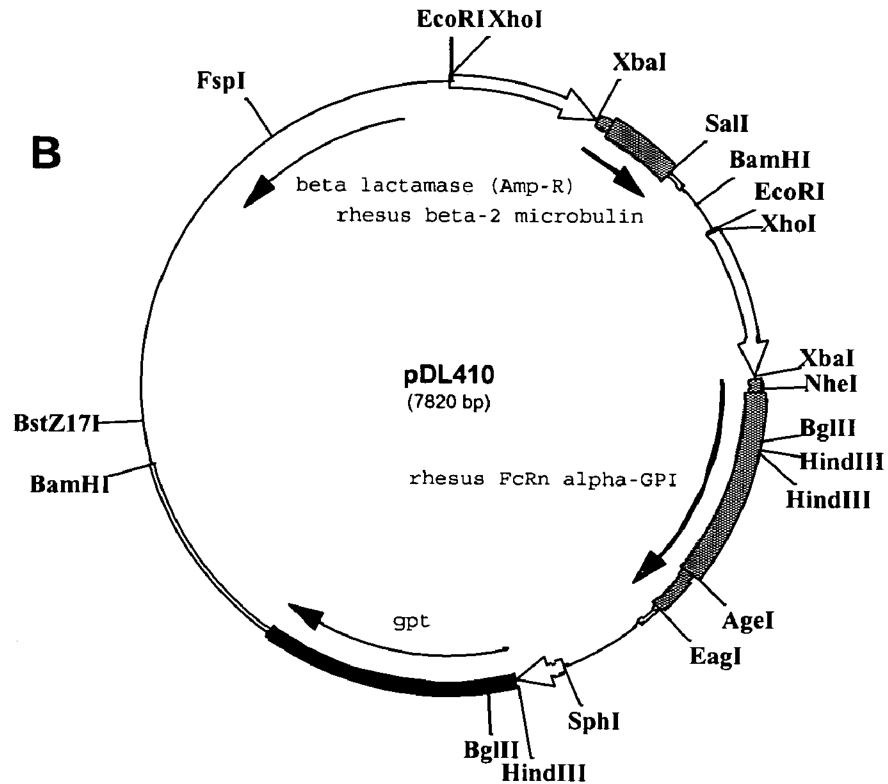
FIG. 9

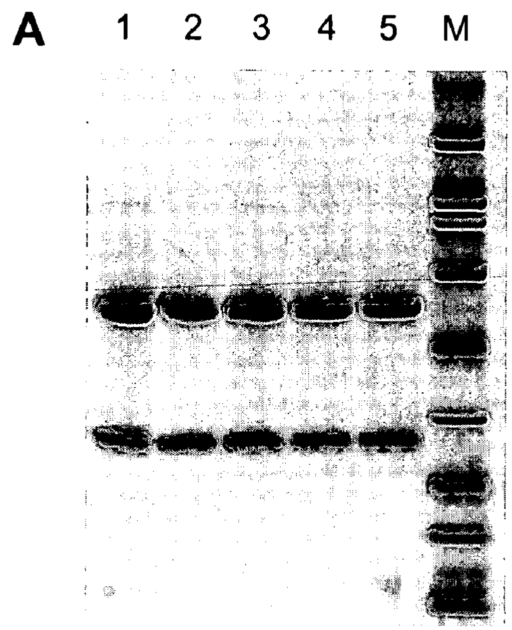
1 OST577-IgG2M3
2 T250Q
3 M428L
4 T250Q/M428L
5 T250Q/M428F
M Molecular weight standards
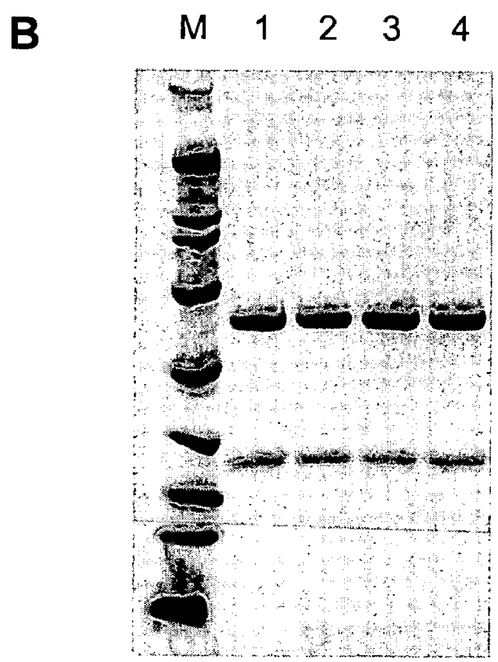
M Molecular weight standards
1 OST577-IgG1
2 T250E
3 M428F
4 T250E/M428F
FIG. 10

Daclizumab (IgG1)

Mature kappa light chain (SEQ ID NO:118)

DIQMTQSPSTLSASVGDRVTITCSASSSISYMHWYQQKPGKAPKLLIYTTSNLASGVPARFSGSGSGTEFTLTISS
LQPDDFATYYCHQRSTYPLTFGQGTKVEVKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Mature gamma-1 heavy chain with T250D (SEQ ID NO:119)

QVQLVQSGAEVKKPGSSVKVSCKASGYTFTSYRMHWVRQAPGQGLEWIGYINPSTGYTEYNQKFKDKATITADEST
NTAYMELSSLRSEDTAVYYCARGGGVFDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPC
PAPELLGGPSVFLFPPKPKDDLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

Mature gamma-1 heavy chain with T250Q (SEQ ID NO:120)

QVQLVQSGAEVKKPGSSVKVSCKASGYTFTSYRMHWVRQAPGQGLEWIGYINPSTGYTEYNQKFKDKATITADEST
NTAYMELSSLRSEDTAVYYCARGGGVFDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPC
PAPELLGGPSVFLFPPKPKDQLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK

Mature gamma-1 heavy chain with M428L (SEQ ID NO:121)

QVQLVQSGAEVKKPGSSVKVSCKASGYTFTSYRMHWVRQAPGQGLEWIGYINPSTGYTEYNQKFKDKATITADEST
NTAYMELSSLRSEDTAVYYCARGGGVFDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVLHEALHNHYTQKSLSLSPGK

Mature gamma-1 heavy chain with T250Q/M428L (SEQ ID NO:122)

QVQLVQSGAEVKKPGSSVKVSCKASGYTFTSYRMHWVRQAPGQGLEWIGYINPSTGYTEYNQKFKDKATITADEST
NTAYMELSSLRSEDTAVYYCARGGGVFDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPC
PAPELLGGPSVFLFPPKPKDQLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVLHEALHNHYTQKSLSLSPGK

Mature gamma-1 heavy chain with T250Q/M428F (SEQ ID NO:123)

QVQLVQSGAEVKKPGSSVKVSCKASGYTFTSYRMHWVRQAPGQGLEWIGYINPSTGYTEYNQKFKDKATITADEST
NTAYMELSSLRSEDTAVYYCARGGGVFDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKKVEPKSCDKTHTCPPC
PAPELLGGPSVFLFPPKPKDQLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVFHEALHNHYTQKSLSLSPGK

FIG. 22

Daclizumab (Ig2M3)

Mature gamma-2M3 heavy chain with T250D (SEQ ID NO:124)

QVQLVQSGAEVKKPGSSVKVSCKASGYTFTSYRMHWVRQAPGQGLEWIGYINPSTGYTEYNQKFKDKATITADEST
NTAYMELSSLRSEDTAVYYCARGGGVFDYWGQGTLVTVSSASTKGPSVFPLAPCSRSTSESTAALGCLVKDYFPEP
VTVSWNSGALTSGVHTFPAVLQSSGLYSLSSVVTVPSSNFGTQTYTCNVDHKPSNTKVDKTVERKCCVECPPCPAP
PAAAPSVFLFPPKPKDDLMISRTPEVTCVVVDVSHEDPEVQFNWYVDGVEVHNAKTKPREEQFNSTFRVVSVLTVV
HQDWLNGKEYKCKVSNKGLPAPIEKTISKTKGQPREPQVYTLPPSREEMTKNQVSLTCLVKGFYPSDIAVEWESNG
QPENNYKTTPPMLDSDGSFFLYSKLTVDKSRWQQGNVFSCSVMHEALHNHYTQKSLSLSPGK

Mature gamma-2M3 heavy chain with T250Q (SEQ ID NO:125)

QVQLVQSGAEVKKPGSSVKVSCKASGYTFTSYRMHWVRQAPGQGLEWIGYINPSTGYTEYNQKFKDKATITADEST
NTAYMELSSLRSEDTAVYYCARGGGVFDYWGQGTLVTVSSASTKGPSVFPLAPCSRSTSESTAALGCLVKDYFPEP
VTVSWNSGALTSGVHTFPAVLQSSGLYSLSSVVTVPSSNFGTQTYTCNVDHKPSNTKVDKTVERKCCVECPPCPAP
PAAAPSVFLFPPKPKDQLMISRTPEVTCVVVDVSHEDPEVQFNWYVDGVEVHNAKTKPREEQFNSTFRVVSVLTVV
HQDWLNGKEYKCKVSNKGLPAPIEKTISKTKGQPREPQVYTLPPSREEMTKNQVSLTCLVKGFYPSDIAVEWESNG
QPENNYKTTPPMLDSDGSFFLYSKLTVDKSRWQQGNVFSCSVMHEALHNHYTQKSLSLSPGK

Mature gamma-2M3 heavy chain with M428L (SEQ ID NO:126)

QVQLVQSGAEVKKPGSSVKVSCKASGYTFTSYRMHWVRQAPGQGLEWIGYINPSTGYTEYNQKFKDKATITADEST
NTAYMELSSLRSEDTAVYYCARGGGVFDYWGQGTLVTVSSASTKGPSVFPLAPCSRSTSESTAALGCLVKDYFPEP
VTVSWNSGALTSGVHTFPAVLQSSGLYSLSSVVTVPSSNFGTQTYTCNVDHKPSNTKVDKTVERKCCVECPPCPAP
PAAAPSVFLFPPKPKDTLMISRTPEVTCVVVDVSHEDPEVQFNWYVDGVEVHNAKTKPREEQFNSTFRVVSVLTVV
HQDWLNGKEYKCKVSNKGLPAPIEKTISKTKGQPREPQVYTLPPSREEMTKNQVSLTCLVKGFYPSDIAVEWESNG
QPENNYKTTPPMLDSDGSFFLYSKLTVDKSRWQQGNVFSCSVLHEALHNHYTQKSLSLSPGK

Mature gamma-2M3 heavy chain with T250Q/M428L (SEQ ID NO:127)

QVQLVQSGAEVKKPGSSVKVSCKASGYTFTSYRMHWVRQAPGQGLEWIGYINPSTGYTEYNQKFKDKATITADEST
NTAYMELSSLRSEDTAVYYCARGGGVFDYWGQGTLVTVSSASTKGPSVFPLAPCSRSTSESTAALGCLVKDYFPEP
VTVSWNSGALTSGVHTFPAVLQSSGLYSLSSVVTVPSSNFGTQTYTCNVDHKPSNTKVDKTVERKCCVECPPCPAP
PAAAPSVFLFPPKPKDQLMISRTPEVTCVVVDVSHEDPEVQFNWYVDGVEVHNAKTKPREEQFNSTFRVVSVLTVV
HQDWLNGKEYKCKVSNKGLPAPIEKTISKTKGQPREPQVYTLPPSREEMTKNQVSLTCLVKGFYPSDIAVEWESNG
QPENNYKTTPPMLDSDGSFFLYSKLTVDKSRWQQGNVFSCSVLHEALHNHYTQKSLSLSPGK

Mature gamma-2M3 heavy chain with T250Q/M428F (SEQ ID NO:128)

QVQLVQSGAEVKKPGSSVKVSCKASGYTFTSYRMHWVRQAPGQGLEWIGYINPSTGYTEYNQKFKDKATITADEST
NTAYMELSSLRSEDTAVYYCARGGGVFDYWGQGTLVTVSSASTKGPSVFPLAPCSRSTSESTAALGCLVKDYFPEP
VTVSWNSGALTSGVHTFPAVLQSSGLYSLSSVVTVPSSNFGTQTYTCNVDHKPSNTKVDKTVERKCCVECPPCPAP
PAAAPSVFLFPPKPKDQLMISRTPEVTCVVVDVSHEDPEVQFNWYVDGVEVHNAKTKPREEQFNSTFRVVSVLTVV
HQDWLNGKEYKCKVSNKGLPAPIEKTISKTKGQPREPQVYTLPPSREEMTKNQVSLTCLVKGFYPSDIAVEWESNG
QPENNYKTTPPMLDSDGSFFLYSKLTVDKSRWQQGNVFSCSVFHEALHNHYTQKSLSLSPGK

FIG. 22

Fontolizumab (HuZAF®)

Mature kappa light chain (SEQ ID NO:129)

DIQMTQSPSTLSASVGDRVTITCKASENVDTYVSWYQQKPGKAPKLLIYGASNRYTGVPSRFSGSGSGTDFTLTIS
SLQPDDFATYYCGQSYNYPFTFGQGTKVEVKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC

Mature gamma-1 heavy chain with T250D (SEQ ID NO:130)

QVQLVQSGAELKKPGSSVKVSCKASGYIFTSSWINWVKQAPGQGLEWIGRIDPSDGEVHYNQDFKDKATLTVDKST
NTAYMELSSLRSEDTAVYYCARGFLPWFADWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPP
CPAPELLGGPSVFLFPPKPKDDLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYTQKSLSLSPGK

Mature gamma-1 heavy chain with T250Q (SEQ ID NO:131)

QVQLVQSGAELKKPGSSVKVSCKASGYIFTSSWINWVKQAPGQGLEWIGRIDPSDGEVHYNQDFKDKATLTVDKST
NTAYMELSSLRSEDTAVYYCARGFLPWFADWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPP
CPAPELLGGPSVFLFPPKPKDQLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMHEALHNHYTQKSLSLSPGK

Mature gamma-1 heavy chain with M428L (SEQ ID NO:132)

QVQLVQSGAELKKPGSSVKVSCKASGYIFTSSWINWVKQAPGQGLEWIGRIDPSDGEVHYNQDFKDKATLTVDKST
NTAYMELSSLRSEDTAVYYCARGFLPWFADWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVLHEALHNHYTQKSLSLSPGK

Mature gamma-1 heavy chain with T250Q/M428L (SEQ ID NO:133)

QVQLVQSGAELKKPGSSVKVSCKASGYIFTSSWINWVKQAPGQGLEWIGRIDPSDGEVHYNQDFKDKATLTVDKST
NTAYMELSSLRSEDTAVYYCARGFLPWFADWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPP
CPAPELLGGPSVFLFPPKPKDQLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVLHEALHNHYTQKSLSLSPGK

Mature gamma-1 heavy chain with T250Q/M428F (SEQ ID NO:134)

QVQLVQSGAELKKPGSSVKVSCKASGYIFTSSWINWVKQAPGQGLEWIGRIDPSDGEVHYNQDFKDKATLTVDKST
NTAYMELSSLRSEDTAVYYCARGFLPWFADWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVDKKVEPKSCDKTHTCPP
CPAPELLGGPSVFLFPPKPKDQLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVFHEALHNHYTQKSLSLSPGK

FIG. 23

Visilizumab (Nuvion®)

Mature kappa light chain (SEQ ID NO:135)

DIQMTQSPSSLSASVGDRVTITCSASSSVSYMNWYQQKPGKAPKRLIYDTSKLASGVPSRFSGSGSGTDFTLTISS
LQPEDFATYYCQQWSSNPPTFGGGTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC

Mature gamma-2M3 heavy chain with T250D (SEQ ID NO:136)

QVQLVQSGAEVKKPGASVKVSCKASGYTFISYTMHWVRQAPGQGLEWMGYINPRSGYTHYNQKLKDKATLTADKSA
STAYMELSSLRSEDTAVYYCARSAYYDYDGFAYWGQGTLVTVSSASTKGPSVFPLAPCSRSTSESTAALGCLVKDY
FPEPVTVSWNSGALTSGVHTFPAVLQSSGLYSLSSVVTVPSSNFGTQTYTCNVDHKPSNTKVDKTVERKCCVECPP
CPAPPAAAPSVFLFPPKPKDDLMISRTPEVTCVVVDVSHEDPEVQFNWYVDGVEVHNAKTKPREEQFNSTFRVVSV
LTVVHQDWLNGKEYKCKVSNKGLPAPIEKTISKTKGQPREPQVYTLPPSREEMTKNQVSLTCLVKGFYPSDIAVEW
ESNGQPENNYKTTPPMLDSDGSFFLYSKLTVDKSRWQQGNVFSCSVMHEALHNHYTQKSLSLSPSK

Mature gamma-2M3 heavy chain with T250Q (SEQ ID NO:137)

QVQLVQSGAEVKKPGASVKVSCKASGYTFISYTMHWVRQAPGQGLEWMGYINPRSGYTHYNQKLKDKATLTADKSA
STAYMELSSLRSEDTAVYYCARSAYYDYDGFAYWGQGTLVTVSSASTKGPSVFPLAPCSRSTSESTAALGCLVKDY
FPEPVTVSWNSGALTSGVHTFPAVLQSSGLYSLSSVVTVPSSNFGTQTYTCNVDHKPSNTKVDKTVERKCCVECPP
CPAPPAAAPSVFLFPPKPKDQLMISRTPEVTCVVVDVSHEDPEVQFNWYVDGVEVHNAKTKPREEQFNSTFRVVSV
LTVVHQDWLNGKEYKCKVSNKGLPAPIEKTISKTKGQPREPQVYTLPPSREEMTKNQVSLTCLVKGFYPSDIAVEW
ESNGQPENNYKTTPPMLDSDGSFFLYSKLTVDKSRWQQGNVFSCSVMHEALHNHYTQKSLSLSPSK

Mature gamma-2M3 heavy chain with M428L (SEQ ID NO:138)

QVQLVQSGAEVKKPGASVKVSCKASGYTFISYTMHWVRQAPGQGLEWMGYINPRSGYTHYNQKLKDKATLTADKSA
STAYMELSSLRSEDTAVYYCARSAYYDYDGFAYWGQGTLVTVSSASTKGPSVFPLAPCSRSTSESTAALGCLVKDY
FPEPVTVSWNSGALTSGVHTFPAVLQSSGLYSLSSVVTVPSSNFGTQTYTCNVDHKPSNTKVDKTVERKCCVECPP
CPAPPAAAPSVFLFPPKPKDTLMISRTPEVTCVVVDVSHEDPEVQFNWYVDGVEVHNAKTKPREEQFNSTFRVVSV
LTVVHQDWLNGKEYKCKVSNKGLPAPIEKTISKTKGQPREPQVYTLPPSREEMTKNQVSLTCLVKGFYPSDIAVEW
ESNGQPENNYKTTPPMLDSDGSFFLYSKLTVDKSRWQQGNVFSCSVLHEALHNHYTQKSLSLSPSK

Mature gamma-2M3 heavy chain with T250Q/M428L (SEQ ID NO:139)

QVQLVQSGAEVKKPGASVKVSCKASGYTFISYTMHWVRQAPGQGLEWMGYINPRSGYTHYNQKLKDKATLTADKSA
STAYMELSSLRSEDTAVYYCARSAYYDYDGFAYWGQGTLVTVSSASTKGPSVFPLAPCSRSTSESTAALGCLVKDY
FPEPVTVSWNSGALTSGVHTFPAVLQSSGLYSLSSVVTVPSSNFGTQTYTCNVDHKPSNTKVDKTVERKCCVECPP
CPAPPAAAPSVFLFPPKPKDQLMISRTPEVTCVVVDVSHEDPEVQFNWYVDGVEVHNAKTKPREEQFNSTFRVVSV
LTVVHQDWLNGKEYKCKVSNKGLPAPIEKTISKTKGQPREPQVYTLPPSREEMTKNQVSLTCLVKGFYPSDIAVEW
ESNGQPENNYKTTPPMLDSDGSFFLYSKLTVDKSRWQQGNVFSCSVLHEALHNHYTQKSLSLSPSK

Mature gamma-2M3 heavy chain with T250Q/M428F (SEQ ID NO:140)

QVQLVQSGAEVKKPGASVKVSCKASGYTFISYTMHWVRQAPGQGLEWMGYINPRSGYTHYNQKLKDKATLTADKSA
STAYMELSSLRSEDTAVYYCARSAYYDYDGFAYWGQGTLVTVSSASTKGPSVFPLAPCSRSTSESTAALGCLVKDY
FPEPVTVSWNSGALTSGVHTFPAVLQSSGLYSLSSVVTVPSSNFGTQTYTCNVDHKPSNTKVDKTVERKCCVECPP
CPAPPAAAPSVFLFPPKPKDQLMISRTPEVTCVVVDVSHEDPEVQFNWYVDGVEVHNAKTKPREEQFNSTFRVVSV
LTVVHQDWLNGKEYKCKVSNKGLPAPIEKTISKTKGQPREPQVYTLPPSREEMTKNQVSLTCLVKGFYPSDIAVEW
ESNGQPENNYKTTPPMLDSDGSFFLYSKLTVDKSRWQQGNVFSCSVFHEALHNHYTQKSLSLSPSK

FIG. 24

Volociximab (M200)

Mature kappa light chain (SEQ ID NO:141)

QIVLTQSPAIMSASLGERVTMTCTASSSVSSNYLHWYQQKPGSAPNLWIYSTSNLASGVPARFSGSGSGTSYSLTI
SSMEAEDAATYYCHQYLRSPPTFGGGTKLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKSFNRGEC

Mature gamma-4 heavy chain with T250D (SEQ ID NO:142)

QVQLKESGPGLVAPSQSLSITCTISGFSLTDYGVHWVRQPPGKGLEWLVVIWSDGSSTYNSALKSRMTIRKDNSKS
QVFLIMNSLQTDDSAMYYCARHGTYYGMTTTGDALDYWGQGTSVTVSSASTKGPSVFPLAPCSRSTSESTAALGCL
VKDYFPEPVTVSWNSGALTSGVHTFPAVLQSSGLYSLSSVVTVPSSSLGTKTYTCNVDHKPSNTKVDKRVESKYGP
PCPSCPAPEFLGGPSVFLFPPKPKDDLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVMHEALHNHYTQKSLSLSLGK

Mature gamma-4 heavy chain with T250Q (SEQ ID NO:143)

QVQLKESGPGLVAPSQSLSITCTISGFSLTDYGVHWVRQPPGKGLEWLVVIWSDGSSTYNSALKSRMTIRKDNSKS
QVFLIMNSLQTDDSAMYYCARHGTYYGMTTTGDALDYWGQGTSVTVSSASTKGPSVFPLAPCSRSTSESTAALGCL
VKDYFPEPVTVSWNSGALTSGVHTFPAVLQSSGLYSLSSVVTVPSSSLGTKTYTCNVDHKPSNTKVDKRVESKYGP
PCPSCPAPEFLGGPSVFLFPPKPKDQLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVMHEALHNHYTQKSLSLSLGK

Mature gamma-4 heavy chain with M428L (SEQ ID NO:144)

QVQLKESGPGLVAPSQSLSITCTISGFSLTDYGVHWVRQPPGKGLEWLVVIWSDGSSTYNSALKSRMTIRKDNSKS
QVFLIMNSLQTDDSAMYYCARHGTYYGMTTTGDALDYWGQGTSVTVSSASTKGPSVFPLAPCSRSTSESTAALGCL
VKDYFPEPVTVSWNSGALTSGVHTFPAVLQSSGLYSLSSVVTVPSSSLGTKTYTCNVDHKPSNTKVDKRVESKYGP
PCPSCPAPEFLGGPSVFLFPPKPKDTLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVLHEALHNHYTQKSLSLSLGK

Mature gamma-4 heavy chain with T250Q/M428L (SEQ ID NO:145)

QVQLKESGPGLVAPSQSLSITCTISGFSLTDYGVHWVRQPPGKGLEWLVVIWSDGSSTYNSALKSRMTIRKDNSKS
QVFLIMNSLQTDDSAMYYCARHGTYYGMTTTGDALDYWGQGTSVTVSSASTKGPSVFPLAPCSRSTSESTAALGCL
VKDYFPEPVTVSWNSGALTSGVHTFPAVLQSSGLYSLSSVVTVPSSSLGTKTYTCNVDHKPSNTKVDKRVESKYGP
PCPSCPAPEFLGGPSVFLFPPKPKDQLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVLHEALHNHYTQKSLSLSLGK

Mature gamma-4 heavy chain with T250Q/M428F (SEQ ID NO:146)

QVQLKESGPGLVAPSQSLSITCTISGFSLTDYGVHWVRQPPGKGLEWLVVIWSDGSSTYNSALKSRMTIRKDNSKS
QVFLIMNSLQTDDSAMYYCARHGTYYGMTTTGDALDYWGQGTSVTVSSASTKGPSVFPLAPCSRSTSESTAALGCL
VKDYFPEPVTVSWNSGALTSGVHTFPAVLQSSGLYSLSSVVTVPSSSLGTKTYTCNVDHKPSNTKVDKRVESKYGP
PCPSCPAPEFLGGPSVFLFPPKPKDQLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTKNQVSLTCLVKGFYPSD
IAVEWESNGQPENNYKTTPPVLDSDGSFFLYSRLTVDKSRWQEGNVFSCSVFHEALHNHYTQKSLSLSLGK

FIG. 25

SEQUENCE LISTING

```
<160> NUMBER OF SEQ ID NOS: 146

<210> SEQ ID NO 1
<211> LENGTH: 122
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Trp Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met His Ser Leu Arg Ala Ala Asp Thr Gly Val Tyr Phe Cys
                85                  90                  95

Ala Lys Asp Gln Leu Tyr Phe Gly Ser Gln Ser Pro Gly His Tyr Trp
            100                 105                 110

Gly Gln Gly Thr Leu Val Thr Val Ser Ser
        115                 120


<210> SEQ ID NO 2
<211> LENGTH: 326
<212> TYPE: PRT
<213> ORGANISM: Homo sapiens
```

-continued

<400> SEQUENCE: 2

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325
```

<210> SEQ ID NO 3
<211> LENGTH: 330
<212> TYPE: PRT
<213> ORGANISM: Homo sapiens

<400> SEQUENCE: 3

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 4
<211> LENGTH: 109
<212> TYPE: PRT
<213> ORGANISM: Homo sapiens

<400> SEQUENCE: 4

Ser Tyr Val Leu Thr Gln Pro Pro Ser Val Ser Val Ala Pro Gly Gln
1               5                   10                  15

Thr Ala Arg Ile Thr Cys Gly Gly Asp Asn Ile Gly Ser Lys Ser Val
            20                  25                  30

Asn Trp Phe Gln Gln Lys Pro Gly Gln Ala Pro Val Leu Val Val Tyr
        35                  40                  45

Asp Asp Asn Glu Arg Pro Ser Gly Ile Ser Glu Arg Phe Ser Gly Ser
    50                  55                  60

Asn Ser Gly Asn Thr Ala Thr Leu Thr Ile Ser Arg Val Glu Ala Gly
65                  70                  75                  80
```

```
Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly
            100                 105


<210> SEQ ID NO 5
<211> LENGTH: 105
<212> TYPE: PRT
<213> ORGANISM: Homo sapiens

<400> SEQUENCE: 5

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105


<210> SEQ ID NO 6
<211> LENGTH: 116
<212> TYPE: PRT
<213> ORGANISM: Artificial
<220> FEATURE:
<223> OTHER INFORMATION: Humanized antibody

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Val Arg Gln Ser Pro Gly Lys Gly Leu Glu Trp Ile
        35                  40                  45

Gly Val Lys Trp Ser Gly Gly Ser Thr Glu Tyr Asn Ala Ala Phe Ile
    50                  55                  60

Ser Arg Leu Thr Ile Ser Lys Asp Thr Ser Lys Asn Gln Val Ser Leu
65                  70                  75                  80

Lys Leu Asn Ser Leu Thr Ala Ala Asp Thr Ala Val Tyr Tyr Cys Ala
                85                  90                  95

Arg Asn Asp Arg Tyr Ala Met Asp Tyr Trp Gly Gln Gly Thr Leu Val
            100                 105                 110

Thr Val Ser Ser
        115


<210> SEQ ID NO 7
<211> LENGTH: 330
<212> TYPE: PRT
<213> ORGANISM: artificial
<220> FEATURE:
<223> OTHER INFORMATION: Humanized antibody

<400> SEQUENCE: 7
```

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 8
<211> LENGTH: 107
<212> TYPE: PRT
<213> ORGANISM: artificial
<220> FEATURE:
<223> OTHER INFORMATION: Humanized antibody

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30
```

```
Leu Ala Trp Tyr Gln Gln Lys Pro Gly Lys Ala Pro Lys Leu Leu Val
        35                  40                  45

Ser Asn Ala Lys Thr Leu Ala Glu Gly Val Pro Ser Arg Phe Ser Gly
    50                  55                  60

Ser Gly Ser Gly Lys Gln Phe Thr Leu Thr Ile Ser Ser Leu Gln Pro
65                  70                  75                  80

Glu Asp Phe Ala Thr Tyr Tyr Cys Gln His His Tyr Gly Asn Ser Tyr
                85                  90                  95

Pro Phe Gly Gln Gly Thr Lys Leu Glu Ile Lys
            100                 105


<210> SEQ ID NO 9
<211> LENGTH: 107
<212> TYPE: PRT
<213> ORGANISM: artificial
<220> FEATURE:
<223> OTHER INFORMATION: Humanized antibody

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 10
<211> LENGTH: 326
<212> TYPE: PRT
<213> ORGANISM: Homo sapiens

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125
```

-continued

```
Ala Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 11
<211> LENGTH: 326
<212> TYPE: PRT
<213> ORGANISM: Homo sapiens

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Cys Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

```
Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 12
<211> LENGTH: 326
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Asp Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
```

-continued

```
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 13
<211> LENGTH: 326
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Glu Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

-continued

```
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 14
<211> LENGTH: 326
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Phe Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

```
Ser Val Met His Glu Ala Leu His Asn His Tyr Thr Gln Lys Ser Leu
305                 310                 315                 320

Ser Leu Ser Pro Ser Lys
                325


<210> SEQ ID NO 15
<211> LENGTH: 326
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Gly Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325
```

<210> SEQ ID NO 16
<211> LENGTH: 326
<212> TYPE: PRT
<213> ORGANISM: Homo sapiens

<400> SEQUENCE: 16

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

His Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325
```

<210> SEQ ID NO 17
<211> LENGTH: 326
<212> TYPE: PRT
<213> ORGANISM: Homo sapiens

<400> SEQUENCE: 17

```
Ala Ser Thr Lys Gly Pro Ser Val Phe Pro Leu Ala Pro Cys Ser Arg
```

-continued

```
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Ile Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 18
<211> LENGTH: 326
<212> TYPE: PRT
<213> ORGANISM: Homo sapiens

<400> SEQUENCE: 18

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

-continued

```
Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Lys Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 19
<211> LENGTH: 326
<212> TYPE: PRT
<213> ORGANISM: Homo sapiens

<400> SEQUENCE: 19

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95
```

```
Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Leu Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 20
<211> LENGTH: 326
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Met Leu Met Ile Ser Arg Thr Pro Glu Val Thr Cys Val Val Val Asp
```

```
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 21
<211> LENGTH: 326
<212> TYPE: PRT
<213> ORGANISM: Homo sapiens

<400> SEQUENCE: 21

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Asn Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

-continued

Ser Thr Phe Arg Val Val Ser Val Leu Thr Val Val His Gln Asp Trp
180 185 190

Leu Asn Gly Lys Glu Tyr Lys Cys Lys Val Ser Asn Lys Gly Leu Pro
195 200 205

Ala Pro Ile Glu Lys Thr Ile Ser Lys Thr Lys Gly Gln Pro Arg Glu
210 215 220

Pro Gln Val Tyr Thr Leu Pro Pro Ser Arg Glu Glu Met Thr Lys Asn
225 230 235 240

Gln Val Ser Leu Thr Cys Leu Val Lys Gly Phe Tyr Pro Ser Asp Ile
245 250 255

Ala Val Glu Trp Glu Ser Asn Gly Gln Pro Glu Asn Asn Tyr Lys Thr
260 265 270

Thr Pro Pro Met Leu Asp Ser Asp Gly Ser Phe Phe Leu Tyr Ser Lys
275 280 285

Leu Thr Val Asp Lys Ser Arg Trp Gln Gln Gly Asn Val Phe Ser Cys
290 295 300

Ser Val Met His Glu Ala Leu His Asn His Tyr Thr Gln Lys Ser Leu
305 310 315 320

Ser Leu Ser Pro Ser Lys
325

<210> SEQ ID NO 22
<211> LENGTH: 326
<212> TYPE: PRT
<213> ORGANISM: Homo sapiens

<400> SEQUENCE: 22

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Cys Val Glu Cys Pro Pro Cys Pro Ala Pro
100 105 110

Pro Ala Ala Ala Pro Ser Val Phe Leu Phe Pro Pro Lys Pro Lys Asp
115 120 125

Pro Leu Met Ile Ser Arg Thr Pro Glu Val Thr Cys Val Val Val Asp
130 135 140

Val Ser His Glu Asp Pro Glu Val Gln Phe Asn Trp Tyr Val Asp Gly
145 150 155 160

Val Glu Val His Asn Ala Lys Thr Lys Pro Arg Glu Glu Gln Phe Asn
165 170 175

Ser Thr Phe Arg Val Val Ser Val Leu Thr Val Val His Gln Asp Trp
180 185 190

Leu Asn Gly Lys Glu Tyr Lys Cys Lys Val Ser Asn Lys Gly Leu Pro
195 200 205

Ala Pro Ile Glu Lys Thr Ile Ser Lys Thr Lys Gly Gln Pro Arg Glu
210 215 220

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 23
<211> LENGTH: 326
<212> TYPE: PRT
<213> ORGANISM: Homo sapiens

<400> SEQUENCE: 23

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Gln Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
```

```
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 24
<211> LENGTH: 326
<212> TYPE: PRT
<213> ORGANISM: Homo sapiens

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Arg Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

```
Ser Val Met His Glu Ala Leu His Asn His Tyr Thr Gln Lys Ser Leu
305                 310                 315                 320

Ser Leu Ser Pro Ser Lys
                325


<210> SEQ ID NO 25
<211> LENGTH: 326
<212> TYPE: PRT
<213> ORGANISM: Homo sapiens

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Ser Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 26
```

<211> LENGTH: 326
<212> TYPE: PRT
<213> ORGANISM: Homo sapiens

<400> SEQUENCE: 26

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Val Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325
```

<210> SEQ ID NO 27
<211> LENGTH: 326
<212> TYPE: PRT
<213> ORGANISM: Homo sapiens

<400> SEQUENCE: 27

```
Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Trp Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 28
<211> LENGTH: 326
<212> TYPE: PRT
<213> ORGANISM: Homo sapiens

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

-continued

```
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Tyr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 29
<211> LENGTH: 326
<212> TYPE: PRT
<213> ORGANISM: Homo sapiens

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95
```

```
Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Ala Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 30
<211> LENGTH: 326
<212> TYPE: PRT
<213> ORGANISM: Homo sapiens

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

-continued

```
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Cys Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 31
<211> LENGTH: 326
<212> TYPE: PRT
<213> ORGANISM: Homo sapiens

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
```

```
            180                 185                 190

Asp Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 32
<211> LENGTH: 326
<212> TYPE: PRT
<213> ORGANISM: Homo sapiens

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Glu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

-continued

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 33
<211> LENGTH: 326
<212> TYPE: PRT
<213> ORGANISM: Homo sapiens

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Phe Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

```
Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 34
<211> LENGTH: 326
<212> TYPE: PRT
<213> ORGANISM: Homo sapiens

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Gly Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
```

```
305                 310                 315                 320

Ser Leu Ser Pro Ser Lys
                325


<210> SEQ ID NO 35
<211> LENGTH: 326
<212> TYPE: PRT
<213> ORGANISM: Homo sapiens

<400> SEQUENCE: 35

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

His Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 36
<211> LENGTH: 326
```

<212> TYPE: PRT
<213> ORGANISM: Homo sapiens

<400> SEQUENCE: 36

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Ile Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325
```

<210> SEQ ID NO 37
<211> LENGTH: 326
<212> TYPE: PRT
<213> ORGANISM: Homo sapiens

<400> SEQUENCE: 37

```
Ala Ser Thr Lys Gly Pro Ser Val Phe Pro Leu Ala Pro Cys Ser Arg
1               5                   10                  15
```

-continued

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Lys Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 38
<211> LENGTH: 326
<212> TYPE: PRT
<213> ORGANISM: Homo sapiens

<400> SEQUENCE: 38

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Met Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 39
<211> LENGTH: 326
<212> TYPE: PRT
<213> ORGANISM: Homo sapiens

<400> SEQUENCE: 39

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
```

```
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Asn Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 40
<211> LENGTH: 326
<212> TYPE: PRT
<213> ORGANISM: Homo sapiens

<400> SEQUENCE: 40

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

```
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Pro Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 41
<211> LENGTH: 326
<212> TYPE: PRT
<213> ORGANISM: Homo sapiens

<400> SEQUENCE: 41

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190
```

```
Gln Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 42
<211> LENGTH: 326
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Arg Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
```

-continued

```
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 43
<211> LENGTH: 326
<212> TYPE: PRT
<213> ORGANISM: Homo sapiens

<400> SEQUENCE: 43

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Ser Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

-continued

```
Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 44
<211> LENGTH: 326
<212> TYPE: PRT
<213> ORGANISM: Homo sapiens

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Thr Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320
```

```
Ser Leu Ser Pro Ser Lys
                325


<210> SEQ ID NO 45
<211> LENGTH: 326
<212> TYPE: PRT
<213> ORGANISM: Homo sapiens

<400> SEQUENCE: 45

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Val Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 46
<211> LENGTH: 326
<212> TYPE: PRT
```

<213> ORGANISM: Homo sapiens

<400> SEQUENCE: 46

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Trp Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325
```

<210> SEQ ID NO 47
<211> LENGTH: 326
<212> TYPE: PRT
<213> ORGANISM: Homo sapiens

<400> SEQUENCE: 47

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
```

-continued

```
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Tyr Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Ser Lys
                325


<210> SEQ ID NO 48
<211> LENGTH: 326
<212> TYPE: PRT
<213> ORGANISM: Homo sapiens

<400> SEQUENCE: 48

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

-continued

```
Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Ala His Glu Ala Leu His Asn His Tyr Thr Gln Lys Ser Leu
305                 310                 315                 320

Ser Leu Ser Pro Ser Lys
                325


<210> SEQ ID NO 49
<211> LENGTH: 326
<212> TYPE: PRT
<213> ORGANISM: Homo sapiens

<400> SEQUENCE: 49

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110
```

-continued

```
Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Cys His Glu Ala Leu His Asn His Tyr Thr Gln Lys Ser Leu
305                 310                 315                 320

Ser Leu Ser Pro Ser Lys
                325


<210> SEQ ID NO 50
<211> LENGTH: 326
<212> TYPE: PRT
<213> ORGANISM: Homo sapiens

<400> SEQUENCE: 50

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
```

-continued

```
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Asp His Glu Ala Leu His Asn His Tyr Thr Gln Lys Ser Leu
305                 310                 315                 320

Ser Leu Ser Pro Ser Lys
                325


<210> SEQ ID NO 51
<211> LENGTH: 326
<212> TYPE: PRT
<213> ORGANISM: Homo sapiens

<400> SEQUENCE: 51

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190
```

```
Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Glu His Glu Ala Leu His Asn His Tyr Thr Gln Lys Ser Leu
305                 310                 315                 320

Ser Leu Ser Pro Ser Lys
                325


<210> SEQ ID NO 52
<211> LENGTH: 326
<212> TYPE: PRT
<213> ORGANISM: Homo sapiens

<400> SEQUENCE: 52

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240
```

```
Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Phe His Glu Ala Leu His Asn His Tyr Thr Gln Lys Ser Leu
305                 310                 315                 320

Ser Leu Ser Pro Ser Lys
                325


<210> SEQ ID NO 53
<211> LENGTH: 326
<212> TYPE: PRT
<213> ORGANISM: Homo sapiens

<400> SEQUENCE: 53

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
```

-continued

```
        275                 280                 285

Leu Thr Val Asp Lys Ser Arg Trp Gln Gln Gly Asn Val Phe Ser Cys
    290                 295                 300

Ser Val Gly His Glu Ala Leu His Asn His Tyr Thr Gln Lys Ser Leu
305                 310                 315                 320

Ser Leu Ser Pro Ser Lys
                325


<210> SEQ ID NO 54
<211> LENGTH: 326
<212> TYPE: PRT
<213> ORGANISM: Homo sapiens

<400> SEQUENCE: 54

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val His His Glu Ala Leu His Asn His Tyr Thr Gln Lys Ser Leu
305                 310                 315                 320
```

```
Ser Leu Ser Pro Ser Lys
                325


<210> SEQ ID NO 55
<211> LENGTH: 326
<212> TYPE: PRT
<213> ORGANISM: Homo sapiens

<400> SEQUENCE: 55

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Ile His Glu Ala Leu His Asn His Tyr Thr Gln Lys Ser Leu
305                 310                 315                 320

Ser Leu Ser Pro Ser Lys
                325


<210> SEQ ID NO 56
<211> LENGTH: 326
<212> TYPE: PRT
<213> ORGANISM: Homo sapiens
```

<400> SEQUENCE: 56

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Lys His Glu Ala Leu His Asn His Tyr Thr Gln Lys Ser Leu
305                 310                 315                 320

Ser Leu Ser Pro Ser Lys
                325
```

<210> SEQ ID NO 57
<211> LENGTH: 326
<212> TYPE: PRT
<213> ORGANISM: Homo sapiens

<400> SEQUENCE: 57

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Leu His Glu Ala Leu His Asn His Tyr Thr Gln Lys Ser Leu
305                 310                 315                 320

Ser Leu Ser Pro Ser Lys
                325


<210> SEQ ID NO 58
<211> LENGTH: 326
<212> TYPE: PRT
<213> ORGANISM: Homo sapiens

<400> SEQUENCE: 58

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
```

-continued

```
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Asn His Glu Ala Leu His Asn His Tyr Thr Gln Lys Ser Leu
305                 310                 315                 320

Ser Leu Ser Pro Ser Lys
                325


<210> SEQ ID NO 59
<211> LENGTH: 326
<212> TYPE: PRT
<213> ORGANISM: Homo sapiens

<400> SEQUENCE: 59

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110
```

-continued

```
Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Pro His Glu Ala Leu His Asn His Tyr Thr Gln Lys Ser Leu
305                 310                 315                 320

Ser Leu Ser Pro Ser Lys
                325


<210> SEQ ID NO 60
<211> LENGTH: 326
<212> TYPE: PRT
<213> ORGANISM: Homo sapiens

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160
```

```
Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Gln His Glu Ala Leu His Asn His Tyr Thr Gln Lys Ser Leu
305                 310                 315                 320

Ser Leu Ser Pro Ser Lys
                325


<210> SEQ ID NO 61
<211> LENGTH: 326
<212> TYPE: PRT
<213> ORGANISM: Homo sapiens

<400> SEQUENCE: 61

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
```

-continued

```
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Arg His Glu Ala Leu His Asn His Tyr Thr Gln Lys Ser Leu
305                 310                 315                 320

Ser Leu Ser Pro Ser Lys
                325


<210> SEQ ID NO 62
<211> LENGTH: 326
<212> TYPE: PRT
<213> ORGANISM: Homo sapiens

<400> SEQUENCE: 62

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240
```

```
Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Ser His Glu Ala Leu His Asn His Tyr Thr Gln Lys Ser Leu
305                 310                 315                 320

Ser Leu Ser Pro Ser Lys
                325


<210> SEQ ID NO 63
<211> LENGTH: 326
<212> TYPE: PRT
<213> ORGANISM: Homo sapiens

<400> SEQUENCE: 63

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

-continued

```
Leu Thr Val Asp Lys Ser Arg Trp Gln Gln Gly Asn Val Phe Ser Cys
    290                 295                 300

Ser Val Thr His Glu Ala Leu His Asn His Tyr Thr Gln Lys Ser Leu
305                 310                 315                 320

Ser Leu Ser Pro Ser Lys
                325


<210> SEQ ID NO 64
<211> LENGTH: 326
<212> TYPE: PRT
<213> ORGANISM: Homo sapiens

<400> SEQUENCE: 64

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Val His Glu Ala Leu His Asn His Tyr Thr Gln Lys Ser Leu
305                 310                 315                 320

Ser Leu Ser Pro Ser Lys
```

325

<210> SEQ ID NO 65
<211> LENGTH: 326
<212> TYPE: PRT
<213> ORGANISM: Homo sapiens

<400> SEQUENCE: 65

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Trp His Glu Ala Leu His Asn His Tyr Thr Gln Lys Ser Leu
305                 310                 315                 320

Ser Leu Ser Pro Ser Lys
                325
```

<210> SEQ ID NO 66
<211> LENGTH: 326
<212> TYPE: PRT
<213> ORGANISM: Homo sapiens -continued

<400> SEQUENCE: 66

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Tyr His Glu Ala Leu His Asn His Tyr Thr Gln Lys Ser Leu
305                 310                 315                 320

Ser Leu Ser Pro Ser Lys
                325
```

<210> SEQ ID NO 67
<211> LENGTH: 330
<212> TYPE: PRT
<213> ORGANISM: Homo sapiens

<400> SEQUENCE: 67

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Asp Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 68
<211> LENGTH: 330
<212> TYPE: PRT
<213> ORGANISM: Homo sapiens

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Glu Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 69
<211> LENGTH: 330
<212> TYPE: PRT
<213> ORGANISM: Homo sapiens

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
        115                 120                 125

Lys Pro Lys Asp Gln Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 70
<211> LENGTH: 330
<212> TYPE: PRT
<213> ORGANISM: Homo sapiens

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

-continued

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Phe His Glu Ala Leu His Asn His Tyr Thr
305                 310                 315                 320

Gln Lys Ser Leu Ser Leu Ser Pro Gly Lys
                325                 330


<210> SEQ ID NO 71
<211> LENGTH: 330
<212> TYPE: PRT
<213> ORGANISM: Homo sapiens

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Asn His Tyr Thr
305                 310                 315                 320

Gln Lys Ser Leu Ser Leu Ser Pro Gly Lys
                325                 330


<210> SEQ ID NO 72
<211> LENGTH: 326
<212> TYPE: PRT
<213> ORGANISM: Homo sapiens

<400> SEQUENCE: 72

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Glu Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
```

-continued

```
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Phe His Glu Ala Leu His Asn His Tyr Thr Gln Lys Ser Leu
305                 310                 315                 320

Ser Leu Ser Pro Ser Lys
                325


<210> SEQ ID NO 73
<211> LENGTH: 326
<212> TYPE: PRT
<213> ORGANISM: Homo sapiens

<400> SEQUENCE: 73

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Gln Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

-continued

```
Leu Thr Val Asp Lys Ser Arg Trp Gln Gln Gly Asn Val Phe Ser Cys
    290                 295                 300

Ser Val Phe His Glu Ala Leu His Asn His Tyr Thr Gln Lys Ser Leu
305                 310                 315                 320

Ser Leu Ser Pro Ser Lys
                325
```

```
<210> SEQ ID NO 74
<211> LENGTH: 326
<212> TYPE: PRT
<213> ORGANISM: Homo sapiens

<400> SEQUENCE: 74

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Pro Ser Val Phe Leu Phe Pro Pro Lys Pro Lys Asp
        115                 120                 125

Gln Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Leu His Glu Ala Leu His Asn His Tyr Thr Gln Lys Ser Leu
305                 310                 315                 320

Ser Leu Ser Pro Ser Lys
                325
```

<210> SEQ ID NO 75
<211> LENGTH: 330
<212> TYPE: PRT
<213> ORGANISM: Homo sapiens

<400> SEQUENCE: 75

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Glu Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Phe His Glu Ala Leu His Asn His Tyr Thr
305                 310                 315                 320

Gln Lys Ser Leu Ser Leu Ser Pro Gly Lys
                325                 330
```

<210> SEQ ID NO 76
<211> LENGTH: 330
<212> TYPE: PRT
<213> ORGANISM: Homo sapiens

<400> SEQUENCE: 76

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Gln Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Asn His Tyr Thr
305                 310                 315                 320

Gln Lys Ser Leu Ser Leu Ser Pro Gly Lys
                325                 330
```

<210> SEQ ID NO 77
<211> LENGTH: 38
<212> TYPE: DNA
<213> ORGANISM: artificial
<220> FEATURE:
<223> OTHER INFORMATION: primer
<220> FEATURE:
<221> NAME/KEY: variation
<222> LOCATION: (28)..(28)
<223> OTHER INFORMATION: m is a or c
<220> FEATURE:
<221> NAME/KEY: misc_feature
<222> LOCATION: (29)..(30)
<223> OTHER INFORMATION: n is a, c, g, or t -continued

<400> SEQUENCE: 77
gacctcaggg gtccgggaga tcatgagmnn gtccttgg 38

<210> SEQ ID NO 78
<211> LENGTH: 27
<212> TYPE: DNA
<213> ORGANISM: artificial
<220> FEATURE:
<223> OTHER INFORMATION: primer

<400> SEQUENCE: 78
ctcatgatct cccggacccc tgaggtc 27

<210> SEQ ID NO 79
<211> LENGTH: 19
<212> TYPE: DNA
<213> ORGANISM: artificial
<220> FEATURE:
<223> OTHER INFORMATION: primer

<400> SEQUENCE: 79
ccagctctgt cccacaccg 19

<210> SEQ ID NO 80
<211> LENGTH: 18
<212> TYPE: DNA
<213> ORGANISM: artificial
<220> FEATURE:
<223> OTHER INFORMATION: primer

<400> SEQUENCE: 80
gccaggatcc gacccact 18

<210> SEQ ID NO 81
<211> LENGTH: 38
<212> TYPE: DNA
<213> ORGANISM: artificial
<220> FEATURE:
<223> OTHER INFORMATION: primer
<220> FEATURE:
<221> NAME/KEY: variation
<222> LOCATION: (30)..(30)
<223> OTHER INFORMATION: k is g or t

<400> SEQUENCE: 81
gacctcaggg gtccgggaga tcatgagaak gtccttgg 38

<210> SEQ ID NO 82
<211> LENGTH: 27
<212> TYPE: DNA
<213> ORGANISM: artificial
<220> FEATURE:
<223> OTHER INFORMATION: primer

<400> SEQUENCE: 82
ctcatgatct cccggacccc tgaggtc 27

<210> SEQ ID NO 83
<211> LENGTH: 38
<212> TYPE: DNA
<213> ORGANISM: artificial
<220> FEATURE:
<223> OTHER INFORMATION: primer
<220> FEATURE:
<221> NAME/KEY: variation
<222> LOCATION: (30)..(30)

<223> OTHER INFORMATION: m is a or c

<400> SEQUENCE: 83
gacctcaggg gtccgggaga tcatgaggcm gtccttgg 38

<210> SEQ ID NO 84
<211> LENGTH: 38
<212> TYPE: DNA
<213> ORGANISM: artificial
<220> FEATURE:
<223> OTHER INFORMATION: primer
<220> FEATURE:
<221> NAME/KEY: variation
<222> LOCATION: (30)..(30)
<223> OTHER INFORMATION: k is g or t
<220> FEATURE:
<221> NAME/KEY: misc_feature
<222> LOCATION: (28)..(28)
<223> OTHER INFORMATION: n is a, c, g, or t

<400> SEQUENCE: 84
gacctcaggg gtccgggaga tcatgagntk gtccttgg 38

<210> SEQ ID NO 85
<211> LENGTH: 18
<212> TYPE: DNA
<213> ORGANISM: artificial
<220> FEATURE:
<223> OTHER INFORMATION: primer

<400> SEQUENCE: 85
gccaggatcc gacccact 18

<210> SEQ ID NO 86
<211> LENGTH: 36
<212> TYPE: DNA
<213> ORGANISM: artificial
<220> FEATURE:
<223> OTHER INFORMATION: primer
<220> FEATURE:
<221> NAME/KEY: variation
<222> LOCATION: (24)..(24)
<223> OTHER INFORMATION: k is g or t
<220> FEATURE:
<221> NAME/KEY: misc_feature
<222> LOCATION: (22)..(23)
<223> OTHER INFORMATION: n is a, c, g, or t

<400> SEQUENCE: 86
accgttgtgc accaggactg gnnkaacggc aaggag 36

<210> SEQ ID NO 87
<211> LENGTH: 20
<212> TYPE: DNA
<213> ORGANISM: artificial
<220> FEATURE:
<223> OTHER INFORMATION: primer

<400> SEQUENCE: 87
ccagtcctgg tgcacaacgg 20

<210> SEQ ID NO 88
<211> LENGTH: 19
<212> TYPE: DNA
<213> ORGANISM: artificial
<220> FEATURE:
<223> OTHER INFORMATION: primer

<400> SEQUENCE: 88
ctcccggacc cctgaggtc 19

<210> SEQ ID NO 89
<211> LENGTH: 35
<212> TYPE: DNA
<213> ORGANISM: artificial
<220> FEATURE:
<223> OTHER INFORMATION: primer

<400> SEQUENCE: 89
accgttgtgc accaggactg gatcaacggc aagga 35

<210> SEQ ID NO 90
<211> LENGTH: 35
<212> TYPE: DNA
<213> ORGANISM: artificial
<220> FEATURE:
<223> OTHER INFORMATION: primer

<400> SEQUENCE: 90
accgttgtgc accaggactg gtataacggc aagga 35

<210> SEQ ID NO 91
<211> LENGTH: 35
<212> TYPE: DNA
<213> ORGANISM: artificial
<220> FEATURE:
<223> OTHER INFORMATION: primer

<400> SEQUENCE: 91
accgttgtgc accaggactg gcacaacggc aagga 35

<210> SEQ ID NO 92
<211> LENGTH: 35
<212> TYPE: DNA
<213> ORGANISM: artificial
<220> FEATURE:
<223> OTHER INFORMATION: primer

<400> SEQUENCE: 92
accgttgtgc accaggactg gatgaacggc aagga 35

<210> SEQ ID NO 93
<211> LENGTH: 35
<212> TYPE: DNA
<213> ORGANISM: artificial
<220> FEATURE:
<223> OTHER INFORMATION: primer

<400> SEQUENCE: 93
accgttgtgc accaggactg gaataacggc aagga 35

<210> SEQ ID NO 94
<211> LENGTH: 19
<212> TYPE: DNA
<213> ORGANISM: artificial
<220> FEATURE:
<223> OTHER INFORMATION: primer

<400> SEQUENCE: 94
ggacaccttc tctcctccc 19

<210> SEQ ID NO 95
<211> LENGTH: 20
<212> TYPE: DNA

```
<213> ORGANISM: artificial
<220> FEATURE:
<223> OTHER INFORMATION: primer

<400> SEQUENCE: 95

attctagttg tggtttgtcc                                                  20


<210> SEQ ID NO 96
<211> LENGTH: 37
<212> TYPE: DNA
<213> ORGANISM: artificial
<220> FEATURE:
<223> OTHER INFORMATION: primer
<220> FEATURE:
<221> NAME/KEY: variation
<222> LOCATION: (25)..(25)
<223> OTHER INFORMATION: k is g or t
<220> FEATURE:
<221> NAME/KEY: misc_feature
<222> LOCATION: (23)..(24)
<223> OTHER INFORMATION: n is a, c, g, or t

<400> SEQUENCE: 96

gaacgtcttc tcatgctccg tgnnkcatga ggctctg                               37


<210> SEQ ID NO 97
<211> LENGTH: 22
<212> TYPE: DNA
<213> ORGANISM: artificial
<220> FEATURE:
<223> OTHER INFORMATION: primer

<400> SEQUENCE: 97

cacggagcat gagaagacgt tc                                               22


<210> SEQ ID NO 98
<211> LENGTH: 45
<212> TYPE: DNA
<213> ORGANISM: artificial
<220> FEATURE:
<223> OTHER INFORMATION: primer
<220> FEATURE:
<221> NAME/KEY: variation
<222> LOCATION: (27)..(27)
<223> OTHER INFORMATION: m is a or c
<220> FEATURE:
<221> NAME/KEY: misc_feature
<222> LOCATION: (28)..(29)
<223> OTHER INFORMATION: n is a, c, g, or t

<400> SEQUENCE: 98

gtgtagtggt tgtgcagagc ctcatgmnnc acggagcatg agaag                      45


<210> SEQ ID NO 99
<211> LENGTH: 26
<212> TYPE: DNA
<213> ORGANISM: artificial
<220> FEATURE:
<223> OTHER INFORMATION: primer

<400> SEQUENCE: 99

catgaggctc tgcacaacca ctacac                                           26


<210> SEQ ID NO 100
<211> LENGTH: 45
<212> TYPE: DNA
<213> ORGANISM: artificial
<220> FEATURE:
<223> OTHER INFORMATION: primer
```

-continued

<400> SEQUENCE: 100
gtgtagtggt tgtgcagagc ctcatgttcc acggagcatg agaag 45

<210> SEQ ID NO 101
<211> LENGTH: 28
<212> TYPE: DNA
<213> ORGANISM: artificial
<220> FEATURE:
<223> OTHER INFORMATION: primer

<400> SEQUENCE: 101
aacccaagga cgaactcatg atctcccg 28

<210> SEQ ID NO 102
<211> LENGTH: 29
<212> TYPE: DNA
<213> ORGANISM: artificial
<220> FEATURE:
<223> OTHER INFORMATION: primer

<400> SEQUENCE: 102
ggagatcatg agttcgtcct tgggttttg 29

<210> SEQ ID NO 103
<211> LENGTH: 21
<212> TYPE: DNA
<213> ORGANISM: artificial
<220> FEATURE:
<223> OTHER INFORMATION: primer

<400> SEQUENCE: 103
cctcagctcg gacaccttct c 21

<210> SEQ ID NO 104
<211> LENGTH: 19
<212> TYPE: DNA
<213> ORGANISM: artificial
<220> FEATURE:
<223> OTHER INFORMATION: primer

<400> SEQUENCE: 104
gcctccctca tgccactca 19

<210> SEQ ID NO 105
<211> LENGTH: 28
<212> TYPE: DNA
<213> ORGANISM: artificial
<220> FEATURE:
<223> OTHER INFORMATION: primer

<400> SEQUENCE: 105
aacccaagga cgacctcatg atctcccg 28

<210> SEQ ID NO 106
<211> LENGTH: 29
<212> TYPE: DNA
<213> ORGANISM: artificial
<220> FEATURE:
<223> OTHER INFORMATION: primer

<400> SEQUENCE: 106
ggagatcatg aggtcgtcct tgggttttg 29

<210> SEQ ID NO 107

-continued

<211> LENGTH: 29
<212> TYPE: DNA
<213> ORGANISM: artificial
<220> FEATURE:
<223> OTHER INFORMATION: primer

<400> SEQUENCE: 107
ctcatgctcc gtgttccatg aggctctgc 29

<210> SEQ ID NO 108
<211> LENGTH: 27
<212> TYPE: DNA
<213> ORGANISM: artificial
<220> FEATURE:
<223> OTHER INFORMATION: primer

<400> SEQUENCE: 108
agagcctcat ggaacacgga gcatgag 27

<210> SEQ ID NO 109
<211> LENGTH: 29
<212> TYPE: DNA
<213> ORGANISM: artificial
<220> FEATURE:
<223> OTHER INFORMATION: primer

<400> SEQUENCE: 109
ctcatgctcc gtgttgcatg aggctctgc 29

<210> SEQ ID NO 110
<211> LENGTH: 27
<212> TYPE: DNA
<213> ORGANISM: artificial
<220> FEATURE:
<223> OTHER INFORMATION: primer

<400> SEQUENCE: 110
agagcctcat gcaacacgga gcatgag 27

<210> SEQ ID NO 111
<211> LENGTH: 28
<212> TYPE: DNA
<213> ORGANISM: artificial
<220> FEATURE:
<223> OTHER INFORMATION: primer

<400> SEQUENCE: 111
aacccaagga ccaactcatg atctcccg 28

<210> SEQ ID NO 112
<211> LENGTH: 29
<212> TYPE: DNA
<213> ORGANISM: artificial
<220> FEATURE:
<223> OTHER INFORMATION: primer

<400> SEQUENCE: 112
ggagatcatg agttggtcct tgggttttg 29

<210> SEQ ID NO 113
<211> LENGTH: 377
<212> TYPE: PRT
<213> ORGANISM: Homo sapiens

<400> SEQUENCE: 113

Ala Ser Thr Lys Gly Pro Ser Val Phe Pro Leu Ala Pro Cys Ser Arg

-continued

```
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Leu Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Tyr Thr Gln
        355                 360                 365

Lys Ser Leu Ser Leu Ser Pro Gly Lys
    370                 375
```

<210> SEQ ID NO 114
<211> LENGTH: 327
<212> TYPE: PRT
<213> ORGANISM: Homo sapiens

<400> SEQUENCE: 114

-continued

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 115
<211> LENGTH: 377
<212> TYPE: PRT
<213> ORGANISM: Homo sapiens

<400> SEQUENCE: 115

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

-continued

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Leu Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Ala Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Asn Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Leu His Glu Ala Leu His Asn Arg Tyr Thr Gln
        355                 360                 365

Lys Ser Leu Ser Leu Ser Pro Gly Lys
    370                 375


<210> SEQ ID NO 116
<211> LENGTH: 327
<212> TYPE: PRT
<213> ORGANISM: Homo sapiens

<400> SEQUENCE: 116

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

-continued

```
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Leu His Glu Ala Leu His Asn His Tyr Thr Gln Lys Ser
305                 310                 315                 320

Leu Ser Leu Ser Leu Gly Lys
                325


<210> SEQ ID NO 117
<211> LENGTH: 327
<212> TYPE: PRT
<213> ORGANISM: Homo sapiens

<400> SEQUENCE: 117

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

-continued

```
Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Gln Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Leu His Glu Ala Leu His Asn His Tyr Thr Gln Lys Ser
305                 310                 315                 320

Leu Ser Leu Ser Leu Gly Lys
                325


<210> SEQ ID NO 118
<211> LENGTH: 213
<212> TYPE: PRT
<213> ORGANISM: Homo sapiens

<400> SEQUENCE: 118

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala Ser Gly Val Pro Ala Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Arg Ser Thr Tyr Pro Leu Thr
                85                  90                  95

Phe Gly Gln Gly Thr Lys Val Glu Val Lys Arg Thr Val Ala Ala Pro
            100                 105                 110

Ser Val Phe Ile Phe Pro Pro Ser Asp Glu Gln Leu Lys Ser Gly Thr
        115                 120                 125
```

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 119
<211> LENGTH: 446
<212> TYPE: PRT
<213> ORGANISM: Homo sapiens

<400> SEQUENCE: 119

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Asp Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
```

```
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 120
<211> LENGTH: 446
<212> TYPE: PRT
<213> ORGANISM: Homo sapiens

<400> SEQUENCE: 120

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

-continued

```
Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Gln Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 121
<211> LENGTH: 446
<212> TYPE: PRT
<213> ORGANISM: Homo sapiens

<400> SEQUENCE: 121

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140
```

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Leu His Glu Ala Leu His
            420                 425                 430

Asn His Tyr Thr Gln Lys Ser Leu Ser Leu Ser Pro Gly Lys
        435                 440                 445


<210> SEQ ID NO 122
<211> LENGTH: 446
<212> TYPE: PRT
<213> ORGANISM: Homo sapiens

<400> SEQUENCE: 122

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
```

-continued

```
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Gln Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Leu His Glu Ala Leu His
            420                 425                 430

Asn His Tyr Thr Gln Lys Ser Leu Ser Leu Ser Pro Gly Lys
        435                 440                 445
```

<210> SEQ ID NO 123
<211> LENGTH: 446
<212> TYPE: PRT
<213> ORGANISM: Homo sapiens

<400> SEQUENCE: 123

-continued

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Gln Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Phe His Glu Ala Leu His
```

```
            420                 425                 430

Asn His Tyr Thr Gln Lys Ser Leu Ser Leu Ser Pro Gly Lys
        435                 440                 445


<210> SEQ ID NO 124
<211> LENGTH: 442
<212> TYPE: PRT
<213> ORGANISM: Homo sapiens

<400> SEQUENCE: 124

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Ala Ala Ala Pro Ser Val Phe Leu Phe Pro Pro
225                 230                 235                 240

Lys Pro Lys Asp Asp Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350
```

Met Thr Lys Asn Gln Val Ser Leu Thr Cys Leu Val Lys Gly Phe Tyr
355 360 365

Pro Ser Asp Ile Ala Val Glu Trp Glu Ser Asn Gly Gln Pro Glu Asn
370 375 380

Asn Tyr Lys Thr Thr Pro Pro Met Leu Asp Ser Asp Gly Ser Phe Phe
385 390 395 400

Leu Tyr Ser Lys Leu Thr Val Asp Lys Ser Arg Trp Gln Gln Gly Asn
405 410 415

Val Phe Ser Cys Ser Val Met His Glu Ala Leu His Asn His Tyr Thr
420 425 430

Gln Lys Ser Leu Ser Leu Ser Pro Gly Lys
435 440

<210> SEQ ID NO 125
<211> LENGTH: 442
<212> TYPE: PRT
<213> ORGANISM: Homo sapiens

<400> SEQUENCE: 125

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Arg Met His Trp Val Arg Gln Ala Pro Gly Gln Gly Leu Glu Trp Ile
35 40 45

Gly Tyr Ile Asn Pro Ser Thr Gly Tyr Thr Glu Tyr Asn Gln Lys Phe
50 55 60

Lys Asp Lys Ala Thr Ile Thr Ala Asp Glu Ser Thr Asn Thr Ala Tyr
65 70 75 80

Met Glu Leu Ser Ser Leu Arg Ser Glu Asp Thr Ala Val Tyr Tyr Cys
85 90 95

Ala Arg Gly Gly Gly Val Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Cys Ser Arg Ser Thr Ser Glu Ser Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Asn Phe
180 185 190

Gly Thr Gln Thr Tyr Thr Cys Asn Val Asp His Lys Pro Ser Asn Thr
195 200 205

Lys Val Asp Lys Thr Val Glu Arg Lys Cys Cys Val Glu Cys Pro Pro
210 215 220

Cys Pro Ala Pro Pro Ala Ala Ala Pro Ser Val Phe Leu Phe Pro Pro
225 230 235 240

Lys Pro Lys Asp Gln Leu Met Ile Ser Arg Thr Pro Glu Val Thr Cys
245 250 255

Val Val Val Asp Val Ser His Glu Asp Pro Glu Val Gln Phe Asn Trp
260 265 270

Tyr Val Asp Gly Val Glu Val His Asn Ala Lys Thr Lys Pro Arg Glu
275 280 285

-continued

```
Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440


<210> SEQ ID NO 126
<211> LENGTH: 442
<212> TYPE: PRT
<213> ORGANISM: Homo sapiens

<400> SEQUENCE: 126

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
```

```
    210                 215                 220

Cys Pro Ala Pro Pro Ala Ala Ala Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Leu His Glu Ala Leu His Asn His Tyr Thr
            420                 425                 430

Gln Lys Ser Leu Ser Leu Ser Pro Gly Lys
        435                 440


<210> SEQ ID NO 127
<211> LENGTH: 442
<212> TYPE: PRT
<213> ORGANISM: Homo sapiens

<400> SEQUENCE: 127

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140
```

-continued

```
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Ala Ala Ala Pro Ser Val Phe Leu Phe Pro Pro
225                 230                 235                 240

Lys Pro Lys Asp Gln Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Leu His Glu Ala Leu His Asn His Tyr Thr
            420                 425                 430

Gln Lys Ser Leu Ser Leu Ser Pro Gly Lys
        435                 440


<210> SEQ ID NO 128
<211> LENGTH: 442
<212> TYPE: PRT
<213> ORGANISM: Homo sapiens

<400> SEQUENCE: 128

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Ala Ala Ala Pro Ser Val Phe Leu Phe Pro Pro
225                 230                 235                 240

Lys Pro Lys Asp Gln Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Phe His Glu Ala Leu His Asn His Tyr Thr
            420                 425                 430

Gln Lys Ser Leu Ser Leu Ser Pro Gly Lys
        435                 440
```

<210> SEQ ID NO 129
<211> LENGTH: 214
<212> TYPE: PRT
<213> ORGANISM: Homo sapiens

<400> SEQUENCE: 129

```
Asp Ile Gln Met Thr Gln Ser Pro Ser Thr Leu Ser Ala Ser Val Gly
```

-continued

```
1               5                   10                  15

Asp Arg Val Thr Ile Thr Cys Lys Ala Ser Glu Asn Val Asp Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gly Gln Ser Tyr Asn Tyr Pro Phe
                85                  90                  95

Thr Phe Gly Gln Gly Thr Lys Val Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 130
<211> LENGTH: 447
<212> TYPE: PRT
<213> ORGANISM: Homo sapiens

<400> SEQUENCE: 130

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Ile Phe Thr Ser Ser
            20                  25                  30

Trp Ile Asn Trp Val Lys Gln Ala Pro Gly Gln Gly Leu Glu Trp Ile
        35                  40                  45

Gly Arg Ile Asp Pro Ser Asp Gly Glu Val His Tyr Asn Gln Asp Phe
    50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Phe Leu Pro Trp Phe Ala Asp Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Asp Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 131
<211> LENGTH: 447
<212> TYPE: PRT
<213> ORGANISM: Homo sapiens

<400> SEQUENCE: 131

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Ile Phe Thr Ser Ser
            20                  25                  30

Trp Ile Asn Trp Val Lys Gln Ala Pro Gly Gln Gly Leu Glu Trp Ile
        35                  40                  45

Gly Arg Ile Asp Pro Ser Asp Gly Glu Val His Tyr Asn Gln Asp Phe
    50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Gly Phe Leu Pro Trp Phe Ala Asp Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Gln Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 132
<211> LENGTH: 447
<212> TYPE: PRT
<213> ORGANISM: Homo sapiens

<400> SEQUENCE: 132

```
Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Ile Phe Thr Ser Ser
```

```
            20                  25                  30

Trp Ile Asn Trp Val Lys Gln Ala Pro Gly Gln Gly Leu Glu Trp Ile
        35                  40                  45

Gly Arg Ile Asp Pro Ser Asp Gly Glu Val His Tyr Asn Gln Asp Phe
    50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Phe Leu Pro Trp Phe Ala Asp Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Leu His Glu Ala Leu
            420                 425                 430

His Asn His Tyr Thr Gln Lys Ser Leu Ser Leu Ser Pro Gly Lys
        435                 440                 445
```

<210> SEQ ID NO 133
<211> LENGTH: 447
<212> TYPE: PRT
<213> ORGANISM: Homo sapiens

<400> SEQUENCE: 133

```
Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Ile Phe Thr Ser Ser
            20                  25                  30

Trp Ile Asn Trp Val Lys Gln Ala Pro Gly Gln Gly Leu Glu Trp Ile
        35                  40                  45

Gly Arg Ile Asp Pro Ser Asp Gly Glu Val His Tyr Asn Gln Asp Phe
    50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Phe Leu Pro Trp Phe Ala Asp Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Gln Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
```

```
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Leu His Glu Ala Leu
            420                 425                 430

His Asn His Tyr Thr Gln Lys Ser Leu Ser Leu Ser Pro Gly Lys
        435                 440                 445


<210> SEQ ID NO 134
<211> LENGTH: 447
<212> TYPE: PRT
<213> ORGANISM: Homo sapiens

<400> SEQUENCE: 134

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Ile Phe Thr Ser Ser
            20                  25                  30

Trp Ile Asn Trp Val Lys Gln Ala Pro Gly Gln Gly Leu Glu Trp Ile
        35                  40                  45

Gly Arg Ile Asp Pro Ser Asp Gly Glu Val His Tyr Asn Gln Asp Phe
    50                  55                  60

Lys Asp Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Phe Leu Pro Trp Phe Ala Asp Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Gln Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

-continued

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Phe His Glu Ala Leu
            420                 425                 430

His Asn His Tyr Thr Gln Lys Ser Leu Ser Leu Ser Pro Gly Lys
        435                 440                 445


<210> SEQ ID NO 135
<211> LENGTH: 213
<212> TYPE: PRT
<213> ORGANISM: Homo sapiens

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 136
```

```
<211> LENGTH: 446
<212> TYPE: PRT
<213> ORGANISM: Homo sapiens

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Ala Ala Ala Pro Ser Val Phe
225                 230                 235                 240

Leu Phe Pro Pro Lys Pro Lys Asp Asp Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
```

-continued

```
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Ser Lys
        435                 440                 445


<210> SEQ ID NO 137
<211> LENGTH: 446
<212> TYPE: PRT
<213> ORGANISM: Homo sapiens

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Ala Ala Ala Pro Ser Val Phe
225                 230                 235                 240

Leu Phe Pro Pro Lys Pro Lys Asp Gln Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320
```

-continued

```
Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Ser Lys
        435                 440                 445


<210> SEQ ID NO 138
<211> LENGTH: 446
<212> TYPE: PRT
<213> ORGANISM: Homo sapiens

<400> SEQUENCE: 138

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Ala Ala Ala Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Leu His Glu Ala Leu His
            420                 425                 430

Asn His Tyr Thr Gln Lys Ser Leu Ser Leu Ser Pro Ser Lys
        435                 440                 445


<210> SEQ ID NO 139
<211> LENGTH: 446
<212> TYPE: PRT
<213> ORGANISM: Homo sapiens

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Ala Ala Ala Pro Ser Val Phe
225                 230                 235                 240

Leu Phe Pro Pro Lys Pro Lys Asp Gln Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Leu His Glu Ala Leu His
            420                 425                 430

Asn His Tyr Thr Gln Lys Ser Leu Ser Leu Ser Pro Ser Lys
        435                 440                 445


<210> SEQ ID NO 140
<211> LENGTH: 446
<212> TYPE: PRT
<213> ORGANISM: Homo sapiens

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110
```

```
Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Ala Ala Ala Pro Ser Val Phe
225                 230                 235                 240

Leu Phe Pro Pro Lys Pro Lys Asp Gln Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Phe His Glu Ala Leu His
            420                 425                 430

Asn His Tyr Thr Gln Lys Ser Leu Ser Leu Ser Pro Ser Lys
        435                 440                 445


<210> SEQ ID NO 141
<211> LENGTH: 215
<212> TYPE: PRT
<213> ORGANISM: Homo sapiens

<400> SEQUENCE: 141

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Asn
            20                  25                  30

Tyr Leu His Trp Tyr Gln Gln Lys Pro Gly Ser Ala Pro Asn Leu Trp
        35                  40                  45
```

```
Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr Leu Arg Ser Pro
                85                  90                  95

Pro Thr Phe Gly Gly Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 142
<211> LENGTH: 451
<212> TYPE: PRT
<213> ORGANISM: Homo sapiens

<400> SEQUENCE: 142

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asp Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Arg Lys Asp Asn Ser Lys Ser Gln Val Phe Leu
65                  70                  75                  80

Ile Met Asn Ser Leu Gln Thr Asp Asp Ser Ala Met Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Ser Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
```

```
        195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Asp Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450


<210> SEQ ID NO 143
<211> LENGTH: 451
<212> TYPE: PRT
<213> ORGANISM: Homo sapiens

<400> SEQUENCE: 143

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asp Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Arg Lys Asp Asn Ser Lys Ser Gln Val Phe Leu
65                  70                  75                  80

Ile Met Asn Ser Leu Gln Thr Asp Asp Ser Ala Met Tyr Tyr Cys Ala
                85                  90                  95

Arg His Gly Thr Tyr Tyr Gly Met Thr Thr Thr Gly Asp Ala Leu Asp
            100                 105                 110
```

-continued

```
Tyr Trp Gly Gln Gly Thr Ser Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Gln Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450


<210> SEQ ID NO 144
<211> LENGTH: 451
<212> TYPE: PRT
<213> ORGANISM: Homo sapiens

<400> SEQUENCE: 144

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asp Tyr
            20                  25                  30
```

-continued

```
Gly Val His Trp Val Arg Gln Pro Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Arg Lys Asp Asn Ser Lys Ser Gln Val Phe Leu
65                  70                  75                  80

Ile Met Asn Ser Leu Gln Thr Asp Asp Ser Ala Met Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Ser Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Leu
            420                 425                 430

His Glu Ala Leu His Asn His Tyr Thr Gln Lys Ser Leu Ser Leu Ser
        435                 440                 445
```

```
Leu Gly Lys
    450


<210> SEQ ID NO 145
<211> LENGTH: 451
<212> TYPE: PRT
<213> ORGANISM: Homo sapiens

<400> SEQUENCE: 145

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asp Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Arg Lys Asp Asn Ser Lys Ser Gln Val Phe Leu
65                  70                  75                  80

Ile Met Asn Ser Leu Gln Thr Asp Asp Ser Ala Met Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Ser Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Gln Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Leu
            420                 425                 430

His Glu Ala Leu His Asn His Tyr Thr Gln Lys Ser Leu Ser Leu Ser
        435                 440                 445

Leu Gly Lys
    450


<210> SEQ ID NO 146
<211> LENGTH: 451
<212> TYPE: PRT
<213> ORGANISM: Homo sapiens

<400> SEQUENCE: 146

Gln Val Gln Leu Lys Glu Ser Gly Pro Gly Leu Val Ala Pro Ser Gln
1               5                   10                  15

Ser Leu Ser Ile Thr Cys Thr Ile Ser Gly Phe Ser Leu Thr Asp Tyr
            20                  25                  30

Gly Val His Trp Val Arg Gln Pro Pro Gly Lys Gly Leu Glu Trp Leu
        35                  40                  45

Val Val Ile Trp Ser Asp Gly Ser Ser Thr Tyr Asn Ser Ala Leu Lys
    50                  55                  60

Ser Arg Met Thr Ile Arg Lys Asp Asn Ser Lys Ser Gln Val Phe Leu
65                  70                  75                  80

Ile Met Asn Ser Leu Gln Thr Asp Asp Ser Ala Met Tyr Tyr Cys Ala
                85                  90                  95

Arg His Gly Thr Tyr Tyr Gly Met Thr Thr Thr Gly Asp Ala Leu Asp
            100                 105                 110

Tyr Trp Gly Gln Gly Thr Ser Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Ser Cys Pro Ala Pro Glu Phe Leu Gly
225                 230                 235                 240

Gly Pro Ser Val Phe Leu Phe Pro Pro Lys Pro Lys Asp Gln Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
```

-continued

```
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Phe
            420                 425                 430

His Glu Ala Leu His Asn His Tyr Thr Gln Lys Ser Leu Ser Leu Ser
        435                 440                 445

Leu Gly Lys
    450
```

ALTERATION OF FCRN BINDING AFFINITIES OR SERUM HALF-LIVES OF ANTIBODIES BY MUTAGENESIS

RELATED APPLICATIONS

This application is a continuation-in-part of U.S. Ser. No. 10/822,300 filed Apr. 9, 2004, which is a continuation-in-part of U.S. Ser. No. 10/687,118 filed Oct. 15, 2003, which claims priority from U.S. Provisional Application Nos. 60/418,972 filed Oct. 15, 2002, 60/462,014 filed Apr. 10, 2003, 60/475,762 filed Jun. 3, 2003, and 60/499,048 filed Aug. 29, 2003, each of which is hereby incorporated by reference in its entirety.

FIELD OF THE INVENTION

The present invention relates to the fields of immunology and protein engineering. In particular, it concerns modified antibodies of class IgG that have altered binding affinities for FcRn, or altered serum half-lives as a consequence of one or more amino acid modifications in the Fc region thereof.

BACKGROUND OF THE INVENTION

Antibodies are proteins that exhibit binding specificity to a particular antigen. Native (i.e., naturally occurring or wild-type) antibodies are usually heterotetrameric glycoproteins of about 150,000 daltons, composed of two identical light (L) chains and two identical heavy (H) chains. As shown in FIG. 1, each light chain is linked to a heavy chain by one covalent disulfide bond, while the number of disulfide linkages varies between the heavy chains of different immunoglobulin isotypes. Each heavy chain has at one end a variable domain ($V_H$) followed by a number of constant domains. Each light chain has a variable domain ($V_L$) at one end and a constant domain at the other end. The constant domain of the light chain is aligned with the first constant domain of the heavy chain.

Certain portions of the variable domains differ extensively in sequence among antibodies and are responsible for the binding specificity of each particular antibody to its particular antigen. The constant domains are not involved directly in binding of an antibody to an antigen, but exhibit various effector functions. Depending on the amino acid sequence of the constant region of the heavy chains, antibodies or immunoglobulins can be assigned to different classes. There are five major classes (isotypes) of immunoglobulins in humans: IgA, IgD, IgE, IgG, and IgM, and several of these may be further divided into subclasses (subtypes), such as IgG1, IgG2, IgG3, and IgG4 as well as IgA1 and IgA2.

A schematic representation of the native IgG structure is shown in FIG. 1, where the various portions of the native antibody molecule are indicated. The heavy chain constant region includes $C_H1$, the hinge region, $C_H2$, and $C_H3$. Papain digestion of antibodies produces two fragments, Fab and Fc. The Fc fragment consists of $C_H2$, $C_H3$, and part of the hinge region. The crystal structure of the human IgG1 Fc fragment has been determined (Deisenhofer, Biochemistry 20:2361-2370 (1981)). In human IgG molecules, the Fc fragment is generated by papain cleavage of the hinge region N-terminal to Cys 226. Therefore, the human IgG heavy chain Fc region is usually defined as stretching from the amino acid residue at position 226 to the C-terminus (numbered according to the EU index of Kabat, et al., "Sequences of Proteins of Immunological Interest", $5^{th}$ ed., National Institutes of Health, Bethesda, Md. (1991); the EU numbering scheme is used hereinafter).

The Fc region is essential to the effector functions of antibodies. The effector functions include initiating complement-dependent cytotoxicity (CDC), initiating phagocytosis and antibody-dependent cell-mediated cytotoxicity (ADCC), and transferring antibodies across cellular barriers by transcytosis. In addition, the Fc region is critical for maintaining the serum half-life of an antibody of class IgG (Ward and Ghetie, Ther. Immunol. 2:77-94 (1995)).

Studies have found that the serum half-life of an IgG antibody is mediated by binding of Fc to the neonatal Fc receptor (FcRn). FcRn is a heterodimer consisting of a transmembrane $\alpha$ chain and a soluble $\beta$ chain ($\beta$2-microglobulin). FcRn shares 22-29% sequence identity with Class I MHC molecules and has a non-functional version of the MHC peptide-binding groove (Simister and Mostov, Nature 337:184-187 (1989)). The $\alpha$1 and $\alpha$2 domains of FcRn interact with the $C_H2$ and $C_H3$ domains of the Fc region (Raghavan et al., Immunity 1:303-315 (1994)).

A model has been proposed for how FcRn might regulate the serum half-life of an antibody. As shown in FIG. 2, IgGs are taken up by endothelial cells through non-specific pinocytosis and then enter acidic endosomes. FcRn binds IgG at acidic pH (<6.5) in endosomes and releases IgG at basic pH (>7.4) in the bloodstream. Accordingly, FcRn salvages IgG from a lysosomal degradation pathway. When serum IgG levels decrease, more FcRn molecules are available for IgG binding so that an increased amount of IgG is salvaged. Conversely, if serum IgG levels rise, FcRn becomes saturated, thereby increasing the proportion of pinocytosed IgG that is degraded (Ghetie and Ward, Annu. Rev. Immunol. 18:739-766 (2000)).

Consistent with the above model, the results of numerous studies support a correlation between the affinity for FcRn binding and the serum half-life of an antibody (Ghetie and Ward, ibid.). Significantly, such a correlation has been extended to engineered antibodies with higher affinity for FcRn than their wild-type parent molecules.

Ghetie et al. randomly mutagenized position 252, position 254, and position 256 in a mouse IgG1 Fc-hinge fragment. One mutant showed an affinity three and a half times higher for mouse FcRn and a half-life about 23% or 65% longer in two mouse strains, respectively, as compared to that of the wild-type (Ghetie et al., Nat. Biotechnol. 15:637-640 (1997)).

Shields et al. used alanine scanning mutagenesis to alter residues in the Fc region of a human IgG1 antibody and then assessed the binding to human FcRn. They found several mutants with a higher binding affinity for human FcRn than the wild-type, but did not identify mutations at positions 250, 314, or 428 (Shields et al., J. Biol. Chem. 276:6591-6604 (2001)).

Martin et al. proposed mutagenesis at a number of positions in the human IgG Fc to increase binding to FcRn including, among many others, positions 250, 314, and 428. However, none of the mutants proposed by Martin et al. was constructed or tested for binding to FcRn (Martin et al., Mol. Cell 7:867-877 (2001)).

Dall'Acqua et al. described random mutagenesis and screening of human IgG1 hinge-Fc fragment phage display libraries against mouse FcRn. They disclosed random mutagenesis of positions 428-436 but did not identify mutagenesis at position 428 as having any effect on mouse FcRn binding affinity and stated that the wild-type methionine amino acid at this position is favorable for efficient binding (Dall'Acqua et al., J. Immunol. 169:5171-5180 (2002)).

Kim et al. mutagenized human IgG1 by amino acid substitutions at position 253, position 310, or position 435 of the Fc region. They found that the mutant Fc-hinge fragments have reduced serum half-lives in mice compared to the wild-type IgG1 Fc-hinge fragment, and concluded that Ile253, His310, and His435 play a central role in regulating the serum half-life of IgG (Kim et al., Eur. J. Immunol. 29:2819-2825 (1999)).

Hornick et al. showed that a single amino acid substitution at position 253 in the Fc region of a chimeric human IgG1 antibody accelerates clearance in mice and improves immunoscintigraphy of solid tumors (Hornick et al., J. Nucl. Med. 41:355-362 (2000)).

U.S. Pat. No. 6,165,745 discloses a method of producing an antibody with a decreased biological half-life by introducing a mutation into the DNA segment encoding the antibody. The mutation includes an amino acid substitution at position 253, 310, 311, 433, or 434 of the Fc-hinge domain. The full disclosure of U.S. Pat. No. 6,165,745, as well as the full disclosure of all other U.S. patent references cited herein, are hereby incorporated by reference.

U.S. Pat. Nos. 5,530,101; 5,585,089; 5,693,761; 5,693,762; and 6,180,370 disclose the humanization of immunoglobulins.

U.S. Pat. No. 6,277,375 B1 discloses a composition comprising a mutant IgG molecule having an increased serum half-life relative to the wild-type IgG, wherein the mutant IgG molecule comprises the amino acid substitutions: threonine to leucine at position 252, threonine to serine at position 254, or threonine to phenylalanine at position 256. A mutant IgG with an amino acid substitution at position 433, 435, or 436 is also disclosed.

U.S. Patent Application No. 20020098193 A1 and PCT Publication No. WO 97/34621 disclose mutant IgG molecules having increased serum half-lives relative to IgG wherein the mutant IgG molecule has at least one amino acid substitution in the Fc-hinge region. However, no experimental support is provided for mutations at positions 250, 314, or 428.

U.S. Pat. No. 6,528,624 discloses a variant of an antibody comprising a human IgG Fc region, which variant comprises an amino acid substitution at one or more of amino acid positions 270, 322, 326, 327, 329, 331, 333, and 334 of the human IgG Fc region.

PCT Publication No. WO 98/05787 discloses deleting or substituting amino acids at positions 310-331 of the BR96 antibody in order to reduce its induced toxicity, but does not disclose amino acid modifications that result in altered binding to FcRn.

PCT Publication No. WO 00/42072 discloses a polypeptide comprising a variant Fc region with altered FcRn binding affinity, which polypeptide comprises an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 386, 388, 400, 413, 415, 424, 433, 434, 435, 436, 439, and 447 of the Fc region, wherein the numbering of the residues in the Fc region is that of the EU index (Kabat et al., op. cit.).

PCT Publication No. WO 02/060919 A2 discloses a modified IgG comprising an IgG constant domain comprising one or more amino acid modifications relative to a wild-type IgG constant domain, wherein the modified IgG has an increased half-life compared to the half-life of an IgG having the wild-type IgG constant domain, and wherein the one or more amino acid modifications are at one or more of positions 251, 253, 255, 285-290, 308-314, 385-389, and 428-435. However, no examples of mutations at positions 314 or 428 with altered binding to FcRn are disclosed.

Martin, W. L. (Doctoral dissertation entitled, "Protein-Protein Recognition: The Neonatal Fc Receptor and Immunoglobulin G," California Institute of Technology (2001)) proposes theoretical mutations at several Fc positions of the rat gamma-2a constant region, including positions 250 and 428, that may increase FcRn binding affinity. Martin suggests the possibility of substituting, among others, isoleucine for valine at position 250, or substituting phenylalanine for leucine at position 428. Martin does not suggest any substitution for position 314. Martin does not demonstrate increased binding affinity to FcRn for any of these proposed mutations.

The above-referenced publications have not showed that the serum half-life or FcRn binding affinity of an antibody of the IgG class can be altered by the amino acid modifications at position 250, position 314, or position 428 of the Fc region. The present invention used molecular modeling to select Fc residues near the FcRn contact site that might have an effect on binding, but may not be necessary for pH-dependent binding. Amino acid modifications were made at position 250, 314, or 428 of the constant region of an immunoglobulin heavy chain of class IgG. The serum half-lives or FcRn binding affinities of antibodies comprising said modifications were altered and, therefore, were different from those of unmodified antibodies.

SUMMARY OF THE INVENTION

The present invention is based upon the inventors' identification of several mutations in the constant domain of a human IgG molecule that alter (i.e., increase or decrease) the affinity of the IgG molecule for FcRn. The present invention provides for modified antibodies having altered FcRn binding affinity and/or serum half-life relative to the corresponding unmodified antibody. The in vivo half-life (i.e. persistence in serum or other tissues of a subject) of antibodies, and other bioactive molecules, is an important clinical parameter that determines the amount and frequency of antibody (or any other pharmaceutical molecule) administration. Accordingly, such molecules, including antibodies, with increased (or decreased) half-life are of significant pharmaceutical importance.

The present invention relates to a modified molecule (preferably an antibody), that has an increased (or decreased) in vivo half-life by virtue of the presence of a modified IgG constant domain (preferably from a human IgG), or FcRn-binding portion thereof (preferably the Fc or hinge-Fc domain) wherein the IgG constant domain, or fragment thereof, is modified (preferably by an amino acid substitution) to increase (or decrease) the affinity for the FcRn.

In a particular embodiment, the present invention relates to modified class IgG antibodies, whose in vivo half-lives are extended (or reduced) by the changes in amino acid residues at positions identified by structural studies to be involved either directly or indirectly in the interaction of the hinge-Fc domain with the FcRn receptor. In a preferred embodiment the modified class IgG antibody is selected from the group consisting of daclizumab, fontolizumab, visilizumab and M200 (volociximab).

In preferred embodiments, the constant domain (or fragment thereof) has a higher affinity for FcRn at pH 6.0 than at pH 7.4. That is, the pH dependency of FcRn binding affinity mimics the wild-type pH dependency. In alternative embodiments, the modified antibodies of the present invention may exhibit altered pH dependence profiles relative to that of the unmodified antibody. Such altered pH dependence profiles may be useful in some therapeutic or diagnostic applications.

In some embodiments, the antibody modifications of the present invention will alter FcRn binding and/or serum half-life without altering other antibody effector functions such as ADCC or CDC. In particularly preferred embodiments, the modified antibodies of the invention exhibit no changes in binding to Fc-gamma receptors or C1q. In alternative embodiments, the antibody modifications of the present invention may result in increased (or decreased) effector functions as well as increased serum half-life. In particularly preferred embodiments, the modified antibodies of the invention may have increased (or decreased) ADCC activities as well as increased serum half-life.

It should be noted that the modifications of the present invention may also alter (i.e., increase or decrease) the bioavailability (e.g., transport to mucosal surfaces, or other target tissues) of the modified antibodies (or other molecules).

In preferred embodiments, the present invention provides for a modified antibody of class IgG, in which at least one amino acid from the heavy chain constant region selected from the group consisting of amino acid residues 250, 314, and 428 is substituted with an amino acid residue different from that present in the unmodified antibody. Preferably this substitution alters the binding affinity for FcRn and/or the serum half-life of said modified antibody relative to the unmodified wild-type antibody. The present invention further provides for a modified antibody having an increased binding affinity for FcRn and an increased serum half-life as compared with the unmodified antibody, wherein amino acid residue 250 from the heavy chain constant region is substituted with glutamic acid or glutamine; or amino acid residue 428 from the heavy chain constant region is substituted with phenylalanine or leucine.

The present invention further provides for a modified antibody having an increased binding affinity for FcRn and/or an increased serum half-life as compared with the unmodified antibody, wherein (a) amino acid residue 250 from the heavy chain constant region is substituted with glutamic acid and amino acid residue 428 from the heavy chain constant region is substituted with phenylalanine; (b) amino acid residue 250 from the heavy chain constant region is substituted with glutamine and amino acid residue 428 from the heavy chain constant region is substituted with phenylalanine; or (c) amino acid residue 250 from the heavy chain constant region is substituted with glutamine and amino acid residue 428 from the heavy chain constant region is substituted with leucine.

The present invention further provides for a modified antibody having a reduced binding affinity for FcRn and/or a reduced serum half-life as compared with the unmodified antibody, wherein amino acid residue 314 from the heavy chain constant region is substituted with another amino acid which is different from that present in an unmodified antibody.

The present invention further provides for a modified antibody having a reduced binding affinity for FcRn and/or a reduced serum half-life as compared with the unmodified antibody, wherein amino acid residue 250 from the heavy chain constant region is substituted with arginine, asparagine, aspartic acid, lysine, phenylalanine, proline, tryptophan, or tyrosine; or amino acid residue 428 from the heavy chain constant region is substituted with alanine, arginine, asparagine, aspartic acid, cysteine, glutamic acid, glutamine, glycine, histidine, lysine, proline, serine, threonine, tyrosine, or valine.

The present invention also provides for an antibody having a constant region substantially identical to a naturally occurring class IgG antibody constant region wherein at least one amino acid residue selected from the group consisting of residues 250, 314, and 428 is different from that present in the naturally occurring class IgG antibody, thereby altering FcRn binding affinity and/or serum half-life of said antibody relative to the naturally occurring antibody. In preferred embodiments, the naturally occurring class IgG antibody comprises a heavy chain constant region of a human IgG1, IgG2, IgG2M3, IgG3 or IgG4 molecule. Also in preferred embodiments, amino acid residue 250 from the heavy chain constant region of the antibody having a constant region substantially identical to the naturally occurring class IgG antibody is glutamic acid or glutamine; or amino acid residue 428 from the heavy chain constant region is phenylalanine or leucine. In other preferred embodiments, the antibody having a constant region substantially identical to a naturally occurring class IgG antibody has a glutamic acid residue at position 250 and, phenylalanine residue at position 428; or amino acid residue 250 is glutamine and amino acid residue 428 is phenylalanine; or amino acid residue 250 is glutamine and amino acid residue 428 is leucine.

In some embodiments, the antibody having a constant region substantially identical to a naturally occurring class IgG antibody constant region includes an amino acid residue at position 314 different from that present in the naturally occurring antibody, thereby reducing FcRn binding affinity and/or reducing serum half-life relative to the naturally occurring antibody. Embodiments include antibodies wherein amino acid residue 314 is alanine, arginine, aspartic acid, asparagine, cysteine, glutamic acid, glutamine, glycine, histidine, lysine, methionine, phenylalanine, proline, serine, threonine, tryptophan, tyrosine, or valine. In one preferred embodiment amino acid residue 314 is arginine.

In other embodiments, the antibody having a constant region substantially identical to a naturally occurring class IgG antibody constant region includes an amino acid residue at position 250 selected from the group consisting of arginine, asparagine, aspartic acid, lysine, phenylalanine, proline, tryptophan, or tyrosine, thereby reducing FcRn binding affinity and/or reducing serum half-life relative to the naturally occurring antibody. Similarly, the amino acid residue at position 428 may be substituted with an amino acid residue selected from the group consisting of alanine, arginine, asparagine, aspartic acid, cysteine, glutamic acid, glutamine, glycine, histidine, lysine, proline, serine, threonine, tyrosine, or valine, thereby reducing FcRn binding affinity and/or reducing serum half-life relative to the naturally occurring antibody.

The present invention further provides for a method of modifying an antibody of class IgG, wherein said method comprises substituting at least one amino acid from the heavy chain constant region selected from the group consisting of amino acid residues 250, 314, and 428 with an amino acid which is different from that present in an unmodified antibody, thereby causing an alteration of the binding affinity for FcRn and/or the serum half-life of said unmodified antibody.

The present invention further provides for a method of producing a modified antibody of class IgG with an altered binding affinity for FcRn and/or an altered serum half-life as compared with an unmodified antibody, wherein said method comprises:

(a) preparing an expression vector (preferably a replicable expression vector) comprising a suitable promoter operably linked to DNA encoding at least a constant region of an immunoglobulin heavy chain wherein at least one amino acid from the heavy chain constant region selected from the group consisting of amino acid residues 250, 314, and 428 is substituted with an amino acid which is different from that present in an unmodified antibody thereby causing an alteration in FcRn binding affinity and/or serum half-life;

(b) transforming host cells with said vector; and (c) culturing said transformed host cells to produce said modified antibody.

Optionally, such a method further comprises: preparing a second expression vector (preferably a replicable expression vector) comprising a promoter operably linked to DNA encoding a complementary immunoglobulin light chain and further transforming said cell line with said second vector.

The present invention also includes pharmaceutical compositions and methods of prophylaxis and therapy using modified immunoglobulins (including immunoglobulins conjugated with toxins and radionuclides), proteins and other bioactive molecules of the invention having altered half-lives. Also included are methods of diagnosis using modified immunoglobulins, proteins and other bioactive molecules of the invention having altered half-lives. In preferred embodiments, the amino acid modifications of the present invention may be used to extend the serum half-life of a therapeutic or diagnostic antibody. For example, the present invention provides for a modified therapeutic or diagnostic antibody of class IgG with an in vivo elimination half-life at least about 1.3-fold longer than that of the corresponding unmodified antibody. The modified therapeutic or diagnostic antibody wherein at least one amino acid residue selected from the group consisting of residues 250, 314, and 428 is different from that present in the unmodified antibody. In preferred embodiments the modified therapeutic or diagnostic antibody has an in vivo elimination half-life at least about 1.3-fold, 1.5-fold, 1.8-fold, 1.9-fold, or greater than 2.0-fold longer than that of the corresponding unmodified antibody.

The present invention also provides for a modified therapeutic or diagnostic antibody of class IgG with an in vivo clearance at least about 1.3-fold lower than that of the corresponding unmodified antibody. The modified therapeutic or diagnostic antibody wherein at least one amino acid residue selected from the group consisting of residues 250, 314, and 428 is different from that present in the unmodified antibody. In preferred embodiments the modified therapeutic or diagnostic antibody has an in vivo clearance at least about 1.3-fold, 1.5-fold, 1.8-fold, 2.0-fold, 2.3-fold, 2.5-fold, 2.8-fold, or greater than 3.0-fold lower than that of the corresponding unmodified antibody. In a preferred embodiment the therapeutic antibody is selected from the group consisting of daclizumab, fontolizumab, visilizumab and volociximab.

The present invention further provides for a modified therapeutic or diagnostic antibody of class IgG with an in vivo area under the concentration-time curve at least about 1.3-fold higher than that of the corresponding unmodified antibody. The modified therapeutic or diagnostic antibody wherein at least one amino acid residue selected from the group consisting of residues 250, 314, and 428 is different from that present in the unmodified antibody. In preferred embodiments the modified therapeutic or diagnostic antibody has an in vivo elimination half-life at least about 1.3-fold, 1.5-fold, 1.8-fold, 2.0-fold, 2.3-fold, 2.6-fold, 2.8-fold, or greater than 3.0-fold higher than that of the corresponding unmodified antibody.

In alternative preferred embodiments, the amino acid modifications of the present invention may also be used to reduce the serum half-life of a therapeutic or diagnostic antibody. Such therapeutic or diagnostic antibodies are well-known in the art and listed in the following description of the invention.

The invention also provides a modified therapeutic antibody comprising a light chain amino acid sequence of SEQ ID NO: 118 and a heavy chain amino acid sequence selected from SEQ ID NOs: 119-128. The invention also provides a vector comprising a polynucleotide encoding one or more of these light or heavy chain amino acid sequences. This invention further provides a host cell comprising this vector.

In addition the invention provides: a modified therapeutic antibody comprising a light chain amino acid sequence of SEQ ID NO: 129 and a heavy chain amino acid sequence selected from SEQ ID NOs: 130-134; a modified therapeutic antibody comprising a light chain amino acid sequence of SEQ ID NO: 135 and a heavy chain amino acid sequence selected from SEQ ID NOs: 136-140; and a modified therapeutic antibody comprising a light chain amino acid sequence of SEQ ID NO: 141 and a heavy chain amino acid sequence selected from SEQ ID NOs: 142-146. The invention also provides vectors comprising one or more of the heavy and/or light chain amino acid sequences of the above-listed modified therapeutic antibodies; and the invention provides a host cell comprising any of the above listed vectors.

BRIEF DESCRIPTION OF THE DRAWINGS

FIG. 3. Amino Acid Sequences of Hu1D10-IgG2M3, Hu1D10-IgG1, Hu1D10-IgG3 and Hu1D10-IgG4 with Positions 250, 314, and 428 of the Heavy Chain Highlighted. "Hu1D10-VH" (SEQ ID NO: 6) depicts the amino acid sequence of the heavy chain variable region of Hu1D10-IgG2M3, Hu1D10-IgG1, Hu1D10-IgG3, or Hu1D10-IgG4. "IgG2M3-CH" (SEQ ID NO: 2) depicts the amino acid sequence of the heavy chain constant region of Hu1D10-IgG2M3. "IgG1-CH" (SEQ ID NO: 7) depicts the amino acid sequence of the heavy chain constant region of Hu1D10-IgG1. "IgG3-CH" (SEQ ID NO: 113) depicts the amino acid sequence of the heavy chain constant region of Hu1D10-IgG3. "IgG4-CH" (SEQ ID NO: 114) depicts the amino acid sequence of the heavy chain constant region of Hu1D10-IgG4. "Hu1D10-VL" (SEQ ID NO: 8) depicts the amino acid sequence of the light chain variable region of Hu1D10-IgG2M3, Hu1D10-IgG1, Hu1D10-IgG3, or Hu D10-IgG4. "KAPPA-CL" (SEQ ID NO: 9) depicts the amino acid sequence of the light chain constant region of Hu1D10-IgG2M3, Hu1D10-IgG1, Hu1D10-IgG3, or Hu1D10-IgG4.

FIG. 5A. Restriction Map of Heavy Chain Vector pVAg2M3-OST577

FIG. 5B. Restriction Map of Heavy Chain Vector pVAg1.N-OST577

FIG. 7A. Restriction Map of Heavy Chain Vector pVAg2M3-Hu1D10

FIG. 7B. Restriction Map of Heavy Chain Vector pVAg1.N-Hu1D10

FIG. 7C. Restriction Map of Heavy Chain Vector pHuHCg3.Tt.D-Hu1D10

FIG. 7D. Restriction Map of Heavy Chain Vector pHuHCg4.Tt.D-Hu1D10

FIG. 9A. Restriction Map of Human FcRn Vector pDL208

FIG. 9B. Restriction Map of Rhesus FcRn Vector pDL410

FIG. 10A. SDS-PAGE Analysis of OST577-IgG2M3 Wild-Type and Mutant Antibodies Purified OST577-IgG2M3 wild-type and mutant antibodies were analyzed by SDS-PAGE under reducing conditions, as described in Example 5.

FIG. 10B. SDS-PAGE Analysis of OST577-IgG1 Wild-Type and Mutant Antibodies Purified OST577-IgG1 wild-type and mutant antibodies were analyzed by SDS-PAGE under reducing conditions, as described in Example 5.

FIG. 22. Amino acid sequences of Daclizumab with various FcRn binding mutations.

FIG. 23. Amino acid sequences of Fontolizumab with various FcRn binding mutations.

FIG. 24. Amino acid sequences of Visilizumab with various FcRn binding mutations.

FIG. 25. Amino acid sequences of M200 (volociximab) with various FcRn binding mutations.

DETAILED DESCRIPTION OF THE INVENTION

Figure 1:
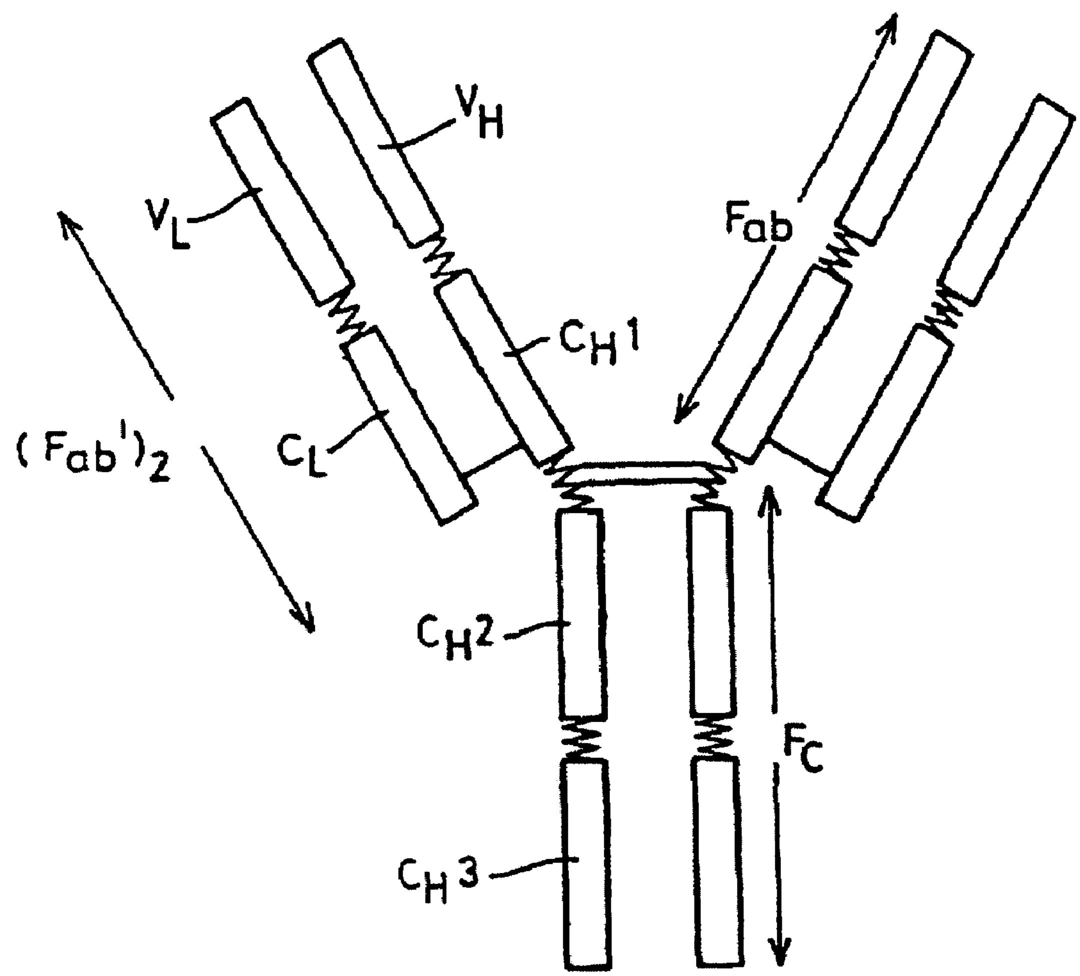
FIG. 1. Illustration of the Structure of an IgG Molecule
Figure 2:
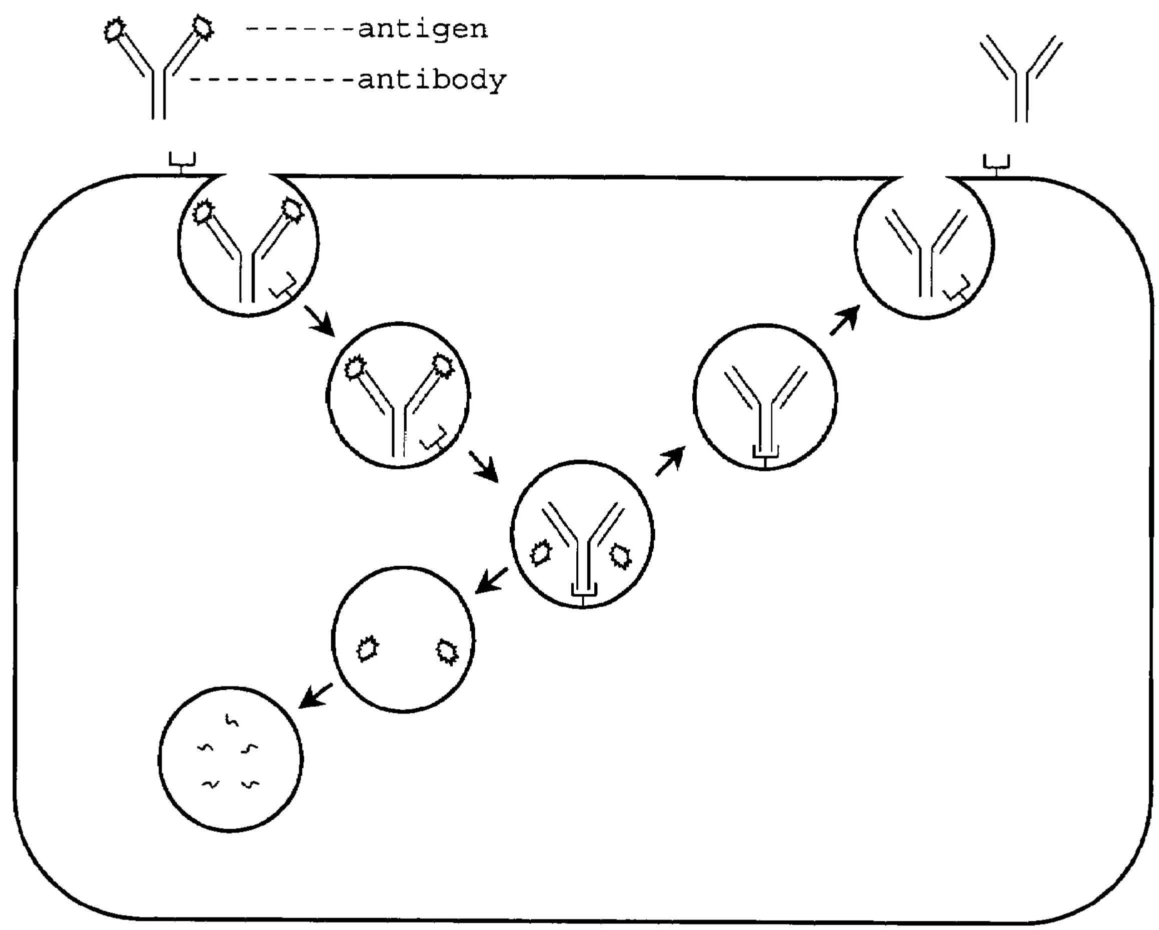
FIG. 2. Salvage Pathway of IgG Molecules

I. Modified Antibodies with Altered FcRn Binding Affinity and/or Serum Half-Lives In order that the invention may be more completely understood, several definitions are set forth.

As used herein, the terms "immunoglobulin" and "antibody" refer to proteins consisting of one or more polypeptides substantially encoded by immunoglobulin genes. The recognized immunoglobulin genes include the kappa, lambda, alpha, gamma (γ1, γ2, γ3, γ4), delta, epsilon, and mu constant region genes, as well as the myriad immunoglobulin variable region genes. Full-length immunoglobulin "light chains" (about 25 Kd or 214 amino acids) are encoded by a kappa or lambda variable region gene at the NH2-terminus (about 110 amino acids) and a kappa or lambda constant region gene at the COOH-terminus. Full-length immunoglobulin "heavy chains" (about 50 Kd or 446 amino acids) are similarly encoded by a heavy chain variable region gene (about 116 amino acids) and one of the other aforementioned constant region genes, e.g., gamma (encoding about 330 amino acids).

One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to tetrameric antibodies, immunoglobulins may exist in a variety of other forms including, for example, Fv, Fab, and $(Fab')_2$, as well as bifunctional hybrid antibodies (e.g., Lanzavecchia and Scheidegger, Eur. J. Immunol. 17:105-111 (1987)) and in single chains (e.g., Huston et al., Proc. Natl. Acad. Sci. USA, 85:5879-5883 (1988), and Bird et al., Science, 242:423-426 (1988), which are incorporated herein by reference). (See, generally, Hood et al., "Immunology", $2^{nd}$ ed., Benjamin, New York (1984), and Hunkapiller and Hood, Nature, 323:15-16 (1986), which are incorporated herein by reference).

The term "genetically altered antibodies" refers to antibodies wherein the sequence of amino acid residues has been changed from that of a native or wild-type antibody. Because of the relevance of recombinant DNA techniques, the present invention is not limited to modification of amino acid sequences found in natural antibodies. As described below, previously engineered antibodies may be redesigned according to present invention in order to obtain the desired characteristics of altered FcRn binding affinity and/or serum half-life. The possible variants of modified antibodies useful with the present invention are many and range from changing just one or a few amino acids to the complete redesign of, for example, the variable or constant region. Changes in the constant region will, in general, be made in order to improve or alter characteristics, such as complement fixation, interaction with various Fc-gamma receptors and other effector functions. Changes in the variable region will be made in order to improve the antigen binding characteristics.

An antibody having a constant region substantially identical to a naturally occurring class IgG antibody constant region refers to an antibody in which any constant region present is substantially identical, i.e., at least about 85-90%, and preferably at least 95% identical, to the amino acid sequence of the naturally occurring class IgG antibody's constant region.

In many preferred uses of the present invention, including in vivo use of the modified antibodies in humans for and in vitro detection assays, it may be preferable to use chimeric, primatized, humanized, or human antibodies that have been modified (i.e., mutated) according to the present invention.

The term "chimeric antibody" refers to an antibody in which the constant region comes from an antibody of one species (typically human) and the variable region comes from an antibody of another species (typically rodent). Methods for producing chimeric antibodies are known in the art. See e.g., Morrison, Science 229:1202-1207 (1985); Oi et al., BioTechniques 4:214-221 (1986); Gillies et al., J. Immunol. Methods 125:191-202 (1989); U.S. Pat. Nos. 5,807,715; 4,816,567; and 4,816,397, which are incorporated herein by reference in their entireties.

The term "primatized antibody" refers to an antibody comprising monkey variable regions and human constant regions. Methods for producing primatized antibodies are known in the art. See e.g., U.S. Pat. Nos. 5,658,570; 5,681,722; and 5,693,780, which are incorporated herein by reference in their entireties.

The term "humanized antibody" or "humanized immunoglobulin" refers to an immunoglobulin comprising a human framework, at least one and preferably all complementarity determining regions (CDRs) from a non-human antibody, and in which any constant region present is substantially identical to a human immunoglobulin constant region, i.e., at least about 85-90%, and preferably at least 95% identical. Hence, all parts of a humanized immunoglobulin, except possibly the CDRs, are substantially identical to corresponding parts of one or more native human immunoglobulin sequences. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. Nos. 5,530,101; 5,585,089; 5,693,761; 5,693,762; 6,180,370 (each of which is incorporated by reference in its entirety). Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, Mol. Immunol., 28:489-498 (1991); Studnicka et al., Prot. Eng. 7:805-814 (1994); Roguska et al., Proc. Natl. Acad. Sci. 91:969-973 (1994), and chain shuffling (U.S. Pat. No. 5,565,332), all of which are hereby incorporated by reference in their entireties.

Completely human antibodies may be desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Fremont, Calif.) and Medarex (Princeton, N.J.) can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., Biotechnology 12:899-903 (1988).

As used herein the term "altering" may refer to "increasing" or "reducing".

The present invention provides for a modified antibody of class IgG, in which at least one amino acid from the heavy chain constant region, selected from the group consisting of amino acid residues 250, 314, and 428, is substituted with an amino acid residue different from that present in the unmodified antibody.

The antibodies of IgG class include antibodies of IgG1, IgG2, IgG3, and IgG4. The constant region of the heavy chain of an IgG molecule is indicated in FIG. 1. The numbering of the residues in the heavy chain is that of the EU index (Kabat et al., op. cit.). The substitution can be made at position 250, 314, or 428 alone, or in any combinations thereof, such as at positions 250 and 428, or at positions 250 and 314, or at positions 314 and 428, or at positions 250, 314, and 428, with positions 250 and 428 as a preferred combination.

For each position, the substituting amino acid may be any amino acid residue different from that present in that position of the unmodified antibody.

For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine.

For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine.

For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. The present invention provides for antibodies of class IgG comprising at least one of the above-described amino acid substitutions. For example, the present invention provides for the mutated IgG2M3 constant regions comprising two of the above-mentioned substitutions at position 250, 314, and/or 428. The amino acid sequences of some specific substitutions (i.e., mutations) of the constant region provided by the present invention are disclosed in Table 1 (SEQ ID NOs: 10-66).

TABLE 1

| Substituting Amino Acid | 250 | 314 | 428 |
|---|---|---|---|
| Alanine (A) | T250A; SEQ ID NO: 10 | L314A; SEQ ID NO: 29 | M428A; SEQ ID NO: 48 |
| Cysteine (C) | T250C; SEQ ID NO: 11 | L314C; SEQ ID NO: 30 | M428C; SEQ ID NO: 49 |
| Aspartic acid (D) | T250D; SEQ ID NO: 12 | L314D; SEQ ID NO: 31 | M428D; SEQ ID NO: 50 |
| Glutamic acid (E) | T250E; SEQ ID NO 13 | L314E; SEQ ID NO: 32 | M428E; SEQ ID NO: 51 |
| Phenylalanine (F) | T250F; SEQ ID NO: 14 | L314F; SEQ ID NO: 33 | M428F; SEQ ID NO: 52 |
| Glycine (G) | T250G; SEQ ID NO: 15 | L314G; SEQ ID NO: 34 | M428G; SEQ ID NO: 53 |
| Histidine (H) | T250H; SEQ ID NO: 16 | L314H; SEQ ID NO: 35 | M428H; SEQ ID NO: 54 |
| Isoleucine (I) | T250I; SEQ ID NO: 17 | L314I; SEQ ID NO: 36 | M428I; SEQ ID NO: 55 |
| Lysine (K) | T250K; SEQ ID NO: 18 | L314K; SEQ ID NO: 37 | M428K; SEQ ID NO: 56 |
| Leucine (L) | T250L; SEQ ID NO: 19 | Wild Type | M428L; SEQ ID NO: 57 |
| Methionine (M) | T250M; SEQ ID NO: 20 | L314M; SEQ ID NO: 38 | Wild Type |
| Asparagine (N) | T250N; SEQ ID NO: 21 | L314N; SEQ ID NO: 39 | M428N; SEQ ID NO: 58 |
| Proline (P) | T250P; SEQ ID NO: 22 | L314P; SEQ ID NO: 40 | M428P; SEQ ID NO: 59 |
| Glutamine (Q) | T250Q; SEQ ID NO: 23 | L314Q; SEQ ID NO: 41 | M428Q; SEQ ID NO: 60 |
| Arginine (R) | T250R; SEQ ID NO: 24 | L314R; SEQ ID NO: 42 | M428R; SEQ ID NO: 61 |
| Serine (S) | T250S; SEQ ID NO: 25 | L314S; SEQ ID NO: 43 | M428S; SEQ ID NO: 62 |
| Threonine (T) | Wild Type | L314T; SEQ ID NO: 44 | M428T; SEQ ID NO: 63 |
| Valine (V) | T250V; SEQ ID NO: 26 | L314V; SEQ ID NO: 45 | M428V; SEQ ID NO: 64 |
| Tryptophan (W) | T250W; SEQ ID NO: 27 | L314W; SEQ ID NO: 46 | M428W; SEQ ID NO: 65 |
| Tyrosine (Y) | T250Y; SEQ ID NO: 28 | L314Y; SEQ ID NO: 47 | M428Y; SEQ ID NO: 66 |

In a preferred embodiment, the present invention provides for a modified antibody having an altered serum half-life or FcRn binding affinity relative to the unmodified antibody. The present invention further provides for a modified antibody of class IgG, in which at least one amino acid from the heavy chain constant region, selected from the group consisting of amino acid residues 250, 314, and 428, is substituted with another amino acid which is different from that present in the unmodified antibody, thereby altering the binding affinity for FcRn and/or the serum half-life of the modified antibody compared to the binding affinity and/or serum half-life of said unmodified antibody.

The unmodified antibodies of the present invention include natural antibodies of all species. The term "natural antibodies" refers to all antibodies produced by a host animal. Non-limiting exemplary natural antibodies of the present invention include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati et al., WO91/10741; U.S. Pat. No. 6,150,584, which are herein incorporated by reference in their entirety).

The unmodified antibodies of the present invention also includes recombinant antibodies having the same amino acid sequences as a natural antibody, or genetically-altered antibodies that have changed amino acid sequences compared to the natural antibodies. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety).

The unmodified antibodies of the present invention also include chimeric, primatized, humanized and human antibodies (see discussion above). Consequently, a modified antibody of the present invention may be produced by substituting an amino acid residue at position 250, 314, or 428 in a humanized, primatized, or chimeric antibody, wherein the humanized, primatized, or chimeric antibody previously has been derived from a native antibody.

Preferably, the chimeric antibodies comprise variable regions derived from rodents and constant regions derived from humans so that the chimeric antibodies have longer half-lives and are less immunogenic when administered to a human subject. The primatized antibodies comprise variable regions derived from primates and constant regions derived from humans. The humanized antibodies typically comprise at least one CDR from the donor antibodies (for example, murine or chicken antibodies) and heavy and/or light chain human frameworks. Sometimes, some amino acid residues in the human frameworks will be replaced by the residues at the equivalent positions of the donor antibodies to ensure the proper binding of the humanized antibodies to their antigens. The detailed guidelines of antibody humanization are disclosed in U.S. Pat. Nos. 5,530,101; 5,585,089; 5,693,761; 5,693,762; and 6,180,370, each of which is incorporated by reference herein.

The unmodified antibodies of the present invention may include genetically-altered antibodies that are functionally equivalent to the corresponding natural antibodies. Unmodified antibodies that are genetically-altered to provide improved stability and/or therapeutic efficacy are preferred. Examples of altered antibodies include those with conservative substitutions of amino acid residues, and one or more deletions or additions of amino acids that do not significantly alter the antigen binding utility. Substitutions can range from changing or modifying one or more amino acid residues to complete redesign of a region as long as the binding or functional utility is maintained. Antibodies of this invention can be altered post-translationally (e.g., acetylation, and phosphorylation) or can be altered synthetically (e.g., the attachment of a labeling group).

The unmodified antibodies of the present invention may include antibodies having enhanced binding affinities for their antigens through genetic alterations of the variable regions (see, e.g., U.S. Pat. No. 6,350,861, which is herein incorporated by reference in its entirety). In one alternative embodiment, the modified IgGs of the present invention that have longer half-lives than wild-type (or unmodified) IgGs may also include IgGs whose bioactive sites, such as antigen-binding sites, Fc-receptor binding sites, or complement-binding sites, are modified by genetic engineering to increase or reduce such activities compared to the wild type.

The unmodified and modified antibodies of the present invention may be of any of the recognized isotypes, but the four IgG isotypes are preferred, with IgG1 and IgG2 especially preferred. Antibodies with constant regions mutated to have reduced effector functions, for example the IgG2M3 and other IgG2 mutants described in U.S. Pat. No. 5,834,597 (which is incorporated by reference in its entirety), are included. In a preferred aspect, the unmodified and modified antibodies in the present invention comprise heavy chain constant regions of human IgGs.

The present invention may be applied to any antibody comprising heavy chain constant regions of IgG class, preferably IgG1, IgG2, IgG2M3, IgG3, and IgG4. The heavy chain variable regions of such antibodies can be derived from any selected antibodies. Exemplary antibodies disclosed herein include OST577-IgG1 and OST577-IgG2M3, which comprise the heavy chain and light chain variable regions of the human anti-hepatitis B virus antibody OST577 (Ehrlich et al., Hum. Antibodies Hybridomas 3:2-7 (1992)), the light chain constant region of human lambda-2, and the heavy chain constant region of human IgG1 and IgG2M3, respectively. Also disclosed herein are Hu1D10-IgG1 and Hu1D10-IgG2M3, Hu1D10-IgG3 and Hu1D10-IgG4 which comprise the heavy and light chain variable regions of the humanized anti-HLA-DR β chain allele antibody Hu1D10 (Kostelny et al., Int. J. Cancer 93:556-565 (2001)), the light chain constant region of human kappa, and the aforementioned heavy chain constant regions of human IgG1, IgG2M3, IgG3 and IgG4, respectively (See, FIG. 3).

Further exemplifications of the present invention disclosed herein include mutants of the human IgG1, IgG2M3 (a genetically altered variant of IgG2), IgG3 and IgG4 antibodies, illustrating alteration of the serum half-life of an antibody of class IgG. The constant region of the heavy chain of IgG2M3 is derived from that of the IgG2 by replacing residues 234 and 237 of the IgG2 heavy chain constant region with alanine. The generation of the heavy chain constant region of IgG2M3 is disclosed in U.S. Pat. No. 5,834,597, which is incorporated herein by reference.

Generally, the modified antibodies of the present invention include any immunoglobulin molecule that binds (preferably, immunospecifically, i.e., competes off non-specific binding, as determined by immunoassays well known in the art for assaying specific antigen-antibody binding) an antigen and contains an FcRn-binding fragment. Such antibodies include, but are not limited to, polyclonal, monoclonal, bi-specific, multi-specific, human, humanized, chimeric antibodies, single chain antibodies, Fab fragments, $F(ab')_2$ fragments, disulfide-linked Fvs, and fragments containing either a $V_L$ or $V_H$ domain or even a complementary determining region (CDR) that specifically binds an antigen, in certain cases, engineered to contain or fused to an FcRn binding domain.

The modified IgG molecules of the invention may include IgG subclasses of any given animals. For example, in humans, the IgG class includes IgG1, IgG2, IgG3, and IgG4; and the mouse IgG class includes IgG1, IgG2a, IgG2b, and IgG3; and the rat IgG class includes IgG1, IgG2a, IgG2b, IgG2c, and IgG3. It is known that certain IgG subclasses, for example, rat IgG2b and IgG2c, have higher clearance rates than, for example, IgG1 (Medesan et al., Eur. J. Immunol., 28:2092-2100 (1998)). Thus, when using IgG subclasses other than IgG lit may be advantageous to substitute one or more of the residues, particularly in the $C_H2$ and $C_H3$ domains, which differ from the IgG1 sequence with those of IgG1, thereby increasing the in vivo half-life of the other types of IgG.

The immunoglobulins of the present invention may be from any animal origin including birds and mammals. Preferably, the antibodies are human, rodent, donkey, sheep, rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin, as described infra and, for example, in U.S. Pat. No. 5,939,598 by Kucherlapati et al.

In addition, the modified antibodies of the present invention may be monospecific, bispecific, trispecific antibodies or of greater multispecificity. Multispecific antibodies may be specific for different epitopes of a polypeptide or may be specific for heterologous epitopes, such as a heterologous polypeptide or solid support material. See, e.g., PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

The modified antibodies of the invention include derivatives that are otherwise modified, i.e., by the covalent attachment of any type of molecule to the antibody such that covalent attachment does not prevent the antibody from binding antigen and/or generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Monoclonal antibodies useful with the present invention can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow and Lane, "Antibodies: A Laboratory Manual," Cold Spring Harbor Laboratory Press, New York (1988); Hammerling et al., in: "Monoclonal Antibodies and T-Cell Hybridomas," Elsevier, New York (1981), pp. 563-681 (both of which are incorporated herein by reference in their entireties).

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well-known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments that recognize specific epitopes may also be useful with the present invention and may be generated by well-known techniques. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the complete light chain, and the variable region, the CH1 region and the hinge region of the heavy chain.

For example, antibodies can also be generated using various display methods known in the art, including phage display. In phage display methods, functional antibody domains are displayed on the surface of phage particles that carry the polynucleotide sequences encoding them. In a particular embodiment, such phage can be utilized to display antigen-binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Alternatively, the modified FcRn binding portion of immunoglobulins of the present invention can be also expressed in a phage display system. Examples of phage display methods that can be used to make the immunoglobulins, or fragments thereof, of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187:9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab', and $F(ab')_2$ fragments can also be employed using methods known in the art such as those disclosed in PCT publication WO 92/22324; Mullinax et al., BioTechniques 12:864-869 (1992); Sawai et al., Amer. J. Reprod. Immunol. 34:26-34 (1995); and Better et al., Science 240:1041-1043 (1988), each of which is incorporated by reference in its entirety. Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., Proc. Natl. Acad. Sci. 90:7995-7999 (1993); and Skerra et al., Science 240:1038-1040 (1988).

In particular embodiments, the modified antibodies have in vivo therapeutic and/or prophylactic uses. Examples of therapeutic and prophylactic antibodies which may be so modified include, but are not limited to, SYNAGIS® (palivizumab) (Medimmune, MD) which is a humanized anti-respiratory syncytial virus (RSV) monoclonal antibody for the treatment of patients with RSV infection; HERCEPTIN® (trastuzumab) (Genentech, CA) which is a humanized anti-HER2 monoclonal antibody for the treatment of patients with metastatic breast cancer; REMICADE® (infliximab) (Centocor, Pa.) which is a chimeric anti-TNF-α monoclonal antibody for the treatment of patients with Crohn's disease; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD18 $F(ab')_2$ (Genentech); CDP860 which is a humanized anti-CD18 $F(ab')_2$ (Celltech, UK); PR0542 which is an anti-HIV gp120 antibody fused with CD4 (Progenics/Genzyme Transgenics); OSTAVIR™ which is a human anti Hepatitis B virus antibody (Protein Design Labs/Novartis); PROTOVIR™ which is a humanized anti-CMV IgG1 antibody (Protein Design Labs/Novartis); IC14 which is an anti-CD14 antibody (ICOS); AVASTIN™ which is a humanized anti-VEGF IgG1 antibody (Genentech); ERBITUX™ which is a chimeric anti-EGFR IgG antibody (ImClone Systems); VITAXIN™ which is a humanized anti-αVβ3 integrin antibody (Applied Molecular Evolution/Medimmune); Campath-1H/LDP-03 which is a humanized anti-CD52 IgG1 antibody (Leukosite); ZAMYL™ which is a humanized anti-CD33 IgG antibody (Protein Design Labs/Kanebo); RITUXAN™ which is a chimeric anti-CD20 IgG1 antibody (IDEC Pharmaceuticals/Genentech, Roche/Zenyaku); LYMPHOCIDE™ which is a humanized anti-CD22 IgG antibody (Immunomedics); REMITOGEN™ which is a humanized anti-HLA-DR antibody (Protein Design Labs); ABX-IL8 which is a human anti-IL8 antibody (Abgenix); RAPTIVA™ which is a humanized IgG1 antibody (Genetech/Xoma); ICM3 which is a humanized anti-ICAM3 antibody (ICOS); IDEC-114 which is a primatized anti-CD80 antibody (IDEC Pharmaceuticals/Mitsubishi); IDEC-131 which is a humanized anti-CD40L antibody (IDEC/Eisai); IDEC-151 which is a primatized anti-CD4 antibody (IDEC); IDEC-152 which is a primatized anti-CD23 antibody (IDEC/Seikagaku); NUVION™ which is a humanized anti-CD3 IgG2M3 antibody (Protein Design Labs); 5G1.1 which is a humanized anti-complement factor 5 (C5) antibody (Alexion Pharmaceuticals); HUMIRA™ which is a human anti-TNF-α antibody (CAT/BASF); CDP870 which is a humanized anti-TNF-α Fab fragment (Celltech); IDEC-151 which is a primatized anti-CD4 IgG1 antibody (IDEC Pharmaceuticals/Smith-Kline Beecham); MDX-CD4 which is a human anti-CD4 IgG antibody (Medarex/Eisai/Genmab); CDP571 which is a humanized anti-TNF-α IgG4 antibody (Celltech); LDP-02 which is a humanized anti-α4β7 antibody (LeukoSite/Genentech); OrthoClone OKT4A which is a humanized anti-CD4 IgG antibody (Ortho Biotech); ANTOVA™ which is a humanized anti-CD40L IgG antibody (Biogen); TYSABRI® which is a humanized anti-VLA-4 IgG antibody (Elan); MDX-33 which is a human anti-CD64 (FcγR) antibody (Medarex/Centeon); SCH55700 which is a humanized anti-IL-5 IgG4 antibody (Celltech/Schering); SB-240563 and SB-240683 which are humanized anti-IL-5 and IL-4 antibodies, respectively (SmithKline Beecham); rhuMab- E25 which is a humanized anti-IgE IgG1 antibody (Genentech/Novartis/Tanox Biosystems); IDEC-152 which is a primatized anti-CD23 antibody (IDEC Pharmaceuticals); SIMULECT™ which is a chimeric anti-CD25 IgG1 antibody (Novartis Pharmaceuticals); LDP-01 which is a humanized anti-β2-integrin IgG antibody (Leukosite); CAT-152 which is a human anti-TGF-β2 antibody (Cambridge Antibody Technology); and Corsevin M which is a chimeric anti-Factor VII antibody (Centocor).

The present invention permits modification of these and other therapeutic antibodies to increase the in vivo half-life, allowing administration of lower effective dosages and/or less frequent dosing of the therapeutic antibody. Such modification to increase in vivo half-life can also be useful to improve diagnostic immunoglobulins as well. For example, increased serum half-life of a diagnostic antibody may permit administration of lower doses to achieve sufficient diagnostic sensitivity. Alternatively, decreased serum half-life may be advantageous in applications where rapid clearance of a diagnostic antibody is desired.

Disclosed herein is the amino acid sequence of OST577-IgG2M3, including the amino acid sequence of its heavy chain variable region (SEQ ID NO: 1) (OST577-VH) and constant region (SEQ ID NO: 2) (IgG2M3-CH) with positions 250, 314, and 428 highlighted, and the amino acid sequence of its light chain variable region (SEQ ID NO: 4) (OST577-VL) and constant region (SEQ ID NO: 5) (LAMBDA2-CL).

Disclosed herein is the amino acid sequence of the heavy chain constant region of OST577-IgG1 (SEQ ID NO: 3).

The present invention provides for a modified antibody having an increased binding affinity for FcRn and/or an increased serum half-life as compared with the unmodified antibody, wherein amino acid residue 250 or 428 from the heavy chain constant region is substituted with another amino acid residue that is different from that present in the unmodified antibody. Preferably, amino acid residue 250 from the heavy chain constant region is substituted with glutamic acid or glutamine. Alternatively, amino acid residue 428 from the heavy chain constant region is substituted with phenylalanine or leucine.

In one example, said unmodified antibody comprises the heavy chain constant region of an IgG1, or IgG2, or IgG2M3 molecule, including, but not limited to, OST577-IgG2M3 or OST577-IgG1. IgG1, IgG2, and IgG2M3 have a threonine residue at position 250 and a methionine residue at position 428. Preferably, the threonine residue at position 250 is substituted with glutamic acid (T250E) or glutamine (T250Q), and the methionine residue at position 428 is substituted with phenylalanine (M428F) or leucine (M428L). The amino acid sequences of the heavy chain constant region of the modified IgG2M3 having the amino acid substitutions of T250E (SEQ ID NO: 13), T250Q (SEQ ID NO: 23), M428F (SEQ ID NO: 52), or M428L (SEQ ID NO: 57) are disclosed herein. The amino acid sequences of the constant region of the heavy chain of the modified IgG1 having the amino acid substitutions of T250D (SEQ ID NO: 67), T250E (SEQ ID NO: 68), T250Q (SEQ ID NO: 69), M428F (SEQ ID NO: 70), or M428L (SEQ ID NO. 71) are also disclosed herein.

The present invention provides for a modified antibody having an increased binding affinity for FcRn and/or an increased serum half-life as compared with the unmodified antibody. The amino acid modification can be any one of the following substitutions:

1) Amino acid residue 250 from the heavy chain constant region is substituted with glutamic acid and amino acid residue 428 from the heavy chain constant region is substituted with phenylalanine.
2) Amino acid residue 250 from the heavy chain constant region is substituted with glutamine and amino acid residue 428 from the heavy chain constant region is substituted with phenylalanine.
3) Amino acid residue 250 from the heavy chain constant region is substituted with glutamine and amino acid residue 428 from the heavy chain constant region is substituted with leucine.

The amino acid sequences of the heavy chain constant region of the modified IgG2M3 having the double amino acid substitutions of T250E/M428F (SEQ ID NO: 72), T250Q/M428F (SEQ ID NO: 73), or T250Q/M428L (SEQ ID NO: 74) are disclosed herein.

The amino acid sequences of the heavy chain constant region of the modified IgG1 having the double amino acid substitutions of T250E/M428F (SEQ ID NO: 75) or T250Q/M428L (SEQ ID NO: 76) are disclosed herein.

The modified antibodies with the described double amino acid substitutions at positions 250 and 428 display exceedingly high binding affinities for FcRn compared to that of the unmodified antibodies.

In a preferred embodiment of the present invention, the binding affinity for FcRn and/or the serum half-life of the modified antibody is increased by at least about 30%, 50%, 80%, 2-fold, 3-fold, 4-fold, 5-fold, 10-fold, 15-fold, 20-fold, 25-fold, 30-fold, 40-fold, 50-fold, 60-fold, 70-fold, 80-fold, 90-fold, or 100-fold.

The present invention provides for a modified antibody having a reduced binding affinity for FcRn and/or a reduced serum half-life as compared with the unmodified antibody, wherein amino acid residue 314 from the heavy chain constant region is substituted with another amino acid which is different from that present in an unmodified antibody. The modified antibodies having an amino acid substitution at position 314 have been shown to display a reduced binding affinity, suggesting that position 314 should be modified if a reduced serum half-life of an antibody is desired. Preferably, the amino acid residue 314 from the heavy chain constant region is substituted with alanine, arginine, aspartic acid, asparagine, cysteine, glutamic acid, glutamine, glycine, histidine, lysine, methionine, phenylalanine, proline, serine, threonine, tryptophan, tyrosine, or valine. More preferably, the amino acid substitution is from leucine to alanine or arginine at position 314. As shown in the Examples, the binding affinity for FcRn of the modified OST577-IgG2M3 comprising a substitution from leucine to arginine is reduced to 11% of that of the unmodified OST577-IgG2M3.

The amino acid sequence of the heavy chain constant region of the modified IgG2M3, having the amino acid substitution from leucine to alanine at position 314 is disclosed herein as SEQ ID NO: 29. The amino acid sequence of the heavy chain constant region of the modified IgG2M3, having the amino acid substitution from leucine to arginine at position 314 is disclosed herein as SEQ ID NO: 42.

The present invention provides for a modified antibody having a reduced binding affinity for FcRn and/or a reduced serum half-life as compared with the unmodified antibody, wherein (1) amino acid residue 250 from the heavy chain constant region is substituted with arginine, asparagine, aspartic acid, lysine, phenylalanine, proline, tryptophan, or tyrosine; or (2) amino acid residue 428 from the heavy chain constant region is substituted with alanine, arginine, asparagine, aspartic acid, cysteine, glutamic acid, glutamine, glycine, histidine, lysine, proline, serine, threonine, tyrosine, or valine. Preferably, amino acid residue 250 from the heavy chain constant region is substituted with aspartic acid, or amino acid residue 428 from the heavy chain constant region is substituted with glycine. Such an amino acid substitution can dramatically reduce the serum half-life of an antibody. As shown in the Examples, the binding affinity for FcRn of the modified OST577-IgG2M3 having such amino acid substitutions is reduced to about 5-7% of that of the unmodified OST577-IgG2M3.

The amino acid sequence of the heavy chain constant region of the modified IgG2M3 having the amino acid substitution from threonine to aspartic acid at position 250 is disclosed herein as SEQ ID NO: 12. The amino acid sequence of the heavy chain constant region of the modified IgG2M3 having the amino acid substitution from methionine to glycine at position 428 is disclosed herein as SEQ ID NO: 53.

In a preferred embodiment of the present invention, the binding affinity for FcRn and/or the serum half-life of said modified antibody is reduced by at least about 20%, 30%, 40%, 50%, 60%, 70%, 80%, 85%, 90%, 95%, 97%, 98%, or 99%.

The present invention includes the heavy chain constant regions, Fc regions, or $C_H2$-$C_H3$ regions of the modified IgG antibodies described herein, preferably, of the modified IgG1, IgG2 or IgG2M3 antibodies having the amino acid substitutions described herein.

The present invention also includes a polypeptide comprising an amino acid sequence of any one of the SEQ ID Nos: 10-76. In a preferred embodiment, these polypeptides are mutated IgG1, IgG2, or IgG2M3 constant regions.

The heavy chain constant regions of the modified antibodies of the present invention can be linked to the heavy chain variable region of any selected antibody to generate the desired hybrid heavy chain. Examples of the selected antibodies include, but are not limited to, antibodies against IL-2, IL-4, IL-10, IL-12, HSV, CD3, CD33, CMV, and IFN-γ. In addition, the variable regions can be those of natural antibodies of any species such as a human, a primate, or a rodent. Alternatively, they can be that of genetically-altered antibodies, including, but not limited to, humanized antibodies, antibodies having increased binding affinities to their antigen through genetic modification, or fully human antibodies. Such a hybrid heavy chain can be linked to a variety of light chains to produce the desired antibody. The light chains can be either lambda or kappa light chains. Since the serum half-life of an antibody is determined primarily by its heavy chain constant region, a desired serum half-life of a produced antibody can be accomplished through the amino acid substitutions in the heavy chain constant region described herein.

II. Production of Modified Antibodies with Altered FcRn Binding Affinity and/or Serum Half-lives The present invention provides for methods of producing proteins, particularly antibodies with altered FcRn binding affinity and/or serum half-lives. Preferably, the present invention provides for methods to modify a given antibody of class IgG at one or more of the positions disclosed herein. This may be achieved chemically, or by random or site-directed mutagenesis and recombinant production using any known production methods.

The present invention provides for a method of modifying an antibody of class IgG, comprising substituting at least one amino acid from the heavy chain constant region selected from the group consisting of amino acid residues 250, 314, and 428 with an amino acid which is different from that present in an unmodified antibody, thereby causing alteration of the binding affinity for FcRn and/or the serum half-life of said unmodified antibody.

The substitution can be made at position 250, 314, or 428 alone, or in any combinations thereof, such as at positions 250 and 428.

To increase the binding affinity for FcRn and/or increase the serum half-life of an antibody, amino acid residue 250 from the heavy chain constant region is substituted with glutamic acid or glutamine, or amino acid residue 428 from the heavy chain constant region is substituted with phenylalanine or leucine. Alternatively, amino acid residue 250 from the heavy chain constant region is substituted with glutamic acid and amino acid residue 428 from the heavy chain constant region is substituted with phenylalanine; or amino acid residue 250 from the heavy chain constant region is substituted with glutamine and amino acid residue 428 from the heavy chain constant region is substituted with phenylalanine; or amino acid residue 250 from the heavy chain constant region is substituted with glutamine and amino acid residue 428 from the heavy chain constant region is substituted with leucine. Modification at both 250 and 428 is preferred since antibodies having such double mutations display exceptionally high binding affinities for FcRn.

To produce a modified antibody having a reduced binding affinity for FcRn and/or reduced serum half-life, as compared with the unmodified antibody, amino acid residue 314 from the heavy chain constant region is substituted with another amino acid, which is different from that present in an unmodified antibody. Preferably, amino acid residue 314 from the heavy chain constant region is substituted with alanine, arginine, aspartic acid, asparagine, cysteine, glutamic acid, glutamine, glycine, histidine, lysine, methionine, phenylalanine, proline, serine, threonine, tryptophan, tyrosine, or valine. More preferably, amino acid residue 314 from the heavy chain constant region is substituted with alanine or arginine.

To produce a modified antibody having a reduced binding affinity for FcRn and a reduced serum half-life as compared with the unmodified antibody, amino acid residue 250 from the heavy chain constant region is substituted with arginine, asparagine, aspartic acid, lysine, phenylalanine, proline, tryptophan, or tyrosine; or amino acid residue 428 from the heavy chain constant region is substituted with alanine, arginine, asparagine, aspartic acid, cysteine, glutamic acid, glutamine, glycine, histidine, lysine, proline, serine, threonine, tyrosine, or valine. More preferably, amino acid residue 250 is substituted with aspartic acid or amino acid 428 is substituted with glycine.

The amino acid substitutions described herein are achieved by standard recombinant DNA technology. In one embodiment, site-directed mutagenesis may be used to introduce the amino acid substitutions into the DNA encoding an unmodified antibody. The resulting DNAs of modified antibodies are then delivered into host cells and the modified antibodies are so produced. The desired alteration of binding affinity for FcRn of the modified antibodies can be selected by using phage display technology or any other suitable methods known in the art and confirmed by measuring the binding affinity.

Preferably, a method of producing modified antibody of class IgG with an altered binding affinity for FcRn and an altered serum half-life as compared with unmodified antibody comprises:

(a) preparing a replicable expression vector comprising a suitable promoter operably linked to a DNA which encodes at least a constant region of an immunoglobulin heavy chain and in which at least one amino acid from the heavy chain constant region selected from the group consisting of amino acid residues 250, 314, and 428 is substituted with an amino acid which is different from that present in an unmodified antibody thereby causing an alteration in serum half-life;

(b) transforming host cells with said vector; and (c) culturing said transformed host cells to produce said modified antibody.

Such a method optionally further comprises after Step (a): preparing a second replicable expression vector comprising a promoter operably linked to a DNA which encodes a complementary immunoglobulin light chain and wherein said cell line is further transformed with said vector.

To generate the DNA in Step (a), the amino acid substitutions can be introduced by mutagenesis, including, but not limited to, site-directed mutagenesis (Kunkel, Proc. Natl. Acad. Sci. USA 82:488-492 (1985)), PCR mutagenesis (Higuchi, in "PCR Protocols: A Guide to Methods and Applications", Academic Press, San Diego (1990) pp. 177-183), and cassette mutagenesis (Wells et al., Gene 34:315-323 (1985)). Preferably, site-directed mutagenesis is performed by the overlap-extension PCR method, which is disclosed in the Examples (Higuchi, in "PCR Technology: Principles and Applications for DNA Amplification", Stockton Press, New York (1989), pp. 61-70).

Figure 4:
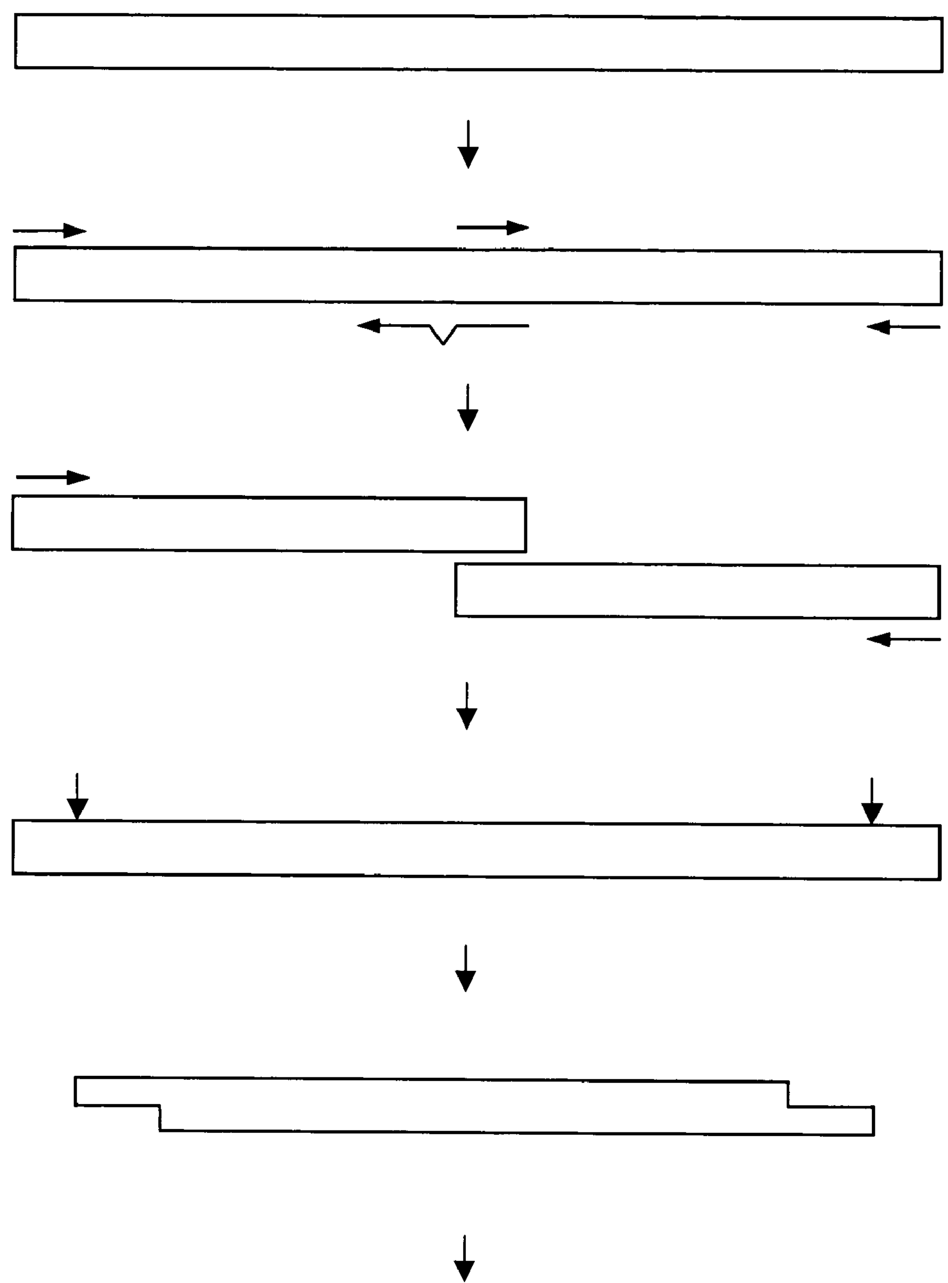
FIG. 4. Illustration of the Overlap-Extension PCR Method

The technique of overlap-extension PCR (Higuchi, ibid.) can be used to introduce any desired mutation(s) into a target sequence (the starting DNA). For example, as shown in FIG. 4, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector.

As the first step of mutagenesis, the starting DNA is operably cloned into a mutagenesis vector. The primers are designed to reflect the desired amino acid substitution (see more details in the Examples). In one example, the vectors used for in vitro mutagenesis can be used for directing protein expression. Thus, the resulting DNA of the overlap-extension PCR can be cloned back into the mutagenesis vector so that an expression vector comprising the DNA with the desired mutation is created. An example of the mutagenesis vector comprising the starting DNA includes, but is not limited to, pVAg2M3-OST577.

For example, the mutations at position 250 were made by amplifying the region surrounding the PinAI-BamHI fragment of pVAg2M3-OST577 (see the restriction map in FIG. 5A) in a two step process using the overlap-extension method described above, then digesting the resulting PCR segment with PinAI and BamHI, and cloning the resulting restriction fragment into pVAg2M3-OST577. Similarly, the mutations at position 314 or 428 were made by amplifying the region surrounding the PmlI-BamHI fragment by overlap-extension PCR, then digesting the resulting PCR segments with PmlI and BamHI, and cloning the resulting restriction fragments into pVAg2M3-OST577.

The starting DNA can be a DNA encoding an entire unmodified antibody, an entire immunoglobulin heavy chain of an unmodified antibody, the constant region of a heavy chain, or part of the heavy chain constant region of an unmodified antibody as long as the amino acid residue that is going to be modified is included.

If the DNA encoding an entire unmodified antibody is used as the starting DNA for mutagenesis, the entire modified antibody can be produced by performing Steps (a), (b), and (c) of the method described herein. The step between Step (a) and Step (b) of said method for generating the complementary light chain would not be necessary.

If the starting DNA for mutagenesis is a DNA encoding the entire heavy chain of an unmodified antibody, mutagenesis will give rise to a vector comprising the DNA encoding the entire modified heavy chain. In order to produce an entire modified antibody, the step between Steps (a) and (b) of the method disclosed herein is performed. That is, another replicable expression vector comprising a suitable promoter operably linked to a DNA encoding the complementary immunoglobulin light chain is co-transfected into the same host cells. As a result, both the complementary light chain and the modified heavy chain are expressed in the same host cells and assembled properly to give rise to the entire modified antibody. An example of said expression vector comprising a DNA encoding an immunoglobulin light chain includes, but is not limited to, pVAλ2-OST577.

If the starting DNA for mutagenesis is a DNA encoding part of the heavy chain constant region, such as a $C_H2$-$C_H3$ segment or an Fc domain, the resulting DNA encoding such a modified partial heavy chain is first connected in frame with the remaining unmodified heavy chain, so that the DNA encoding an entire heavy chain with the modification described herein in Step (a) is generated. An entire modified antibody is then produced by co-transfecting host cells with the vector comprising the DNA encoding a complementary light chain and the vector comprising the DNA encoding such modified heavy chain. The connection of the DNA encoding the modified partial heavy chain and the remaining unmodified heavy chain can be achieved by using the standard molecular cloning techniques known in the art of molecular biology, such as restriction digestions and ligations (Sambrook and Russell, "Molecular Cloning: A Laboratory Manual", 3rd edition, Cold Spring Harbor Laboratory Press, New York (2001)).

The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence (see Queen et al., Proc. Natl. Acad. Sci. USA 86:10029-10033 (1989); WO90/07861; Co et al., J. Immunol. 148:1149-1154 (1992); "Antibody Engineering: A Practical Guide", Borrebaeck, Ed., Freeman, New York (1997)) which are incorporated herein by reference in their entirety for all purposes).

Host cells are transformed by using the techniques known in the art, such as liposome, calcium phosphate, electroporation, etc. (Sambrook and Russell, op. cit.). Preferably, the host cells are transiently transfected using the liposome method.

The host cells used to produce the modified antibody of the present invention may be cultured in a variety of media known in the arts.

Modified antibodies described herein can be produced intracellularly, in the periplasmic space, or directly secreted into the medium. Preferably, the modified antibodies in the present invention are secreted into culture media. The media of the host cell culture producing modified antibodies are collected and cell debris is spun down by centrifugation. The supernatants are collected and subjected to the protein expression assays (see more details in the Examples).

The expression of a modified antibody is confirmed by gel electrophoresis using SDS-PAGE reducing or non-reducing protein gel analysis, or any other techniques known in the art. ELISA can also be used to detect both the expression of a modified antibody and the quantity of that antibody.

Modified antibodies should retain proper binding to antigens as compared with the unmodified antibodies. Accordingly, proper antibody-antigen binding is tested by the procedures known in the art of immunology, such as ELISA. Additional experiments can be performed to confirm that modified antibodies have structural properties similar to those of unmodified antibodies. These experiments include, but are not limited to, SDS-PAGE, SEC, ELISA, and protein A binding assays. The protein A binding assay is preferred since protein A binds to the same region of the $C_H2$-$C_H3$ junction as FcRn, although the binding involves different residues.

Modified antibodies prepared from host cells can be purified using the techniques known in the art, including, but not limited to, gel filtration and column chromatography (e.g., affinity chromatography by protein A, cation exchange chromatography, anion exchange chromatography, and gel filtration). The minimum acceptable purity of the antibody for use in pharmaceutical formulation will be 90%, with 95% preferred, 98% more preferred and 99% or higher the most preferred.

The binding affinities of the produced antibodies for FcRn can be detected by performing a competitive binding assay at pH 6.0, the optimal condition for binding to FcRn. The binding affinities can be tested by immobilizing FcRn on a solid substrate such as a Sepharose® bead. Alternatively, the binding affinities can be evaluated using an ELISA. Preferably, the present invention tests the binding affinities by carrying out a competitive binding assay in a cell-based system. A dilution series of a produced modified antibody and the unmodified antibody are compared for binding to FcRn expressed on a cell line, preferably an NS0 cell line. The experimental procedures for carrying out a competitive binding assay are described in detail in the Examples.

The experiments in the present invention show that similar binding affinity results can be achieved with purified antibodies or culture supernatants of the cells producing antibodies. Accordingly, supernatants can be used directly to test the binding affinities for FcRn of the produced antibodies in order to confirm that the desired alteration of the binding affinities has been accomplished. After such a confirmation, the produced antibody is subjected to more complex purification procedures.

Direct binding assays should also be performed to confirm that the modified antibodies bind to the FcRn in a pH-dependent manner. In particular, the binding affinity of the modified antibodies for FcRn is tested both at pH 6.0 and at pH 8.0 (see more details in Examples). In general, the binding affinity at pH 6.0 should exceed that at pH 8.0.

Biological stability (or serum half-life) may be measured by a variety of in vitro or in vivo means, for example, by using a radiolabeled protein and measuring levels of serum radioactivity as a function of time, or by assaying the levels of intact antibody (of known specificity) present in the serum using ELISA as a function of time, with a particularly preferred measure of increased biological stability being evidenced by increased serum half-life and decreased clearance rates.

The present invention provides for the polynucleotide molecules encoding the modified antibodies, or the polynucleotide molecules encoding a modified partial or full heavy chain of the modified antibodies, such as the constant regions, Fc regions or $C_H2$-$C_H3$ regions, with the mutations described herein.

The present invention provides for the vectors comprising the polynucleotide molecules encoding the modified antibodies, or the polynucleotide molecules encoding the modified partial or full heavy chains of the modified antibodies, such as the constant regions, Fc regions or $C_H2$-$C_H3$ regions, with the mutations (substitutions) described herein.

The present invention includes a host cell containing said vectors comprising said nucleic acid molecules as described herein. Suitable host cells for the expression of the modified antibodies described herein are derived from prokaryotic organisms such as *Escherichia coli*, or eukaryotic multicellular organisms, including yeasts, plants, insects, and mammals.

*E. coli* is one prokaryotic host particularly useful for cloning and/or expressing the DNA sequences of the present invention. Other microbial hosts suitable for use include bacilli, such as *Bacillus subtilis*, and other *enterobacteriaceae*, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters can be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation.

Other microbes, such as yeast, can also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired.

Plants and plant cell cultures can be used for expression of the DNA sequence of the invention (Larrick and Fry, Hum. Antibodies Hybridomas 2:172-189 (1991); Benvenuto et al., Plant Mol. Biol. 17:865-874 (1991); During et al., Plant Mol. Biol. 15:281-293 (1990); Hiatt et al., Nature 342:76-78 (1989)). Preferable plant hosts include, for example: *Arabidopsis, Nicotiana tabacum, Nicotiana rustica*, and *Solanum tuberosum*. A preferred expression cassette for expressing polynucleotide sequences encoding the modified antibodies of the invention is the plasmid pMOG18 in which the inserted polynucleotide sequence encoding the modified antibody is operably linked to a CaMV 35S promoter with a duplicated enhancer; pMOG18 is used according to the method of Sijmons et al., Bio/Technology 8:217-221 (1990). Alternatively, a preferred embodiment for the expression of modified antibodies in plants follows the methods of Hiatt et al., supra, with the substitution of polynucleotide sequences encoding the modified antibodies of the invention for the immunoglobulin sequences used by Hiatt et al., supra. *Agrobacterium tumifaciens* T-DNA-based vectors can also be used for expressing the DNA sequences of the invention; preferably such vectors include a marker gene encoding spectinomycin-resistance or another selectable marker.

Insect cell culture can also be used to produce the modified antibodies of the invention, typically using a baculovirus-based expression system. The modified antibodies can be produced by expressing polynucleotide sequences encoding the modified antibodies according to the methods of Putlitz et al., Bio/Technology 8:651-654 (1990).

In addition to microorganisms and plants, mammalian cell culture can also be used to express and produce the polypeptides of the present invention (see Winnacker, "From Genes to Clones", VCH Publishers, New York (1987)). Mammalian cells are actually preferred, because a number of suitable host cell lines capable of secreting intact immunoglobulins have been developed in the art, and include the CHO cell lines, various COS cell lines, HeLa cells, preferably myeloma cell lines, etc., or transformed B-cells or hybridomas. Expression vectors for these cells can include expression control sequences, such as an origin of replication, a promoter, an enhancer (Queen et al., Immunol. Rev. 89:49-68 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. Generally, a selectable marker, such as a neo expression cassette, is included in the expression vector.

The present invention provides for a method of making an agent with altered FcRn binding affinity and/or serum half-life by conjugating or otherwise binding of that agent to a moiety identified as having an increased or reduced serum half-life through its interaction with FcRn. Such a moiety includes, but is not limited to, a modified IgG or a modified partial or full heavy chain comprising the amino acid substitutions described herein. Such agents would include, but are not limited to, antibodies, fragments of antibodies, hormones, receptor ligands, immunotoxins, therapeutic drugs of any kind, T-cell receptor binding antigens, and any other agents that may be bound to the increased serum half-life moieties of the present invention. To create a fusion protein with an altered in vivo stability, DNA segments encoding such proteins may be operatively incorporated into a recombinant vector, in frame with the constant region of a modified antibody, whether upstream or downstream, in a position so as to render the vector capable of expressing a fusion protein comprising such a protein operably linked with the constant region. Techniques for the manipulation of DNA segments in this manner, for example, by genetic engineering using restriction endonucleases, will be known to those of skill in the art in light of both the present disclosure and references such as Sambrook and Russell, supra.

The above method is proposed for use in the generation of a series of therapeutic compounds with improved biological stability. Such compounds include, for example, interleukin-2, insulin, interleukin-4, and interferon gamma, or even T cell receptors. The recombinant Fc domains of this invention are also contemplated to be of use in stabilizing a wide range of drugs, which would likely alleviate the need for their repeated administration. However, the present methods are not limited solely to the production of proteins for human administration, and may be employed to produce large quantities of any protein with increased stability, such as may be used, for example, in immunization protocols, in animal treatment by veterinarians, or in rodent in vivo therapy models.

III. Uses of Modified Antibodies with Altered FcRn Binding Affinity and/or Serum Half-lives The present invention provides for a composition comprising the modified antibodies described herein and a pharmaceutically acceptable carrier. The compositions for parenteral administration commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. The compositions can contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate. The concentration of the antibodies in these formulations can vary widely, i.e., from less than about 0.01%, usually at least about 0.1% to as much as 5% by weight and are selected primarily based on fluid volumes, and viscosities in accordance with the particular mode of administration selected.

A typical composition for intravenous infusion can be made up to contain 250 ml of sterile Ringer's solution, and 10 mg to 100 mg of antibody (see "Remington's Pharmaceutical Science", $15^{th}$ ed., Mack Publishing Company, Easton, Pa. (1980)).

The modified antibodies in the present invention can be used for various non-therapeutic purposes. They may be used as an affinity purification agent. They may also be useful in diagnostic assays, such as detecting expression of an antigen of interest in specific cells, tissues, or serum. For diagnostic applications, the antibodies typically will be labeled with a detectable moiety, including radioisotopes, fluorescent labels, and various enzyme substrate labels. The antibodies may also be employed in any known assay method, such as competitive binding assays, direct and indirect sandwich assays, and immunoprecipitation assays. The antibodies may also be used for in vivo diagnostic assays. Generally, the antibodies are labeled with a radionucleotide so that the antigen or cell expressing it can be localized using immunoscintigraphy.

Kits can also be supplied for use with the modified antibodies in the protection against or detection of a cellular activity or for the presence of a selected cell surface receptor or the diagnosis of disease. Thus, the subject composition of the present invention may be provided, usually in a lyophilized form in a container, either alone or in conjunction with additional antibodies specific for the desired cell type. The modified antibodies, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the modified antibody is employed in an assay, this will usually be present in a separate vial. The second antibody is typically conjugated to a label and formulated in an analogous manner with the antibody formulations described above.

The modified antibodies have various therapeutic applications. The modified antibodies may be used to treat a patient suffering from, or predisposed to, a disease or disorder, who could benefit from administration of the modified antibodies. The conditions that can be treated with the antibodies include cancer; inflammatory conditions such as asthma; autoimmune diseases; and viral infections, etc.

The cancers that can be treated by the antibodies described herein include, but are not limited to, breast cancer, squamous cell cancer, small cell lung cancer, non-small cell lung cancer, gastrointestinal cancer, pancreatic cancer, glioblastoma, cervical cancer, ovarian cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma, and various types of head and neck cancer.

The autoimmune diseases include, but are not limited to, Addison's disease, autoimmune diseases of the ear, autoimmune diseases of the eye such as uveitis, autoimmune hepatitis, Crohn's disease, diabetes (Type I), epididymitis, glomerulonephritis, Graves' disease, Guillain-Barre syndrome, Hashimoto's disease, hemolytic anemia, systemic lupus erythematosus, multiple sclerosis, myasthenia gravis, pemphigus vulgaris, psoriasis, rheumatoid arthritis, sarcoidosis, scleroderma, Sjogren's syndrome, spondyloarthropathies, thyroiditis, ulcerative colitis, and vasculitis.

The modified antibodies with reduced serum half-lives in the present invention may be used in the treatment of diseases or disorders where destruction or elimination of tissue or foreign microorganisms is desired. For example, the antibody may be used to treat cancer; inflammatory disorders; infections; and other conditions where removal of tissue is desired. The antibody would be generally useful in that the quicker biological clearance times would result in reduced immunogenicity of any antibody administered. Other applications would include antibody-based imaging regimens, antibody-based drug removal, or creation of immunotoxins with a shorter life.

The modified antibodies with increased serum half-lives may be an anti-tissue factor (TF) antibody, anti-IgE antibody, and anti-integrin antibody. The desired mechanism of action may be to block ligand-receptor binding pairs. The modified antibodies with increased serum half-lives may also be agonist antibodies. The antibodies can also be used as therapeutic agents such as vaccines. The dosage and frequency of immunization of such vaccines will be reduced due to the extended serum half-lives of the antibodies.

The compositions comprising the present antibodies are administered by any suitable means, including parenteral subcutaneous, intraperitoneal, intrapulmonary, and intranasal, and if desired for local immunosuppressive treatment, intralesional administration. Parenteral infusions include intramuscular, intravenous, intraarterial, intraperitoneal, or subcutaneous administration. In addition, the antibodies are suitably administered by pulse infusion, particularly with declining doses of antibodies.

The compositions containing the present antibodies or a cocktail thereof can be administered for prophylactic and/or therapeutic treatments. In therapeutic application, compositions are administered to a patient already affected by the particular disease, in an amount sufficient to cure or at least partially arrest the condition and its complications. An amount adequate to accomplish this is defined as a "therapeutically effective dose." Amounts effective for this use will depend upon the severity of the condition and the general state of the patient's own immune system, but generally range from about 0.01 to about 100 mg of modified antibody per dose, with dosages of 1 to 10 mg per patient being more commonly used.

In prophylactic applications, compositions containing the modified antibodies or a cocktail thereof are administered to a patient not already in a disease state to enhance the patient's resistance. Such an amount is defined to be a "prophylactically effective dose." In this use, the precise amounts again depend upon the patient's state of health and general level of immunity, but generally range from 0.1 to 100 mg per dose, especially dosages of 1 to 10 mg per patient.

Single or multiple administrations of the compositions can be carried out with dose levels and pattern being selected by the treating physician. In any event, the pharmaceutical formulations should provide a quantity of the mutant antibodies of this invention sufficient to effectively treat the patient.

The following examples are offered by way of illustration and not by way of limitation. The disclosure of all citations in the specification is expressly incorporated herein by reference.

EXAMPLES

Example 1

This example describes the antibody expression vectors used in the present invention.

The components of the heavy chain expression plasmid pVAg2M3-OST577, a derivative of the M3 variant of pVg2.D.Tt (Cole et al., J. Immunol. 159:3613-3621 (1997)), are as follows. As shown in FIG. 5A, proceeding clockwise from the EcoRI site, the heavy chain unit begins with the human cytomegalovirus (hCMV) major immediate early (IE) promoter and enhancer (Boshart et al., Cell 41:521-530 (1985)) as an EcoRI-XbaI fragment. The hCMV region is followed by the OST577 $V_H$ region as an XbaI fragment, including signal sequence, J segment, and splice donor sequence. The $V_H$ region is followed by a modified genomic DNA fragment containing the human gamma-2M3 heavy chain constant region (Cole et al., op. cit.) as an XbaI-BamHI fragment, including the $C_H1$, hinge (H), $C_H2$, and $C_H3$ exons with the intervening introns, part of the intron preceding $C_H1$, and a polyadenylation (polyA) signal for mRNA processing following $C_H3$, followed by the transcriptional terminator of the human complement gene C2 (Ashfield et al., EMBO J. 10:4197-4207 (1991)) as a BamHI-EcoRI fragment. The heavy chain unit is followed by a gene encoding a mutant form of dihydrofolate reductase (dhfr), together with regulatory elements (enhancer, promoter, splice signals, and polyA signal) from Simian Virus 40 (SV40) needed for transcription. This region, which was taken as a BamHI-EcoRI fragment from the plasmid pVg1 (Co et al., op. cit.), was modified by converting the BamHI site to an EcoRI site. Moving counterclockwise within this unit from the original EcoRI site, first there is part of the plasmid pBR322 (Sutcliffe, Cold Spring Harbor Symp. Quant. Biol. 43:77-90 (1979)) comprising the bacterial origin of replication and ampicillin resistance gene for selection in *E. coli*, except the bacterial replication origin was replaced with the corresponding segment from pUC18 (Yanisch-Perron et al., Gene 33:103-119 (1985)) to increase the copy number of the vector in bacterial hosts. Next, there is a segment of SV40 (Reddy et al., Science 200:494-502 (1978)) containing the SV40 enhancer and early promoter to ensure strong transcription initiation. This segment is followed by the coding sequence of the *E. coli* dhfr gene (Simonsen and Levinson, Proc. Natl. Acad. Sci. USA 80:2495-2499 (1983)). The dhfr gene is followed by an SV40 segment containing the small t antigen intron, which is believed to increase mRNA levels, and then the plasmid contains another SV40 segment containing a polyA signal for ending the mRNA transcript.

The components of the heavy chain expression plasmid pVAg1.N-OST577, a derivative of pVg1 (Co et al., op. cit.), are as follows. As shown in FIG. 5B, proceeding clockwise from the EcoRI site, the heavy chain unit begins with the same EcoRI-XbaI fragment containing the hCMV IE promoter and enhancer that was used in the pVAg2M3-OST577 vector, followed by the OST577 $V_H$ region as an XbaI fragment. The $V_H$ region is followed by a genomic DNA fragment containing the human gamma-1 heavy chain constant region (Ellison et al., Nucleic Acids Res. 10:4071-4079 (1982)) as an XbaI-BamHI fragment, including the $C_H1$, hinge (H), $C_H2$, and $C_H3$ exons with the intervening introns, part of the intron preceding $C_H1$, and a polyA signal for mRNA processing following $C_H3$. To facilitate subsequent manipulations of the coding regions, overlap-extension PCR mutagenesis (Higuchi, op. cit.) was used to create an NheI site in the intron between the hinge and $C_H2$ exons. The heavy chain unit is followed by the same BamHI-EcoRI restriction fragment encoding dhfr, together with regulatory elements and a portion of plasmid pBR322, that was used in the pVAg2M3-OST577 vector.

Figure 6:
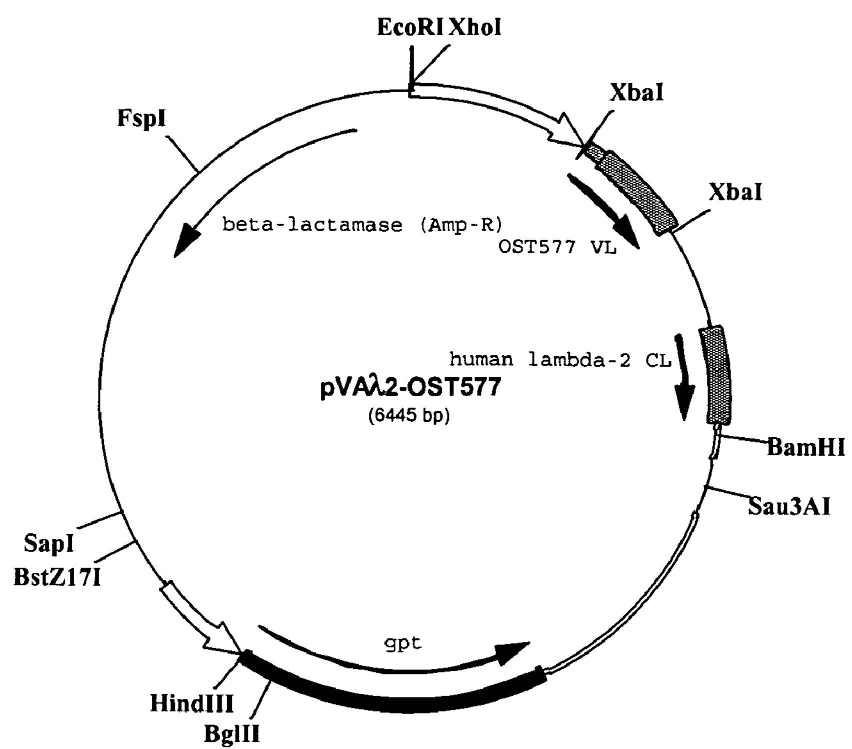
FIG. 6. Restriction Map of Light Chain Vector pVAλ2-OST577

The components of the light chain expression plasmid pVAλ2-OST577, a derivative of pVk (Co et al., op. cit.), are as follows. As shown in FIG. 6, proceeding clockwise from the EcoRI site, the light chain unit begins with the same EcoRI-XbaI fragment containing the hCMV IE promoter and enhancer that was used in the heavy chain vectors, followed by the OST577 $V_L$ region as an XbaI fragment, including signal sequence, J segment, and splice donor sequence. The $V_L$ region is followed by a genomic DNA fragment containing the human lambda-1 light chain constant region (Hieter et al., Nature 294:536-540 (1981)) as an XbaI-Sau3AI fragment that was modified by PCR to encode the human lambda-2 light chain constant region (Hieter et al., ibid.), including the human lambda-1 light chain intron, the human lambda-2 light chain constant region exon ($C_\lambda 2$) and a portion of the 3' untranslated region from the human lambda-2 light chain, and a polyA signal for mRNA processing from the human lambda-1 light chain. The light chain gene is followed by a gene encoding xanthine guanine phosphoribosyl transferase (gpt), together with regulatory elements from SV40 needed for transcription. The function of this region, which was taken as a BamHI-EcoRI fragment from the plasmid pSV2-gpt (Mulligan and Berg, op. cit.), is to provide a selectable drug-resistance marker after transfection of the plasmid into mammalian cells. Moving counterclockwise within this unit from the EcoRI site, first there is part of the plasmid pBR322 (Sutcliffe, op. cit.) comprising the bacterial origin of replication and ampicillin resistance gene for selection in *E. coli*, except the bacterial replication origin was replaced with the corresponding segment from pUC18 (Yanisch-Perron et al., op. cit.) to increase the copy number of the vector in bacterial hosts. Next, there is a segment of SV40 (Reddy et al., op. cit.) containing the SV40 enhancer and early promoter, to ensure strong transcription initiation. This segment is followed by the coding sequence of the *E. coli* gpt gene (Richardson et al., Nucleic Acids Res. 11:8809-8816 (1983)). The gpt gene is followed by an SV40 segment containing the small t antigen intron, which is believed to increase mRNA levels, and then the plasmid contains another SV40 segment containing a polyA signal for ending the mRNA transcript.

The components of the heavy chain expression plasmid pVAg2M3-Hu1D10 (see FIG. 7A) are identical to those of pVAg2M3-OST577 from which it was derived, except the OST577 $V_H$ region was replaced with the Hu1D10 $V_H$ region from plasmid pHu1D10.IgG1.rgpt.dE (Kostelny et al. (2001), op. cit.). The components of the heavy chain expression plasmid pVAg1.N-Hu1D10 (see FIG. 7B) are identical to those of pVAg1.N-OST577 from which it was derived, except the OST577 $V_H$ region was replaced with the Hu1D10 $V_H$ region from plasmid pHu1D10.IgG1.rgpt.dE (Kostelny et al., ibid).

The components of the heavy chain expression plasmid pHuHCg3.Tt.D-Hu1D10 (see FIG. 7C) are identical to those of pVg2.D.Tt (Cole et al., op. cit.), except the XbaI-BamHI fragment containing the human gamma-2M3 heavy chain constant region was replaced with the Hu1D10 $V_H$ region from plasmid pHu1D10.IgG1.rgpt.dE (Kostelny et al. (2001), op. cit.) as an XbaI fragment, followed by a genomic DNA fragment containing the human gamma-3 heavy chain constant region (Huck et al., Nucleic Acids Res. 14:1779-1789 (1986)) as an Xba-BamHI fragment, including the $C_H1$, four hinge (H), $C_H2$, and $C_H3$ exons with the intervening introns, part of the intron preceding $C_H1$, and a polyadenylation (polyA) signal for mRNA processing following $C_H3$. The components of the heavy chain expression plasmid pHuHCg4.Tt.D-Hu1D10 (see FIG. 7D) are identical to those of pHuHCg3.Tt.D-Hu1D10, except the human gamma-3 heavy chain constant region was replaced with a genomic DNA fragment containing the human gamma-4 heavy chain constant region (Ellison et al., op. cit.) as an XbaI-BamHI fragment, including the $C_H1$, hinge (H), $C_H2$, and $C_H3$ exons with the intervening introns, part of the intron preceding $C_H1$, and a polyadenylation (polyA) signal for mRNA processing following $C_H3$.

Figure 8:
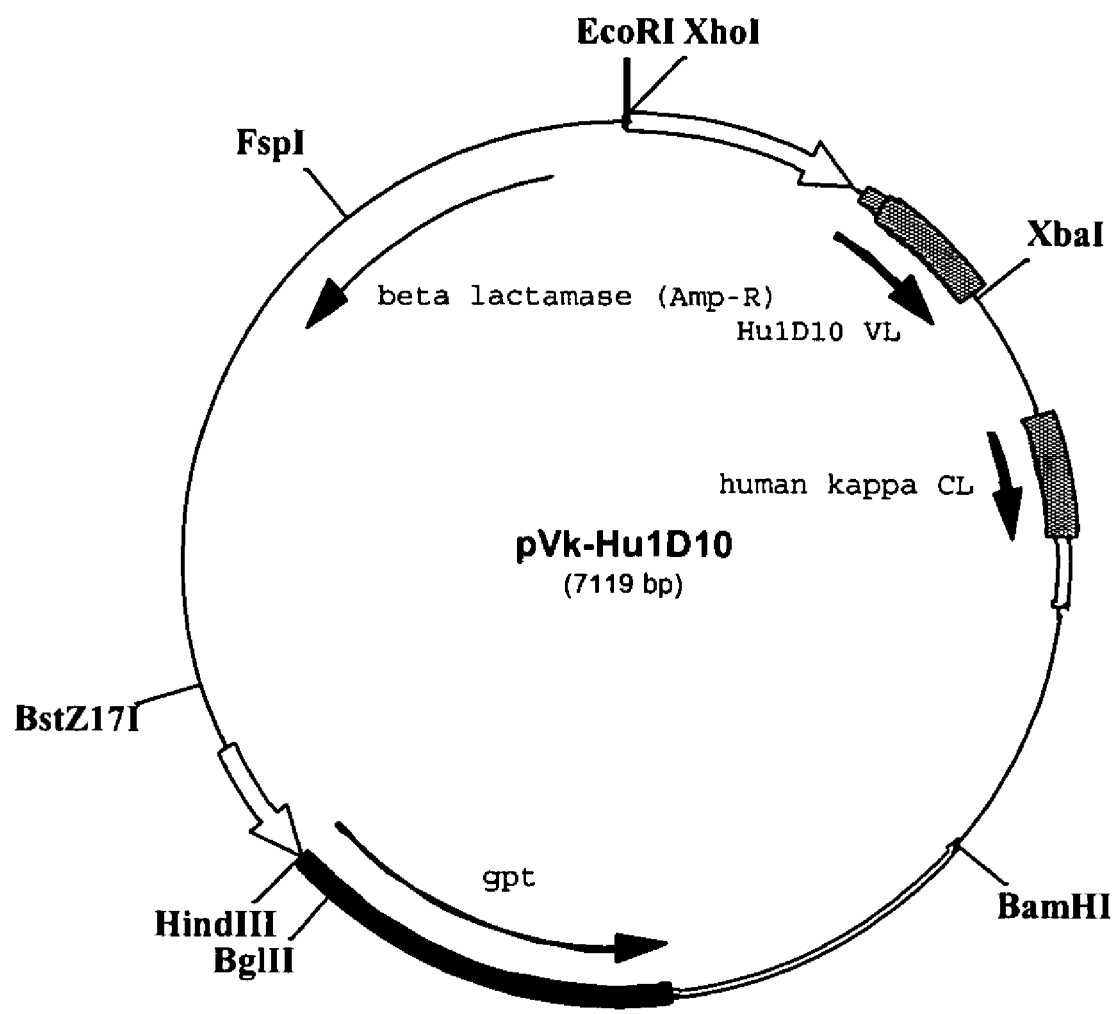
FIG. 8. Restriction Map of Light Chain Vector pVk-Hu1D10.

The components of the light chain expression plasmid pVk-Hu1D10, a derivative of pVk (Co et al., op. cit.), are as follows. As shown in FIG. 8, proceeding clockwise from the EcoRI site, the light chain unit begins with the same EcoRI-XbaI fragment containing the hCMV IE promoter and enhancer that was used in the heavy chain vectors, followed by the Hu1D10 $V_L$ region (Kostelny et al. (2001), op. cit.) as an XbaI fragment, including signal sequence, J segment, and splice donor sequence. The $V_L$ region is followed by a genomic DNA fragment containing the human kappa light chain constant region (Hieter et al., Cell 22:197-207 (1980)) as an XbaI-BamHI fragment, including the human kappa light chain constant region exon ($C_\kappa$), part of the intron preceding $C_\kappa$, and a polyA signal for mRNA processing following $C_\kappa$. The light chain unit is followed by the same BamHI-EcoRI fragment encoding gpt, together with regulatory elements needed for transcription and a portion of plasmid pBR322, that was used in the pVk vector.

Example 2

This example describes the plasmids used in the present invention.

The OST577 heavy and light chain cDNAs were cloned in their entirety by PCR from a trioma cell line expressing human monoclonal anti-HBV antibody OST577 (Ehrlich et al., op. cit.). The heavy and light chain variable regions were converted by PCR into miniexons, flanked by XbaI sites at both ends, comprising the signal sequences, V, (D), and J segments, splice donor sequences, and a portion of the corresponding introns, as outlined in Co et al., supra. The expression vector pVAg2M3-OST577 (see FIG. 5A), a derivative of the M3 variant of pVg2.D.Tt (Cole et al., op. cit.), was constructed by replacing the XbaI fragment containing the OKT3-$V_H$ miniexon with the OST577-$V_H$ miniexon. Then the PciI-FspI fragment containing the bacterial replication origin was replaced with the corresponding PciI-FspI fragment from pUC18 (Yanisch-Perron et al., op. cit.) to increase the copy number of the vector in bacterial hosts. The expression vector pVAg1.N-OST577 (see FIG. 5B), a derivative of pVg1 (Co et al., op. cit.), was constructed by inserting an XbaI fragment containing the OST577-$V_H$ miniexon into the unique XbaI site of pVg1, modifying the hinge-$C_H2$ intron by overlap-extension PCR (Higuchi, op. cit.) to create a unique NheI site, and replacing the HindIII-XhoI fragment containing the bacterial replication origin with the corresponding HindIII-XhoI fragment from pVAg2M3-OST577 to increase the copy number of the vector in bacterial hosts.

The expression vector pVλ2-OST577, a derivative of pVk (Co et al., op. cit.), was constructed by first replacing the XbaI-BamHI fragment of pVk containing the genomic human kappa constant region with an XbaI-BglII PCR product containing the genomic human lambda-1 constant region. The coding region and a portion of the 3' untranslated region were replaced with the corresponding fragment from the OST577 light chain cDNA by PCR, essentially yielding a genomic human lambda-2 constant region exon. Finally, the OST577-$V_L$ miniexon was inserted into the XbaI site of the vector. The expression vector pVAλ2-OST577 (see FIG. 6), a derivative of pVλ2-OST577, was constructed by replacing the SapI-FspI fragment containing the bacterial replication origin with the corresponding SapI-FspI fragment from pVAg2M3-OST577 to increase the copy number of the vector in bacterial hosts.

The expression vector pVAg2M3-Hu1D10 (see FIG. 7A) was constructed by replacing the XhoI-XbaI fragment from plasmid pVAg2M3-OST577, containing the hCMV promoter and enhancer (Boshart et al., op. cit.) and the OST577 $V_H$ region, with the corresponding XhoI-XbaI fragment from plasmid pHu1D10.IgG1.rgpt.dE (Kostelny et al. (2001), op. cit.) containing the hCMV promoter and enhancer and the Hu1D10 $V_H$ region. The expression vector pVAg1.N-Hu1D10 (see FIG. 7B) was constructed by replacing the XhoI-XbaI fragment from plasmid pVAg1.N-OST577, containing the hCMV promoter and enhancer (Boshart et al., op. cit.) and the OST577 $V_H$ region, with the corresponding XhoI-XbaI fragment from plasmid pHu1D10.IgG1.rgpt.dE (Kostelny et al. (2001), op. cit.) containing the hCMV promoter and enhancer and the Hu1D10 $V_H$ region.

The expression vector pHuHC.g3.Tt.D-Hu1D10 (see FIG. 7C) was constructed by replacing the XhoI-BamHI fragment from the M3 variant of pVg2.D.Tt (Cole et al., op. cit.), containing the hCMV promoter and enhancer and the human gamma-2M3 heavy chain constant region, with a XhoI-XbaI fragment from plasmid pHu1D10.IgG1.rgpt.dE (Kostelny et al. (2001), op. cit.) containing the hCMV promoter and enhancer and the Hu1D10 $V_H$ region, and an XbaI-BamHI fragment containing the human gamma-3 heavy chain constant region (Huck et al., op. cit.), respectively. The expression vector pHuHC.g4.Tt.D-Hu1D10 (see FIG. 7D) was constructed by replacing the XhoI-BamHI fragment from the M3 variant of pVg2.D.Tt (Cole et al., op. cit.), containing the hCMV promoter and enhancer and the the human gamma-2M3 heavy chain constant region, with a XhoI-XbaI fragment from plasmid pHu1D10.IgG1.rgpt.dE (Kostelny et al. (2001), op. cit.) containing the hCMV promoter and enhancer and the Hu1D10 $V_H$ region, and an XbaI-BamHI fragment containing the human gamma-4 heavy chain constant region (Ellison et al., op. cit.), respectively.

The expression vector pVk-Hu1D10 (see FIG. 8) was constructed by replacing the XhoI-XbaI fragment from plasmid pVk (Co et al., op. cit.), containing the hCMV promoter and enhancer (Boshart et al., op. cit.), with the XhoI-XbaI fragment from plasmid pHu1D10.IgG1.rgpt.dE (Kostelny et al. (2001), op. cit.) containing the hCMV promoter and enhancer and the Hu1D10 $V_L$ region.

The base expression vector pDL172, a derivative of pVk.rg (Cole et al., op. cit.), was constructed by replacing the XbaI-SphI fragment containing the genomic human kappa constant region with an XbaI-SphI fragment comprised of an XbaI-NheI fragment containing the N-terminal portion of the M195 heavy chain signal sequence (Co et al., op. cit.), a 0.7 kb NheI-AgeI fragment, a synthetic AgeI-EagI fragment encoding a human c-myc decapeptide, flanked by linker peptides, that is recognized by mouse monoclonal antibody 9E10 (Evan et al., Mol. Cell. Biol. 5:3610-3616 (1985)), followed by the GPI linkage signal from human decay accelerating factor (Caras et al., Nature 325:545-549 (1987)), and an EagI-SphI fragment containing the polyA signal of the human immunoglobulin gamma-1 gene (Ellison et al., op. cit.).

Human beta-2 microglobulin (β2m) and the extracellular domains of the human neonatal Fc receptor (FcRn) alpha chain were cloned by PCR from a cDNA library prepared from human peripheral blood mononuclear cells. The human FcRn alpha chain gene was modified by PCR to add a flanking NheI site and the C-terminal portion of the M195 heavy chain signal sequence (Co et al., op. cit.) at the 5' end, and a flanking AgeI site at the 3' end, and used to replace the NheI-AgeI fragment of pDL172, resulting in expression vector pDL172+HuFcRn. The human β2m gene was modified by PCR to add flanking XbaI and SalI sites at the 5' and 3' ends, respectively, and to remove an internal EcoRI site. The resulting XbaI-SalI fragment was subcloned into an intermediate vector, flanked on its 5' end by an EcoRI-XbaI fragment containing the hCMV IE promoter and enhancer (Boshart et al., op. cit.), and on its 3' end by a SalI-BamHI fragment containing the polyadenylation signal of the murine immunoglobulin gamma-2a gene (Kostelny et al. (1992), op. cit.), followed by a BamHI-EcoRI fragment containing the transcriptional terminator of the human complement gene C2 (Ashfield et al., op. cit.). The resulting EcoRI-EcoRI fragment containing a functional human β2m transcriptional unit was cloned into the unique EcoRI site of pDL172+HuFcRn, resulting in expression vector pDL172+HuFcRn+Hufβ2m, hereinafter referred to as pDL208 (see FIG. 9A).

Rhesus β2m and the extracellular domains of the rhesus FcRn alpha chain were cloned by PCR from a cDNA library prepared from rhesus peripheral blood mononuclear cells. The rhesus β2m gene was modified by PCR to add flanking XbaI and SalI sites at the 5' and 3' ends, respectively, and to remove an internal EcoRI site. The resulting XbaI-SalI fragment was subcloned into an intermediate vector, flanked on its 5' end by an EcoRI-XbaI fragment containing the hCMV IE promoter and enhancer (Boshart et al., op. cit.), and on its 3' end by a SalI-BamHI fragment containing the polyadenylation signal of the murine immunoglobulin gamma-2a gene (Kostelny et al. (1992), op. cit.), followed by a BamHI-EcoRI fragment containing the transcriptional terminator of the human complement gene C2 (Ashfield et al., op. cit.). The resulting EcoRI-EcoRI fragment containing a functional rhesus β2m transcriptional unit was used to replace the EcoRI-EcoRI fragment (containing the human β2m transcriptional unit) of pDL172+HuFcRn+Huβ2m, resulting in pDL172+HuFcRn+Rhβ2m. The rhesus FcRn alpha chain gene was modified by PCR to add a flanking NheI site and the C-terminal portion of the M195 heavy chain signal sequence (Co et al., op. cit.) at the 5' end, and a flanking AgeI site at the 3' end, and used to replace the NheI-AgeI fragment (containing the human FcRn alpha chain gene) of pDL172+HuFcRn+Rhβ2m, resulting in expression vector pDL172+RhFcRn+Rhβ2m, hereinafter referred to as pDL410 (see FIG. 9B).

Example 3

This example describes mutagenesis of the Fc region of the human γ2M3 heavy chain gene.

Molecular Modeling:

An initial model of the human Fc/FcRn complex was generated based on a low-resolution crystal structure of the rat Fc/FcRn complex (Burmeister et al., Nature 372:379-383 (1994); RCSB protein databank code 1FRT). First, the rat β2m of the complex was replaced by superimposing the human β2m taken from a high-resolution crystal structure of the human histocompatibility antigen HLA-A2 (Saper et al. J. Mol. Biol. 219:277-319 (1991); RCSB code 3HLA) in the same orientation as that of the rat β2m in the complex. Then, the alpha chain of the rat FcRn was replaced by superimposing the human alpha chain taken from a high-resolution crystal structure of human FcRn (West and Bjorkman, Biochemistry 29:9698-9708 (2000); RCSB code 1EXU) in the same orientation as the rat alpha chain in the complex. Next, the rat residues in the Fc of the complex were replaced with the corresponding residues from the human IgG1 Fc (Kabat et al., op. cit.), and energy minimization calculations were done using the SEGMOD and ENCAD programs (Levitt, J. Mol. Biol. 226:507-533 (1992); Levitt, J. Mol. Biol. 168:595-620 (1983)) to produce a model of the human IgG1 Fc/FcRn complex. Finally, the human IgG1 Fc residues of the model were replaced with the corresponding residues from the human IgG2M3 Fc (Cole et al., op. cit.), and the energy minimization calculations were repeated to produce a model of the human IgG2M3 Fc/FcRn complex, hereinafter referred to as model 1.

A second model of the human IgG2M3 Fc/FcRn complex was generated as described above, based on a model of the rat Fc/FcRn complex (Weng et al., J. Mol. Biol. 282:217-225 (1998); RCSB code 2FRT), hereinafter referred to as model 2.

A third model was generated as described above, based on the high-resolution crystal structure of a heterodimeric rat Fc/FcRn complex (Martin et al., Mol. Cell 7:867-877 (2001); RCSB code 1I1A), hereinafter referred to as model 3.

Mutagenesis:

The overlap-extension polymerase chain reaction (PCR) method (Higuchi, op. cit.) was used to generate random amino acid substitutions at positions 250, 314, and 428 of the OST577-IgG2M3 heavy chain (numbered according to the EU index of Kabat et al., op. cit.). To generate random mutants at position 250, the mutagenesis primers JY24 (5'-GAC CTC AGG GGT CCG GGA GAT CAT GAG MNN GTC CTT GG-3') (SEQ ID NO: 77) and JY25 (5'-CTC ATG ATC TCC CGG ACC CCT GAG GTC-3') (SEQ ID NO: 78) were used, where M=A or C, and N=A, C, G or T. The first round of overlap-extension PCR used outside primer msc g2-1 (5'-CCA GCT CTG TCC CAC ACC G-3') (SEQ ID NO: 79) and JY24 for the left-hand fragment, and outside primer kco8 (5'-GCC AGG ATC CGA CCC ACT-3') (SEQ ID NO: 80) and JY25 for the right-hand fragment. The PCR reaction was done using the Expand™ High Fidelity PCR System (Roche Diagnostics Corporation, Indianapolis, Ind.), following the manufacturer's recommendations, by incubating at 94° C. for 5 minutes, followed by 25 cycles of 94° C. for 5 seconds, 55° C. for 5 seconds and 72° C. for 60 seconds, followed by incubating at 72° C. for 7 minutes in a GeneAmp® PCR System 9600 (Applied Biosystems®, Foster City, Calif.). The PCR products were run on a low-melting point agarose gel, excised from the gel, and melted at 70° C. The second round of PCR to combine the left-hand and right-hand fragments was done as described above, using outside primers msc g2-1 and kco8, for 35 cycles. The final PCR products were run on a low-melting point agarose gel and DNA fragments of the expected size were excised and purified using the QIAEX™II Gel Extraction Kit (QIAGEN®, Valencia, Calif.). The purified fragments were digested with PinAI and BamHI, gel-purified as described above, and cloned between the corresponding sites in pVAg2M3-OST577.

To generate the T2501 and T250L mutants, the mutagenesis primers KH4 (5'-GAC CTC AGG GGT CCG GGA GAT CAT GAG AAK GTC CTT GG-3') (SEQ ID NO: 81) and KH3 (5'-CTC ATG ATC TCC CGG ACC CCT GAG GTC-3') (SEQ ID NO: 82) were used, where K=G or T. To generate the T250C and T250G mutants, the mutagenesis primers KH5 (5'-GAC CTC AGG GGT CCG GGA GAT CAT GAG GCM GTC CTT GG-3') (SEQ ID NO: 83) and KH3 were used, where M=A or C. To generate the T250N and T250Q mutants, the mutagenesis primers KH6 (5'-GAC CTC AGG GGT CCG GGA GAT CAT GAG NTK GTC CTT GG-3') (SEQ ID NO: 84) and KH3 were used, where K=G or T, and N=A, C, G or T. The first round of PCR used outside primer msc g2-1 and KH4, KH5 or KH6 for the left-hand fragment, and outside primer MGD-1 (5'-GCC AGG ATC CGA CCC ACT-3') (SEQ ID NO: 85) and KH3 for the right-hand fragment. The PCR reactions were done using the Expand™ High Fidelity PCR System (Roche Diagnostics Corporation) by incubating at 94° C. for 5 minutes, followed by 25 cycles of 94° C. for 5 seconds, 60° C. for 5 seconds and 72° C. for 60 seconds, followed by incubating at 72° C. for 7 minutes. The PCR products were run on a low-melting point agarose gel, excised from the gel, and melted at 70° C. The second round of PCR to combine the left-hand and right-hand fragments was done as described above, using outside primers msc g2-1 and MGD-1, by incubating at 94° C. for 5 minutes, followed by 35 cycles of 94° C. for 5 seconds, 60° C. for 5 seconds and 72° C. for 105 seconds, followed by incubating at 72° C. for 7 minutes. The final PCR products were run on a low-melting point agarose gel and DNA fragments of the expected size were excised and purified using the QIAquick™ Gel Extraction Kit (QIAGEN®). The purified fragments were digested with PinAI and BamHI, gel-purified as described above, and cloned between the corresponding sites in pVAg2M3-OST577.

To generate random mutants at position 314, the mutagenesis primers kco78 (5'-ACC GTT GTG CAC CAG GAC TGG NNK AAC GGC AAG GAG-3') (SEQ ID NO: 86) and kco79 (5'-CCA GTC CTG GTG CAC AAC GG-3') (SEQ ID NO: 87) were used, where K=G or T, and N=A, C, G or T. The first round of PCR used outside primer ks g2-5 (5'-CTC CCG GAC CCC TGA GGT C-3') (SEQ ID NO: 88) and kco79 for the left-hand fragment, and outside primer kco8 and kco78 for the right-hand fragment. All subsequent steps were done as described above for position 250 random mutagenesis, except the second round of PCR used outside primers ks g2-5 and kco8, and the final PCR fragments were digested with PmlI and BamHI and cloned into the corresponding sites in pVAg2M3-OST577.

To generate the L314I mutant, the mutagenesis primers MGD-10 (5'-ACC GTT GTG CAC CAG GAC TGG ATC AAC GGC AAG GA-3') (SEQ ID NO: 89) and kco79 were used. To generate the L314Y mutant, the mutagenesis primers MGD-11 (5'-ACC GTT GTG CAC CAG GAC TGG TAT AAC GGC AAG GA-3') (SEQ ID NO: 90) and kco79 were used. To generate the L314H mutant, the mutagenesis primers MGD-12 (5'-ACC GTT GTG CAC CAG GAC TGG CAC AAC GGC AAG GA-3') (SEQ ID NO: 91) and kco79 were used. To generate the L314M mutant, the mutagenesis primers MGD-13 (5'-ACC GTT GTG CAC CAG GAC TGG ATG AAC GGC AAG GA-3') (SEQ ID NO: 92) and kco79 were used. To generate the L314N mutant, the mutagenesis primers MGD-14 (5'-ACC GTT GTG CAC CAG GAC TGG AAT AAC GGC AAG GA-3') (SEQ ID NO: 93) and kco79 were used. The first round of PCR used outside primer jt240 (5'-GGA CAC CTT CTC TCC TCC C-3') (SEQ ID NO: 94) and kco79 for the left-hand fragment, and outside primer kco41 (5'-ATT CTA GTT GTG GTT TGT CC-3') (SEQ ID NO: 95) and MGD-10, MGD-11, MGD-12, MGD-13 or MGD-14 for the right-hand fragment. The PCR reactions were done using the Expand™ High Fidelity PCR System (Roche Diagnostics Corporation) by incubating at 94° C. for 5 minutes, followed by 25 cycles of 94° C. for 5 seconds, 60° C. for 5 seconds and 72° C. for 60 seconds, followed by incubating at 72° C. for 7 minutes. The PCR products were run on a low-melting point agarose gel, excised from the gel, and melted at 70° C. The second round of PCR to combine the left-hand and right-hand fragments was done as described above, using outside primers jt240 and kco41, by incubating at 94° C. for 5 minutes, followed by 35 cycles of 94° C. for 5 seconds, 60° C. for 5 seconds and 72° C. for 90 seconds, followed by incubating at 72° C. for 7 minutes. The final PCR products were run on a low-melting point agarose gel and DNA fragments of the expected size were excised and purified using the QIAquick™ Gel Extraction Kit (QIAGEN®). The purified fragments were subcloned in pCR®4Blunt-TOPO® (Invitrogen™, Carlsbad, Calif.), then digested with PmlI and BamHI, gel-purified as described above, and cloned between the corresponding sites in pVAg2M3-OST577.

To generate random mutants at position 428, the mutagenesis primers JY22 (5'-GAA CGT CTT CTC ATG CTC CGT GNN KCA TGA GGC TCT G-3') (SEQ ID NO: 96) and JY23 (5'-CAC GGA GCA TGA GAA GAC GTT C-3') (SEQ ID NO: 97) were initially used, where K=G or T, and N=A, C, G or T. The first round of PCR used outside primer ks g2-5 and JY23 for the left-hand fragment, and outside primer kco8 and JY22 for the right-hand fragment. All subsequent steps were done as described above for position 314 random mutagenesis.

To generate additional random mutants at position 428, the mutagenesis primers MGD-2 (5'-GTG TAG TGG TTG TGC AGA GCC TCA TGM NNC ACG GAG CAT GAG AAG-3') (SEQ ID NO: 98) and KH1 (5'-CAT GAG GCT CTG CAC AAC CAC TAC AC-3') (SEQ ID NO: 99) were subsequently used, where M=A or C, and N=A, C, G or T. The first round of PCR used outside primer msc g2-1 and MGD-2 for the left-hand fragment, and outside primer MGD-1 and KH1 for the right-hand fragment. The PCR reaction was done using the Expand™ High Fidelity PCR System (Roche Diagnostics Corporation) by incubating at 94° C. for 5 minutes, followed by 25 cycles of 94° C. for 5 seconds, 60° C. for 5 seconds and 72° C. for 90 seconds, followed by incubating at 72° C. for 7 minutes. The PCR products were run on a low-melting point agarose gel, excised from the gel, and melted at 70° C. The second round of PCR to combine the left-hand and right-hand fragments was done as described above, using outside primers msc g2-1 and MGD-1, by incubating at 94° C. for 5 minutes, followed by 35 cycles of 94° C. for 5 seconds, 60° C. for 5 seconds and 72° C. for 75 seconds, followed by incubating at 72° C. for 7 minutes. The final PCR products were run on a low-melting point agarose gel and DNA fragments of the expected size were excised and purified using the QIAquick™ Gel Extraction Kit (QIAGEN®). The purified fragments were digested with PinAI and BamHI, gel-purified as described above, and cloned between the corresponding sites in pVAg2M3-OST577.

To generate the M428E mutant, the mutagenesis primers MGD-8 (5'-GTG TAG TGG TTG TGC AGA GCC TCA TGT TCC ACG GAG CAT GAG AAG-3') (SEQ ID NO: 100) and KH1 were used. The first round of PCR used outside primer msc g2-1 and MGD-8 for the left-hand fragment, and outside primer MGD-1 and KH1 for the right-hand fragment. All subsequent steps were done as described above for position 428 random mutagenesis.

The T250E/M428F double mutant was generated by replacing the PmlI-BamHI fragment in the pVAg2M3-OST577 plasmid containing the T250E mutation with the corresponding PmlI-BamHI fragment from the pVAg2M3-OST577 plasmid containing the M428F mutation. The T250Q/M428F and T250Q/M428L double mutants were generated by replacing the PmlI-BamHI fragment in the pVAg2M3-OST577 plasmid containing the T250Q mutation with the corresponding PmlI-BamHI fragments from the pVAg2M3-OST577 plasmids containing the M428F and M428L mutations, respectively.

Several amino acid substitutions were also created at positions 250 and 428 of the Hu1D10-IgG2M3 heavy chain. To generate the M428L mutant, the XhoI-XbaI fragment from plasmid pVAg2M3-OST577 (M428L), containing the hCMV promoter and enhancer (Boshart et al., op. cit.) and the OST577 $V_H$ region, was replaced with the corresponding XhoI-XbaI fragment from plasmid pHu1D10.IgG1.rgpt.dE (Kostelny et al. (2001), op. cit.) containing the hCMV promoter and enhancer and the Hu1D10 $V_H$ region. To generate the T250Q/M428L mutant, the XhoI-XbaI fragment from plasmid pVAg2M3-OST577 (T250Q/M428L), containing the hCMV promoter and enhancer (Boshart et al., op. cit.) and the OST577 $V_H$ region, was replaced with the corresponding XhoI-XbaI fragment from plasmid pHu1D10.IgG1.rgpt.dE (Kostelny et al. (2001), op. cit.) containing the hCMV promoter and enhancer and the Hu1D10 $V_H$ region.

Plasmid DNA was prepared using the QIAprep™ Spin Miniprep Kit (QIAGEN®), and nucleotide substitutions were identified by sequencing. Large-scale plasmid DNA preparations were made using the EndoFree® Plasmid Maxi Kit (QIAGEN®). The coding regions of the OST577-IgG2M3 expression plasmids were verified by nucleotide sequencing.

Results:

In order to isolate human IgG mutants with higher or lower affinity to the neonatal Fc receptor (FcRn), which would be expected to have altered serum half-lives, random amino acid substitutions were generated at positions 250, 314, and 428 of the human γ2M3 heavy chain (numbered according to the EU index of Kabat et al., op. cit.). These three positions were chosen based on computer modeling of a complex of the human IgG2M3 Fc and human FcRn (see models 1, 2, and 3, which are described earlier in the Example), which was deduced from the X-ray crystal structure of the rat Fc/FcRn complex (Burmeister et al., op. cit.). Although the wild-type amino acids at positions 250, 314, and 428 are located near the Fc/FcRn interface, these residues do not appear to directly contribute to the pH-dependent interaction between Fc and FcRn. Therefore, amino acid substitutions at these positions may increase (or decrease) the affinity of Fc for FcRn while maintaining pH-dependent binding. Among the single mutants generated by PCR-based mutagenesis were 19 mutants that converted the wild-type T at position 250 to A, C, D, E, F, G, H, I, K, L, M, N, P, Q, R, S, V, W, or Y; 19 mutants that converted the wild-type L at position 314 to A, C, D, E, F, G, H, I, K, M, N, P, Q, R, S, T, V, W, or Y; and 19 mutants that converted the wild-type M at position 428 to A, C, D, E, F, G, H, I, K, L, N, P, Q, R, S, T, V, W, or Y (see Table 1). Some of the single mutants with increased binding to FcRn were combined to generate several double mutants, including T250E/M428F, T250Q/M428F, and T250Q/M428L.

Example 4

This example describes mutagenesis of the Fc region of the human γ1 heavy chain gene.

Mutagenesis:

The overlap-extension PCR method (Higuchi, op. cit.) was used to generate amino acid substitutions at positions 250 and 428 of the OST577-IgG1 heavy chain (numbered according to the EU index of Kabat et al., op. cit.). To generate the T250E mutant, the mutagenesis primers JX076 (5'-AAC CCA AGG ACG AAC TCA TGA TCT CCC G-3') (SEQ ID NO: 101) and JX077 (5'-GGA GAT CAT GAG TTC GTC CTT GGG TTT TG-3') (SEQ ID NO: 102) were used. The first round of overlap-extension PCR used outside primer JX080 (5'-CCT CAG CTC GGA CAC CTT CTC-3') (SEQ ID NO: 103) and JX077 for the left-hand fragment, and outside primer NT244 (5'-GCC TCC CTC ATG CCA CTC A-3') (SEQ ID NO: 104) and JX076 for the right-hand fragment. The PCR reaction was done using the Expand™ High Fidelity PCR System (Roche Diagnostics Corporation), following the manufacturer's recommendations, by incubating at 94° C. for 5 minutes, followed by 35 cycles of 94° C. for 20 seconds, 55° C. for 20 seconds and 72° C. for 90 seconds, followed by incubating at 72° C. for 7 minutes in a GeneAmp® PCR System 9600 (Applied Biosystems®). The PCR products were run on a low-melting point agarose gel, excised from the gel, and melted at 70° C. The second round of PCR to combine the left-hand and right-hand fragments was done as described above, using outside primers JX080 and NT244, for 35 cycles. The final PCR products were run on a low-melting point agarose gel and DNA fragments of the expected size were excised and purified using the QIAquick™II Gel Extraction Kit (QIAGEN®). The purified fragments were digested with NheI and EagI, gel-purified as described above, and cloned between the corresponding sites in pVAg1.N-OST577.

To generate the T250D mutant, the mutagenesis primers JX087 (5'-AAC CCA AGG ACG ACC TCA TGA TCT CCC G-3') (SEQ ID NO: 105) and JX088 (5'-GGA GAT CAT GAG GTC GTC CTT GGG TTT TG-3') (SEQ ID NO: 106) were used. The first round of PCR used outside primer JX080 and JX088 for the left-hand fragment, and outside primer NT244 and JX087 for the right-hand fragment. All subsequent steps were done as described above.

To generate the M428F mutant, the mutagenesis primers JX078 (5'-CTC ATG CTC CGT GTT CCA TGA GGC TCT GC-3') (SEQ ID NO: 107) and JX079 (5'-AGA GCC TCA TGG AAC ACG GAG CAT GAG-3') (SEQ ID NO: 108) were used. The first round of PCR used outside primer JX080 and JX079 for the left-hand fragment, and outside primer NT244 and JX078 for the right-hand fragment. All subsequent steps were done as described above.

To generate the M428L mutant, the mutagenesis primers JXM428L1 (5'-CTC ATG CTC CGT GTT GCA TGA GGC TCT GC-3') (SEQ ID NO: 109) and JXM428L2 (5'-AGA GCC TCA TGC AAC ACG GAG CAT GAG-3') (SEQ ID NO: 110) were used. The first round of PCR used outside primer JX080 and JXM428L2 for the left-hand fragment, and outside primer NT244 and JXM428L1 for the right-hand fragment. All subsequent steps were done as described above.

To generate the T250Q mutant, the mutagenesis primers JXT250Q1 (5'-AAC CCA AGG ACC AAC TCA TGA TCT CCC G-3') (SEQ ID NO: 111) and JXT250Q2 (5'-GGA GAT CAT GAG TTG GTC CTT GGG TTT TG-3') (SEQ ID NO: 112) were used. The first round of PCR used outside primer JX080 and JXT250Q2 for the left-hand fragment, and outside primer NT244 and JXT250Q1 for the right-hand fragment. All subsequent steps were done as described above.

To generate the T250E/M428F double mutant, the mutagenesis primers JX076 and JX077 were used to create the T250E mutation in a template containing the M428F mutation. The first round of PCR used outside primer JX080 and JX077 for the left-hand fragment, and outside primer NT244 and JX076 for the right-hand fragment. All subsequent steps were done as described above.

To generate the T250Q/M428L double mutant, the mutagenesis primers JXT250Q1 and JXT250Q2 were used to create the T250Q mutation, and the mutagenesis primers JXM428L1 and JXM428L2 were used to create the M428L mutation. The first round of PCR used outside primer JX080 and JXT250Q2 to create the left-hand fragment, JXT250Q1 and JXM428L2 to create the middle fragment, and outside primer NT244 and JXM428L1 to create the right-hand fragment. All subsequent steps were done as described above.

Several amino acid substitutions were also created at positions 250 and 428 of the Hu1D10-IgG1 heavy chain. To generate the M428L mutant, the XhoI-XbaI fragment from plasmid pVAg1.N-OST577 (M428L), containing the hCMV promoter and enhancer (Boshart et al., op. cit.) and the OST577 $V_H$ region, was replaced with the corresponding XhoI-XbaI fragment from plasmid pHu1D10.IgG1.rgpt.dE (Kostelny et al. (2001), op. cit.) containing the hCMV promoter and enhancer and the Hu1D10 $V_H$ region. To generate the T250Q/M428L mutant, the XhoI-XbaI fragment from plasmid pVAg1.N-OST577 (T250Q/M428L), containing the hCMV promoter and enhancer (Boshart et al., op. cit.) and the OST577 $V_H$ region, was replaced with the corresponding XhoI-XbaI fragment from plasmid pHu1D10.IgG1.rgpt.dE (Kostelny et al. (2001), op. cit.) containing the hCMV promoter and enhancer and the Hu1D10 $V_H$ region.

Plasmid DNA was prepared using the QIAprep™ Spin Miniprep Kit (QIAGEN®), and nucleotide substitutions were confirmed by sequencing. Large-scale plasmid DNA preparations were made using the EndoFree™ Plasmid Maxi Kit (QIAGEN®). The coding regions of the OST577-IgG1 expression plasmids were verified by nucleotide sequencing.

Results:

In order to identify human IgG mutants with altered affinity to the neonatal Fc receptor (FcRn), which would be expected to have altered serum half-lives, several amino acid substitutions were generated at positions 250 and 428 of the human γ1 heavy chain (numbered according to the EU index of Kabat et al., op. cit.). These two positions were chosen based on the identification of mutations at these positions in the human γ2M3 heavy chain that resulted in increased or decreased binding to FcRn. Although the wild-type amino acids at positions 250 and 428 are located near the Fc/FcRn interface, these residues do not appear to directly contribute to the pH-dependent interaction between Fc and FcRn. Therefore, amino acid substitutions at these positions may increase (or decrease) the affinity of Fc for FcRn while maintaining pH-dependent binding. Both single and double mutants that exhibited increased binding in the context of the human γ2M3 heavy chain were evaluated in the human γ1 heavy chain, including the single mutants T250E, T250Q, M428F, and M428L, and the double mutants T250E/M428F and T250Q/M428L. A single mutant that exhibited decreased binding in the context of the human γ2M3 heavy chain (T250D) was also evaluated in the human γ1 heavy chain.

Example 5

This example describes the characterization of mutant IgG2M3 and IgG1 antibodies.

Cell Culture:

Human kidney cell line 293-H (Life Technologies®, Rockville, Md.) was maintained in DMEM (BioWhittaker™, Walkersville, Md.) containing 10% Fetal Bovine Serum (FBS) (HyClone®, Logan, Utah), 0.1 mM MEM non-essential amino acids (Invitrogen™) and 2 mM L-glutamine (Invitrogen™), hereinafter referred to as 293 medium, at 37° C. in a 7.5% $CO_2$ incubator. For expression and purification of monoclonal antibodies after transient transfection, 293-H cells were incubated in DMEM containing 10% low-IgG FBS (HyClone®), 0.1 mM MEM non-essential amino acids and 2 mM L-glutamine, hereinafter referred to as low-IgG 293 medium. Mouse myeloma cell line Sp2/0 (American Type Culture Collection, Manassus, Va.) was maintained in DMEM containing 10% FBS and 2 mM L-glutamine. For purification of monoclonal antibodies after stable transfections, Sp2/0 cells were adapted to growth in Hybridoma-SFM (HSFM) (Life Technologies®).

Transient Transfections:

293-H cells were transiently cotransfected with the appropriate light chain plasmid and the appropriate wild-type or one of the various mutated heavy chain plasmids containing a single or double amino acid substitution at position 250, 314 or 428. For small-scale transient transfections, approximately $1\times10^6$ cells per transfection were plated in a 6-well plate in 3 ml of 293 medium and grown overnight to confluence. The next day, 2 μg of light chain plasmid and 2 μg of wild-type or mutated heavy chain plasmid were combined with 0.25 ml of HSFM. In a separate tube, 10 μl of Lipofectamine™ 2000 reagent (Invitrogen™) and 0.25 ml of HSFM were combined and incubated for 5 minutes at room temperature. The 0.25 ml Lipofectamine™ 2000-HSFM mixture was mixed gently with the 0.25 ml DNA-HSFM mixture and incubated at room temperature for 20 minutes. The medium covering the 293-H cells was aspirated and replaced with low-IgG 293 medium, then the lipofectamine-DNA complexes were added dropwise to the cells, mixed gently by swirling, and the cells were incubated for 5-7 days at 37° C. in a 7.5% $CO_2$ incubator before harvesting the supernatants.

For large-scale transient transfections, approximately $7\times10^6$ cells per transfection were plated in a T-75 flask in 25 ml of 293 medium and grown overnight to confluence. The next day, 12 μg of light chain plasmid and 12 μg of wild-type or mutated heavy chain plasmid were combined with 1.5 ml of HSFM. In a separate tube, 60 μl of Lipofectamine™ 2000 reagent and 1.5 ml of HSFM were combined and incubated for 5 minutes at room temperature. The 1.5 ml Lipofectamine™ 2000-HSFM mixture was mixed gently with the 1.5 ml DNA-HSFM mixture and incubated at room temperature for 20 minutes. The medium covering the 293-H cells was aspirated and replaced with low-IgG 293 medium, then the lipofectamine-DNA complexes were added dropwise to the cells, mixed gently by swirling, and the cells were incubated for 5-7 days at 37° C. in a 7.5% $CO_2$ incubator before harvesting the supernatants.

Antibody Concentration:

Supernatants from small-scale transient transfections were harvested by centrifugation at ~1,200 rpm for 5 minutes and sterile filtered using 0.22 μm Millex®-GV microfilters (Millipore® Corporation, Bedford, Mass.). The samples were concentrated approximately 6-fold to 0.5 ml using 6 ml Vivaspin® concentrators (50,000 MWCO) (Vivascience® AG, Hannover, Germany) by centrifugation at 3,000 rpm. Concentrated protein samples were resuspended in 5 ml of PBS, pH 6.0, and concentrated to a volume of 0.5 ml as described above. The ELISA method described below was used to measure the antibody concentration in each sample.

Stable Transfections:

Sp2/0 cells were stably transfected with the appropriate light chain plasmid and the appropriate wild-type or one of the various mutated heavy chain plasmids containing a single or double amino acid substitution at position 250 or 428. Approximately $1\times10^7$ cells were washed with 10 ml of PBS, and resuspended in 1 ml of PBS. Approximately 25-30 μg of light chain plasmid and 50-60 μg of heavy chain plasmid were linearized with FspI, and added to the cells. Cells and DNA were mixed gently, and transferred to a Gene Pulser Cuvette (Bio-Rad® Laboratories, Hercules, Calif.) on ice. The cells were electroporated using a Gene Pulser II (Bio-Rad® Laboratories) set at 0.360 kV, 25 μF, and returned to ice for 10-20 minutes. The cells were diluted in 40 ml of DMEM, 10% FBS, 2 mM L-glutamine, and plated in four 96-well plates at 100 μl/well. After 48 hours, 100 μl/well of 2× mycophenolic acid (MPA) selection medium (DMEM, 10% FBS, 1×HT Media Supplement Hybri-Max® (Sigma®, St. Louis, Mo.), 300 μg/ml xanthine (Sigma®), 2 μg/ml mycophenolic acid (Life Technologies®), and 2 mM L-glutamine) was added. Supernatants from wells apparently containing single colonies were screened by ELISA after 10-14 days. The highest antibody-producing clones were chosen for expansion and adaptation to HSFM (Life Technologies®). Adapted clones were expanded to roller bottles in 450 ml of HSFM, gassed with 5% $CO_2$ in air, supplemented after 2 days with 50 ml of Protein Free Feed Medium-2 (PFFM-2) (Sauer et al., Biotechnol. Bioeng. 67:585-597 (2000)), and grown to exhaustion.

Some of the highest antibody-producing clones were also adapted to Protein-Free Basal Medium-1 (PFBM-1) (Protein Design Labs™, Inc.), expanded to 10 L spinner flasks, supplemented after 2 days with 1/10 volume of PFFM-2, and grown to exhaustion.

ELISA:

To quantitate the amount of OST577 or Hu1D10 antibody present in culture supernatants, an ELISA was performed. Immulon™ 4 plates (DYNEX® Technologies, Inc., Chantilly, Va.) were coated overnight at 4° C. with 1.0 μg/ml of goat $F(ab')_2$ anti-human IgG gamma chain antibody (BioSource International, Camarillo, Calif.) or AffiniPure™ goat anti-human IgG Fcγ fragment specific antibody (Jackson ImmunoResearch Laboratories, Inc., West Grove, Pa.) in 100 μl/well of 0.2 M carbonate-bicarbonate buffer, pH 9.4. The next day, the plates were washed with ELISA Wash Buffer (EWB) (PBS, 0.1% Tween 20) and blocked with 300 μl/well of SuperBlock® Blocking Buffer in TBS (Pierce Chemical Company, Rockford, Ill.) for 20-30 minutes at room temperature. The plates were washed with EWB, and appropriately diluted test samples were added to each well. Purified OST577 or Hu1D10 antibodies, as appropriate, were serially diluted twofold in 100 μl/well of ELISA Buffer (EB) (PBS, 1% bovine serum albumin, 0.1% Tween 20) starting at 0.2 μg/ml, and used as standards. Culture supernatants were initially diluted 1:10 in 100 μl/well of EB, then serially diluted twofold in 100 μl/well of EB. The plates were incubated for 1-2 hours at room temperature, then washed with EWB, and 100 μl/well of goat anti-human lambda light chain HRP-conjugated antibody (BioSource International, or Southern Biotechnology Associates, Inc., Birmingham, Ala.) or goat anti-human kappa light chain HRP-conjugated antibody (Southern Biotechnology Associates, Inc.), as appropriate, was added at 1.0 μg/ml in EB. After incubation for 1 hour at room temperature, the plates were washed with EWB, followed by addition of 100 μl/well of ABTS Peroxidase Substrate/Peroxidase Solution B (Kirkegaard & Perry Laboratories, Gaithersburg, Md.). The reaction was stopped with 100 μl/well of 2% oxalic acid, and the absorbance at 415 nm was measured using a VERSAmax™ microtitre plate reader (Molecular Devices® Corporation, Sunnyvale, Calif.).

Antibody Purification:

Culture supernatants from transient transfections were harvested by centrifugation, and sterile filtered. The pH of the filtered supernatants was adjusted by addition of 1/50 volume of 1 M sodium citrate, pH 7.0. Supernatants were run over a 1 ml HiTrap® Protein A HP column (Amersham Biosciences™ Corporation, Piscataway, N.J.) that was pre-equilibrated with 20 mM sodium citrate, 150 mM NaCl, pH 7.0. The column was washed with the same buffer, and bound antibody was eluted with 20 mM sodium citrate, pH 3.5. After neutralization by addition of 1/50 volume of 1.5 M sodium citrate, pH 6.5, the pooled antibody fractions were run over a 5 ml HiTrap® Desalting column (Amersham Biosciences™ Corporation) that was pre-equilibrated with 20 mM sodium citrate, 120 mM NaCl, pH 6.0. The flow-through was collected and fractions with $OD_{280}$>0.1 were pooled and concentrated to ~0.5-1.0 mg/ml using 2 ml Vivaspin® concentrators (50,000 dalton MWCO) (Vivascience® AG). Samples were then filter sterilized using 0.2 μm Millex®-GV microfilters (Millipore® Corporation). The concentrations of the purified antibodies were determined by UV spectroscopy by measuring the absorbance at 280 nm (1 mg/ml=1.4 $A_{280}$).

For small-scale purification of antibody from stable transfections, culture supernatants were harvested by centrifugation, and sterile filtered. Supernatants were run over a 5 ml POROS® 50A Protein A column (Applied Biosystems®) that was pre-equilibrated with PBS, pH 7.4. The column was washed with the same buffer, and bound antibody was eluted with 0.1 M glycine, 0.1 M NaCl, pH 3.0. After neutralization by addition of 1/20 volume of 1 M Tris base, pooled fractions were buffer exchanged into PBS, pH 7.4, using a PD-10 desalting column (Amersham Biosciences™ Corporation) or by dialysis. Samples were then filter sterilized using 0.2 μm Millex®-GV microfilters (Millipore® Corporation). The concentrations of the purified antibodies were determined by UV spectroscopy by measuring the absorbance at 280 nm (1 mg/ml=1.4 $A_{280}$).

For large-scale purification of antibody from stable transfectants, the cell culture harvest was clarified by dead-end filtration using Sartorius® filtration capsules (Sartorius® AG, Goettingen, Germany). The clarified harvest was concentrated from approximately 10 L to 750 ml using a Pellicon® 2 cassette (30,000 dalton MWCO) (Millipore® Corporation), then purified by protein A affinity chromatography on a rProtein A Sepharose FF column (Amersham Biosciences™ Corporation) using the citrate buffer system described above. The protein A eluate was concentrated in an Amicon® stir cell apparatus using a YM30 membrane (Millipore® Corporation), then the sample was buffer exchanged into 20 mM sodium citrate, 120 mM NaCl, pH 6.0, using a Superdex™ 200 column (Amersham Biosciences™ Corporation). The pH and osmolality were measured, and the concentrations of the purified antibodies were determined by UV spectroscopy by measuring the absorbance at 280 nm (1 mg/ml=1.4 $A_{280}$).

SDS-PAGE:

Five μg samples of purified antibodies were run under reducing or non-reducing conditions on NuPAGE® Novex 4-12% Bis-Tris gels (Invitrogen™) and stained using the SimplyBlue™ SafeStain Kit (Invitrogen™) following the manufacturer's recommendations.

Results:

The IgG2M3 Fc and IgG1 Fc mutants were expressed as anti-HBV antibodies, comprising the light and heavy chain variable regions of OST577 (Ehrlich et al., op. cit.), the light chain constant region of human lambda-2 (Hieter et al. (1981), op. cit.), and the heavy chain constant regions of human gamma-2 mutant 3 (IgG2M3) (Cole et al, op. cit.) and IgG1 (Ellison et al., op. cit.), respectively. The IgG2M3 variant contains two amino acid substitutions in the $C_H2$ region (V234A and G237A), and shows extremely low residual binding to human Fcγ receptors (Cole et al., op. cit.). The IgG2M3 Fc and IgG1 Fc mutants were also expressed as anti-HLA-DR β chain allele antibodies, comprising the light and heavy chain variable regions of Hu1D10 (Kostelny et al. (2001), op. cit.), the light chain constant region of human kappa (Hieter et al. (1980), op. cit.), and the heavy chain constant regions of human IgG2M3 (Cole et al, op. cit.) and IgG1 (Ellison et al., op. cit.), respectively. As described above, the appropriate wild-type or mutant heavy chain expression vector was transiently co-transfected with the appropriate light chain expression vector into 293-H cells for expression of OST577 or Hu1D10 monoclonal antibodies. ELISA analysis of culture supernatants harvested 5-7 days after transient transfection showed that antibody expression levels were typically 5-50 μg/ml in 25 ml of supernatant. OST577 or Hu1D10 antibodies were purified by protein A affinity chromatography for a final yield of approximately 100-1000 μg. Stable expression of OST577 or Hu1D10 antibodies in Sp2/0 cells typically resulted in expression levels of 5-50 μg/ml as determined by ELISA. Yields of approximately 50-80% of the antibody present in culture supernatants were obtained by small-scale protein A affinity chromatography.

Purified antibodies were characterized by SDS polyacrylamide gel electrophoresis (SDS-PAGE) under non-reducing and reducing conditions. SDS-PAGE analysis under non-reducing conditions indicated that the purified antibodies had a molecular weight of about 150-160 kD (data not shown); analysis under reducing conditions indicated that the purified antibodies were comprised of a heavy chain with a molecular weight of about 50 kD and a light chain with a molecular weight of about 25 kD (see FIGS. 10A and 10B). SDS-PAGE analysis of antibodies purified from stable Sp2/0 transfectants gave results similar to those observed with antibodies purified from transient 293-H transfections.

Example 6

This example describes the competitive binding analysis of mutant IgG2M3 and IgG1 antibodies.

Cell Culture:

Mouse myeloma cell line NS0 (European Collection of Animal Cell Cultures, Salisbury, Wiltshire, UK) was maintained in DMEM containing 10% FBS. NS0 transfectants expressing recombinant, GPI-linked human or rhesus FcRn on the surface were maintained in mycophenolic acid (MPA) selection medium (DMEM, 10% FBS, 1×HT Media Supplement Hybri-Max® (Sigma®), 250 μg/ml xanthine (Sigma®), 1 μg/ml mycophenolic acid (Life Technologies®), and 2 mM L-glutamine) or 2×MPA selection medium.

Human FcRn Cell Line:

NS0 cells were stably transfected with pDL208. Approximately $1\times10^7$ cells were washed once and resuspended in 1 ml of plain DMEM, transferred to a Gene Pulser™ Cuvette (Bio-Rad® Laboratories), and incubated on ice for 10 minutes. Forty μg of plasmid pDL208 was linearized with FspI and gently mixed with the cells on ice, then the cells were electroporated by pulsing twice using a Gene Pulser™ II (Bio-Rad® Laboratories) set at 1.5 kV, 3 μF, and returned to ice for 10 minutes. The cells were diluted in 20 ml of DMEM, 10% FBS, and plated in two 96-well plates at 100 μl/well. The medium was replaced after 48 hours with MPA selection medium. Mycophenolic acid-resistant NS0 transfectants from wells apparently containing single colonies were expanded in MPA selection medium and screened after about 3 weeks by FACS™. Approximately $1.5\times10^5$ cells/test were incubated in 100 μl of FACS Staining Buffer (FSB) (PBS, 1% FBS, 0.1% $NaN_3$) containing 10 μg/ml of biotinylated mouse anti-human β-microglobulin antibody (Chromaprobe, Inc., Aptos, Calif.) for 1 hour on ice. The cells were washed once with 4 ml of FSB, then incubated in 25 μl of FSB containing 20 μg/ml of streptavidin-FITC conjugate (Southern Biotechnology Associates, Inc.) for 30 minutes on ice in the dark. The cells were washed once with 4 ml of FSB, and resuspended in 1% formaldehyde. Samples were analyzed for antibody binding to human β2m using a FACScan flow cytometer (BD® Biosciences, San Jose, Calif.). Several clones with the highest apparent staining were subcloned using a FACStar cell sorter (BD® Biosciences), expanded in DMEM, 10% FBS, 2 mM L-glutamine, and retested by FACS™ as described above. One subclone, designated NS0 HuFcRn (memb), clone 7-3, was used in subsequent binding assays.

Rhesus FcRn Cell Line:

NS0 cells were stably transfected with pDL410. Approximately $6\times10^5$ cells were transfected by electroporation as described above. Transfectants were identified by FACS™ as described above by staining with 100 ng/test of a mouse anti-human FcRn alpha chain antibody (Protein Design Labs™, Inc.) that cross-reacts with rhesus FcRn alpha chain, and detecting with goat anti-mouse kappa FITC-conjugated antibody (Southern Biotechnology Associates, Inc.). A cell line designated NS0 RhFcRn, clone R-3, was used in subsequent binding assays.

Single Point Competitive Binding Assay:

Concentrated OST577-IgG2M3 supernatants were tested in a single-point competitive binding assay for binding to human FcRn on cell line NS0 HuFcRn (memb), clone 7-3. Approximately $2\times10^5$ cells/test were washed once in FACS Binding Buffer (FBB) (PBS containing 0.5% BSA, 0.1% $NaN_3$), pH 8.0, once in FBB, pH 6.0, and resuspended in 120 μl of pre-mixed biotinylated OST577-IgG2M3 antibody (8.3 μg/ml) and concentrated supernatant (containing 8.3 μg/ml of competitor antibody) in FBB, pH 6.0. The cells were incubated for 1 hour on ice, washed twice in FBB, pH 6.0, and resuspended in 25 μl of streptavidin-RPE conjugate (BioSource International) diluted to 2.5 μg/ml in FBB, pH 6.0. After incubation for 30 minutes on ice in the dark, the cells were washed twice in FBB, pH 6.0, and resuspended in 1% formaldehyde. Samples were analyzed for antibody binding to FcRn by FACS™ using a FACSCalibur flow cytometer (BD® Biosciences). Mean channel fluorescence (MCF) of each mutant was compared to that of the wild-type antibody and plotted using Excel (Microsoft® Corporation, Redmond, Wash.).

Competitive Binding Assays:

A dilution series of each purified OST577-IgG2M3 antibody was competed against biotinylated HuEP5C7-IgG2M3 antibody (He et al., J. Immunol. 160:1029-1035 (1998)) for binding to human FcRn on cell line NS0 HuFcRn (memb), clone 7-3. For initial screening experiments, approximately $2\times10^5$ cells/test were washed once in FSB, pH 6.0, and resuspended in 100 μl of pre-mixed biotinylated HuEP5C7-IgG2M3 antibody (10 μg/ml) and OST577-IgG2M3 competitor antibody (twofold serial dilutions from 208 μg/ml to 0.102 μg/ml) in FSB, pH 6.0. The cells were incubated with the antibody mixture for 1 hour on ice, washed twice in FSB, pH 6.0, and resuspended in 25 μl of streptavidin-RPE conjugate (BioSource International) diluted to 2.5 μg/ml in FSB, pH 6.0. After incubation for 30 minutes on ice in the dark, the cells were washed twice in FSB, pH 6.0, and resuspended in 1% formaldehyde. Samples were analyzed for antibody binding to FcRn by FACS™ using a FACScan flow cytometer (BD® Biosciences). Mean channel fluorescence (MCF) was plotted against competitor concentration, and IC50 values were calculated using GraphPad Prism® (GraphPad™ Software, Inc., San Diego, Calif.). For consistency, the IC50 values shown in the Tables are based on the final competitor concentrations.

Subsequent competitive binding experiments were done as described above, except the cells were washed once in FBB, pH 8.0, and once in FBB, pH 6.0, then resuspended in 100 μl of pre-mixed biotinylated HuEP5C7-IgG2M3 antibody (10 μg/ml) and OST577-IgG2M3 competitor antibody (twofold serial dilutions from 208 μg/ml to 0.102 μg/ml) in FBB, pH 6.0. All subsequent incubations and washes were done using FBB, pH 6.0, as described above. One group of experiments was done in 120 μl of pre-mixed biotinylated OST577-IgG2M3 antibody (8.3 μg/ml) and OST577-IgG2M3 competitor antibody (twofold serial dilutions from 208 μg/ml to 0.102 μg/ml) in FBB, pH 6.0, as described above. Another group of experiments was done in 200 μl of pre-mixed biotinylated OST577-IgG1 antibody (5.0 μg/ml) and OST577-IgG1 competitor antibody (twofold serial dilutions starting from 125 μg/ml, or threefold serial dilutions starting from 250 μg/ml) in FBB, pH 6.0, as described above. A further group of experiments was done in 200 μl of pre-mixed biotinylated OST577-IgG1 antibody (5.0 μg/ml) and OST577-IgG1 competitor antibody (threefold serial dilutions starting from 750 μg/ml) in FBB, pH 6.0, as described above.

A dilution series of each purified OST577-IgG2M3 antibody was competed against biotinylated OST577-IgG2M3 antibody for binding to rhesus FcRn on cell line NS0 RhFcRn, clone R-3. In one group of experiments, approximately $2\times10^5$ cells/test were washed once in FBB, pH 8.0, and once in FBB, pH 6.0, then resuspended in 120 μl of pre-mixed biotinylated OST577-IgG2M3 antibody (8.3 μg/ml) and OST577-IgG2M3 competitor antibody (twofold serial dilutions from 208 μg/ml to 0.102 μg/ml) in FBB, pH 6.0. The cells were incubated with the antibody mixture for 1 hour on ice, washed twice in FBB, pH 6.0, and resuspended in 25 μl of streptavidin-RPE conjugate (BioSource International) diluted to 2.5 μg/ml in FBB, pH 6.0. After incubation for 30 minutes on ice in the dark, the cells were washed twice in FBB, pH 6.0, and resuspended in 1% formaldehyde. Samples were analyzed for antibody binding to FcRn by FACS™ using a FACSCalibur flow cytometer (BD® Biosciences). Another group of experiments was done in 200 μl of pre-mixed biotinylated OST577-IgG1 antibody (5.0 μg/ml) and OST577-IgG1 competitor antibody (threefold serial dilutions starting from 500 μg/ml) in FBB, pH 6.0, as described above.

Results:

The relative binding of wild-type OST577-IgG2M3 or OST577-IgG1 antibodies and their various mutants to FcRn was determined using a transfected NS0 cell line stably expressing human FcRn on its surface. As described above, the concentrated supernatants were tested for binding to human FcRn according to the single point competitive binding assay and the purified antibodies were tested for FcRn binding in the competitive binding assays. Increasing concentrations of unlabeled competitor antibodies were incubated with cells in the presence of a sub-saturating concentration of labeled IgG2M3 or IgG1 antibody in FSB or FBB, pH 6.0.

Figure 11:
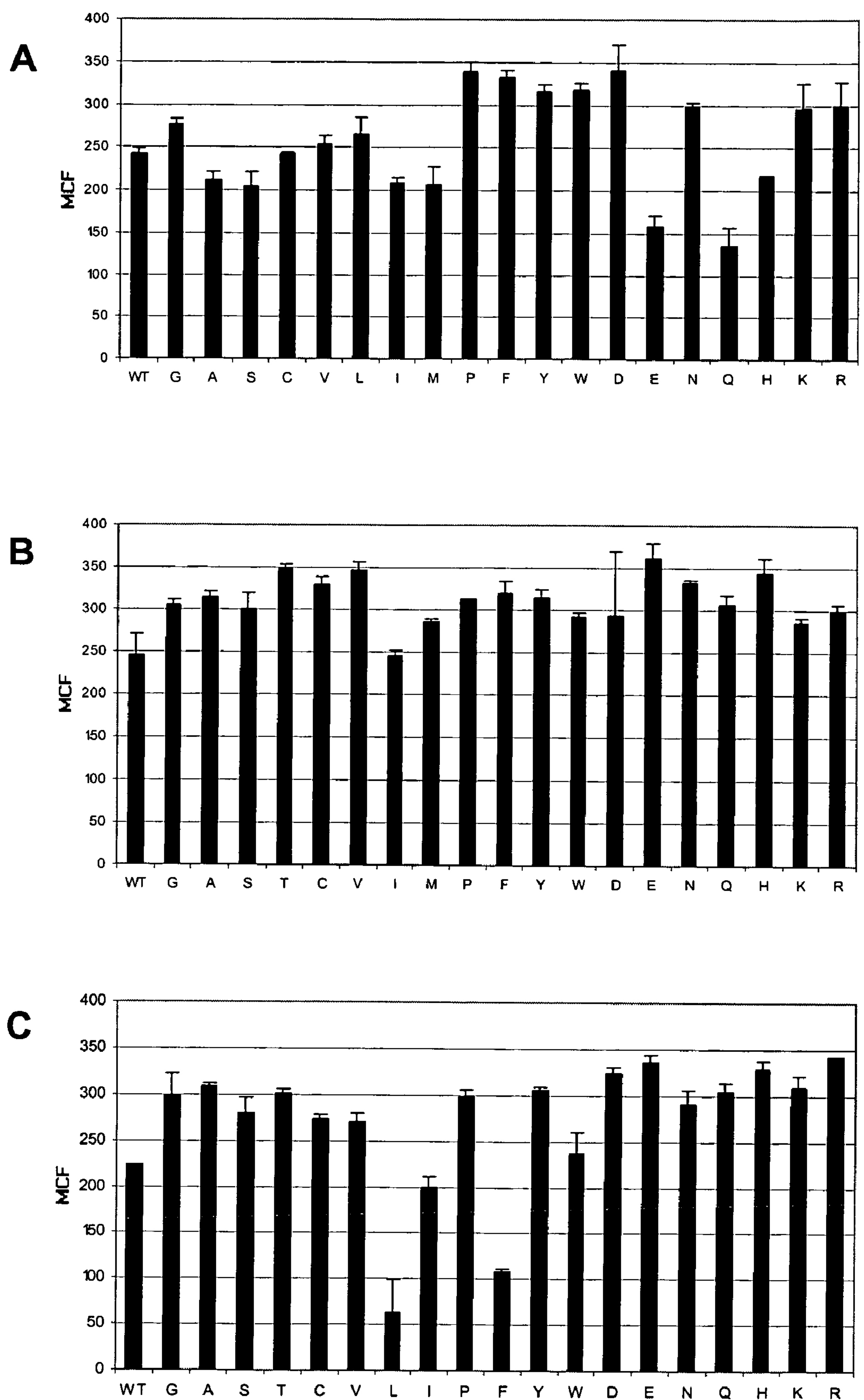
FIG. 11A. Single Point Competitive Binding Assay of the Various Mutants of Position 250 of OST577-IgG2M3 to Human FcRn. The binding of biotinylated OST577-IgG2M3 antibody to human FcRn on transfected NS0 cells in the presence of the wild-type or position 250 mutant OST577-IgG2M3 competitor antibodies in FBB, at pH 6.0, was detected with streptavidin-conjugated RPE and analyzed by flow cytometry, as described in Example 6.
FIG. 11B. Single Point Competitive Binding Assay of the Various Mutants of Position 314 of OST577-IgG2M3 to Human FcRn. The binding of biotinylated OST577-IgG2M3 antibody to human FcRn on transfected NS0 cells in the presence of the wild-type or position 314 mutant OST577-IgG2M3 competitor antibodies in FBB, at pH 6.0, was detected with streptavidin-conjugated RPE and analyzed by flow cytometry, as described in Example 6.
FIG. 11C. Single Point Competitive Binding Assay of the Various Mutants of Position 428 of OST577-IgG2M3 to Human FcRn. The binding of biotinylated OST577-IgG2M3 antibody to human FcRn on transfected NS0 cells in the presence of the wild-type or position 428 mutant OST577-IgG2M3 competitor antibodies in FBB, at pH 6.0, was detected with streptavidin-conjugated RPE and analyzed by flow cytometry, as described in Example 6.

The results of typical experiments with concentrated OST577-IgG2M3 supernatants are shown in FIGS. 11A, 11B, and 11C. As shown in FIG. 11A, some of the mutants at position 250 (e.g., T250E, T250Q) were stronger competitors than the wild-type, suggesting that these mutants have increased binding to human FcRn as compared to the wild-type antibody. Other mutants at this position (e.g., T250D, T250F, T250K, T250N, T250P, T250R, T250W, T250Y) were weaker competitors than the wild-type, suggesting that these mutants have reduced binding to human FcRn as compared to the wild-type antibody. As shown in FIG. 11B, none of the mutants at position 314 was a stronger competitor than the wild-type, suggesting that none of these mutants has increased binding to human FcRn as compared to the wild-type antibody. Most of the mutants at this position (e.g., L314A, L314C, L314D, L314E, L314F, L314G, L314H, L314K, L314M, L314N, L314P, L314Q, L314R, L314S, L314T, L314V, L314W, L314Y) were weaker competitors than the wild-type, suggesting that these mutants have reduced binding to human FcRn as compared to the wild-type antibody. As shown in FIG. 11C, some of the mutants at position 428 (e.g., M428F, M428L) were stronger competitors than the wild-type, suggesting that these mutants have increased binding to human FcRn as compared to the wild-type antibody. Other mutants at this position (e.g., M428A, M428C, M428D, M428E, M428G, M428H, M428K, M428N, M428P, M428Q, M428R, M428S, M428T, M428V, M428Y) were weaker competitors than the wild-type, suggesting that these mutants have reduced binding to human FcRn as compared to the wild-type antibody.

Table 2 summarizes the IC50 values (the amount of competitor antibody necessary to inhibit binding of the labeled antibody to FcRn by 50%) of the purified wild-type OST577-IgG2M3 antibody and some of its mutants for binding to human FcRn. Relative binding values were calculated as the ratio of the IC50 value of the wild-type OST577-IgG2M3 antibody to that of each of the mutants. At amino acid position 314, none of the purified mutants showed an increase in binding to human FcRn relative to the wild-type antibody. In fact, all four of the purified mutants at position 314 showed reduced binding relative to the wild-type antibody. However, at amino acid position 250, one of the mutants (T250E) showed approximately 3-fold better binding to human FcRn than the wild-type antibody. Several mutants at position 250 showed slightly reduced binding relative to the wild-type antibody, and one mutant (T250D) showed substantially reduced binding to human FcRn relative to the wild-type antibody. At amino acid position 428, one of the mutants (M428F) also showed approximately 3-fold better binding to human FcRn than the wild-type antibody, while another mutant (M428G) showed substantially reduced binding to human FcRn relative to the wild-type antibody.

Since two amino acid substitutions at two different positions were identified, namely T250E, T250Q, M428F, and M428L, each showing an increase in binding to human FcRn, the double mutants T250E/M428F, T250Q/M428F, and T250Q/M428L were constructed, transiently transfected into 293-H cells, purified, and tested for binding to human FcRn. As described above, increasing concentrations of unlabeled competitor antibodies were incubated with cells expressing human FcRn in the presence of a sub-saturating concentration of labeled HuEP5C7-IgG2M3 or OST577-IgG2M3 antibody in FBB, pH 6.0.

Figure 12:
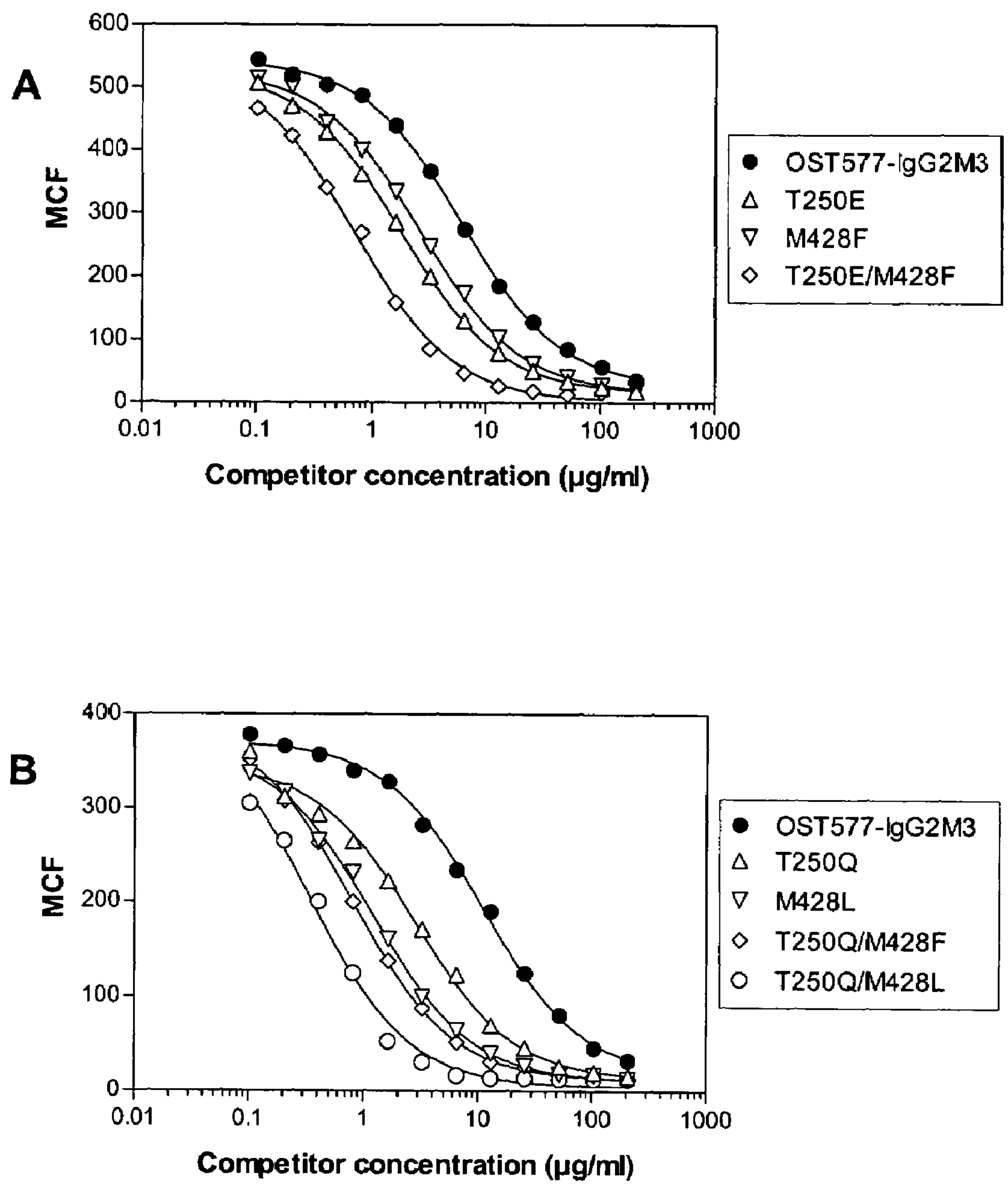
FIG. 12A. Competitive Binding Assay of OST577-IgG2M3 Wild-Type and Mutant Antibodies to Human FcRn. The binding of biotinylated HuEP5C7-IgG2M3 antibody to human FcRn on transfected NS0 cells in the presence of increasing concentrations of the wild-type or mutant OST577-IgG2M3 competitor antibodies in FBB, at pH 6.0, was detected with streptavidin-conjugated RPE and analyzed by flow cytometry, as described in Example 6.
FIG. 12B. Competitive Binding Assay of OST577-IgG2M3 Wild-Type and Mutant Antibodies to Human FcRn. The binding of biotinylated OST577-IgG2M3 antibody to human FcRn on transfected NS0 cells in the presence of increasing concentrations of the wild-type or mutant OST577-IgG2M3 competitor antibodies in FBB, at pH 6.0, was detected with streptavidin-conjugated RPE and analyzed by flow cytometry, as described in Example 6.

As shown in FIG. 12A, the double mutant (T250E/M428F) showed better binding to human FcRn than either of the single mutants (T250E or M428F) and showed approximately 15-fold better binding to human FcRn than the wild-type antibody. As shown in FIG. 12B, the double mutant (T250Q/M428L) showed better binding to human FcRn than either of the single mutants (T250Q or M428L) or the double mutant (T250Q/M428F), and showed approximately 28-fold better binding to human FcRn than the wild-type antibody. As summarized in Table 3, in one group of experiments, the IC50 for the wild-type OST577-IgG2M3 antibody is ~9 μg/ml, whereas the IC50 for each of the single mutants (T250E and M428F) is ~3 μg/ml, and the IC50 for the double mutant (T250E/M428F) is less than 1 μg/ml. As summarized in Table 4, in another group of experiments, the IC50 for the wild-type OST577-IgG2M3 antibody is ~12 μg/ml, whereas the IC50 for each of the single mutants (T250Q and M428L) and the double mutant (T250Q/M428F) is ~2-4 μg/ml, and the IC50 for the double mutant (T250Q/M428L) is less than 1 μg/ml.

Wild-type OST577-IgG1, the single mutants T250E, T250Q, M428F, M428L, and the double mutants T250E/M428F and T250Q/M428L were also created. As summarized in Table 5, in one group of experiments, the IC50 for the wild-type OST577-IgG1 antibody is ~14 μg/ml, whereas the IC50 for each of the single mutants (T250E and M428F) is ~3-5 μg/ml, and the IC50 for the double mutant (T250E/M428F) is less than 1 μg/ml. As summarized in Table 6, in another group of experiments, the IC50 for the wild-type OST577-IgG1 antibody is ~10 μg/ml, whereas the IC50 for the single mutant (T250Q) is ~3 μg/ml, and the IC50 for the single mutant (M428L) and the double mutant (T250Q/M428L) is less than 1 μg/ml.

The binding of OST577-IgG2M3 and some of its mutants to rhesus FcRn were tested in competitive binding experiments. As summarized in Table 7, the IC50 for the wild-type OST577-IgG2M3 antibody is ~15 μg/ml, whereas the IC50 for each of the single mutants (T250Q and M428L) and the double mutant (T250Q/M428F) is ~2-4 μg/ml, and the IC50 for the double mutant (T250Q/M428L) is less than 1 μg/ml. The binding of OST577-IgG1 and some of its mutants to rhesus FcRn were also tested in competitive binding experiments. As summarized in Table 8, the IC50 for the wild-type OST577-IgG1 antibody is ~9 μg/ml, whereas the IC50 for the single mutant (T250Q) is ~3 μg/ml, and the IC50 for the single mutant (M428L) and the double mutant (T250Q/M428L) is less than 1 μg/ml.

TABLE 2

| Name[a] (IgG2M3) | n[b] | IC50 (μg/ml)[c] | Relative Binding[d] |
|---|---|---|---|
| Wild-type | 6 | 10.7 ± 4.6 | 1.0 |
| L314W | 2 | 20.2 ± 2.0 | 0.53 |
| L314Q | 2 | 32.0 ± 2.3 | 0.33 |
| L314A | 2 | 68.7 ± 2.1 | 0.16 |
| L314R | 2 | 102 ± 4 | 0.11 |
| T250E | 1 | 3.82 | 2.8 |
| T250S | 2 | 12.0 ± 0.9 | 0.89 |
| T250A | 2 | 13.3 ± 0.5 | 0.80 |
| T250V | 3 | 19.0 ± 1.8 | 0.56 |
| T250D | 1 | >210 | <0.050 |
| M428F | 2 | 3.40 ± 0.53 | 3.1 |
| M428G | 1 | 147 | 0.072 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated HuEP5C7-IgG2M3 in FSB, pH 6.0, as described in Example 6.
[d]Relative binding to human FcRn was calculated as the ratio of the IC50 value of the wild-type OST577-IgG2M3 to that of each of the mutants.

TABLE 3

| Name[a] (IgG2M3) | n[b] | IC50 (μg/ml)[c] | Relative Binding[d] |
|---|---|---|---|
| Wild-type | 3 | 9.40 ± 2.87 | 1.0 |
| T250E | 3 | 2.71 ± 1.16 | 3.5 |
| M428F | 3 | 2.97 ± 0.30 | 3.2 |
| T250E/M428F | 2 | 0.639 ± 0.094 | 15 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated HuEP5C7-IgG2M3 in FBB, pH 6.0, as described in Example 6.
[d]Relative binding to human FcRn was calculated as the ratio of the IC50 value of the wild-type OST577-IgG2M3 to that of each of the mutants.

TABLE 4

| Name[a] (IgG2M3) | n[b] | IC50 (μg/ml)[c] | Relative Binding[d] |
|---|---|---|---|
| Wild-type | 3 | 11.9 ± 2.5 | 1.0 |
| T250Q | 3 | 4.20 ± 1.02 | 2.8 |
| M428L | 3 | 1.79 ± 0.69 | 6.7 |
| T250Q/M428F | 3 | 1.50 ± 0.31 | 8.0 |
| T250Q/M428L | 3 | 0.430 ± 0.084 | 28 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated OST577-IgG2M3 in FBB, pH 6.0, as described in Example 6.
[d]Relative binding to human FcRn was calculated as the ratio of the IC50 value of the wild-type OST577-IgG2M3 to that of each of the mutants.

TABLE 5

| Name[a] (IgG1) | n[b] | IC50 (μg/ml)[c] | Relative Binding[d] |
|---|---|---|---|
| Wild-type | 6 | 13.9 ± 4.2 | 1.0 |
| T250E | 3 | 5.26 ± 0.87 | 2.6 |
| M428F | 5 | 3.44 ± 1.22 | 4.0 |
| T250E/M428F | 4 | 0.990 ± 0.786 | 14 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated OST577-IgG1 in FBB, pH 6.0, as described in Example 6.
[d]Relative binding to human FcRn was calculated as the ratio of the IC50 value of the wild-type OST577-IgG1 to that of each of the mutants.

TABLE 6

| Name[a] (IgG1) | n[b] | IC50 (μg/ml)[c] | Relative Binding[d] |
|---|---|---|---|
| Wild-type | 5 | 10.3 ± 2.8 | 1.0 |
| T250Q | 5 | 3.14 ± 0.86 | 3.3 |
| M428L | 5 | 0.896 ± 0.304 | 11 |
| T250Q/M428L | 5 | 0.351 ± 0.144 | 29 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated OST577-IgG1 in FBB, pH 6.0, as described in Example 6.
[d]Relative binding to human FcRn was calculated as the ratio of the IC50 value of the wild-type OST577-IgG1 to that of each of the mutants.

TABLE 7

| Name[a] (IgG2M3) | n[b] | IC50 (μg/ml)[c] | Relative Binding[d] |
|---|---|---|---|
| Wild-type | 3 | 14.8 ± 2.7 | 1.0 |
| T250Q | 3 | 4.05 ± 0.24 | 3.6 |
| M428L | 3 | 1.92 ± 0.46 | 7.7 |
| T250Q/M428F | 3 | 1.77 ± 0.60 | 8.4 |
| T250Q/M428L | 3 | 0.554 ± 0.052 | 27 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated OST577-IgG2M3 in FBB, pH 6.0, as described in Example 6.
[d]Relative binding to rhesus FcRn was calculated as the ratio of the IC50 value of the wild-type OST577-IgG2M3 to that of each of the mutants.

TABLE 8

| Name[a] (IgG1) | n[b] | IC50 (μg/ml)[c] | Relative Binding[d] |
|---|---|---|---|
| Wild-type | 3 | 8.86 ± 0.52 | 1.0 |
| T250Q | 3 | 2.97 ± 0.59 | 3.0 |
| M428L | 3 | 0.629 ± 0.060 | 14 |
| T250Q/M428L | 3 | 0.236 ± 0.013 | 37 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated OST577-IgG1 in FBB, pH 6.0, as described in Example 6.
[d]Relative binding to rhesus FcRn was calculated as the ratio of the IC50 value of the wild-type OST577-IgG1 to that of each of the mutants.

Example 7

This example describes confirmation of the properties of the IgG2M3 and IgG1 mutants in FcRn binding.

Direct Binding Assay:

Purified OST577-IgG2M3 antibodies were tested for binding to human FcRn on cell line NS0 HuFcRn (memb), clone 7-3, or to untransfected NS0 cells in FBB at pH 6.0. Approximately $2\times10^5$ cells/test were washed once in FBB, pH 8.0, and once in FBB, pH 6.0, then resuspended in 100 μl of antibody at a concentration of 11 μg/ml in FBB, pH 6.0. The cells were incubated with antibody for 1 hour on ice, washed twice in FBB, pH 6.0, and resuspended in 25 μl of goat anti-human IgG RPE-conjugated antibody (Southern Biotechnology Associates, Inc.) diluted to 5 μg/ml in FBB, pH 6.0. After incubation for 30 minutes on ice in the dark, the cells were washed twice in FBB, pH 6.0, and resuspended in 1% formaldehyde. Samples were analyzed for antibody binding to FcRn by FACS™ using a FACScan flow cytometer (BD® Biosciences). Mean channel fluorescence (MCF) of each mutant was plotted using Excel (Microsoft® Corporation).

Competitive Binding Assay at 37° C.:

A dilution series of each purified OST577-IgG2M3 antibody was competed against biotinylated OST577-IgG2M3 antibody for binding to human FcRn on cell line NS0 HuFcRn (memb), clone 7-3 at 37° C. Approximately $2\times10^5$ cells/test were washed once in FBB, pH 8.0, and once in FBB, pH 6.0, then resuspended in 100 μl of pre-mixed biotinylated OST577-IgG2M3 antibody (10 μg/ml) and OST577-IgG2M3 competitor antibody (twofold serial dilutions, from 208 μg/ml to 0.102 μg/ml) in FBB, pH 6.0. The cells were incubated with the antibody mixture for 1 hour at 37° C., washed twice in FBB, pH 6.0, and resuspended in 25 μl of streptavidin-RPE conjugate (BioSource International) diluted to 2.5 μg/ml in FBB, pH 6.0. After incubation for 30 minutes in the dark, the cells were washed twice in FBB, pH 6.0, and resuspended in 1% formaldehyde. Samples were analyzed for antibody binding to FcRn by FACS™ using a FACScan flow cytometer (BD® Biosciences). Mean channel fluorescence (MCF) was plotted against competitor concentration, and IC50 values were calculated using GraphPad Prism® (GraphPad™ Software).

pH-Dependent Binding and Release Assay:

Purified OST577-IgG2M3 and OST577-IgG1 mutant antibodies were compared to the respective wild-type antibodies for binding to human FcRn and then released at various pH values in single-point binding and release assays using cell line NS0 HuFcRn (memb), clone 7-3. Approximately $2\times10^5$ cells/test were washed once in FBB, pH 8.0, and once in FBB, pH 6.0, then resuspended in 100 μl of purified antibody (10 μg/ml) in FBB, pH 6.0. The cells were incubated for 1 hour on ice, washed twice in FBB, pH 6.0, 6.5, 7.0, 7.5, or 8.0, and resuspended in 25/t of goat $F(ab')_2$ anti-human IgG FITC-conjugated antibody (Southern Biotechnology Associates, Inc.) diluted to 1.25 μg/ml in FBB of the appropriate pH. After incubation for 30 minutes on ice in the dark, the cells were washed twice in FBB of the appropriate pH, and resuspended in 1% formaldehyde. Samples were analyzed for antibody binding to FcRn by FACS™ using a FACSCalibur flow cytometer (BD® Biosciences). Mean channel fluorescence (MCF) of each mutant was plotted using Excel (Microsoft® Corporation).

Purified OST577-IgG2M3 and OST577-IgG1 mutant antibodies were compared to the respective wild-type antibodies for binding to rhesus FcRn and then released at various pH values in single-point binding and release assays using cell line NS0 RhFcRn, clone R-3, as described above.

Figure 13:
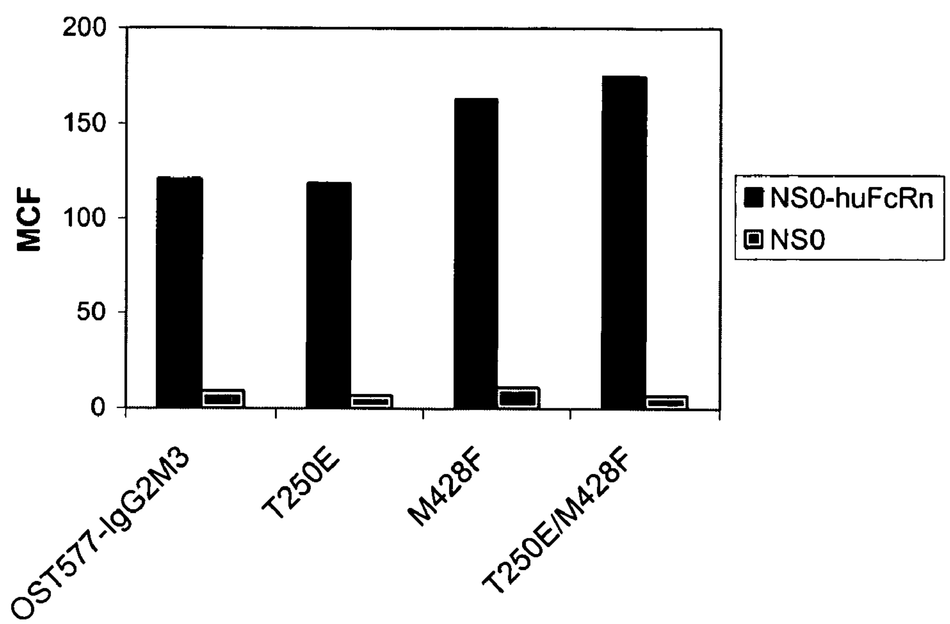
FIG. 13. Antibody Binding to Cells Transfected with Human FcRn versus Untransfected Cells. The binding of the wild-type or mutant OST577-IgG2M3 antibodies to human FcRn on transfected NS0 cells or to untransfected NS0 cells in FBB, at pH 6.0, was analyzed by flow cytometry, as described in Example 7.

Results:

The binding properties of wild-type OST577-IgG2M3 or OST577-IgG1 antibodies and their various mutants to human FcRn were confirmed using a transfected NS0 cell line stably expressing human FcRn on its surface. To confirm that binding of the mutant antibodies was specific for human FcRn on the transfected NS0 cell line, rather than occurring via some other receptor or by an unknown mechanism, the antibodies were tested for binding to untransfected NS0 cells versus a transfected NS0 cell line stably expressing human FcRn. As described above, the cells were incubated with a sub-saturating concentration of antibody in FBB, pH 6.0, and binding was analyzed by FACS™. As shown in FIG. 13, the results indicated that there was no apparent binding to the parent NS0 cell line, suggesting that the antibodies bind specifically to the transfected cells via human FcRn.

Figure 14:
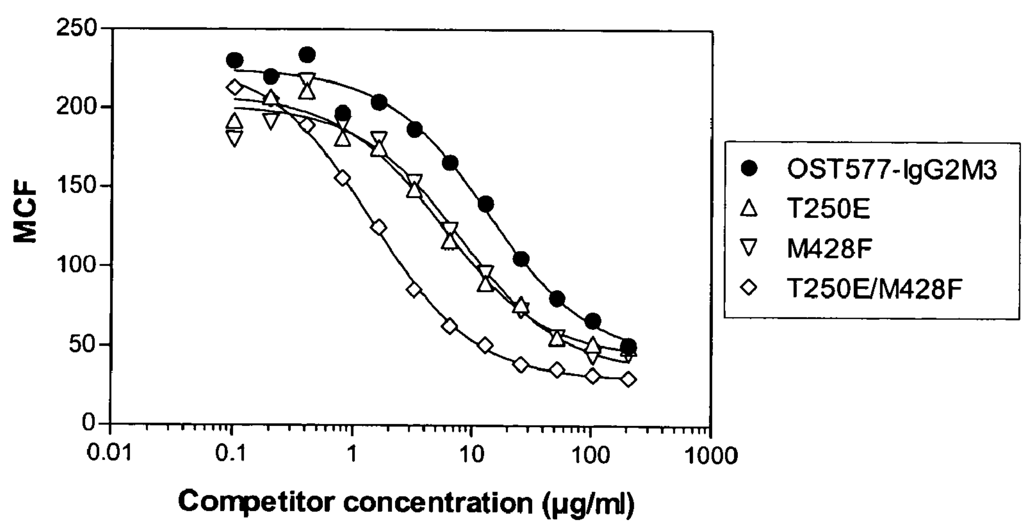
FIG. 14. Competitive Binding Assay of OST577-IgG2M3 Wild-Type and Mutant Antibodies to Human FcRn at 37° C. The binding of biotinylated OST577-IgG2M3 antibody to human FcRn on transfected NS0 cells in the presence of increasing concentrations of the wild-type or mutant OST577-IgG2M3 competitor antibodies in FBB, at pH 6.0, was detected with streptavidin-conjugated RPE and analyzed by flow cytometry, as described in Example 7. All incubations were done at 37° C.

To confirm that each of the mutants generated in the present invention behaved in a physiologically relevant manner, the effects of temperature and pH on binding to human FcRn were examined more closely. Because the initial competitive binding assays were performed at 4° C., the experiments were repeated at the more physiologically relevant temperature of 37° C. to show that the mutants were still active at this temperature. As described above, increasing concentrations of unlabeled competitor antibodies were incubated with cells expressing human FcRn in the presence of a sub-saturating concentration of labeled OST577-IgG2M3 antibody at 37° C. in FBB, pH 6.0. As shown in FIG. 14, the results indicated that the antibodies maintained their relative pattern of binding to human FcRn at 37° C.

Figure 15:
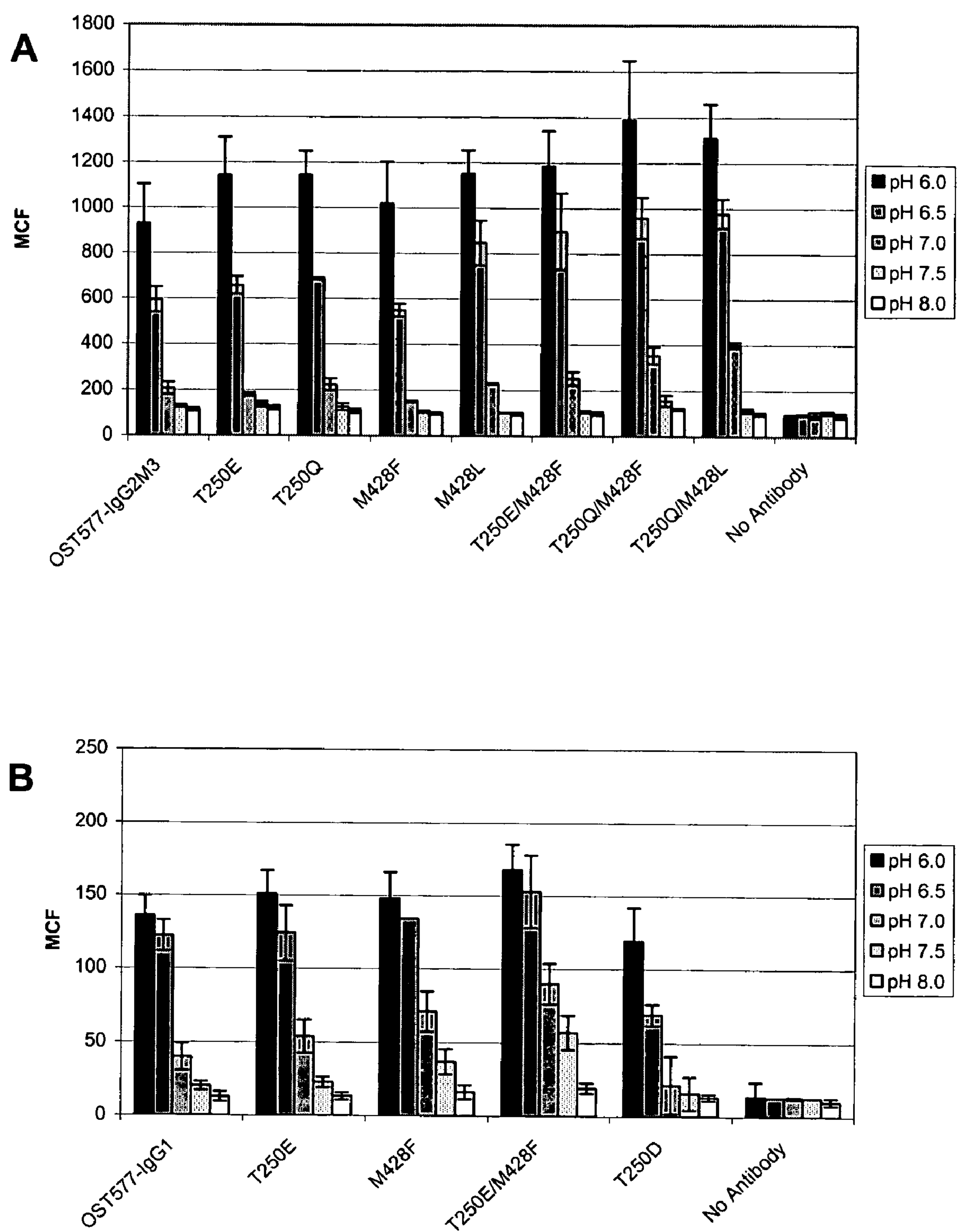
FIG. 15A. pH-Dependent Binding and Release of OST577-IgG2M3 Wild-Type and Mutant Antibodies to Human FcRn. The binding and release of the wild-type or mutant OST577-IgG2M3 antibodies to human FcRn on transfected NS0 cells in FBB, at pH 6.0, 6.5, 7.0, 7.5, or 8.0, was analyzed by flow cytometry, as described in Example 7.
FIG. 15B. pH-Dependent Binding and Release of OST577-IgG1 Wild-Type and Mutant Antibodies to Human FcRn. The binding and release of the wild-type or mutant OST577-IgG1 antibodies to human FcRn on transfected NS0 cells in FBB, at pH 6.0, 6.5, 7.0, 7.5, or 8.0, was analyzed by flow cytometry, as described in Example 7.
FIG. 15C. pH-Dependent Binding and Release of OST577-IgG1 Wild-Type and Mutant Antibodies to Human FcRn. The binding and release of the wild-type or mutant OST577-IgG1 antibodies to human FcRn on transfected NS0 cells in FBB, at pH 6.0, 6.5, 7.0, 7.5, or 8.0, was analyzed by flow cytometry, as described in Example 7.
FIG. 15D. pH-Dependent Binding and Release of OST577-IgG2M3 Wild-Type and Mutant Antibodies to Rhesus FcRn. The binding and release of the wild-type or mutant OST577-IgG2M3 antibodies to rhesus FcRn on transfected NS0 cells in FBB, at pH 6.0, 6.5, 7.0, 7.5, or 8.0, was analyzed by flow cytometry, as described in Example 7.
FIG. 15E. pH-Dependent Binding and Release of OST577-IgG1 Wild-Type and Mutant Antibodies to Rhesus FcRn. The binding and release of the wild-type or mutant OST577-IgG1 antibodies to rhesus FcRn on transfected NS0 cells in FBB, at pH 6.0, 6.5, 7.0, 7.5, or 8.0, was analyzed by flow cytometry, as described in Example 7.
Figure 15:
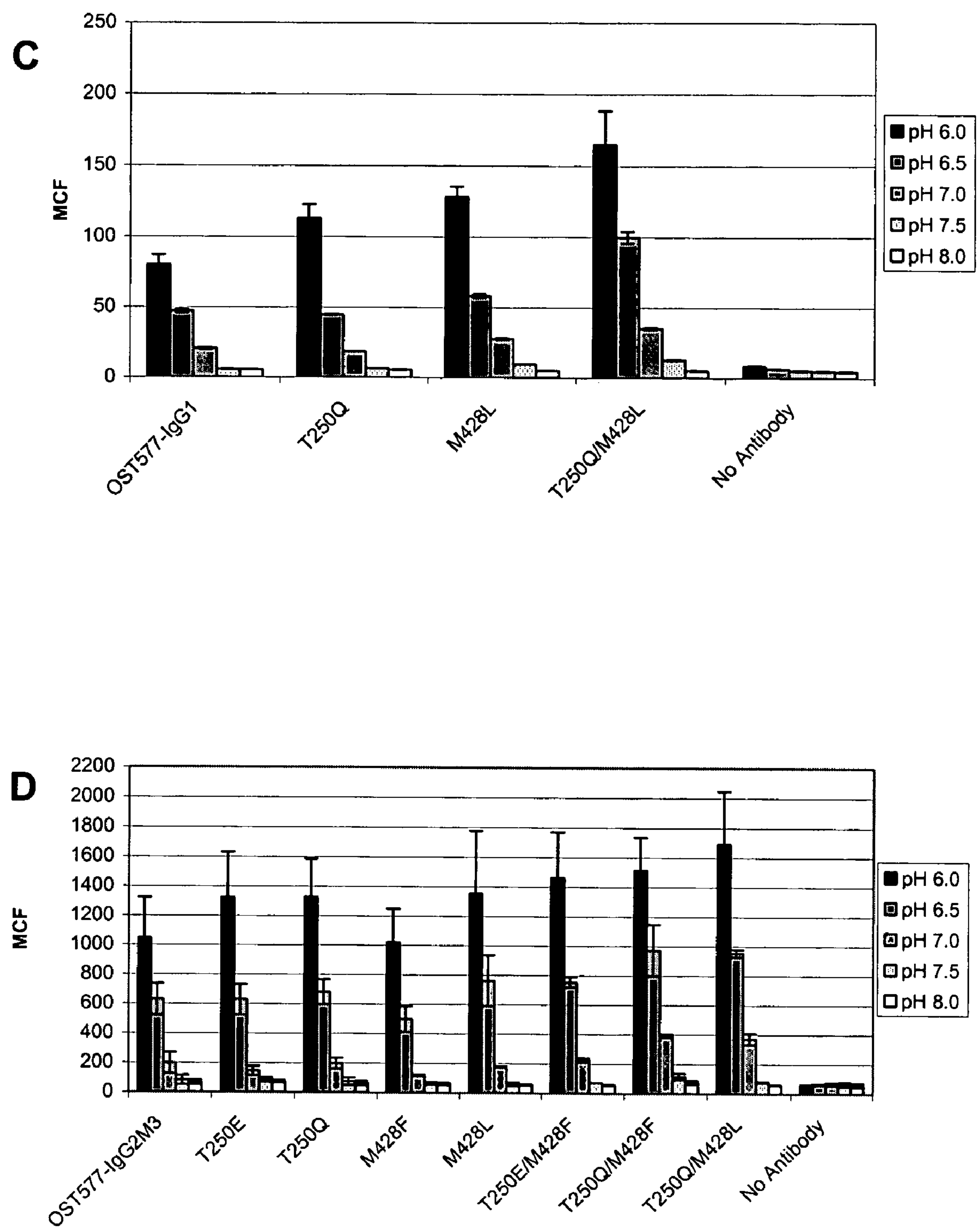
Figure 15:
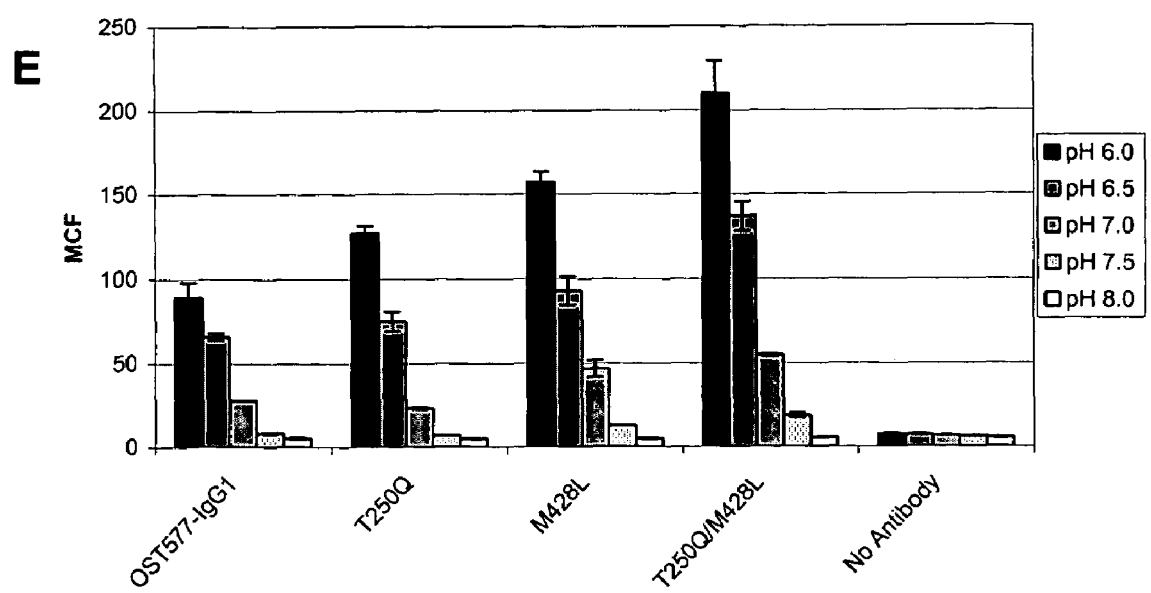

The binding of IgG to FcRn is known to be pH-dependent: IgG binds strongly to FcRn at pH 6.0 but weakly at pH 8.0. In order to engineer mutant antibodies with longer serum half-lives, it is desirable to increase binding to FcRn at pH 6.0, while retaining pH-dependent release from FcRn at pH 8.0. To confirm that binding was pH-dependent, the antibodies were tested for binding to a transfected NS0 cell line stably expressing human FcRn and then released at pH values ranging from pH 6.0 to pH 8.0. As described above, the cells were incubated with a sub-saturating concentration of antibody in FBB, pH 6.0, washed with FBB, pH 6.0, 6.5, 7.0, 7.5, or 8.0, and binding was analyzed by FACS™. As shown in FIG. 15A, the results indicated that the modified OST577-IgG2M3 antibodies having the T250E, T250Q, M428F, M428L, T250E/M428F, T250Q/M428F, or T250Q/M428L mutations all showed strong binding to human FcRn at pH 6.0, with diminishing binding as the pH values increased to pH 8.0. As shown in FIG. 15B, the results indicated that the modified OST577-IgG1 antibodies having the T250E, M428F, or T250E/M428F mutations all showed strong binding to human FcRn at pH 6.0, with diminishing binding as the pH values increased to pH 8.0. The OST577-IgG1 antibody having the T250D mutation showed weaker binding (compared to wild-type) to human FcRn at pH 6.0, with diminishing binding as the pH values increased to pH 8.0. As shown in FIG. 15C, the results indicated that the modified OST577-IgG1 antibodies having the T250Q, M428L, or T250Q/M428L mutations all showed strong binding to human FcRn at pH 6.0, with diminishing binding as the pH values increased to pH 8.0. These results indicated that the binding of the antibodies to human FcRn was indeed pH-dependent.

Similarly, the antibodies were tested for binding to a transfected NS0 cell line stably expressing rhesus FcRn and then released at pH values ranging from pH 6.0 to pH 8.0. As shown in FIG. 15D, the results indicated that the modified OST577-IgG2M3 antibodies having the T250E, T250Q, M428F, M428L, T250E/M428F, T250Q/M428F, or T250Q/M428L mutations all showed strong binding to rhesus FcRn at pH 6.0, with diminishing binding as the pH values increased to pH 8.0. As shown in FIG. 15E, the results indicated that the modified OST577-IgG1 antibodies having the T250Q, M428L, or T250Q/M428L mutations all showed strong binding to rhesus FcRn at pH 6.0, with diminishing binding as the pH values increased to pH 8.0. These results indicated that the binding of the antibodies to rhesus FcRn was also pH-dependent.

Example 8

This example describes confirmation of additional properties of the IgG2M3 and IgG1 mutants.

Cell Culture:

Human Burkitt's lymphoma cell line Raji (American Type Culture Collection) was maintained in RPMI 1640 with L-glutamine (BioWhittaker™) containing 10% FBS (HyClone®) and 1% penicillin-streptomycin (Life Technologies®).

Antigen Binding Assays:

The antigen binding activity of OST577 wild-type and mutant antibodies was confirmed in a competitive binding ELISA. Immulon™ 2 plates (DYNEX® Technologies) were coated overnight at 4° C. with 1.0 μg/ml of recombinant Hepatitis B Surface Antigen (HBsAg) (Advanced ImmunoChemical, Inc., Long Beach, Calif.). The next day, the plates were washed with EWB and blocked with 300 μl/well of SuperBlock® Blocking Buffer in TBS (Pierce Chemical Company) for 30 minutes at room temperature. The plates were washed with EWB, and premixed biotinylated OST577-IgG2M3 antibody (0.25 μg/ml) and competitor OST577-IgG2M3 antibody (twofold serial dilutions from 33 μg/ml to 0.033 μg/ml) or premixed biotinylated OST577-IgG1 antibody (0.25 μg/ml) and competitor OST577-IgG1 antibody (twofold serial dilutions from 67 μg/ml to 0.067 μg/ml) in 100 μl of EB were added to each well. The plates were incubated for 1 hour at room temperature, then washed with EWB, and 100 μl/well of streptavidin-HRP conjugate (Pierce Chemical Company) was added at 1 μg/ml in EB. After incubation for 30 minutes at room temperature, the plates were washed with EWB, followed by addition of 100 μl/well of ABTS Peroxidase Substrate/Peroxidase Solution B (Kirkegaard & Perry Laboratories). The reaction was stopped with 100 μl/well of 2% oxalic acid, and the absorbance at 415 nm was measured using a VERSAmax™ microtitre plate reader (Molecular Devices® Corporation).

The antigen binding activity of Hu1D10-IgG2M3 wild-type and mutant antibodies was confirmed in a FACS™ binding assay using Raji cells, which express an allele of the HLA-DR β chain that is recognized by Hu1D10 (Kostelny et al. (2001), op. cit.). Approximately $2.5\times10^5$ cells/test were washed once in FBB, pH 7.4, and resuspended in 140 μl of Hu1D10-IgG2M3 antibody (threefold serial dilutions from 60 μg/ml to 0.027 μg/ml) in FBB, pH 7.4. The cells were incubated with antibody for 1 hour on ice, washed twice in FBB, pH 7.4, and resuspended in 25 μl of goat $F(ab')_2$ anti-human kappa RPE-conjugated antibody (Southern Biotechnology Associates, Inc.) diluted to 10 μg/ml in FBB, pH 7.4. After incubation for 30 minutes on ice in the dark, the cells were washed twice in FBB, pH 7.4, and resuspended in 1% formaldehyde. Samples were analyzed for antibody binding to the HLA-DR β chain allele by FACS™ using a FACSCalibur flow cytometer (BD® Biosciences).

Similarly, the antigen binding activity of Hu1D10-IgG1 wild-type and mutant antibodies was confirmed in a FACS™ binding assay using Raji cells. Approximately $2.0\times10^5$ cells/test were washed once in FBB, pH 7.4, and resuspended in 100 μl of Hu1D10-IgG1 antibody (twofold serial dilutions from 25 μg/ml to 12.5 μg/ml, then threefold serial dilutions from 12.5 μg/ml to 0.0020 μg/ml) in FBB, pH 7.4. A dilution series of HuFd79-IgG1 antibody (Co et al., Proc. Natl. Acad. Sci. 88:2869-2873 (1991)) was prepared as described above and used as a negative control. The cells were incubated with antibody for 1 hour on ice, washed twice in FBB, pH 7.4, and resuspended in 25 μl of goat $F(ab')_2$ anti-human IgG FITC-conjugated antibody (Southern Biotechnology Associates, Inc.) diluted to 20 μg/ml in FBB, pH 7.4. After incubation for 30 minutes on ice in the dark, the cells were washed twice in FBB, pH 7.4, and resuspended in 1% formaldehyde. Samples were analyzed for antibody binding to the HLA-DR β chain allele by FACS™ using a FACSCalibur flow cytometer (BD® Biosciences).

ADCC Assay:

The antibody-dependent cell-mediated cytotoxicity (ADCC) activity of Hu1D10 wild-type and mutant antibodies was confirmed by measuring lactate dehydrogenase (LDH) release using human peripheral blood mononuclear cells (PBMC) as effectors and Raji cells as targets following a published method (Shields et al., op. cit.). PBMC were prepared from fresh whole blood using a Ficoll-Paque® Plus gradient (Amersham Biosciences™ Corporation) and resuspended at a density of $8\times10^6$ cells/ml in assay medium (RPMI 1640, 1% BSA). Raji cells were washed three times in assay medium and resuspended at a density of $0.4\times10^6$ cells/ml in assay medium. Hu1D10 wild-type and mutant antibodies were diluted to 4 μg/ml, 0.25 μg/ml, and 0.016 μg/ml in assay medium. Raji cells (50 μl/well) and Hu1D10 antibody (50 μl/well, i.e., 200 ng/test, 12.5 ng/test, or 0.8 ng/test) were combined in the wells of a Falcon 96-well U-bottom assay plate (BD® Biosciences) and incubated for 30 minutes at room temperature. PBMC (100 μl/well, i.e., 40:1 effector/target ratio) were added to the opsonized cells and incubated for 4 hours at 37° C. in a $CO_2$ incubator. Antibody independent cell-mediated cytotoxicity (AICC) was measured by incubating effector and target cells in the absence of antibody. Spontaneous release was measured by incubating target cells ($SR_{target}$) or effector cells ($SR_{effector}$)

in the absence of antibody. Maximum release (MR) was measured by adding 2% Triton X-100 to target cells. The plates were gently centrifuged, and the supernatants (100 μl/well) were transferred to a Falcon 96-well flat-bottom plate. LDH activity was measured by incubating the supernatants with 100 μl/well of LDH reaction mixture from the Cytotoxicity Detection Kit (Roche Diagnostics Corporation) for 30 minutes at room temperature. The reaction was stopped with 50 μl/well of 1 N HCl, and the absorbance at 490 nm was measured using a VERSAmax™ microtitre plate reader (Molecular Devices® Corporation). The percent cytotoxicity was calculated as (LDH release$_{sample}$−SR$_{effector}$−SR$_{target}$)/(MR$_{target}$−SR$_{target}$)×100.

Figure 16:
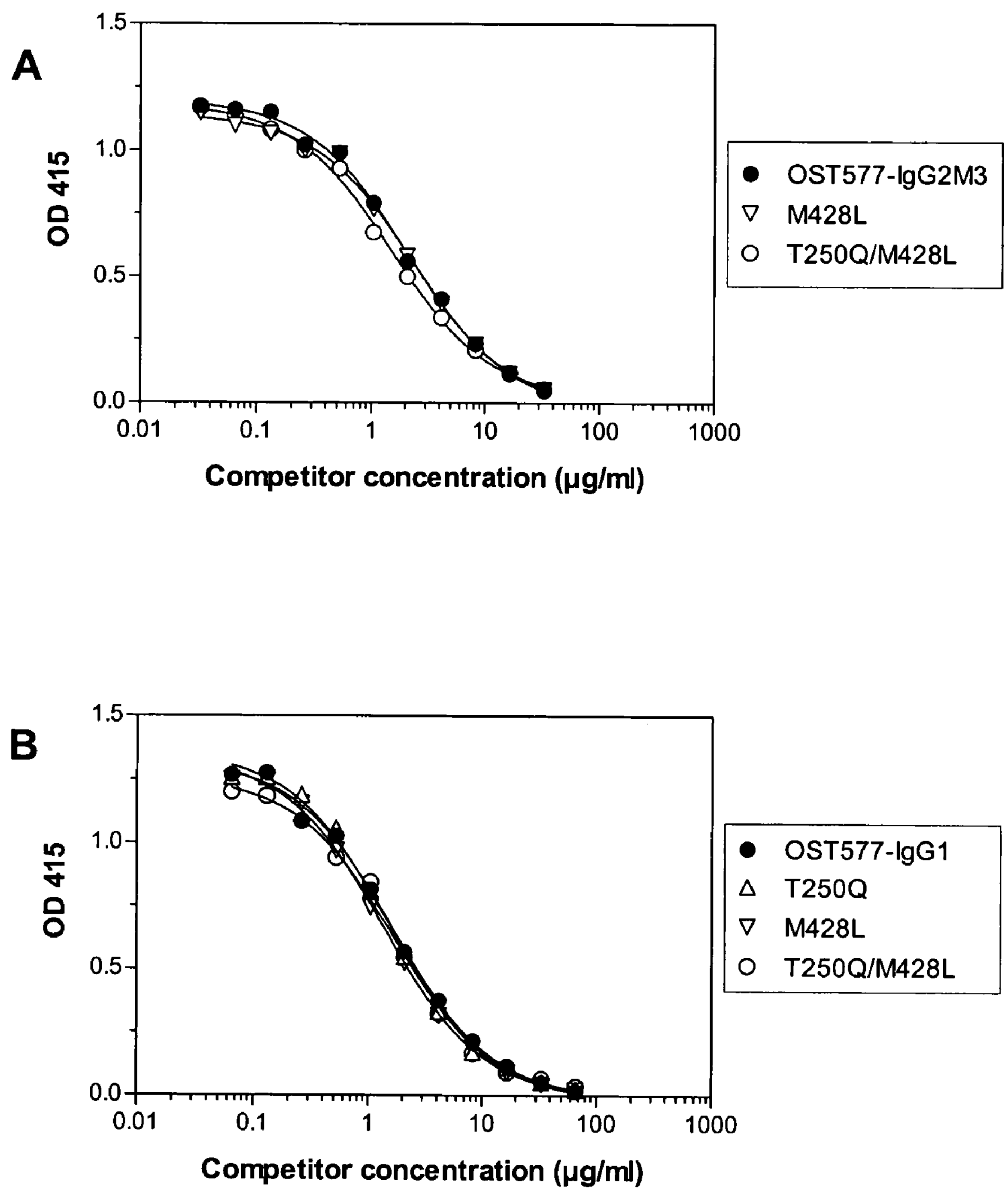
FIG. 16A. Competitive Binding Assay of OST577-IgG2M3 Wild-Type and Mutant Antibodies to HbsAg. The binding of the wild-type or mutant OST577-IgG2M3 antibodies to HBsAg was analyzed in an ELISA competition, as described in Example 8.
FIG. 16B. Competitive Binding Assay of OST577-IgG1 Wild-Type and Mutant Antibodies to HbsAg. The binding of the wild-type or mutant OST577-IgG1 antibodies to HBsAg was analyzed in an ELISA competition, as described in Example 8.

Results:

The antigen binding properties of wild-type and mutant OST577 and Hu1D10 antibodies to their respective antigens were confirmed using appropriate binding assays. As described above, the binding of OST577 antibodies to HBsAg was determined in a competitive ELISA. As shown in FIG. 16A, the binding of the wild-type and mutant OST577-IgG2M3 antibodies to HBsAg was essentially identical. Similarly, as shown in FIG. 16B, the binding of the wild-type and mutant OST577-IgG1 antibodies to HBsAg was essentially identical.

Figure 17:
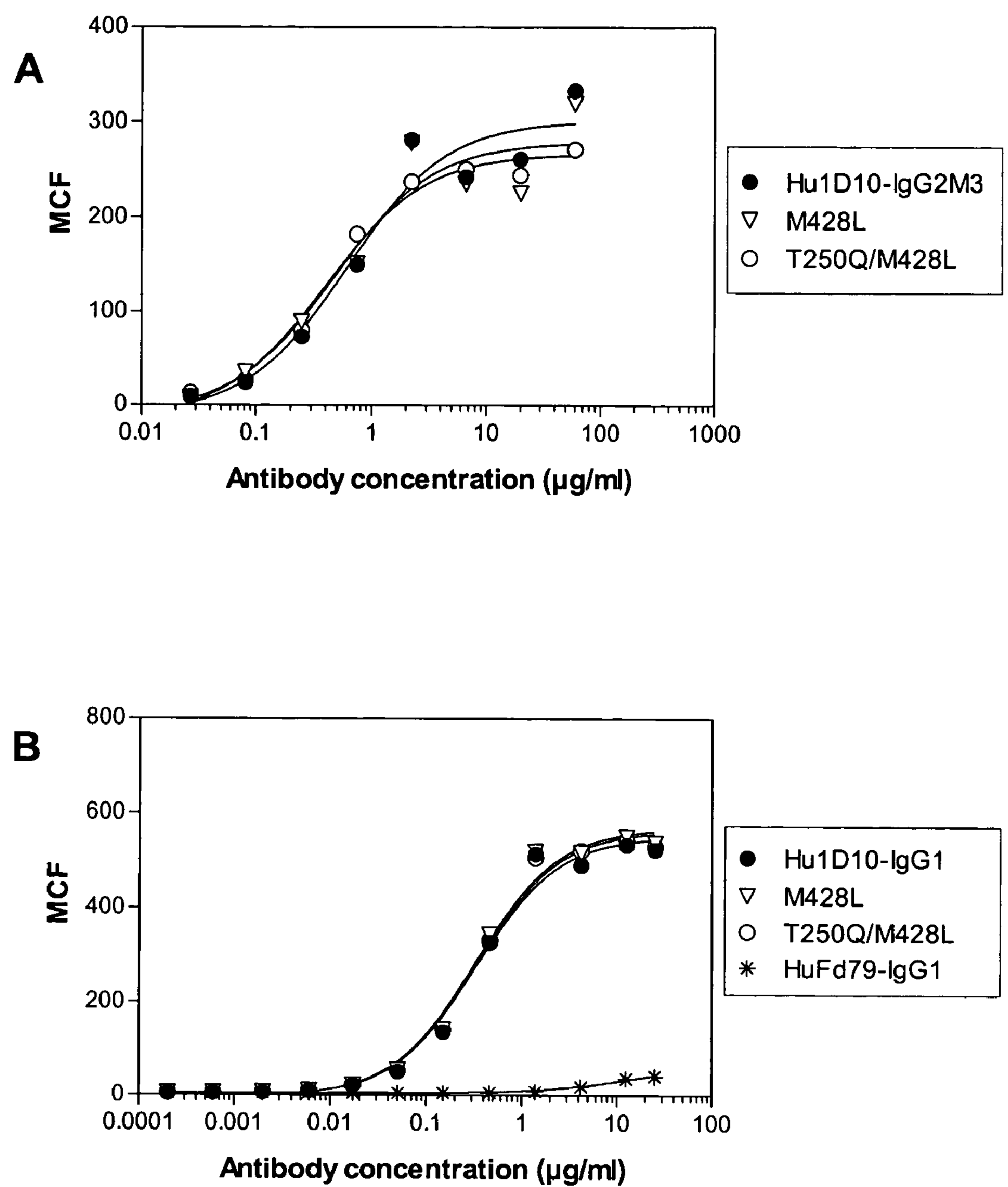
FIG. 17A. Binding Assay of Hu1D10-IgG2M3 Wild-Type and Mutant Antibodies to HLA-DR β Chain Allele. The binding of the wild-type or mutant Hu1D10-IgG2M3 antibodies to Raji cells was analyzed in a FACS binding assay, as described in Example 8.
FIG. 17B. Binding Assay of Hu1D10-IgG1 Wild-Type and Mutant Antibodies to HLA-DR β Chain Allele. The binding of the wild-type or mutant Hu1D10-IgG1 antibodies to Raji cells was analyzed in a FACS binding assay, as described in Example 8.

As described above, the binding of Hu1D10 antibodies to an allele of the HLA-DR β chain was determined in a FACS binding assay. As shown in FIG. 17A, the binding of the wild-type and mutant Hu1D10-IgG2M3 antibodies to the HLA-DR β chain allele was essentially identical. Similarly, as shown in FIG. 17B, the binding of the wild-type and mutant Hu1D10-IgG1 antibodies to the HLA-DR β chain allele was essentially identical. These results indicate that, as expected, the mutations described at positions 250 and 428 do not affect antigen binding.

Figure 18:
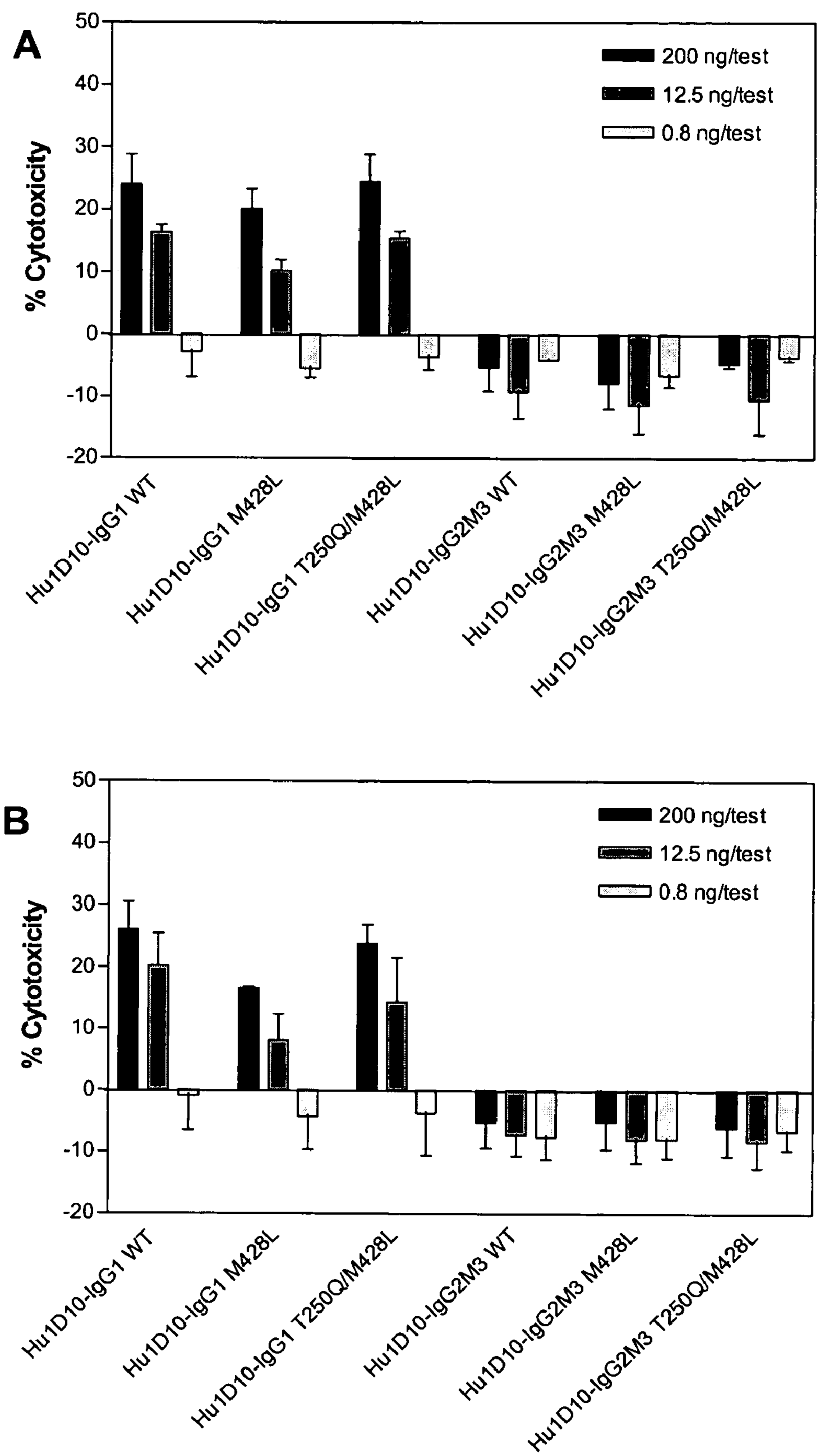
FIG. 18A. ADCC Assay of Hu1D10-IgG1 and Hu1D10-IgG2M3 Wild-Type and Mutant Antibodies Using PBMC From a 158V/V Donor. The ADCC activity of the wild-type or mutant Hu1D10-IgG1 and Hu1D10-IgG2M3 antibodies on Raji cells was determined using PBMC isolated from a donor carrying homozygous 158V/V FcγRIII alleles, as described in Example 8.
FIG. 18B. ADCC Assay of Hu1D10-IgG1 and Hu1D10-IgG2M3 Wild-Type and Mutant Antibodies Using PBMC From a 158F/F Donor. The ADCC activity of the wild-type or mutant Hu1D10-IgG1 and Hu1D10-IgG2M3 antibodies on Raji cells was determined using PBMC isolated from a donor carrying homozygous 158F/F FcγRIII alleles, as described in Example 8.

The ADCC activity of Hu1D10 wild-type and mutant antibodies was confirmed in an LDH release assay using human PBMC as effectors and Raji cells as targets. As shown in FIG. 18A, using a donor carrying homozygous 158 V/V FcγRIII alleles, the ADCC activity of the double mutant (T250Q/M428L) Hu1D10-IgG1 antibody was very similar to that of the wild-type antibody while the ADCC activity of the single mutant (M428L) Hu1D10-IgG1 antibody was slightly diminished compared to the wild-type antibody. As expected, the wild-type and mutant Hu1D10-IgG2M3 antibodies lacked ADCC activity. Similarly, as shown in FIG. 18B, using a donor carrying homozygous 158 F/F FcγRIII alleles, the ADCC activity of the double mutant (T250Q/M428L) Hu1D10-IgG1 antibody was very similar to that of the wild-type antibody while the ADCC activity of the single mutant (M428L) Hu1D10-IgG1 antibody was somewhat diminished compared to the wild-type antibody. The wild-type and mutant Hu1D10-IgG2M3 antibodies lacked ADCC activity. These results indicate that the T250Q/M428L mutation described in this invention does not affect the ADCC activity of the IgG1 form of the antibody, while the M428L mutation slightly reduces the ADCC activity of the IgG1 form. The mutations described at positions 250 and 428 do not affect the ADCC activity of the IgG2M3 form of the antibody.

Example 9

This example describes in vitro and in vivo serum half-life assays.

Human IgG antibodies with higher (or lower) affinity to FcRn in vitro are expected to have longer (or shorter) serum half-life in vivo, respectively. The affinity of human IgG mutants to FcRn may be measured in vitro by various methods such as surface plasmon resonance (SPR) using soluble FcRn conjugated to a suitable biosensor chip, or by performing a competitive binding experiment using FcRn expressed on the surface of transfected cells. The FcRn used in the in vitro affinity experiments may be of murine, rhesus, or human origin. The serum half-life of human IgG mutants with the desired properties may be measured in vivo by injecting suitable experimental animals (e.g., mice or monkeys) or humans with a dose of antibody in the range 0.1-10 mg of antibody per kg of body weight, then withdrawing serum samples at various time intervals spanning the expected serum half-life of the antibody, and assaying the samples for the presence of intact IgG by a suitable technique such as ELISA.

Rhesus Pharmacokinetics Study:

A non-GLP pharmacokinetics study entitled "Pharmacokinetic Comparison of Three Variants of OST577" was conducted at the California National Primate Research Center (CNPRC) at the University of California, Davis. Twelve male rhesus macaques were randomized by weight and assigned to one of three study groups. The four animals comprising each study group each received a single intravenous dose of wild-type or one of two variants of OST577 at 1 mg/kg administered over fifteen minutes. The OST577 antibodies were wild-type OST577-IgG2M3, a variant of OST577-IgG2M3 containing the single mutation M428L, and a variant of OST577-IgG2M3 containing the double mutation T250Q/M428L. All three antibodies were expressed by transfection of Sp2/0 cells and purified as described in Example 5.

Blood samples were drawn prior to dosing on day 0, at 1 and 4 hours after dosing, and at 1, 7, 14, 21, 28, 42, and 56 days. At each time point, 4 mls of blood was drawn from a saphenous vein, serum was prepared, and 2 aliquots were frozen and maintained at −20° C. until use. For serum chemistry and hematology determinations, blood samples were drawn 16 days prior to the study, prior to dosing on day 0, and at the conclusion of the study on day 56.

ELISA:

The concentration of the OST577-IgG2M3 antibodies in rhesus serum samples was determined by ELISA using a qualified assay. Pooled normal rhesus serum (PNRS) was obtained from the CNPRC. The same lot of PNRS was used to prepare calibrators, positive serum controls, and for pre-dilution of rhesus serum samples. Calibrators were prepared by standard dilution of OST577-IgG2M3 in PNRS at 3000, 1500, 750, 375, 187.5, 93.75, 46.88, 23.44, and 0 ng/ml, equilibrated for 2 hours at room temperature, and frozen in aliquots at −20° C. Positive serum controls were prepared by spiking PNRS with OST577-IgG2M3 at 0.2 μg/ml for the low positive serum control, 0.4 μg/ml for the medium positive serum control, and 0.8 μg/ml for the high positive serum control, equilibrated for 2 hours at room temperature, and frozen in aliquots at −20° C. Predose serum samples from each animal were used as negative serum controls.

Immulon™ 2 plates (DYNEX® Technologies, Inc.) were coated overnight at 2-8° C. with 100 μl/well of a mouse anti-OST577-IgG1 idiotype monoclonal antibody (OST577-γ1 anti-id, Protein Design Labs™, Inc.) at 1.0 μg/ml in PBS. The next day the plates were washed three times with 300 μl/well of PBS/Tween (Phosphate Buffered Saline, 0.1% Tween 20), tapped dry on a paper towel, and blocked with 300 μl/well of SuperBlock® Blocking Buffer in PBS (Pierce Chemical Company) for 60±5 minutes at room temperature. Calibrators, positive and negative serum controls, and serum samples were thawed and brought to room temperature before use. Calibrators, and positive and negative serum controls were diluted 1:10 in SuperBlock® Blocking Buffer in PBS. Serum samples were appropriately pre-diluted (1:10 to 1:80) in PNRS, then diluted 1:10 in SuperBlock® Blocking Buffer in PBS. The plates were washed three times with 300 μl/well of PBS/Tween and tapped dry on a paper towel. Diluted calibrators, positive and negative serum controls, and serum samples were then added at 100 μl/well in duplicate wells and incubated for 60±5 minutes at room temperature. The plates were washed three times with 300 μl/well of PBS/Tween and tapped dry on a paper towel. Goat anti-human lambda light chain HRP-conjugated antibody (Southern Biotechnology Associates, Inc.) was prepared by 1:1000 dilution in PBS/BSA/Tween (Phosphate Buffered Saline, 0.5% Bovine Serum Albumin, 0.1% Tween 20), added at 100 μl/well, and incubated for 60±5 minutes at room temperature. The plates were washed three times with 300 μl/well of PBS/Tween and tapped dry on a paper towel. ABTS Peroxidase Substrate/Peroxidase Solution B (Kirkegaard & Perry Laboratories) was added at 100 μl/well, and incubated for 7±1 minutes. Development was stopped by addition of Substrate Stop Solution (2% Oxalic Acid) at 100 μl/well. Absorbance values at 415 nm were measured within 30 minutes after adding the Substrate Stop Solution using a VERSAmax™ microtitre plate reader (Molecular Devices® Corporation).

A calibration curve was prepared using the mean absorbance values obtained from the calibrators and fitting the data to a four parameter logistic regression curve using SOFTmax® PRO, version 4.0 (Molecular Devices® Corporation). The mean absorbance value for the negative serum control (i.e., predose sample mean for each animal) was subtracted from each absorbance value obtained for the calibrators. The positive serum control concentrations were determined after subtracting the mean absorbance value obtained for the negative serum control from each absorbance value obtained for the positive serum controls. Concentrations corresponding to the resulting mean absorbance values were derived by interpolation from the calibration curve. The concentrations of serum samples were determined by subtracting the mean absorbance value of the negative serum control from the absorbance value of each sample, averaging the resulting absorbance values, deriving the concentration corresponding to the mean absorbance value by interpolation from the calibration curve, and multiplying the resulting concentration by the pre-dilution factor, if any, to arrive at the final concentration for each sample.

The estimated quantitative range of the assay was 0.10-0.90 μg/ml. The assay was considered suitable when the following two conditions were met: (1) the mean back-calculated concentration of all three calibrators in the quantitative range was within 20% of their nominal value; and (2) the mean calculated results of four of six positive serum controls was within 30% of their nominal value, and at least one mean result from each concentration level was within 30% of its nominal value. Data from plates that did not meet the above criteria were rejected. Data from individual serum samples was rejected when any of the following three conditions was met: (1) the absorbance values in duplicate wells differed from each other by more than 40%; (2) the mean calculated concentration was below the lower limit of quantitation (LLOQ) of the assay (0.10 μg/ml); (3) the mean calculated concentration was above the upper limit of quantitation (ULOQ) of the assay (0.90 μg/ml).

Figure 19:
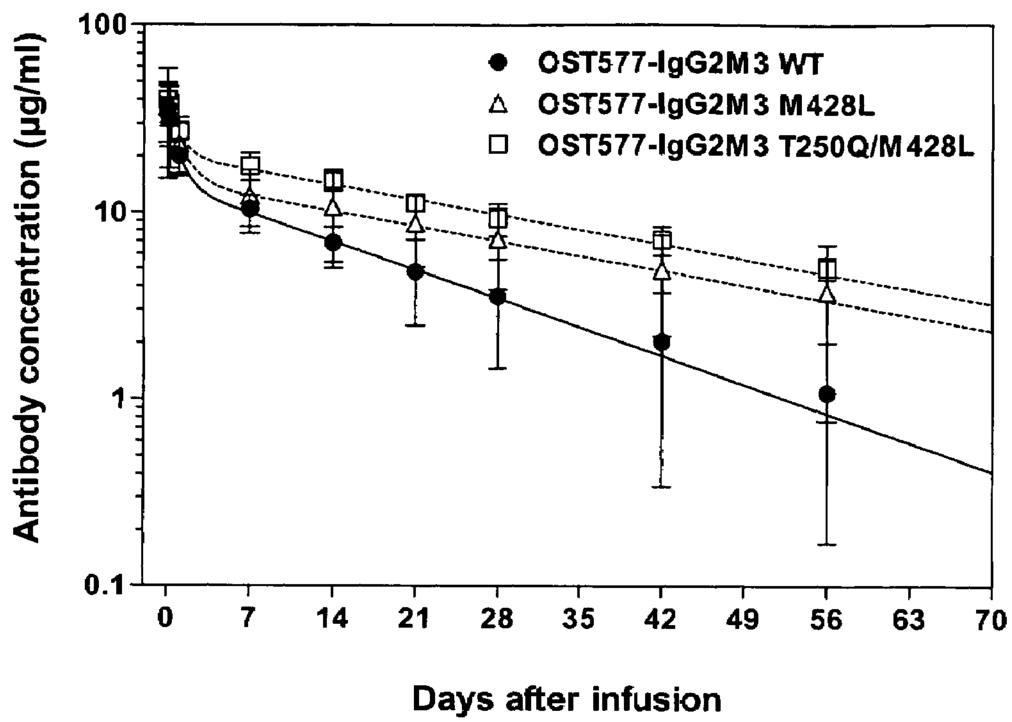
FIG. 19. Pharmacokinetics of OST577-IgG2M3 wild-type and variant antibodies in rhesus macaque. The observed and modeled mean serum concentrations (μg/ml) and standard deviations of OST577-IgG2M3 wild-type and variant antibodies administered by infusion at a dose of 1 mg/kg to groups of four rhesus macaques were plotted as a function of time (days after infusion), as described in Example 9.

Results:

The serum antibody concentration data were fitted with a two-compartment model using WinNonlin® Enterprise Edition, version 3.2 (Pharsight® Corporation, Mountain View, Calif.). The model assumes a first order distribution and first order elimination rate and fits the data well. The modeled data (simulated based on each group's geometric mean of the primary pharmacokinetic parameters) as well as the observed mean serum antibody concentration (μg/ml) and the standard deviation for each group of four animals were plotted as a function of time (days after infusion) using GraphPad Prism®, version 3.02 (GraphPad™ Software, Inc.). As shown in FIG. 19, the data indicate that the mean serum antibody concentrations of the M428L and T250Q/M428L variants of OST577-IgG2M3 were maintained at higher levels than wild-type OST577-IgG2M3 at all time points.

Various pharmacokinetic parameters were calculated from the data using WinNonlin® Enterprise Edition, version 3.2 (Pharsight® Corporation). Statistical analyses of the pharmacokinetic parameters were calculated using GraphPad Prism®, version 3.02 (GraphPad™ Software, Inc.). As shown in Table 9, the mean maximum serum antibody concentration (Cmax) was very similar among the three test groups, indicating that the administered antibodies were distributed to the circulation in a similar manner. Thus, the higher antibody concentrations of the mutant IgG2M3 antibodies following the distribution phase are attributable to their increased persistence in the serum. Analysis of the mean clearance (CL) indicated that this was the case. The mean CL, the volume of serum antibody cleared per unit of time, was approximately 1.8-fold lower for the M428L variant (0.0811±0.0384 ml/hr/kg; p=0.057), and approximately 2.8-fold lower for the T250Q/M428L variant (0.0514±0.0075 ml/hr/kg; p=0.029) compared to wild-type OST577-IgG2M3 (0.144±0.047 ml/hr/kg) (Table 9), indicating a significant decrease in the clearance of the OST577-IgG2M3 M428L and T250Q/M428L variants from the circulation of rhesus monkeys compared to the wild-type.

The PK profiles of the OST577-IgG2M3 variants were further analyzed by calculating other parameters (Table 9). Since the AUC (Area Under the Curve) is inversely proportional to CL, it follows that the mean AUC, the area under the concentration-time curve extrapolated from time zero to infinity, was approximately 2-fold higher for the M428L variant (15,200±8,700 hr*μg/ml; p=0.057), and approximately 2.6-fold higher for the T250Q/M428L variant (19,800±2,900 hr*μg/ml; p=0.029) compared to wild-type OST577-IgG2M3 (7,710±3,110 hr*μg/ml) (Table 9), indicating a significant increase in the total exposure of the OST577-IgG2M3 M428L and T250Q/M428L variants compared to the wild-type.

Finally, the mean elimination (β-phase) half-life was approximately 1.8-fold longer for the M428L variant (642±205 hr), and approximately 1.9-fold longer for the T250Q/M428L variant (652±28 hr; p=0.029) compared to wild-type OST577-IgG2M3 (351±121 hr) (Table 9). The elimination half-life for wild-type OST577-IgG2M3 in this study is similar to that for OST577-IgG1 (324±85 hr) in a previous PK study in rhesus monkeys (Ehrlich et al., op. cit.).

TABLE 9

| Name[a] (IgG2M3) | Cmax[b] (μg/ml) | CL[c] (ml/hr/kg) | AUC[d] (hr * μg/ml) | Elimination half-life[e] (hr) |
|---|---|---|---|---|
| Wild-type | 36.7 ± 12.8 | 0.144 ± 0.047 | 7710 ± 3110 | 351 ± 121 |
| M428L | 36.5 ± 20.1 | 0.0811* ± 0.0384 | 15200* ± 8700 | 642 ± 205 |
| T250Q/M428L | 39.9 ± 6.8 | 0.0514* ± 0.0075 | 19800* ± 2900 | 652* ± 28 |

[a]For each mutant, the first letter indicates the wild-type amino acid, the number indicates the position according to the EU index (Kabat et al., op. cit.), and the second letter indicates the mutant amino acid.
[b]Cmax values (±S.D.) are expressed in μg/ml and were calculated from the PK data using WinNonlin as described in Example 9.
[c]CL values (±S.D.) are expressed in ml/hr/kg and were calculated from the PK data using WinNonlin as described in Example 9.
[d]AUC values (±S.D.) are expressed in hr * μg/ml and were calculated from the PK data using WinNonlin as described in Example 9.
[e]Elimination half-life values (±S.D.) are expressed in hr and were calculated from the PK data using WinNonlin as described in Example 9.
*Indicates a significant difference ($p < 0.060$) between the wild-type group and each mutant group. Mann-Whitney tests were done using GraphPad Prism as described in Example 9.

Example 10

This example describes application of the in vitro and in vivo serum half-life assays described in Example 9 to mutants of IgG1 antibodies.

Rhesus Pharmacokinetics Study:

A non-GLP pharmacokinetics study entitled "Pharmacokinetic Comparison of Two Variants of OST577" was conducted at the California National Primate Research Center (CNPRC) at the University of California, Davis. Eight male rhesus macaques were randomized by weight and assigned to one of two study groups. The four animals comprising each study group each received a single intravenous dose of wild-type or a variant of OST577 at 1 mg/kg administered over fifteen minutes. The OST577 antibodies were wild-type OST577-IgG1, and a variant of OST577-IgG1 containing the double mutation T250Q/M428L. Both antibodies were expressed by transfection of Sp2/0 cells and purified as described in Example 5.

Blood samples were drawn prior to dosing on day 0, at 1 and 4 hours after dosing, and at 1, 7, 14, 21, 28, 42, and 56 days. At each time point, 4 mls of blood was drawn from a saphenous vein, serum was prepared, and 2 aliquots were frozen and maintained at −20° C. until use. For serum chemistry and hematology determinations, blood samples were drawn prior to dosing on day 0, and at the conclusion of the study on day 56.

ELISA:

The concentration of the OST577-IgG1 antibodies in rhesus serum samples was determined by ELISA using a validated assay. Pooled normal rhesus serum (PNRS) was obtained from the CNPRC. The same lot of PNRS was used to prepare calibrators, positive and negative serum controls, and for pre-dilution of rhesus serum samples. Calibrators were prepared by standard dilution of OST577-IgG1 in PNRS at 3200, 1600, 800, 400, 200, 100, 50, 25, and 0 ng/ml, equilibrated for 2 hours at room temperature, and frozen in aliquots at −80° C. Positive serum controls were prepared by spiking PNRS with OST577-IgG1 at 0.2 μg/ml for the low positive serum control, 0.4 μg/ml for the medium positive serum control, and 0.8 μg/ml for the high positive serum control, equilibrated for 2 hours at room temperature, and frozen in aliquots at −80° C. PNRS was used as a negative serum control.

Immulon™ 2 plates (DYNEX® Technologies, Inc.) were coated overnight at 2-8° C. with 100 μl/well of a mouse anti-OST577-IgG1 idiotype monoclonal antibody (OST577-γ1 anti-id, Protein Design Labs™, Inc.) at 1.0 μg/ml in PBS. The next day the plates were washed three times with 300 μl/well of PBS/Tween (Phosphate Buffered Saline, 0.1% Tween 20), tapped dry on a paper towel, and blocked with 300 μl/well of SuperBlock® Blocking Buffer in PBS (Pierce Chemical Company) for 60±5 minutes at room temperature. Calibrators, positive and negative serum controls, and serum samples were thawed and brought to room temperature before use. Calibrators, and positive and negative serum controls were diluted 1:10 in SuperBlock® Blocking Buffer in PBS. Serum samples were appropriately pre-diluted (1:5 to 1:80) in PNRS, then diluted 1:10 in SuperBlock® Blocking Buffer in PBS. The plates were washed three times with 300 μl/well of PBS/Tween and tapped dry on a paper towel. Diluted calibrators, positive and negative serum controls, and serum samples were then added at 100 μl/well in duplicate wells and incubated for 60±5 minutes at room temperature. The plates were washed three times with 300 μl/well of PBS/Tween and tapped dry on a paper towel. Goat anti-human lambda light chain HRP-conjugated antibody (Southern Biotechnology Associates, Inc.) was prepared by 1:1000 dilution in PBS/BSA/Tween (Phosphate Buffered Saline, 0.5% Bovine Serum Albumin, 0.1% Tween 20), added at 100 μl/well, and incubated for 60±5 minutes at room temperature. The plates were washed three times with 300 μl/well of PBS/Tween and tapped dry on a paper towel. ABTS Peroxidase Substrate/Peroxidase Solution B (Kirkegaard & Perry Laboratories) was added at 100 μl/well, and incubated for 7±1 minutes. Development was stopped by addition of Substrate Stop Solution (2% Oxalic Acid) at 100 μl/well. Absorbance values at 415 nm were measured within 30 minutes after adding the Substrate Stop Solution using a VERSAmax™ microtitre plate reader (Molecular Devices® Corporation).

A calibration curve was prepared using the mean absorbance values obtained from the calibrators and fitting the data to a four parameter logistic regression curve using SOFTmax® PRO, version 4.0 (Molecular Devices® Corporation). The mean absorbance value for the 0.0 ng/mL calibrator was subtracted from each absorbance value obtained for the remaining calibrators. The positive serum control concentrations were determined after subtracting the mean absorbance value obtained for the negative serum control from each absorbance value obtained for the positive serum controls. Concentrations corresponding to the resulting mean absorbance values were derived by interpolation from the calibration curve. The concentrations of serum samples were determined by subtracting the mean absorbance value of the appropriate predose sample from the absorbance value of each study sample, averaging the resulting absorbance values, deriving the concentration corresponding to the mean absorbance value by interpolation from the calibration curve, and multiplying the resulting concentration by the pre-dilution factor, if any, to arrive at the final concentration for each sample.

The estimated quantitative range of the assay was 0.10-0.90 μg/ml. The assay was considered suitable when the following two conditions were met: (1) the mean back-calculated concentration of all four calibrators in the quantitative range was within 20% of their nominal value; and (2) the mean calculated results of four of six positive serum controls was within 30% of their nominal value, and at least one mean result from each concentration level was within 30% of its nominal value. Data from plates that did not meet the above criteria were rejected. Data from individual serum samples was rejected when either of the following conditions was met: (1) the mean calculated concentration was below the lower limit of quantitation (LLOQ) of the assay (0.10 μg/ml); or (2) the mean calculated concentration was above the upper limit of quantitation (ULOQ) of the assay (0.90 μg/ml). If the calculated result of duplicate samples differed by more than 40% from each other, the sample was retested in a second independent assay. If the mean calculated result of the second assay was within 15% of the mean calculated result of the first assay for the sample in question, the mean calculated result of the first assay was used. Otherwise, the sample was retested in a third independent assay, and the results of all three assays were averaged, unless one value could be removed by outlier testing. In this case, the mean of the two remaining values was reported.

Figure 20:
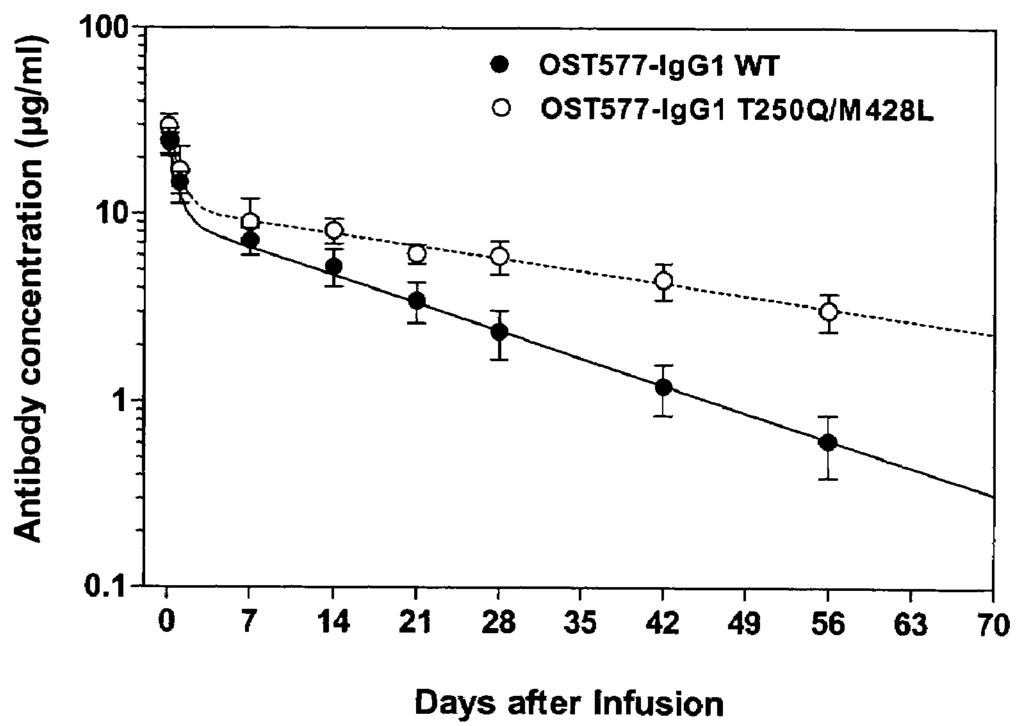
FIG. 20. Pharmacokinetics of OST577-IgG1 wild-type and variant antibodies in rhesus macaque. The observed and modeled mean serum concentrations (μg/ml) and standard deviations of OST577-IgG1 wild-type and variant antibodies administered by infusion at a dose of 1 mg/kg to groups of four rhesus macaques were plotted as a function of time (days after infusion), as described in Example 10.

Results:

The serum antibody concentration data were fitted with a two-compartment model using WinNonlin® Enterprise Edition, version 3.2 (Pharsight® Corporation, Mountain View, Calif.). The model assumes a first order distribution and first order elimination rate and fits the data well. The modeled data (simulated based on the median values of each group's primary pharmacokinetic parameters) as well as the observed mean serum antibody concentration (μg/ml) and the standard deviation for each group of four animals were plotted as a function of time (days after infusion) using GraphPad Prism®, version 3.02 (GraphPad™ Software, Inc.). As shown in FIG. 20, the data indicate that the mean serum antibody concentrations of the T250Q/M428L variant of OST577-IgG1 were maintained at higher levels than wild-type OST577-IgG1 at all time points.

Various pharmacokinetic parameters were calculated from the data using WinNonlin® Enterprise Edition, version 3.2 (Pharsight® Corporation). Statistical analyses of the pharmacokinetic parameters were calculated using GraphPad Prism®, version 3.02 (GraphPad™ Software, Inc.). As shown in Table 10, the Cmax was very similar between both test groups, indicating that the administered antibodies were distributed to the circulation in a similar manner. Thus, the higher antibody concentrations of the mutant IgG1 antibody following the distribution phase are attributable to its increased persistence in the serum. Analysis of the mean CL indicated that this was the case. The mean CL was approximately 2.3-fold lower for the T250Q/M428L variant (0.0811±0.0191 ml/hr/kg; p=0.029) compared to wild-type OST577-IgG1 (0.190±0.022 ml/hr/kg) (Table 10), indicating a significant decrease in the clearance of the OST577-IgG1 T250Q/M428L variant from the circulation of rhesus monkeys compared to the wild-type.

The PK profile of the OST577-IgG1 variant was further analyzed by calculating other parameters (Table 10). The mean AUC was approximately 2.4-fold higher for the T250Q/M428L variant (12,900±3,000 hr*μg/ml; p=0.029) compared to wild-type OST577-IgG1 (5,320±590 hr*μg/ml) (Table 10), indicating a significant increase in the total exposure of the OST577-IgG1 T250Q/M428L variant compared to the wild-type.

Finally, the mean elimination (β-phase) half-life was approximately 2.5-fold longer for the T250Q/M428L variant (838±187 hr; p=0.029) compared to wild-type OST577-IgG1 (336±34 hr) (Table 10). The elimination half-life for wild-type OST577-IgG1 in this study is similar to that for OST577-IgG1 (324±85 hr) in a previous PK study in rhesus monkeys (Ehrlich et al., op. cit.).

TABLE 10

| Name[a] (IgG1) | Cmax[b] (μg/ml) | CL[c] (ml/hr/kg) | AUC[d] (hr * μg/ml) | Elimination half-life[e] (hr) |
|---|---|---|---|---|
| Wild-type | 26.0 ± 4.1 | 0.190 ± 0.022 | 5320 ± 590 | 336 ± 34 |
| T250Q/M428L | 29.1 ± 3.7 | 0.0811* ± 0.0191 | 12900* ± 3000 | 838* ± 187 |

[a]For each mutant, the first letter indicates the wild-type amino acid, the number indicates the position according to the EU index (Kabat et al., op. cit.), and the second letter indicates the mutant amino acid.
[b]Cmax values (±S.D.) are expressed in μg/ml and were calculated from the PK data using WinNonlin as described in Example 10.
[c]CL values (±S.D.) are expressed in ml/hr/kg and were calculated from the PK data using WinNonlin as described in Example 10.
[d]AUC values (±S.D.) are expressed in hr * μg/ml and were calculated from the PK data using WinNonlin as described in Example 10.
[e]Elimination half-life values (±S.D.) are expressed in hr and were calculated from the PK data using WinNonlin as described in Example 10.
*Indicates a significant difference ($p < 0.060$) between the wild-type group and each mutant group. Mann-Whitney tests were done using GraphPad Prism as described in Example 10.

Example 11

This example describes application of the various binding analyses described in Examples 6 and 7 to mutants of IgG3 and IgG4 antibodies.

Mutagenesis:

The overlap-extension PCR method (Higuchi, op. cit.) was used to generate site-directed amino acid substitutions at position 428 of the Hu1D10-IgG3 heavy chain, or positions 250 and 428 of the Hu1D10-IgG4 heavy chain (numbered according to the EU index of Kabat et al., op. cit.). An M428L mutant was generated in the Hu1D10-IgG3 heavy chain. Both an M428L and a T250QM428L mutant were generated in the Hu1D10-IgG4 heavy chain.

Transfections:

The wild-type or mutant Hu1D10-IgG3 or Hu1D10-IgG4 heavy chain expression vectors, described in detail in Examples 1 and 2, were transiently co-transfected with the pVk-Hu1D10 light chain expression vector into human kidney cell line 293-H (Life Technologies®). The Hu1D10-IgG3 or Hu1D10-IgG4 expression vectors were also stably co-transfected with the pVk-Hu1D10 expression vector into Sp2/0 cells, as described in Example 5. For stable transfections in Sp2/0, the IgG3 expression vectors were linearized with FspI; however, the IgG4 expression vectors were linearized with BstZ171 since there are two FspI sites in pHuHC.g4.Tt.D-Hu1D10.

Antibody Purification:

Culture supernatants containing human IgG4 antibodies were quantified by ELISA, harvested by centrifugation, sterile filtered, and purified by protein A affinity chromatography, as described in Example 5.

Culture supernatants containing human IgG3 antibodies were quantified by ELISA, harvested by centrifugation, and sterile filtered, as described in Example 5. The pH of the filtered supernatants was adjusted by addition of 1/75 volume of 1 M Tris-HCl, pH 8.0. Supernatants were run over a 1 ml HiTrap® Protein G HP column (Amersham Biosciences™ Corporation) that was pre-equilibrated with 20 mM sodium phosphate, pH 7.0. The column was washed with the same buffer, and bound antibody was eluted with 100 mM glycine-HCl, pH 2.7. After neutralization by addition of ~1/50 volume of 1 M Tris-HCl, pH 8.0, the pooled protein fractions were either dialyzed overnight in 20 mM sodium citrate, 120 mM NaCl, pH 6.0, or run over a 5 ml HiTrap® Desalting column (Amersham Biosciences™ Corporation) that was pre-equilibrated with 20 mM sodium citrate, 120 mM NaCl, pH 6.0. The flow-through from the desalting column was collected and fractions with $OD_{280}$>0.1 were pooled and concentrated to ~0.5-1.0 mg/ml using 2 ml Vivaspin® concentrators (50,000 dalton MWCO) (Vivascience® AG). Dialyzed material was concentrated in the same manner. Samples were then filter sterilized using 0.2 μm Millex®-GV microfilters (Millipore® Corporation). The concentrations of the purified antibodies were determined by UV spectroscopy by measuring the absorbance at 280 nm (1 mg/ml=1.4 $A_{280}$).

SDS-PAGE:

Five μg samples of purified antibodies were run under reducing or non-reducing conditions, as described in Example 5.

Competitive Binding Assays:

As described in Example 6, NS0 transfectants expressing recombinant, GPI-linked human or rhesus FcRn on the surface were maintained in mycophenolic acid (MPA) selection medium (DMEM, 10% FBS, 1×HT Media Supplement Hybri-Max® (Sigma®), 250 μg/ml xanthine (Sigma®), 1 μg/ml mycophenolic acid (Life Technologies®), and 2 mM L-glutamine) or 2×MPA selection medium.

A dilution series of each purified Hu1D10-IgG3 antibody was competed against human IgG (Sigma-Aldrich, St. Louis, Mo.) that had been labeled with biotin (Pierce Biotechnology, Inc., Rockford, Ill.). Antibodies were tested for binding to both human FcRn on cell line NS0 HuFcRn (memb), clone 7-3, and to rhesus FcRn on cell line NS0 RhFcRn, clone R-3. Approximately $2\times10^5$ cells/test were washed once in FBB, pH 8.0, and once in FBB, pH 6.0, then resuspended in 120 μl of pre-mixed biotinylated human IgG antibody (8.3 μg/ml) and Hu1D10-IgG3 competitor antibody (twofold serial dilutions from 625 μg/ml to 0.305 μg/ml) in FBB, pH 6.0. The cells were incubated with the antibody mixture for 1 hour on ice, washed twice in FBB, pH 6.0, and resuspended in 25 μl of streptavidin-RPE conjugate (BioSource International) diluted to 2.5 μg/ml in FBB, pH 6.0. After incubation for 30 minutes on ice in the dark, the cells were washed twice in FBB, pH 6.0, and resuspended in 1% formaldehyde. Samples were analyzed for antibody binding to FcRn by FACS™ using a FACSCalibur flow cytometer (BD® Biosciences).

A dilution series of each purified Hu1D10-IgG4 antibody was competed against human IgG (Sigma-Aldrich) that had been labeled with biotin (Pierce Biotechnology, Inc.). The IgG4 antibodies were tested for binding to both human FcRn on cell line NS0 HuFcRn (memb), clone 7-3, and to rhesus FcRn on cell line NS0 RhFcRn, clone R-3, as described above for the IgG3 antibodies.

pH-Dependent Binding and Release Assay:

Purified Hu1D10-IgG3 and Hu1D10-IgG4 mutant antibodies were compared to the respective wild-type antibodies for binding to human or rhesus FcRn and then released at various pH values in single-point binding and release assays using cell lines NS0 HuFcRn (memb), clone 7-3, and NS0 RhFcRn, clone R-3, respectively, as described in Example 7. To ensure that both subtypes, IgG3 and IgG4, were labeled equivalently, 25 μl of goat $F(ab')_2$ anti-human kappa FITC-conjugated antibody (Southern Biotechnology Associates, Inc.) diluted to 1.25 μg/ml in FBB of the appropriate pH was used as the detecting reagent.

Results:

Amino acid substitutions were generated at position 428 of the human γ3 heavy chain and positions 250 and 428 of the human γ4 heavy chain (numbered according to the EU index of Kabat et al., op. cit.). These two positions were chosen based on the identification of mutations at these positions in the human γ2M3 heavy chain that resulted in increased binding to FcRn. The M428L mutant (SEQ ID NO:115) was evaluated in the human γ3 heavy chain. Both the M428L mutant (SEQ ID NO:116) and the T250Q/M428L mutant (SEQ ID NO:117) were evaluated in the human γ4 heavy chain.

The IgG3 and IgG4 Fc mutants were expressed as anti-HLA-DR β chain allele antibodies, comprising the light and heavy chain variable regions of Hu1D10 (Kostelny et al. (2001), op. cit.), the light chain constant region of human kappa (Hieter et al. (1980), op. cit.), and the heavy chain constant regions of human IgG3 (Huck et al., op. cit.) and IgG4 (Ellison et al, op. cit.), respectively. As described above, the appropriate wild-type or mutant heavy chain expression vector was transiently co-transfected with the appropriate light chain expression vector into 293-H cells for expression of Hu1D10 monoclonal antibodies. ELISA analysis of culture supernatants harvested 5-7 days after transient transfection showed that antibody expression levels were typically 5-25 μg/ml in 25 ml of supernatant. The Hu1D10-IgG3 and Hu1D10-IgG4 antibodies were purified by affinity chromatography using protein G and protein A, respectively, for a final yield of approximately 100-500 μg. Stable expression of Hu1D10 antibodies in Sp2/0 cells typically resulted in expression levels of 30-100 μg/ml as determined by ELISA. Yields of approximately 50-80% of the antibody present in culture supernatants were obtained by small-scale protein G or protein A affinity chromatography.

Purified antibodies were characterized by SDS polyacrylamide gel electrophoresis (SDS-PAGE) under non-reducing and reducing conditions. SDS-PAGE analysis under non-reducing conditions indicated that the purified antibodies had a molecular weight of about 150-170 kD (data not shown); analysis under reducing conditions indicated that the purified antibodies were comprised of a heavy chain with a molecular weight of about 50-60 kD and a light chain with a molecular weight of about 25 kD (data not shown). SDS-PAGE analysis of antibodies purified from stable Sp2/0 transfectants gave results similar to those observed with antibodies purified from transient 293-H transfections.

The relative binding of wild-type Hu1D10-IgG3 and Hu1D10-IgG4 antibodies and their various mutants to FcRn was determined using a transfected NS0 cell line stably expressing human FcRn on its surface. As described above, purified antibodies were tested for FcRn binding in competitive binding assays. Increasing concentrations of unlabeled competitor antibodies were incubated with cells in the presence of a sub-saturating concentration of biotinylated human IgG antibody (Sigma-Aldrich) in FBB, pH 6.0.

The binding of Hu1D10-IgG3 wild-type and the M428L mutant to human FcRn were tested in competitive binding experiments. As summarized in Table 11, the IC50 for the wild-type Hu1D10-IgG3 antibody is ~15 μg/ml, whereas the IC50 for the M428L single mutant is ~2 μg/ml. The binding of Hu1D10-IgG4 and its mutants to human FcRn were also tested in competitive binding experiments. As summarized in Table 12, the IC50 for the wild-type Hu1D10-IgG4 antibody is ~76 μg/ml, whereas the IC50 for the M428L single mutant is ~5 μg/ml, and the IC50 for the T250Q/M428L double mutant is ~1 μg/ml.

The binding of Hu1D10-IgG3 wild-type and the M428L mutant to rhesus FcRn were tested in competitive binding experiments. As summarized in Table 13, the IC50 for the wild-type Hu1D10-IgG3 antibody is ~14 μg/ml, whereas the IC50 for the M428L single mutant is ~3 μg/ml. The binding of Hu1D10-IgG4 and its mutants to rhesus FcRn were also tested in competitive binding experiments. As summarized in Table 14, the IC50 for the wild-type Hu1D10-IgG4 antibody is ~98 μg/ml, whereas the IC50 for the M428L single mutant is ~7 μg/ml, and the IC50 for the T250Q/M428L double mutant is ~1 μg/ml.

Figure 21:
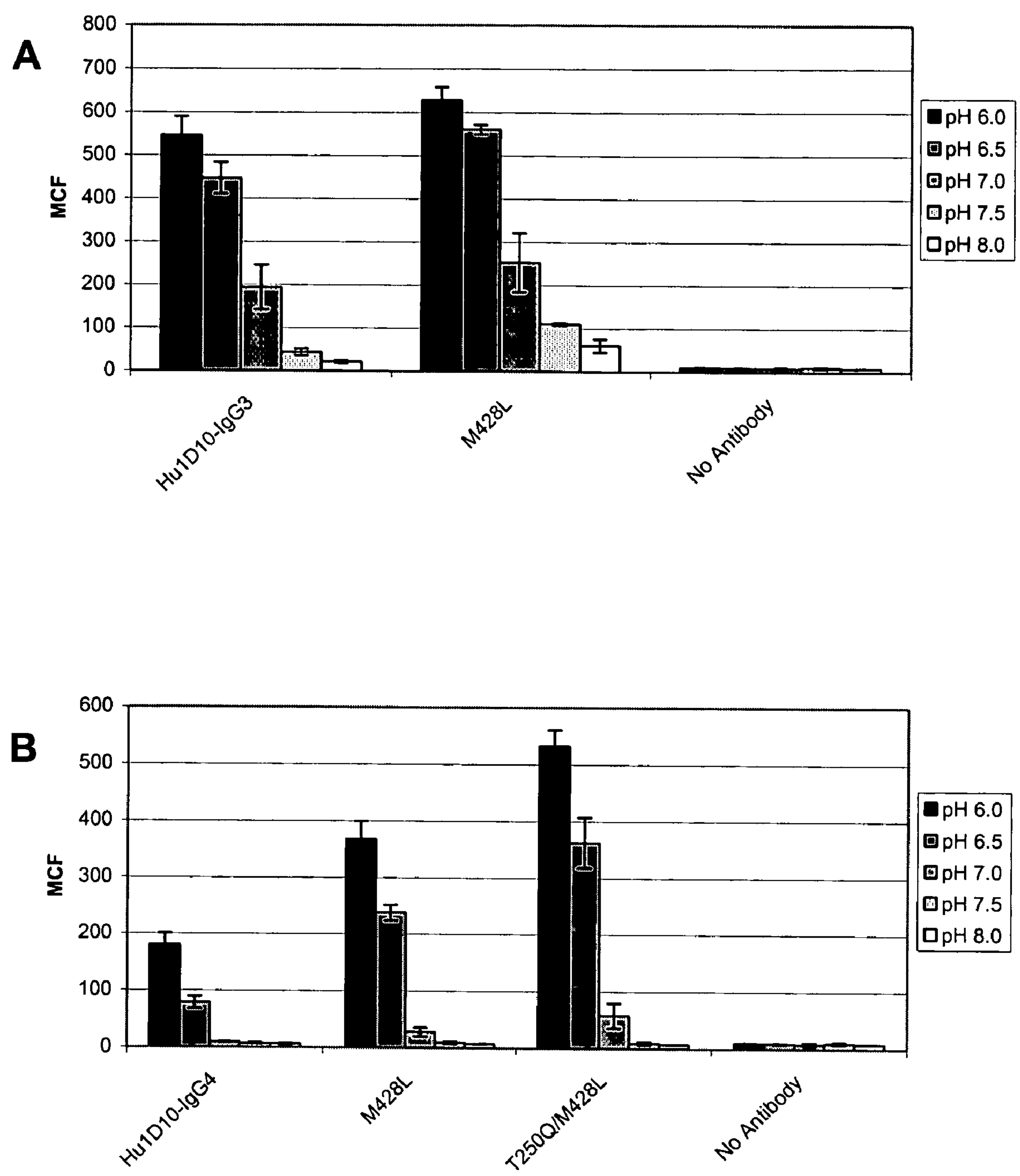
FIG. 21A. pH-Dependent Binding and Release of Hu1D10-IgG3 Wild-Type and Mutant Antibodies to Human FcRn. The binding and release of the wild-type or mutant Hu1D10-IgG3 antibodies to human FcRn on transfected NS0 cells in FBB, at pH 6.0, 6.5, 7.0, 7.5, or 8.0, was analyzed by flow cytometry, as described in Example 11.
FIG. 21B. pH-Dependent Binding and Release of Hu1D10-IgG4 Wild-Type and Mutant Antibodies to Human FcRn. The binding and release of the wild-type or mutant Hu1D10-IgG4 antibodies to human FcRn on transfected NS0 cells in FBB, at pH 6.0, 6.5, 7.0, 7.5, or 8.0, was analyzed by flow cytometry, as described in Example 11.
FIG. 21C. pH-Dependent Binding and Release of Hu1D10-IgG3 Wild-Type and Mutant Antibodies to Rhesus FcRn. The binding and release of the wild-type or mutant Hu1D10-IgG3 antibodies to rhesus FcRn on transfected NS0 cells in FBB, at pH 6.0, 6.5, 7.0, 7.5, or 8.0, was analyzed by flow cytometry, as described in Example 11.
FIG. 21D. pH-Dependent Binding and Release of Hu1D10-IgG4 Wild-Type and Mutant Antibodies to Rhesus FcRn. The binding and release of the wild-type or mutant Hu1D10-IgG4 antibodies to rhesus FcRn on transfected NS0 cells in FBB, at pH 6.0, 6.5, 7.0, 7.5, or 8.0, was analyzed by flow cytometry, as described in Example 11.
Figure 21:
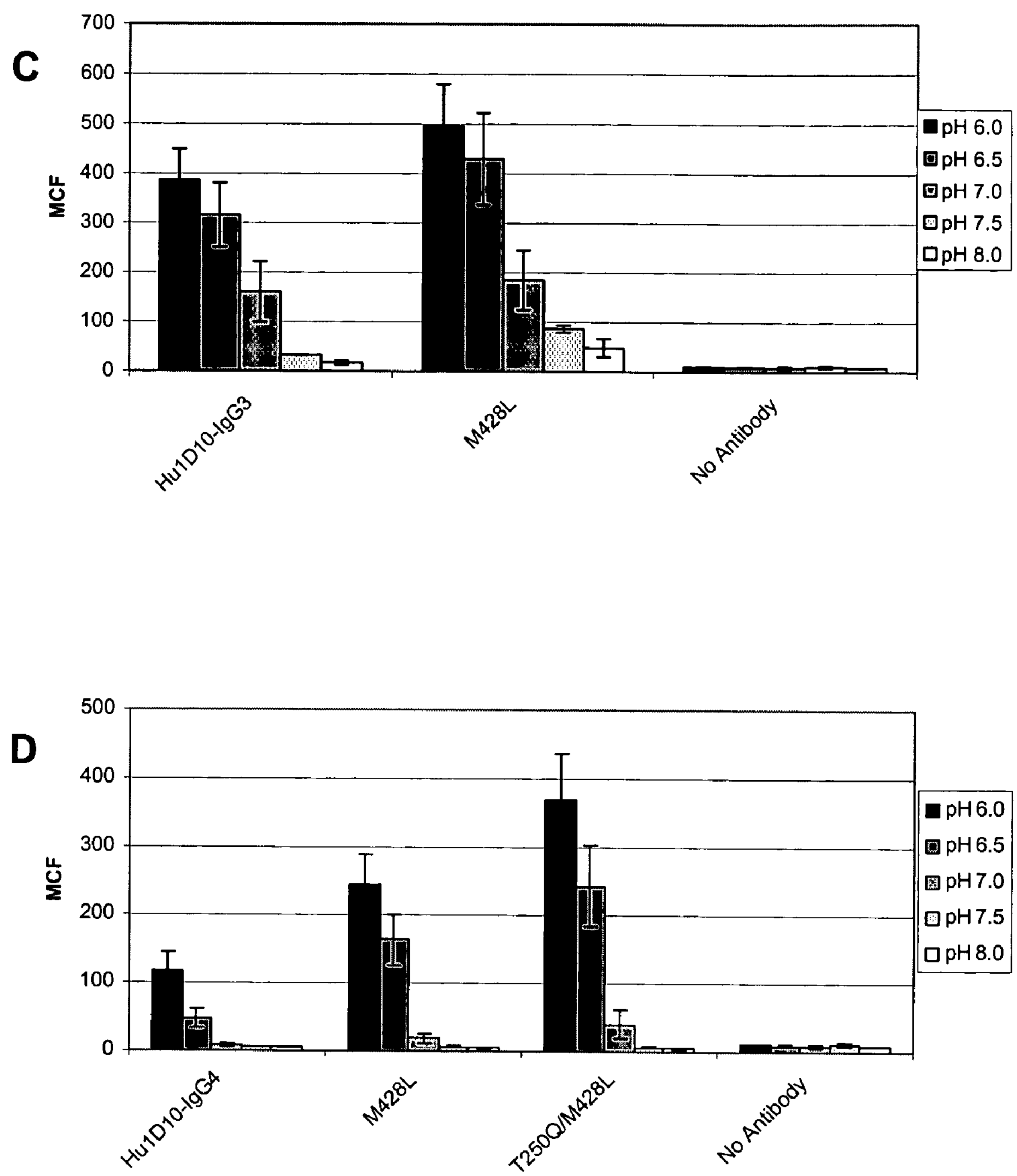

The binding of IgG to FcRn is known to be pH-dependent: IgG binds strongly to FcRn at pH 6.0 but weakly at pH 8.0. In order to engineer mutant antibodies with longer serum half-lives, it is desirable to increase binding to FcRn at pH 6.0, while retaining pH-dependent release from FcRn at pH 8.0. To confirm that binding was pH-dependent, the antibodies were tested for binding to a transfected NS0 cell line stably expressing human FcRn and then released at pH values ranging from pH 6.0 to pH 8.0. As described above, the cells were incubated with a sub-saturating concentration of antibody in FBB, pH 6.0, washed with FBB, pH 6.0, 6.5, 7.0, 7.5, or 8.0, and binding was analyzed by FACS™. As shown in FIG. 21A, the results indicated that the modified Hu1D10-IgG3 antibody with the M428L mutation showed strong binding to human FcRn at pH 6.0, with diminishing binding as the pH values increased to pH 8.0. As shown in FIG. 21B, the results indicated that the modified Hu1D10-IgG4 antibodies with the M428L or T250Q/M428L mutations both showed strong binding to human FcRn at pH 6.0, with diminishing binding as the pH values increased to pH 8.0. These results indicated that the binding of the IgG3 and IgG4 antibodies to human FcRn was pH-dependent.

Similarly, the antibodies were tested for binding to a transfected NS0 cell line stably expressing rhesus FcRn and then released at pH values ranging from pH 6.0 to pH 8.0. As shown in FIG. 21C, the results indicated that the modified Hu1D10-IgG3 antibody with the M428L mutation showed strong binding to rhesus FcRn at pH 6.0, with diminishing binding as the pH values increased to pH 8.0. As shown in FIG. 21D, the results indicated that the modified Hu1D10-IgG4 antibodies with the M428L or T250Q/M428L mutations showed strong binding to rhesus FcRn at pH 6.0, with diminishing binding as the pH values increased to pH 8.0. These results indicated that the binding of the antibodies to rhesus FcRn was also pH-dependent.

TABLE 11

| Name[a] (IgG3) | n[b] | IC50 (μg/ml)[c] | Relative Binding[d] |
|---|---|---|---|
| Wild-type | 3 | 14.5 ± 3.6 | 1.0 |
| M428L | 3 | 2.29 ± 0.39 | 6.3 |

[a]For each mutant, the first letter indicates the wild-type amino acid, the number indicates the position according to the EU index (Kabat et al., op. cit.), and the second letter indicates the mutant amino acid.

[b]n indicates the number of independent assays.

[c]IC50 values (±S.D.) are expressed in μg/ml (based on final competitor concentrations) and were calculated from competitive binding assays versus biotinylated human IgG (Sigma-Aldrich) in FBB, pH 6.0, as described in Example 11.

[d]Relative binding to human FcRn was calculated as the ratio of the IC50 value of the wild-type Hu1D10-IgG3 to that of the mutant.

TABLE 12

| Name[a] (IgG4) | n[b] | IC50 (μg/ml)[c] | Relative Binding[d] |
|---|---|---|---|
| Wild-type | 3 | 76.1 ± 12.7 | 1.0 |
| M428L | 3 | 5.03 ± 0.45 | 15 |
| T250Q/M428L | 3 | 1.07 ± 0.14 | 71 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated human IgG (Sigma-Aldrich) in FBB, pH 6.0, as described in Example 11.
[d]Relative binding to human FcRn was calculated as the ratio of the IC50 value of the wild-type Hu1D10-IgG4 to that of each of the mutants.

TABLE 13

| Name[a] (IgG3) | n[b] | IC50 (μg/ml)[c] | Relative Binding[d] |
|---|---|---|---|
| Wild-type | 3 | 13.8 ± 1.0 | 1.0 |
| M428L | 3 | 3.03 ± 0.44 | 4.6 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated human IgG (Sigma-Aldrich) in FBB, pH 6.0, as described in Example 11.
[d]Relative binding to rhesus FcRn was calculated as the ratio of the IC50 value of the wild-type Hu1D10-IgG3 to that of the mutant.

TABLE 14

| Name[a] (IgG4) | n[b] | IC50 (μg/ml)[c] | Relative Binding[d] |
|---|---|---|---|
| Wild-type | 3 | 98.4 ± 15.8 | 1.0 |
| M428L | 3 | 6.64 ± 1.05 | 15 |
| T250Q/M428L | 3 | 1.27 ± 0.13 | 77 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated human IgG (Sigma-Aldrich) in FBB, pH 6.0, as described in Example 11.
[d]Relative binding to rhesus FcRn was calculated as the ratio of the IC50 value of the wild-type Hu1D10-IgG4 to that of each of the mutants.

Example 12

This example describes application of the in vitro and in vivo serum half-life assays described in Examples 9 and 10 to mutants of IgG3 and IgG4 antibodies.

The protocols of the "Rhesus Pharmacokinetics Study" as described in Examples 9 and 10 are carried out on mutants of IgG3 and IgG4 to confirm the effect of the mutations on in vivo serum half-life and the various pharmacokinetic parameters.

Example 13

This example describes the design and production of FcRn binding mutants of well-known therapeutic antibodies thereby extending (or decreasing) the serum half-life of each so as to allow improved patient treatment regimens.

Daclizumab:

Daclizumab is a humanized anti-CD25 monoclonal antibody that is undergoing clinical development for a number of autoimmune and inflammatory disease indications including asthma, diabetes, uveitis, multiple sclerosis, rheumatoid arthritis and ulcerative colitis. Daclizumab is currently marketed under the trademark Zenapax® for transplant indications only.

The amino acid sequences of the light and heavy chain variable regions for daclizumab have been disclosed in U.S. Pat. No. 5,530,101, which is hereby incorporated by reference herein.

Daclizumab in its current clinical embodiment is an IgG1 isotype antibody, however, an IgG2M3 isotype version of daclizumab may be produced that exhibits similar therapeutic characteristics.

In order to increase the serum half-life of daclizumab, its constant region amino acid sequence may be modified with any of the FcRn binding mutations described above. For example, the T250Q/M428L mutation may be produced in daclizumab using the methods for vector design and mutagenesis described in Examples 1-4 above. The sequence of T250Q/M428L daclizumab is depicted in FIG. 22 (SEQ ID NO: 122).

The increased serum half-life of T250Q/M428L daclizumab may be determined using the in vitro binding assay methods described in Examples 5-7, or using the in vivo assay methods described in Examples 9-10.

It is expected that T250Q/M428L daclizumab will provide the therapeutic benefits of the unaltered daclizumab with the advantage of decreased frequency and amount of dosage.

The other FcRn binding mutations in daclizumab (IgG1 isotype) constant region sequences, as depicted in FIG. 22 (SEQ ID NOs:119-123), may also be produced according to the methods of Examples 1-4 above. It is expected that these mutants will also affect serum half-life of daclizumab as desired based on the effects of these mutations in the OST577 and Hu1D10 antibody examples above.

Similarly, the FcRn binding mutation in an IgG2M3 version of daclizumab constant region sequences, as depicted in FIG. 22 (SEQ ID NOs:124-128), may also be produced according to the methods of Examples 1-4 above.

Fontolizumab:

Fontolizumab is a humanized anti-interferon-gamma (IFN-γ) monoclonal antibody of the IgG1 isotype also known as HuZAF™. Fontolizumab is currently undergoing clinical development as a therapeutic treatment for Crohn's disease. The variable region sequences of fontolizumab are disclosed in U.S. Pat. No. 6,329,511 which is hereby incorporated by reference herein. As described above for daclizumab, the serum half-life of fontolizumab may also be altered by mutating its constant region sequences as shown in FIG. 23 (SEQ ID NOs:130-134), using the methods described above in Examples 1-4.

Visilizumab:

Visilizumab is a humanized anti-CD3 monoclonal antibody of the IgG2M3 isotype, also known as Nuvion®. Visilizumab targets CD3 molecules, which form the antigen-receptor complex on all mature T cells. Visilizumab is currently undergoing clinical development as treatment of steroid refractory ulcerative colitis. As described above for daclizumab and fontolizumab, the serum half-life of visilizumab may also be altered by mutating its constant region sequences as shown in FIG. 24 (SEQ ID NOs:136-140), using the methods described above in Examples 1-4.

Volociximab:

Volociximab is a chimeric IgG4 antibody, also known as M200, directed to the α5β1 integrin that is currently being developed as an angiogenesis inhibitor therapy directed to various proliferative disorders. As described above for daclizumab, fontolizumab, and visilizumab, the serum half-life of volociximab may also be altered by mutating its constant region sequences as shown in FIG. 25 (SEQ ID NOs:142-146), using the methods described above in Examples 1-4.

Example 14

This example describes application of the various binding analyses described in Examples 7 and 11 to mutants of the humanized anti-CD25 antibody, daclizumab, in both IgG1 and IgG2M3 isotypes.

Mutagenesis:

Amino acid substitutions at positions 250 and 428 of the daclizumab (Dac) IgG1 and IgG2M3 heavy chains (numbered according to the EU index of Kabat et al., op. cit.) were generated following the methods described in Examples 3-4 above. The T250Q/M428L mutation was incorporated into Dac-IgG1 and Dac-IgG2M3 expression vectors using the methods for vector design described in Examples 1-2. Wild-type Dac-IgG1 and Dac-IgG2M3 expression vectors were also constructed. The sequences of the T250Q/M428L variants of daclizumab are depicted in FIG. 22 (SEQ ID NOS: 118, 122, and 127).

Transfections:

The Dac-IgG1 wild-type (WT), Dac-IgG2M3 WT, Dac-IgG1 T250Q/M428L, and Dac-IgG2M3 T250Q/M428L expression vectors were stably transfected into NS0 cells, as described in Example 6. The highest antibody-producing clones were chosen for expansion and adaptation to Protein-Free Basal Medium-2 (PFBM-2) (Protein Design Labs™, Inc.). The Dac-IgG1 WT, Dac-IgG1 T250Q/M428L, and Dac-IgG2M3 T250Q/M428L cell lines were cultured in 10 L bioreactors using a fed-batch process (Sauer et al., op. cit.), supplemented volumetrically beginning 2 days after inoculation with Protein-Free Feed Medium-3 (PFFM-3) (Protein Design Labs™, Inc.), and harvested after 10-13 days. The Dac-IgG2M3 WT cell line was expanded to roller bottles in PFBM-2, supplemented after 2 days with 1/10 volume of PFFM-3, and grown to exhaustion. Other protein-free or protein-containing media may also be suitable to support the cell cultures to provide the antibodies.

Antibody Purification:

Culture supernatants containing Dac-IgG1 WT, Dac-IgG1 T250Q/M428L, and Dac-IgG2M3 T250Q/M428L antibodies were purified by protein A affinity chromatography, as follows. The cell culture harvest was adjusted to pH 5.0 using 0.5 M citric acid, clarified by centrifugation, and adjusted to neutral pH. The clarified supernatants were purified by protein A affinity chromatography on a MabSelect Protein A column (GE™ Healthcare, Piscataway, N.J.) using methods similar to those described above in Example 5. The concentrations of the purified antibodies were determined by UV spectroscopy by measuring the absorbance at 280 nm (1 mg/ml=1.34 $A_{280}$).

SDS-PAGE:

Five μg samples of purified antibodies were run under reducing or non-reducing conditions, as described in Example 5.

Competitive Binding Assays:

Antibodies were tested for binding to human FcRn on cell line NS0 HuFcRn (memb), clone 7-3, according to the methods described in Example 11.

pH-Dependent Binding and Release Assay:

The Dac-IgG1 T250Q/M428L and Dac-IgG2M3 T250Q/M428L mutant antibodies were compared to the respective wild-type antibodies for binding to human FcRn and then released at various pH values in single-point binding and release assays using cell line NS0 HuFcRn (memb), clone 7-3, as described in Example 7.

Results:

Amino acid substitutions were generated at positions 250 and 428 (numbered according to the EU index of Kabat et al., op. cit.) of the human γ1 and γ2M3 heavy chains of daclizumab. These two positions were chosen based on the identification of mutations at these positions in the human γ1 and γ2M3 heavy chains of OST577 antibodies that resulted in increased binding affinities to FcRn and longer serum half-lives.

Purified antibodies were characterized by SDS-PAGE under non-reducing and reducing conditions. SDS-PAGE analysis under non-reducing conditions indicated that the purified antibodies had a molecular weight of about 150-160 kD (data not shown); analysis under reducing conditions indicated that the purified antibodies were comprised of a heavy chain with a molecular weight of about 50 kD and a light chain with a molecular weight of about 25 kD (data not shown).

The relative binding of wild-type Dac-IgG1 and Dac-IgG2M3 antibodies and their respective T250Q/M428L mutants to FcRn was determined using a transfected NS0 cell line stably expressing human FcRn on its surface. The purified antibodies were tested for FcRn binding in competitive binding assays. Increasing concentrations of unlabeled competitor antibodies were incubated with cells in the presence of a sub-saturating concentration of biotinylated human IgG antibody (Sigma-Aldrich) in FBB, pH 6.0. As summarized in Table 15, the IC50 for the wild-type Dac-IgG1 antibody is ~20 μg/ml, whereas the IC50 for the T250Q/M428L double mutant is ~0.6 μg/ml. As summarized in Table 16, the IC50 for the wild-type Dac-IgG2M3 antibody is ~71 μg/ml, whereas the IC50 for the T250Q/M428L double mutant is ~4 μg/ml.

To confirm that binding was pH-dependent, the antibodies were tested for binding to a transfected NS0 cell line stably expressing human FcRn and then released at pH values ranging from pH 6.0 to pH 8.0. The cells were incubated with a sub-saturating concentration of antibody in FBB, pH 6.0, washed with FBB, pH 6.0, 6.5, 7.0, 7.5, or 8.0, and binding was analyzed by FACS™. The results indicated that wild-type Dac-IgG1 and Dac-IgG2M3 antibodies and the modified Dac-IgG1 and Dac-IgG2M3 antibodies with the T250Q/M428L mutation all showed strong binding to human FcRn at pH 6.0, with diminishing binding as the pH values increased to pH 8.0. These results confirmed that the binding of the Dac-IgG1 and Dac-IgG2M3 antibodies to human FcRn was pH-dependent.

TABLE 15

| Name[a] (IgG1) | n[b] | IC50 (μg/ml)[c] | Relative Binding[d] |
|---|---|---|---|
| Wild-type | 4 | 20.4 ± 1.6 | 1.0 |
| T250Q/M428L | 3 | 0.626 ± 0.136 | 33 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated human IgG (Sigma-Aldrich) in FBB, pH 6.0, as described in Example 14.
[d]Relative binding to human FcRn was calculated as the ratio of the IC50 value of the wild-type Dac-IgG1 to that of the mutant.

TABLE 16

| Name[a] (IgG2M3) | n[b] | IC50 (μg/ml)[c] | Relative Binding[d] |
|---|---|---|---|
| Wild-type | 3 | 71.4 ± 5.0 | 1.0 |
| T250Q/M428L | 3 | 4.02 ± 0.56 | 18 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated human IgG (Sigma-Aldrich) in FBB, pH 6.0, as described in Example 14.
[d]Relative binding to human FcRn was calculated as the ratio of the IC50 value of the wild-type Dac-IgG2M3 to that of the mutant.

Example 15

This example describes application of the in vitro and in vivo elimination half-life assessment described in Examples 9 and 10 to mutants of the humanized anti-CD25 antibody, daclizumab, in both IgG1 and IgG2M3 isotypes.

Cynomolgus Pharmacokinetics Study:

A non-GLP study of the pharmacokinetics of Dac-IgG1 WT, Dac-IgG1 T250Q/M428L, and Dac-IgG2M3 T250Q/M428L following intravenous administration to cynomolgus monkeys was conducted at Covance Research Products, Inc., Alice, Tex. Thirty male cynomolgus macaques were assigned, based on weight and the baseline level of $CD25^+$ $CD4^+$ T-cells, to one of three study groups. The ten animals comprising each study group each received a single intravenous slow bolus push of wild-type (Dac-IgG1 WT, group 1) or a variant of daclizumab (Dac-IgG1 T250Q/M428L, group 2; and Dac-IgG2M3 T250Q/M428L, group 3) at 10 mg/kg administered within 2 minutes. All three antibodies were expressed by transfection of NS0 cells and purified as described in Example 14.

Blood samples were drawn for determination of daclizumab serum concentration levels prior to dosing on day 0 (predose), at 0.25, 1, 2, and 8 hours after dosing, and at 1, 2, 7, 10, 14, 18, 21, 28, 35, 42, 49, and 56 days. At each time point, approximately 1 ml of blood was drawn via a femoral vein. Serum was prepared and serum samples were frozen and maintained at approximately −70° C. until use. Blood samples (approximately 1 ml) were also drawn for the assessment of antibodies to daclizumab (anti-Ab). These samples were drawn at day 0 (predose), and at 14, 21, 28, 35, 42, 49, and 56 days. For serum chemistry and hematology determinations, blood samples were drawn prior to dosing on day 0, and at the conclusion of the study on day 56.

ELISA for Quantification of Serum Daclizumab:

The concentration of daclizumab (including the variant forms) in serum samples was determined by ELISA. Calibrators and positive quality controls (QC) were prepared by standard dilution of daclizumab in pooled normal cynomolgus serum (PNCS) (Bioreclamation, Inc., East Meadow, N.Y.) at 25, 50, 100, 250, 500, 1000, 2500, and 5000 ng/ml (calibrators); and at 50, 250, and 1000 ng/ml (QC). Separate calibrators and QC's were prepared with each of the three daclizumab materials, equilibrated at room temperature for 2 hours, and frozen in aliquots at −80° C. During sample testing, the calibrators and QC's used for each plate were matched to the serum samples of animals being tested on that plate. For example, samples from animals dosed with Dac-IgG1 WT (Group 1) were tested on plates including calibrators and controls prepared with Dac-IgG1 WT.

Nunc Maxisorp™ 96-well microtiter plates (Nalge Nunc International, Rochester, N.Y.) were coated overnight at 2-8° C. with 100 µl/well of IL-2 Receptor (R&D Systems™, Minneapolis, Minn.) at 25 ng/ml in sodium carbonate buffer. The next day the plates were emptied and tapped dry on a paper towel, and blocked with 300 µl/well of Super Block (ScyTek Laboratories, Inc., Logan, Utah) for 60±5 minutes at room temperature. Calibrators, positive and negative serum controls, and serum samples were thawed and brought to room temperature before use, then diluted 1:5 in Super Block. Serum samples were first appropriately prediluted into the assay quantitative range (1:2 to 1:1000) in PNCS, then diluted 1:5 in Super Block. The plates were washed two times with 300 µl/well of PBS/Tween (PBS, 0.05% Tween 20) and tapped dry on a paper towel. Diluted calibrators, positive and negative serum controls, and serum samples were then added at 100 µl/well in duplicate wells and incubated for 60±5 minutes at room temperature. The plates were washed two times with 300 µl/well of PBS/Tween and tapped dry on a paper towel. Sheep anti-human IgG1 HRP-conjugated antibody (The Binding Site™, Inc., San Diego, Calif.) was diluted 1:3500 in PBS/BSA/Tween (Phosphate Buffered Saline, 1% Bovine Serum Albumin, 0.05% Tween 20) as the detection reagent for samples from animals dosed with Dac-IgG1 WT and Dac-IgG1 T250Q/M428L. Goat anti-human IgG (H+ L) antibody (Zymed™ Laboratories, Inc., South San Francisco, Calif.) was diluted 1:5000 in PBS/BSA/Tween as the detection reagent for samples from animals dosed with Dac-IgG2M3 T250Q/M428L. The detection reagents were added at 150 µl/well, and incubated for 60±5 minutes at room temperature. The plates were washed six times with 300 µl/well of PBS/Tween and tapped dry on a paper towel. TMB substrate (Sigma®) was added at 150 µl/well, and incubated for 10±1 minute. Development was stopped by addition of Substrate Stop Solution (2.5 M Sulfuric Acid) at 50 µl/well. Absorbance values at 450 nm were measured within 30 minutes after adding the Substrate Stop Solution using a Spectramax™ microtiter plate reader (Molecular Devices® Corporation).

A calibration curve was prepared using the mean absorbance values obtained from the calibrators and fitting the data to a four parameter logistic regression curve using SOFTmax® PRO, version 4.0 (Molecular Devices® Corporation). The mean absorbance value for the 0.0 ng/ml calibrator was subtracted from each absorbance value obtained for the remaining calibrators. The positive serum QC concentrations were determined after subtracting the mean absorbance value obtained for the negative QC from each absorbance value obtained for the positive serum controls. Concentrations corresponding to the resulting mean absorbance values were derived by interpolation from the calibration curve. The concentrations of serum samples were determined by subtracting the mean absorbance value of the appropriate predose sample from the absorbance value of each study sample, averaging the resulting absorbance values, deriving the concentration corresponding to the mean absorbance value by interpolation from the calibration curve, and multiplying the resulting concentration by the pre-dilution factor, if any, to arrive at the final concentration for each sample.

The estimated quantitative range of the assay was established as 50 ng/ml (LLOQ) to 1000 ng/ml (ULOQ). Each assay run was considered acceptable when the following two conditions were met: (1) the mean back-calculated concentration of 4 of 5 calibrators in the quantitative range (50, 100, 250, 500, and 1000 ng/ml) was within 20% of their nominal value; and (2) the mean calculated results of four of six positive quality controls was within 30% of their nominal value, and at least one mean result from each concentration level was within 30% of its nominal value. Data from plates that did not meet the above criteria were rejected. Data from individual serum samples was rejected when either of the following conditions was met: (1) the mean calculated concentration of a pre-diluted sample was below the LLOQ of the assay (50 ng/ml); or (2) the mean calculated concentration was above the ULOQ of the assay (1000 ng/ml). If the calculated result of duplicate sample wells differed by more than 40%, the sample was retested.

ELISA Analysis for Anti-Daclizumab Antibodies:

ELISA methods were developed to detect and quantify anti-daclizumab antibodies when present in the serum of study animals. A murine anti-idiotypic antibody (anti-id) against daclizumab (Zid 5.1; Protein Design Labs™, Inc.) was used to prepare calibrators and positive QC's in PNCS (Bioreclamation, Inc.). Calibrators were prepared at 50, 100, 250, 500, 1000, and 2500 ng/ml, and QC's were prepared at 300 and 600 ng/ml of anti-id. An un-spiked negative QC containing PNCS was also included in each assay. Calibrators and controls were equilibrated for 2 hours at room temperature, and frozen in aliquots at −80° C.

Nunc Maxisorp™ 96-well microtiter plates (Nalge Nunc International) were coated overnight at 2-8° C. with 100 µl/well of daclizumab at 0.2 µg/ml in PBS. The next day the plates were emptied and tapped dry on a paper towel, and blocked with 300 µl/well of PBS/BSA (Phosphate Buffered Saline, 1% Bovine Serum Albumin) for 60±5 minutes at room temperature. Calibrators, positive and negative serum controls, and serum samples were thawed and brought to room temperature, then diluted 1:5 in Super Block (Scytek Laboratories). The plates were washed two times with 300 µl/well of PBS/Tween and tapped dry on a paper towel. Diluted calibrators, positive and negative serum controls, and serum samples were then added at 100 µl/well in duplicate wells and incubated for 60±5 minutes at room temperature. The plates were washed two times with 300 µl/well of PBS/Tween and tapped dry on a paper towel. HRP-conjugated daclizumab (Protein Design Labs™, Inc.) was diluted in PBS/BSA/Tween, added at 150 µl/well, and incubated for 60±5 minutes at room temperature. The plates were washed six times with 300 µl/well of PBS/Tween and tapped dry on a paper towel. Enhanced K-Blue® Substrate Solution (TMB) (Neogen™ Corporation, Lansing, Mich.) was added at 150 µl/well, and incubated for 10-12 minutes. Development was stopped by addition of Substrate Stop Solution (2.5 M Sulfuric Acid) at 50 µl/well. Absorbance values at 450 nm were measured within 30 minutes after adding the Substrate Stop Solution using a Spectramax™ microtiter plate reader (Molecular Devices® Corporation).

During sample testing, the specific daclizumab coating antibody and daclizumab-HRP detection reagent used for each plate was matched to the serum samples of animals being tested on that plate. For example, samples from animals dosed with Dac-IgG1 T250Q/M428L (Group 2) were tested on plates coated with Dac-IgG1 T250Q/M428L, and detected with Dac-IgG1 T250Q/M428L-HRP. The dilutions used for the Dac-HRP conjugates during sample testing were 1:1000, 1:3000, or 1:6500 for Dac-IgG1 WT-HRP, Dac-IgG1 T250Q/M428L-HRP, and Dac-IgG2M3 T250Q/M428L-HRP, respectively.

A calibration curve was prepared using the mean absorbance values obtained from the calibrators and fitting the data to a four parameter logistic regression curve using SOFTmax® PRO, version 4.0 (Molecular Devices® Corporation). The mean absorbance value for the 0.0 ng/ml calibrator was subtracted from each absorbance value obtained for the remaining calibrators. The positive QC concentrations were determined after subtracting the mean absorbance value obtained for the negative QC from each absorbance value obtained for the positive QC. Concentrations corresponding to the resulting mean absorbance values were derived by interpolation from the calibration curve. The concentrations of serum samples were determined by subtracting the mean absorbance value of the appropriate predose sample from the absorbance value of each study sample, averaging the resulting absorbance values, deriving the concentration corresponding to the mean absorbance value by interpolation from the calibration curve, and multiplying the resulting concentration by the pre-dilution factor, if any, to arrive at the final concentration for each sample.

The estimated quantitative range of the assay was determined to be between 100 ng/ml (LLOQ) and 2500 ng/ml (ULOQ) of anti-idiotype equivalents. Sample result concentrations equal to or greater than the LLOQ, and equal to or less than the ULOQ were reported in relative anti-idiotype equivalent concentration units. Samples with concentrations >2500 ng/ml were reported as ">2500 ng/ml," without subsequent dilution and retesting. Results below the quantitative range were reported as "BQL" (below quantitative limits). Each assay run was considered acceptable if the mean calculated concentration of the low and high positive QC's was within 60% of their nominal concentration. Data from plates that did not meet this criterion were rejected, and all samples from that run were retested. If absorbance values from duplicate sample wells differed by more than 25%, the sample was retested.

Results:

Among all 30 animals, 9, 6, and 8 animals from groups 1, 2, and 3, respectively, had detectable anti-daclizumab antibodies (anti-Ab). Although the timing of the detectable anti-Ab varied, the majority of the anti-Ab responses occurred after day 28 and were neutralizing in nature as confirmed by the concurrent loss of daclizumab binding to CD25 on peripheral $CD4^+$ T-cells (data not shown). These anti-Ab responses coincided with a significant reduction in serum daclizumab concentrations indicating that these immunogenic responses significantly accelerated the drug clearance after they became detectable. One strategy to minimize the impact of the immunogenicity response on drug elimination is to truncate the data to a time before substantial anti-Ab responses are detected. This truncation cutoff time was determined to be day 28 based on two justifications: 1) the majority of the animals had no detectable anti-Ab response until after the day 28 time point; 2) by day 28, the area under drug concentration-time curve ($AUC_{0-28\ day}$) was at least 80% of the total AUC (AUC extrapolated to infinity), hence the degree of extrapolation in estimating the elimination half-life was minimized and acceptable.

Several animals (n=3, 1, and 3 for groups 1, 2, and 3, respectively) developed high levels of anti-Ab on or earlier than day 28. The impact of the anti-Ab response on the PK profile is so profound in these animals that the evaluation of PK characteristics in these animals cannot be properly done even if the data were truncated to day 28 (data not shown). Hence, these animals were excluded from the data analyses. As a result, 7, 9, and 7 animals were used in the data analyses and statistics for groups 1, 2, and 3, respectively.

Figure 26:
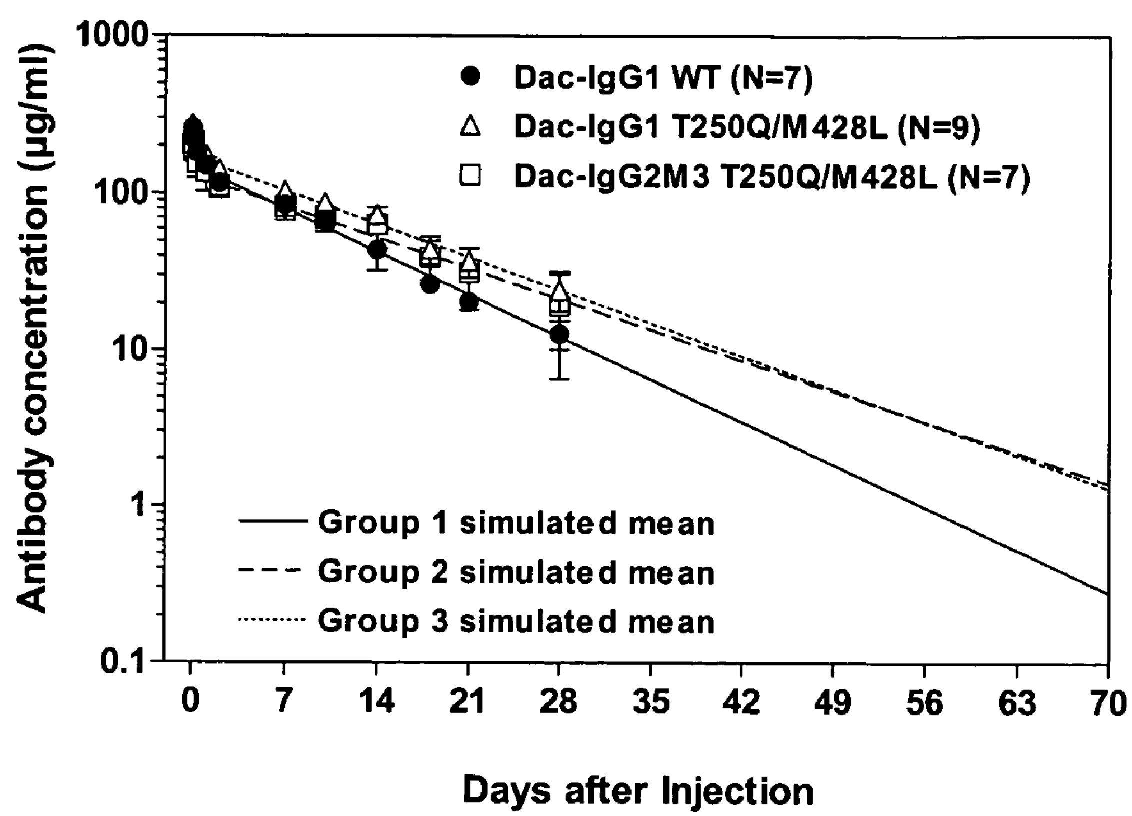
FIG. 26. Pharmacokinetics of Dac-IgG1 wild-type, Dac-IgG1 variant, and Dac-IgG2M3 variant antibodies in cynomolgus monkeys. The observed mean serum antibody concentrations (μg/ml) and standard deviations of Dac-IgG1 wild-type, Dac-IgG1 T250Q/M428L, and Dac-IgG2M3 T250Q/M428L variant antibodies administered by bolus injection at a dose of 10 mg/kg to groups of ten cynomolgus monkeys were plotted as a function of time (days after injection) along with model predicted curves (simulated based on group mean PK parameters), as described in Example 15.

The serum antibody concentration data were fitted with a two-compartment model using WinNonlin® Enterprise Edition, version 4.0.1 (Pharsight® Corporation). The model assumes a first order distribution and first order elimination rate and fits the data well. The modeled data (simulated based on the mean values of each group's primary pharmacokinetic parameters) as well as the observed mean serum antibody concentration (µg/ml) and the standard deviation for each group of evaluable animals were plotted as a function of time (days after infusion) using GraphPad Prism®, version 3.02 (GraphPad™ Software, Inc.). As shown in FIG. 26, the concentration data indicated that the mean serum antibody concentrations of both isotype mutant variants were maintained at higher levels than the wild-type Dac-IgG1 antibody later in the elimination phase.

Various pharmacokinetic parameters were calculated from data up to day 28 using WinNonlin® Enterprise version, 4.0.1 (Pharsight® Corporation). Pair-wise comparisons of PK parameters between the Dac-IgG1 WT and Dac-IgG1 T250Q/M428L mutant antibodies or between the Dac-IgG1 WT and Dac-IgG2M3 T250Q/M428L mutant antibodies were performed by a nonparametric Mann-Whitney test (two-tailed) using GraphPad Prism®, version 3.02 (Graphpad™ Software). P values less than 0.05 were considered significant.

As shown in Table 17, the $C_{max}$ was similar between the Dac-IgG1 WT and Dac-IgG1 T250Q/M428L groups, indicating that the administered antibodies were distributed to the circulation in a similar manner. Thus, the higher antibody concentrations of the mutant IgG1 antibody following the distribution phase are attributable to its increased persistence in the serum. Analysis of the mean CL value indicated that this was the case. The mean CL was approximately 30% slower for the Dac-IgG1 T250Q/M428L variant (0.169±0.020 ml/hr/kg; p=0.0002) compared to Dac-IgG1 WT (0.243±0.018 ml/hr/kg) (Table 17), indicating a significant decrease in the systemic clearance of the Dac-IgG1 T250Q/M428L variant compared to the Dac-IgG1 WT antibody.

The PK profile of the Dac-IgG1 T250Q/M428L variant was further analyzed by calculating other parameters (Table 17). The mean AUC (extrapolated to infinity) was approximately 45% higher for the Dac-IgG1 T250Q/M428L variant (59,800±7,000 hr*μg/ml; p=0.0002) compared to Dac-IgG1 WT (41,300±3,100 hr*μg/ml) (Table 17), indicating a significant increase in the total exposure of the Dac-IgG1 T250Q/M428L variant compared to the wild-type antibody.

As a result of decreased clearance, the mean elimination (β-phase) half-life was approximately 30% longer for the Dac-IgG1 T250Q/M428L variant (240±32 hr; p=0.0052) compared to wild-type Dac-IgG1 (186±26 hr) (Table 17).

For the Dac-IgG2M3 T250Q/M428L variant antibody, however, the $C_{max}$ appeared slightly lower compared to the Dac-IgG1 WT antibody, although the difference was not statistically different (p=0.054). The mean CL was approximately 15% slower for the Dac-IgG2M3 T250Q/M428L variant (0.208±0.067 ml/hr/kg) compared to Dac-IgG1 WT (0.243±0.018 ml/hr/kg) (Table 17). However, the decrease in the clearance of the Dac-IgG2M3 T250Q/M428L variant was not significant compared to Dac-IgG1 WT (p=0.0728).

The mean AUC (extrapolated to infinity) was approximately 27% higher for the Dac-IgG2M3 T250Q/M428L variant (52,400±16,900 hr*μg/ml) compared to Dac-IgG1 WT (41,300±3,100 hr*μg/ml) (Table 17). However, the difference was not significant due to the high inter-individual variability seen in group 3 (p=0.0728).

The mean elimination (β-phase) half-life was significantly (approximately 58%) longer for the Dac-IgG2M3 T250Q/M428L variant (293±140 hr; p=0.0111) compared to Dac-IgG1WT (186±26 hr) (Table 17). Note that the inter-animal variability is also quite high for this parameter (CV % is approximately 48%).

TABLE 17

| Name[a] (Dac) | $C_{max}$[b] (μg/ml) | CL[c] (ml/hr/kg) | AUC[d] (hr * μg/ml) | Elimination half-life[e] (hr) |
|---|---|---|---|---|
| IgG1 WT | 260 ± 27 | 0.243 ± 0.018 | 41300 ± 3100 | 186 ± 26 |
| IgG1 T250Q/M428L | 278 ± 20 | 0.169* ± 0.020 | 59800* ± 7000 | 240* ± 32 |
| IgG2M3 T250Q/M428L | 220 ± 26 | 0.208 ± 0.067 | 52400 ± 16900 | 293* ± 140 |

[a]For each mutant, the first letter indicates the wild-type amino acid, the number indicates the position according to the EU index (Kabat et al., op. cit.), and the second letter indicates the mutant amino acid.

[b]$C_{max}$ values (±S.D.) are expressed in μg/ml and were the observed maximum concentrations.

[c]CL values (±S.D.) are expressed in ml/hr/kg and were calculated from the PK data using WinNonlin as described in Example 15.

[d]AUC values (±S.D.) are expressed in hr * μg/ml and were calculated from the PK data using WinNonlin as described in Example 15.

[e]Elimination half-life values (±S.D.) are expressed in hr and were calculated from the PK data using WinNonlin as described in Example 15.

*Indicates a significant difference (p < 0.050) when comparing the wild-type group to the T250Q/M428L mutant group. Mann-Whitney tests were done using GraphPad Prism as described in Example 15.

Example 16

This example describes application of the various binding analyses described in Examples 7 and 11 to mutants of the humanized anti-CD3 antibody, visilizumab, with the IgG2M3 isotype.

Mutagenesis:

Amino acid substitutions at positions 250 and 428 of the visilizumab (Nuvion®; HuM291) IgG2M3 heavy chain (numbered according to the EU index of Kabat et al., op. cit.) were generated following the methods described in Examples 3-4 above. The T250Q/M428L mutation was incorporated into a HuM291-IgG2M3 heavy chain expression vector using the methods for vector design described in Examples 1-2. Wild-type light chain and HuM291-IgG2M3 heavy chain expression vectors were also constructed. The sequences of the T250Q/M428L variant of HuM291 are depicted in FIG. 24 (SEQ ID NOS: 135 and 139).

Transfections:

293-H cells were transiently cotransfected with the HuM291 light chain plasmid and the HuM291-IgG2M3 WT or HuM291-IgG2M3 T250Q/M428L heavy chain plasmids, as described in Example 5.

Antibody Purification:

Antibodies were purified from culture supernatants containing HuM291-IgG2M3 WT or HuM291-IgG2M3 T250Q/M428L by protein A affinity chromatography, following the methods described in Example 5.

SDS-PAGE:

Five μg samples of purified antibodies were run under reducing or non-reducing conditions, as described in Example 5.

Competitive Binding Assays:

Antibodies were tested for binding to human FcRn on cell line NS0 HuFcRn (memb), clone 7-3, according to the methods described in Example 11.

pH-Dependent Binding and Release Assay:

The HuM291-IgG2M3 WT and HuM291-IgG2M3 T250Q/M428L mutant antibodies were compared for binding to human FcRn and then released at various pH values in single-point binding and release assays using cell line NS0 HuFcRn (memb), clone 7-3, as described in Example 7.

Results:

Amino acid substitutions were generated at positions 250 and 428 (numbered according to the EU index of Kabat et al., op. cit.) of the human γ2M3 heavy chain of HuM291. These two positions were chosen based on the identification of mutations at these positions in the human γ1 and γ2M3 heavy chains of OST577 antibodies that resulted in increased binding affinities to FcRn and longer serum half-lives.

Purified antibodies were characterized by SDS-PAGE under non-reducing and reducing conditions. SDS-PAGE analysis under non-reducing conditions indicated that the purified antibodies had a molecular weight of about 150-160 kD (data not shown); analysis under reducing conditions indicated that the purified antibodies were comprised of a heavy chain with a molecular weight of about 50 kD and a light chain with a molecular weight of about 25 kD (data not shown).

The relative binding of the wild-type HuM291-IgG2M3 antibody and the HuM291-IgG2M3 T250Q/M428L double mutant to FcRn was determined using a transfected NS0 cell line stably expressing human FcRn on its surface. The purified antibodies were tested for FcRn binding in competitive binding assays. Increasing concentrations of unlabeled competitor antibodies were incubated with cells in the presence of a sub-saturating concentration of biotinylated human IgG antibody (Sigma-Aldrich) in FBB, pH 6.0. As summarized in Table 18, the IC50 for the wild-type HuM291-IgG2M3 antibody is ~42 μg/ml, whereas the IC50 for the T250Q/M428L double mutant is ~1.0 μg/ml To confirm that binding was pH-dependent, the antibodies were tested for binding to a transfected NS0 cell line stably expressing human FcRn and then released at pH values ranging from pH 6.0 to pH 8.0. The cells were incubated with a sub-saturating concentration of antibody in FBB, pH 6.0, washed with FBB, pH 6.0, 6.5, 7.0, 7.5, or 8.0, and binding was analyzed by FACS™. The results indicated that wild-type HuM291-IgG2M3 antibody and the modified HuM291-IgG2M3 antibody with the T250Q/M428L mutation both showed strong binding to human FcRn at pH 6.0, with diminishing binding as the pH values increased to pH 8.0. These results confirmed that the binding of the HuM291-IgG2M3 antibodies to human FcRn was pH-dependent.

TABLE 18

| Name[a] (IgG2M3) | n[b] | IC50 (μg/ml)[c] | Relative Binding[d] |
|---|---|---|---|
| Wild-type | 3 | 42.2 ± 7.5 | 1.0 |
| T250Q/M428L | 3 | 0.994 ± 0.200 | 42 |

[a]For each mutant, the first letter indicates the wild-type amino acid, the number indicates the position according to the EU index (Kabat et al., op. cit.), and the second letter indicates the mutant amino acid.
[b]n indicates the number of independent assays.
[c]IC50 values (±S.D.) are expressed in μg/ml (based on final competitor concentrations) and were calculated from competitive binding assays versus biotinylated human IgG (Sigma-Aldrich) in FBB, pH 6.0, as described in Example 16.
[d]Relative binding to human FcRn was calculated as the ratio of the IC50 value of the wild-type HuM291-IgG2M3 to that of the mutant.

Example 17

This example describes application of the various binding analyses described in Examples 7 and 11 to mutants of the chimeric anti-α5β1 integrin antibody, volociximab, with the IgG4 isotype.

Mutagenesis:

Amino acid substitutions at positions 250 and 428 of the volociximab (M200) IgG4 heavy chain (numbered according to the EU index of Kabat et al., op. cit.) were generated following the methods described in Examples 3-4 above. The T250Q/M428L mutation was incorporated into an M200-IgG4 heavy chain expression vector using the methods for vector design described in Examples 1-2. Wild-type light chain and M200-IgG4 heavy chain expression vectors were also constructed. The sequences of the T250Q/M428L variant of M200 are depicted in FIG. 25 (SEQ ID NOS: 141 and 145).

Transfections:

The M200-IgG4 WT and M200-IgG4 T250Q/M428L expression vectors were stably transfected into NS0 cells, as described in Example 6. The highest antibody-producing clones were chosen for expansion and adaptation to Protein-Free Basal Medium-2 (PFBM-2) (Protein Design Labs™, Inc.). The cell lines were expanded to roller bottles in PFBM-2, supplemented after 2 days with 1/10 volume of PFFM-3, and grown to exhaustion.

Antibody Purification:

Antibodies were purified from culture supernatants containing M200-IgG4 WT or M200-IgG4 T250Q/M428L by protein A affinity chromatography, following the methods described in Example 5.

SDS-PAGE:

Five μg samples of purified antibodies were run under reducing or non-reducing conditions, as described in Example 5.

Competitive Binding Assays:

Antibodies were tested for binding to human FcRn on cell line NS0 HuFcRn (memb), clone 7-3, according to the methods described in Example 11.

pH-Dependent Binding and Release Assay:

The M200-IgG4 WT and M200-IgG4 T250Q/M428L mutant antibodies were compared for binding to human FcRn and then released at various pH values in single-point binding and release assays using cell line NS0 HuFcRn (memb), clone 7-3, as described in Example 7.

Results:

Amino acid substitutions were generated at positions 250 and 428 (numbered according to the EU index of Kabat et al., op. cit.) of the human γ4 heavy chain of M200. These two positions were chosen based on the identification of mutations at these positions in the human γ1 and γ2M3 heavy chains of OST577 antibodies that resulted in increased binding affinities to FcRn and longer serum half-lives.

Purified antibodies were characterized by SDS-PAGE under non-reducing and reducing conditions. SDS-PAGE analysis under non-reducing conditions indicated that the purified antibodies had a molecular weight of about 150-160 kD (data not shown); analysis under reducing conditions indicated that the purified antibodies were comprised of a heavy chain with a molecular weight of about 50 kD and a light chain with a molecular weight of about 25 kD (data not shown).

The relative binding of the wild-type M200-IgG4 antibody and the M200-IgG4 T250Q/M428L double mutant to FcRn was determined using a transfected NS0 cell line stably expressing human FcRn on its surface. The purified antibodies were tested for FcRn binding in competitive binding assays. Increasing concentrations of unlabeled competitor antibodies were incubated with cells in the presence of a sub-saturating concentration of biotinylated human IgG antibody (Sigma-Aldrich) in FBB, pH 6.0. As summarized in Table 19, the IC50 for the wild-type M200-IgG4 antibody is ~35 μg/ml, whereas the IC50 for the T250Q/M428L double mutant is ~1.0 μg/ml To confirm that binding was pH-dependent, the antibodies were tested for binding to a transfected NS0 cell line stably expressing human FcRn and then released at pH values ranging from pH 6.0 to pH 8.0. The cells were incubated with a sub-saturating concentration of antibody in FBB, pH 6.0, washed with FBB, pH 6.0, 6.5, 7.0, 7.5, or 8.0, and binding was analyzed by FACS™. The results indicated that wild-type M200-IgG4 antibody and the modified M200-IgG4 antibody with the T250Q/M428L mutation both showed strong binding to human FcRn at pH 6.0, with diminishing binding as the pH values increased to pH 8.0 (data not shown). These results confirmed that the binding of the M200-IgG4 antibodies to human FcRn was pH-dependent.

TABLE 19

| Name[a] (IgG4) | n[b] | IC50 (μg/ml)[c] | Relative Binding[d] |
|---|---|---|---|
| Wild-type | 3 | 34.7 ± 6.3 | 1.0 |
| T250Q/M428L | 3 | 1.00 ± 0.13 | 35 |

[a]For each mutant, the first letter indicates the wild-type amino acid, the number indicates the position according to the EU index (Kabat et al., op. cit.), and the second letter indicates the mutant amino acid.

[b]n indicates the number of independent assays.

[c]IC50 values (±S.D.) are expressed in μg/ml (based on final competitor concentrations) and were calculated from competitive binding assays versus biotinylated human IgG (Sigma-Aldrich) in FBB, pH 6.0, as described in Example 17.

[d]Relative binding to human FcRn was calculated as the ratio of the IC50 value of the wild-type M200-IgG4 to that of the mutant.

Although the invention has been described with reference to the presently preferred embodiments, it should be understood that various modifications may be made without departing from the spirit of the invention.

All publications, patents, patent applications, and web sites are herein incorporated by reference in their entirety to the same extent as if each individual publication, patent, patent application, or web site was specifically and individually indicated to be incorporated by reference in its entirety.

What is claimed is:

1. A modified anti-CD25 monoclonal antibody of class IgG with FcRn binding affinity increased relative to that of an unmodified monoclonal antibody of class IgG, the modified antibody comprising a heavy chain constant region comprising glutamic acid or glutamine at amino acid residue 250 and leucine or phenylalaine at amino acid residue 428.

2. The modified monoclonal antibody according to claim 1, wherein said unmodified monoclonal antibody is of IgG1 or IgG2M3 isotype.

3. The modified monoclonal antibody according to claim 1, wherein said class IgG antibody is a human IgG1.

4. The modified monoclonal antibody according to claim 1, wherein said class IgG antibody is a human IgG2M3.

5. The modified monoclonal antibody according to claim 1, wherein said amino acid residue 250 from the heavy chain constant region is glutamine.

6. The modified monoclonal antibody according to claim 1, wherein said amino acid residue 250 from the heavy chain constant region is glutamic acid.

7. The modified monoclonal antibody according to claim 2, wherein said amino acid residue 428 from the heavy chain constant region is leucine.

8. The modified monoclonal antibody according to claim 2, wherein said amino acid residue 428 from the heavy chain constant region is phenylalanine.

* * * * *